(12) United States Patent
Cho et al.

(10) Patent No.: US 12,378,250 B2
(45) Date of Patent: Aug. 5, 2025

(54) TRICYCLIC COMPOUND AS IRAK4 INHIBITOR

(71) Applicant: KOREA RESEARCH INSTITUTE OF CHEMICAL TECHNOLOGY, Daejeon (KR)

(72) Inventors: Heeyeong Cho, Daejeon (KR); Hee-Jong Lim, Daejeon (KR); Woo Kyu Park, Daejeon (KR); Dae Young Jeong, Daejeon (KR); Hyeon Young Kim, Daejeon (KR); Sae-Bom Yoon, Daejeon (KR); Chong Ock Lee, Daejeon (KR); Heung Kyoung Lee, Daejeon (KR); Victor Sukbong Hong, Daejeon (KR); Ji Hye Choi, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 961 days.

(21) Appl. No.: 17/294,705

(22) PCT Filed: Nov. 20, 2019

(86) PCT No.: PCT/KR2019/015948
§ 371 (c)(1),
(2) Date: May 18, 2021

(87) PCT Pub. No.: WO2020/106059
PCT Pub. Date: May 28, 2020

(65) Prior Publication Data
US 2022/0009933 A1  Jan. 13, 2022

(30) Foreign Application Priority Data

Nov. 21, 2018  (KR) .................. 10-2018-0144188
Nov. 19, 2019  (KR) .................. 10-2019-0148566

(51) Int. Cl.
C07D 487/04 (2006.01)
A23L 33/10 (2016.01)
C07D 487/14 (2006.01)
C07D 519/00 (2006.01)

(52) U.S. Cl.
CPC ............ C07D 487/04 (2013.01); A23L 33/10 (2016.08); C07D 487/14 (2013.01); C07D 519/00 (2013.01); A23V 2002/00 (2013.01)

(58) Field of Classification Search
CPC ... C07D 487/04; C07D 487/14; C07D 519/00
See application file for complete search history.

(56) References Cited

U.S. PATENT DOCUMENTS 8,618,121 B2  12/2013  Collins et al.
2009/0062318 A1  3/2009  Gangjee 2014/0018343 A1  1/2014  Romero et al.
2014/0343051 A1  11/2014  Sauvageau et al.
2015/0246923 A1  9/2015  Wang et al.
2017/0037047 A1  2/2017  Sauvageau et al.

FOREIGN PATENT DOCUMENTS

| CN | 102203092 A | 9/2011 |
|---|---|---|
| CN | 104144931 A | 11/2014 |
| CN | 108676009 A | 10/2018 |
| JP | 2015-504902 A | 2/2015 |
| JP | 2016-505012 A | 2/2016 |
| JP | 2017-511801 A | 4/2017 |
| JP | 2017-513897 A | 6/2017 |
| JP | 2018-525394 A | 9/2018 |
| WO | 2009-004329 A1 | 1/2009 |
| WO | 2010-006032 A1 | 1/2010 |
| WO | 2012-129258 A1 | 9/2012 |
| WO | 2013-066729 A1 | 5/2013 |

(Continued)

OTHER PUBLICATIONS

International Search Report for PCT/KR2019/015948 mailed Mar. 4, 2020 from Korean Intellectual Property Office.
Zhulun Wang et al., "IRAK-4 Inhibitors for Inflammation", Current Topics in Medicinal Chemistry, 2009, 9, 724-737.
Priscilla N. Kelly et al., Selective interleukin-1 receptor-associated kinase 4 inhibitors for the treatment of autoimmune disorders and lymphoid malignancy, J. Exp. Med. 2015 vol. 212 No. 13, pp. 2189-2201.

(Continued)

*Primary Examiner* — Bruck Kifle
(74) *Attorney, Agent, or Firm* — Revolution IP, PLLC

(57) ABSTRACT

The present invention relates to a pharmaceutical composition for preventing or treating autoimmune diseases or tumors, containing, as an active ingredient, a tricyclic compound represented by the following Chemical Formula 1 or a pharmaceutically acceptable salt thereof, and a health food composition for preventing or alleviating autoimmune diseases or tumors, containing the tricyclic compound as an active ingredient,

[Chemical Formula 1]

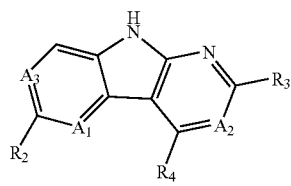

wherein the tricyclic compound represented by Chemical Formula 1 has an excellent inhibitory activity against IRAK4, and thus can be usefully used for the prevention, treatment, or alleviation of autoimmune diseases or tumors.

6 Claims, 4 Drawing Sheets

(56) References Cited

FOREIGN PATENT DOCUMENTS

| WO | 2013-106612 A1 | 7/2013 |
| WO | 2013-110198 A1 | 8/2013 |
| WO | 2014-011902 A1 | 1/2014 |
| WO | 2015-131005 A1 | 9/2015 |
| WO | 2015-161373 A1 | 10/2015 |
| WO | 2017-033093 A1 | 3/2017 |

OTHER PUBLICATIONS

George M. Buckley et al., "IRAK-4 inhibitors. Part 1: A series of amides", Bioorganic & Medicinal Chemistry Letters 18 (2008) 3211-3214.

George M. Buckley et al., "IRAK-4 inhibitors. Part Ii: A structure-based assessment of imidazo[1,2-a]pyridine binding" Bioorganic & Medicinal Chemistry Letters 18 (2008) 3291-3295.

George M. Buckley et al., "IRAK-4 inhibitors. Part III: A series of imidazo[1,2-a]pyridines", ABioorganic & Medicinal Chemistry Letters 18 (2008) 3656-3660.

Graham F. Smith et al., "Identification of quinazoline based inhibitors of IRAK4 for the treatment of inflammation", Bioorganic & Medicinal Chemistry Letters 27 (2017) 2721-2726.

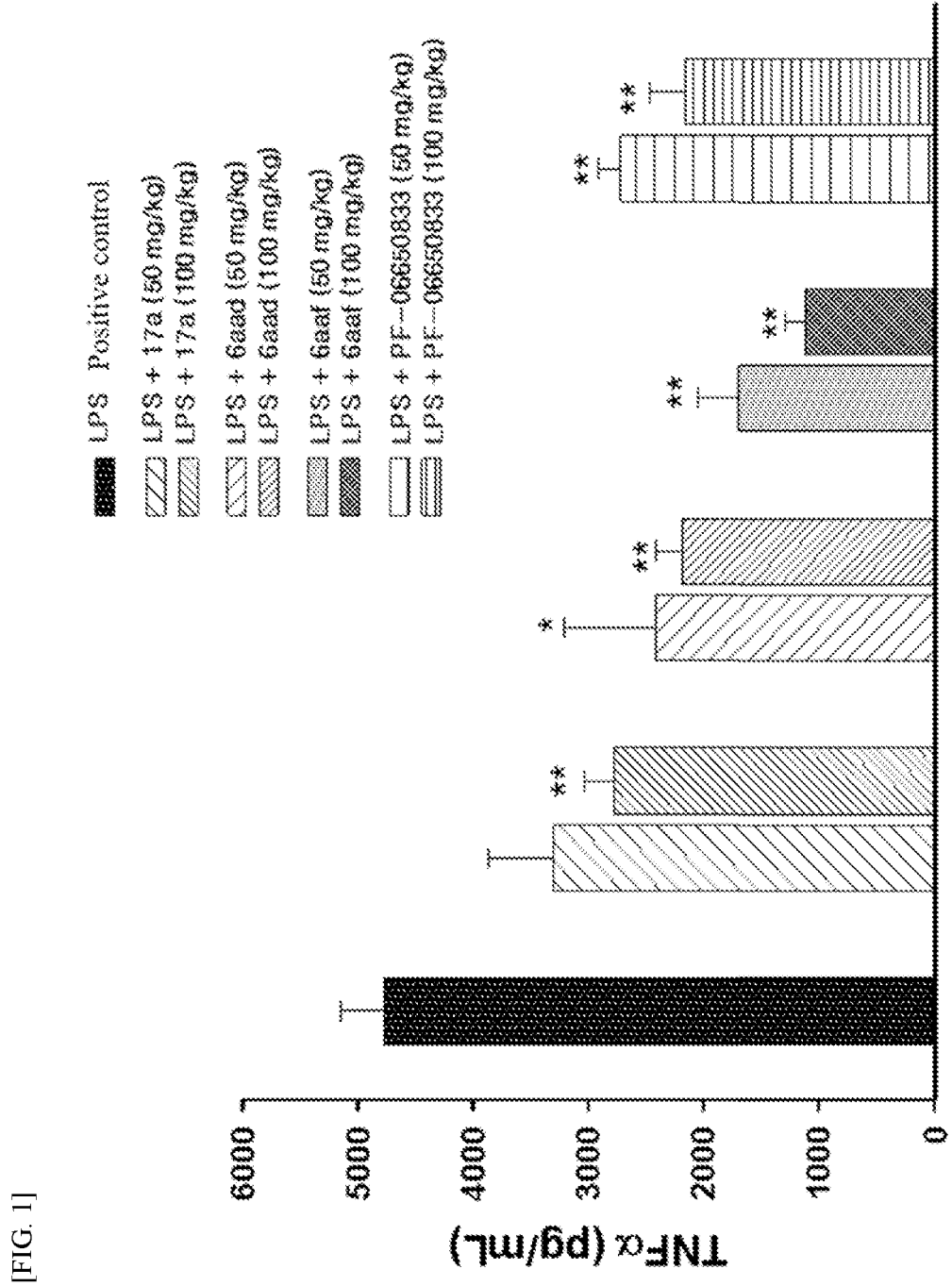
[FIG. 1]

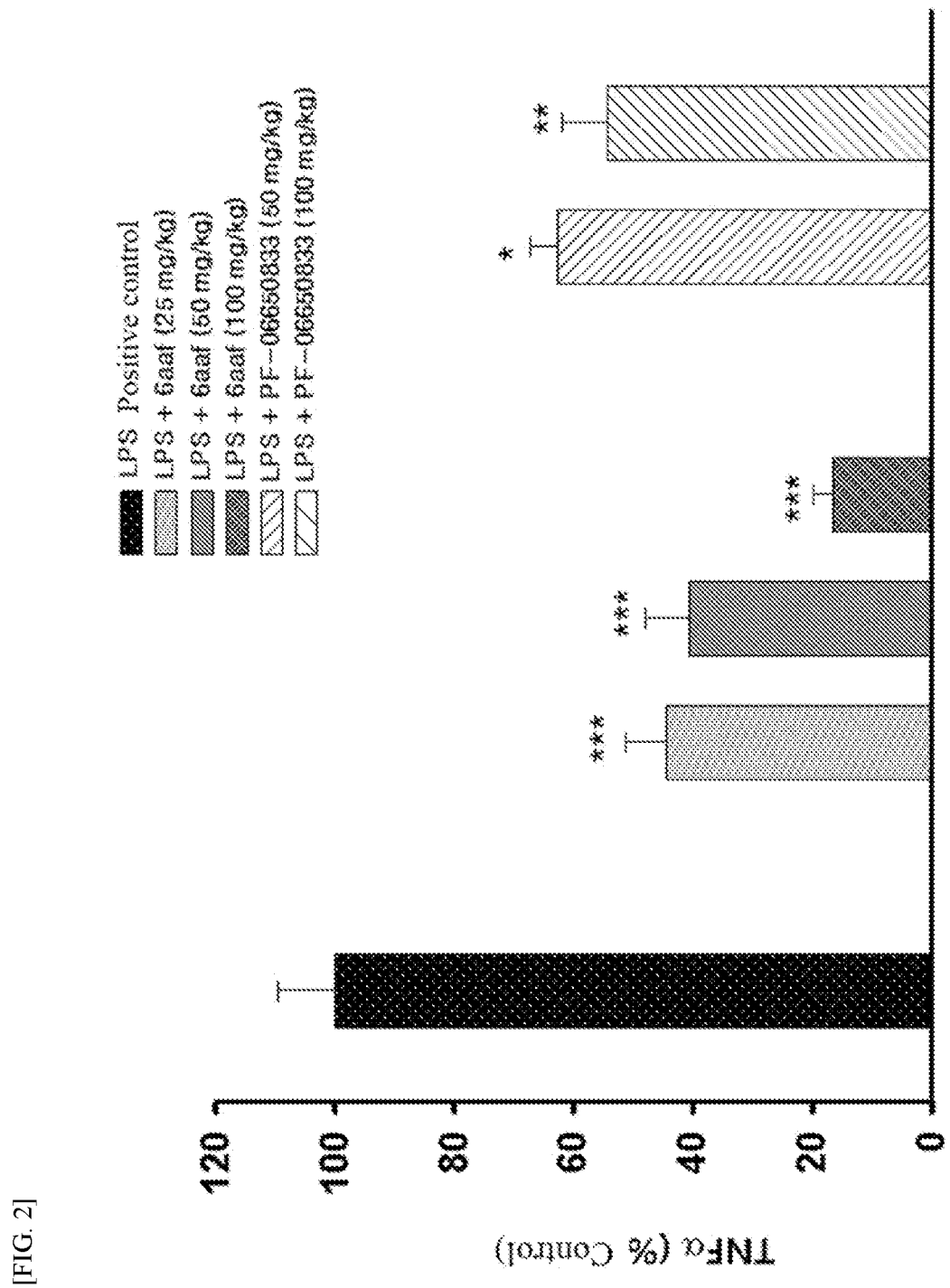
[FIG. 2]

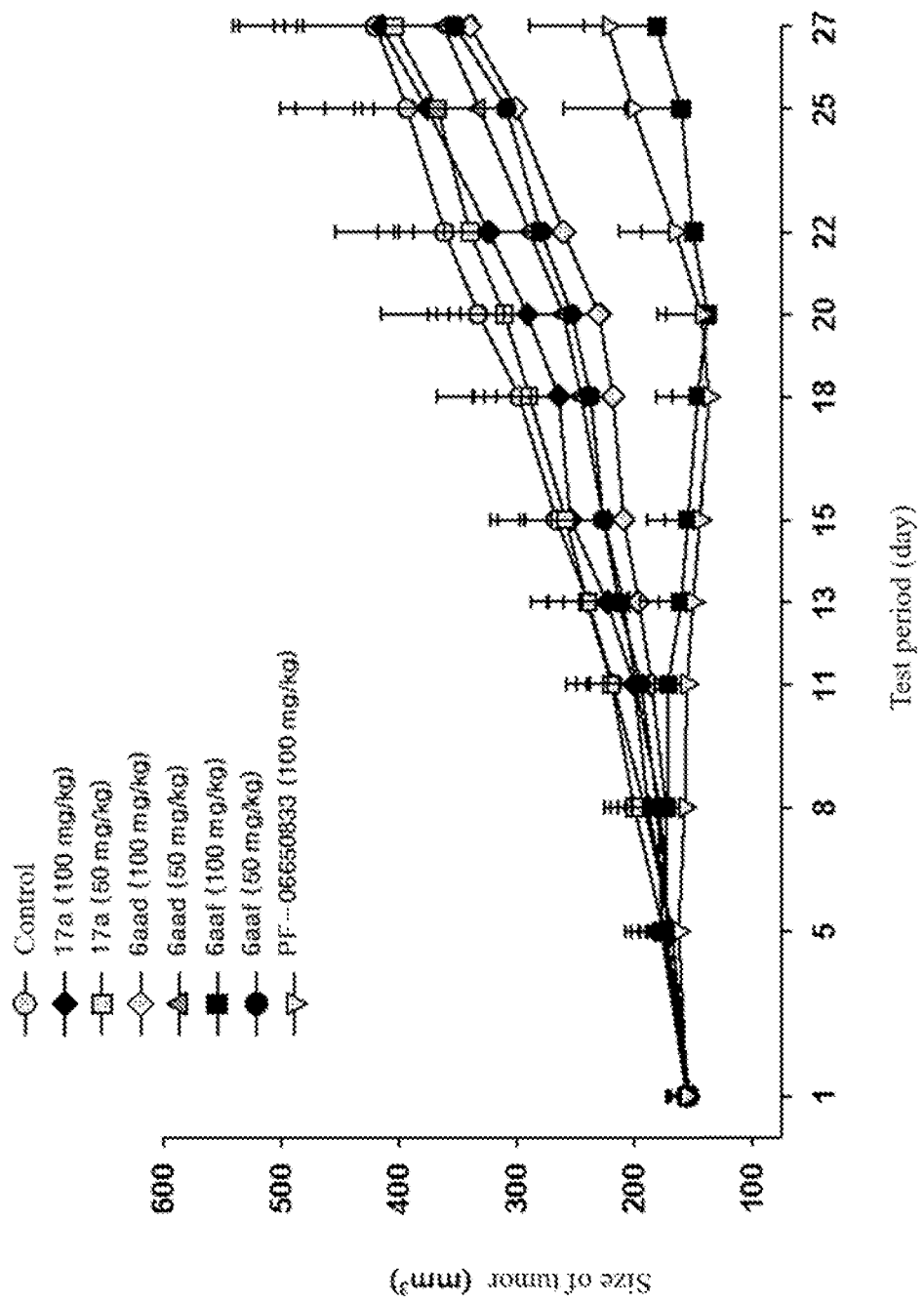
[FIG. 3]

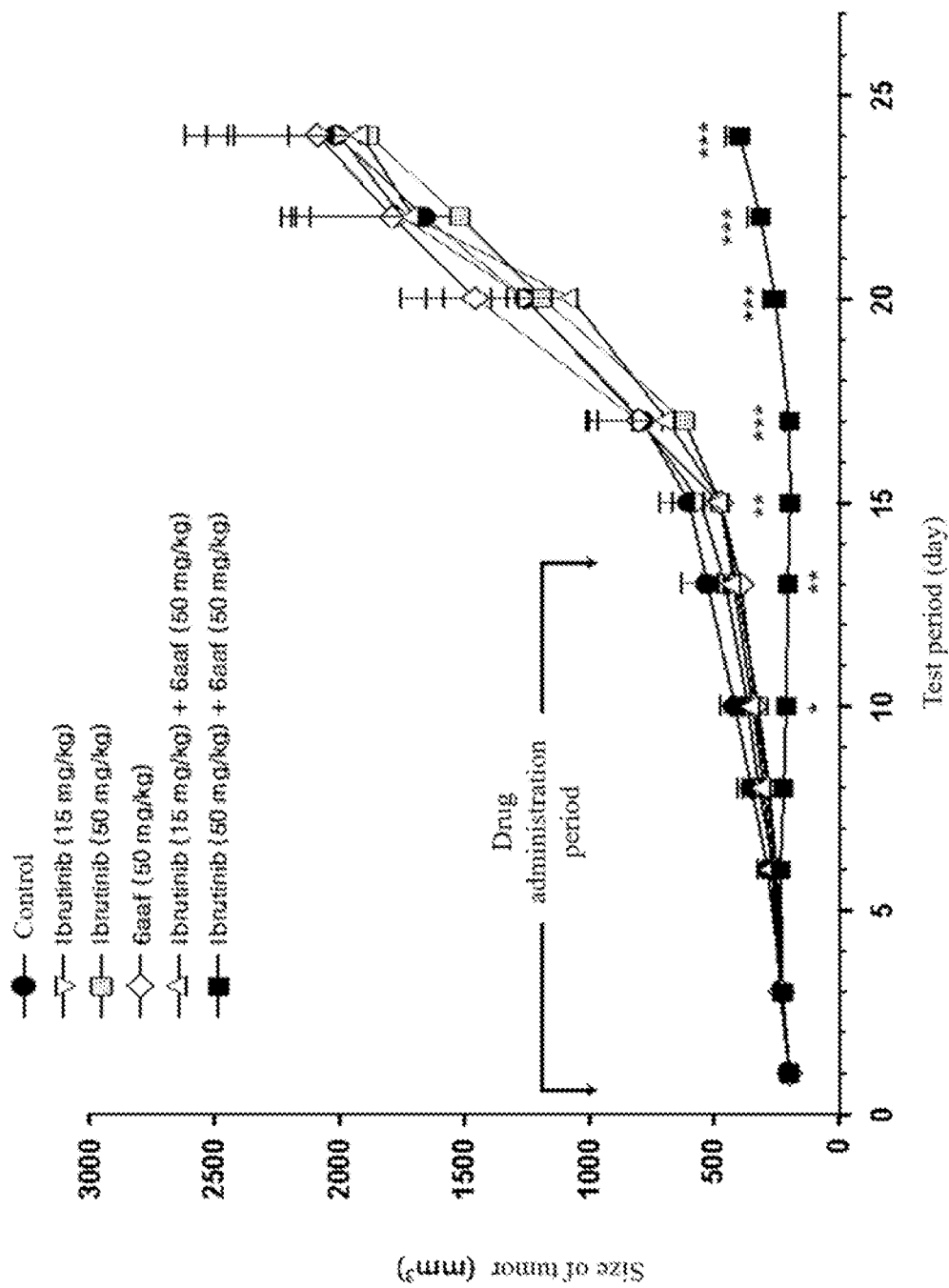
[FIG. 4]

TRICYCLIC COMPOUND AS IRAK4 INHIBITOR

CROSS REFERENCE TO PRIOR APPLICATIONS

This application is the 35 U.S.C. 371 national stage of International application PCT/KR2019/015948 filed on Nov. 20, 2019, which claims priority to Korean Patent Application Nos. 10-2018-0144188 filed on Nov. 21, 2018, and 10-2019-0148566 filed on Nov. 19, 2019. The entire contents of each of the above-identified applications are hereby incorporated by reference.

TECHNICAL FIELD

The present invention relates to a novel tricyclic compound as an IRAK4 inhibitor, a pharmaceutical composition for preventing or treating autoimmune diseases or tumors, containing, as an active ingredient, the tricyclic compound or a pharmaceutically acceptable salt thereof, and a health food composition for preventing or alleviating autoimmune diseases or tumors, containing the tricyclic compound as an active ingredient.

BACKGROUND ART

Interleukin-1 receptor (IL-1R) associated kinase 4 (IRAK4) is a major phosphorylase that mediates the transduction of toll-like receptor (TLR) and interleukin-1 receptor (IL-1R) signals in myeloid cells and lymphoid cells into cells, and has been actively studied as a therapeutic target for systemic lupus erythematosus (SLE) lymphoma, and the like which are rare immune diseases (Current Topics in Medicinal Chemistry, 2009, 9, 724-737).

Lupus is an autoimmune disease of unknown cause, and if a person meets any 4 or more of the 11 criteria of febricity, arthralgia, arthritis, edema, fatigue, facial erythema, photosensitivity, anemia, myocarditis, pleurisy and neurological abnormalities, the person is diagnosed with lupus by comprehensively reviewing the patient's medical history and physical examination, laboratory test, immunological test, and the like. Hydroxychloroquine, which was approved in 1955, is used as a therapeutic agent for lupus, and steroids, non-steroidal anti-inflammatory analgesics (NSAID), Plaquenil, and the like are used as symptomatic preparations. Benlysta (belimumab, GSK, 2010), which is the first new lupus drug, is an antibody injection that suppresses abnormal B lymphocytes by suppressing the binding of BlyS (BAFF) to a B-cell receptor, but has a problem in that the cost thereof is high and the disease cannot be significantly alleviated.

MYD88 L265P mutations have been found in about 30% of diffuse large B cell lymphoma (DLBCL), particularly, an activated B-cell subtype (ABC-DLBCL), and in such mutant cancers, NF-κB is overactivated to secrete high levels of inflammatory cytokines, which are associated with poor prognosis of tumors (J. Exp. Med. 2015: 212, 2189-2201).

IRAK4 is an IRAK family member consisting of 460 amino acids, activates Toll-like receptor 79 (TLR7/9) by a ligand including DNA/RNA to regulate the secretion of interferon (IFN) and inflammatory cytokines, is most abundantly expressed in leukocytes, and after that, the expression is higher in the order of immune organ cells such as adrenal cortex, lymph nodes, and thyroid gland (PLos ONE. 2012. 7. e49771). Since IRAK4 mediates the secretion of inflammatory cytokines such as interferon α (IFN-α) from plasmacytoid dendritic cells (pDCs), IRAK4 inhibition can suppress the secretion of interferon-α, which is a biomarker for lupus disease, and actually, it was observed that mice in which the expression of IRAK4 and IRAK1 was suppressed did not develop lupus and an oligonucleotide inhibitor of TLR7/9 alleviated lupus in an animal model. (J Immunol 2011; 186:1279-1288). Therefore, IRAK4 inhibitory compounds are very likely to treat or alleviate autoimmune diseases and tumors.

IRAK4 inhibitory compounds have been studied over the last ten years.

In 2008, three consecutive reports were published on amide and imidazopyridine derivatives having various structures (Bioorg. Med. Chem. Lett. 2008:18, 3211-3214, 3291-3295, 3656-3660).

Quinazoline derivatives that strongly inhibit IRAK4 have also been reported, and the reported No. 23 compound was found to inhibit R848-induced IL-6 by 30% or more (30 mg/kg) and 90% or more (100 mg/kg) in animal experiments (Bioorg. Med. Chem. Left. 2017: 27, 2721-2726).

Besides, a number of compounds have been known as amidopyrazole and aminopyrimidinone derivatives (WO2012-129258A1, WO2013-066729A1), and furthermore, heterocycle substituted pyridyl compounds having an $IC_{50}$ value of nM level have also been known (WO2013-106612A1).

Meanwhile, in WO2017-033093A1, bicyclic-fused heteroaryl or aryl compounds are disclosed as IRAK4 modulators, and it was confirmed again that inhibitors of IRAK4 kinase activity are potential therapeutic agents for various diseases including autoimmune diseases, tumors, inflammations, cardiovascular diseases, cancers and metabolic diseases.

Further, a US pharmaceutical company Pfizer has been conducting Phase 2 clinical trials of a compound PF-06650833 which inhibits IRAK4 as a therapeutic agent for rheumatoid arthritis.

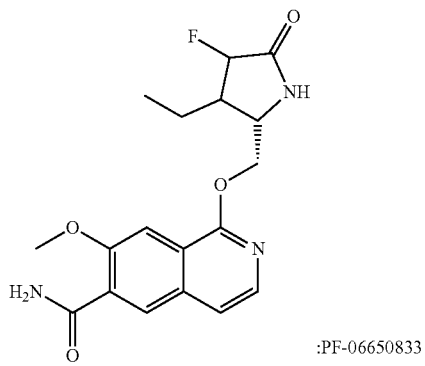

:PF-06650833

Therefore, the present applicant found an optimized novel IRAK4 inhibitory structure by evaluating medicinal effects of IRAK4 enzymes, evaluating changes in secretion of inflammatory cytokines, changes in activity of inflammatory promoters by signaling of TLR4/7/9, and the like, and confirming activities in a systemic infection animal model and a xenotransplanted lymphoma animal model, in order to develop an inhibitor having a new structure, which strongly inhibits IRAK4 and has excellent kinase selectivity.

PRIOR ART DOCUMENT

Patent Document

WO2012-129258A1
WO2013-066729A1

WO2013-106612A1
WO2017-033093A1

DISCLOSURE

Technical Problem

An object of the present invention is to provide a tricyclic compound having a novel structure, which strongly inhibits IRAK4 and has excellent kinase selectivity.

Another object of the present invention is to provide a pharmaceutical composition for preventing or treating autoimmune diseases or tumors, containing, as an active ingredient, the tricyclic compound or a pharmaceutically acceptable salt thereof.

Still another object of the present invention is to provide a health food composition for preventing or alleviating autoimmune diseases or tumors, containing the tricyclic compound as an active ingredient.

Technical Solution

The present invention provides a tricyclic compound represented by the following Chemical Formula 1.

[Chemical Formula 1]

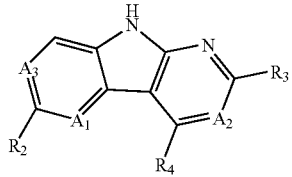

[$A_1$ and $A_2$ are each independently N or CH, $A_3$ is N or $CR_1$, $R_1$ is hydrogen, a halogen, —$COOR_5$ or a (C3-C12) heteroaryl, $R_2$ is hydrogen, an amino group, —$COOR_6$, a (C1-C12) heteroaryl, a (C1-C12)heteroaryl fused to a (C3-C12) cycloalkyl, a (C6-C12)aryl, or a 5- to 7-membered heterocyclic amino comprising one or more heteroatoms selected from nitrogen, oxygen and sulfur, $R_3$ is hydrogen or a (C6-C12)aryl, $R_4$ is -$L_1$-$L_2$-$R_7$, an amino group (—$NH_2$), a (C1-C12)heteroaryl or a (C6-C12)aryl of $R_2$ may be arbitrarily substituted with at least one or more groups selected from the group consisting of a (C1-C4)alkyl, a (C1-C4)alkyl substituted with a halogen, a (C1-C4)thioalkyl, an amino group (—$NH_2$), a methylamino group (—$NHCH_3$), a dimethylamino group (—$N(CH_3)_2$), —$CH_2OH$, a (C1-C4)alkoxy, a hydroxyl group (—OH), a halogen, a methanesulfonyl group (—$SO_2CH_3$), —$SO_2N(CH_3)_2$, a nitro group (—$NO_2$), a cyano group (—CN),

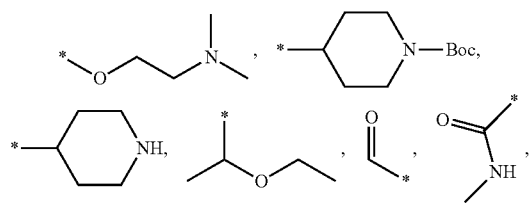

-continued

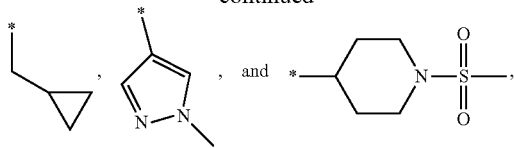

a (C6-C12)aryl of $R_3$ may be arbitrarily substituted with a nitro group (—$NO_2$), $L_1$ is —$N(R_8)$— or —O—, $L_2$ is —$(CH_2)_m$—,

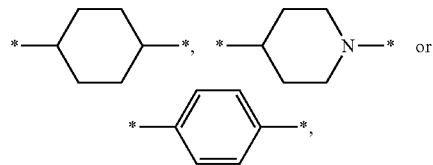

and m is an integer from 2 to 5, $R_7$ is —$N(R_9)_2$, —$OR_{10}$, —$SO_2CH_3$, —$SO_2N(CH_3)_2$, or a 5- to 7-membered heterocyclic amino comprising one or more heteroatoms selected from nitrogen, oxygen and sulfur, $R_5$ is a (C1-C4)alkyl, $R_6$ is a (C1-C4)alkyl, $R_8$ is hydrogen or a (C1-C4), $R_9$ is a (C1-C4)alkyl, $R_{10}$ is a (C1-C4)alkyl, a heterocyclic amino of $R_7$ may be arbitrarily selected from at least one or more groups selected from the group consisting of —$SO_2CH_3$ and —$COOC(CH_3)_3$(-Boc), when $A_3$ is $CR_1$ and $R_1$ is a halogen, —$COOR_5$ or a (C3-C12)heteroaryl, $L_2$ is not —$(CH_2)_m$—, when $L_2$ is —$(CH_2)_m$—, $R_7$ is neither —$N(R_9)_2$ nor —$OR_{10}$, and when $A_3$ is $CR_1$, a case where both $R_1$ and $R_2$ are hydrogen is excluded.]

In Chemical Formula 1, Boc is t-butyloxycarbonyl (—$COOC(CH_3)_3$).

In Chemical Formula 1, the (C3-C12) heteroaryl, which is $R_1$, is preferably

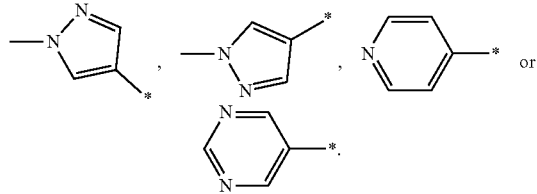

In Chemical, the (C1-C12)heteroaryl, (C1-C12)heteroaryl fused to the (C3-C12)cycloalkyl, or substituted (C1-C12) heteroaryl, which is $R_2$ is preferably any one selected from the followings:

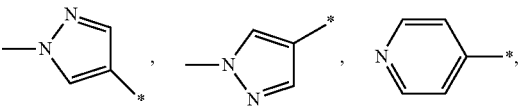

-continued
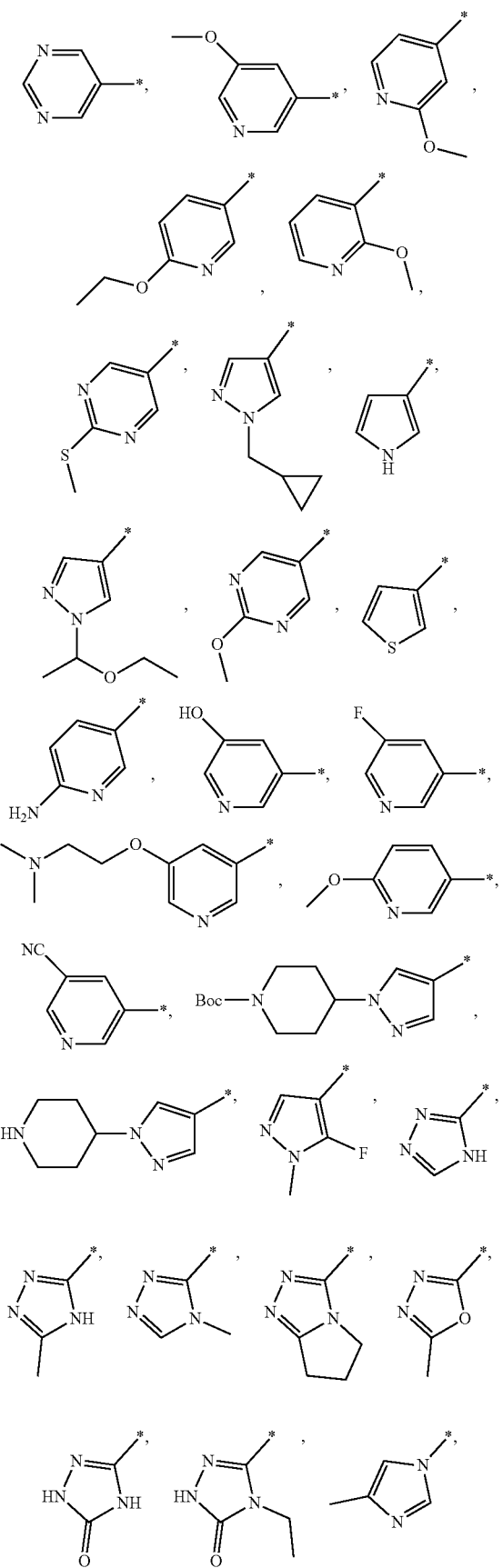
-continued
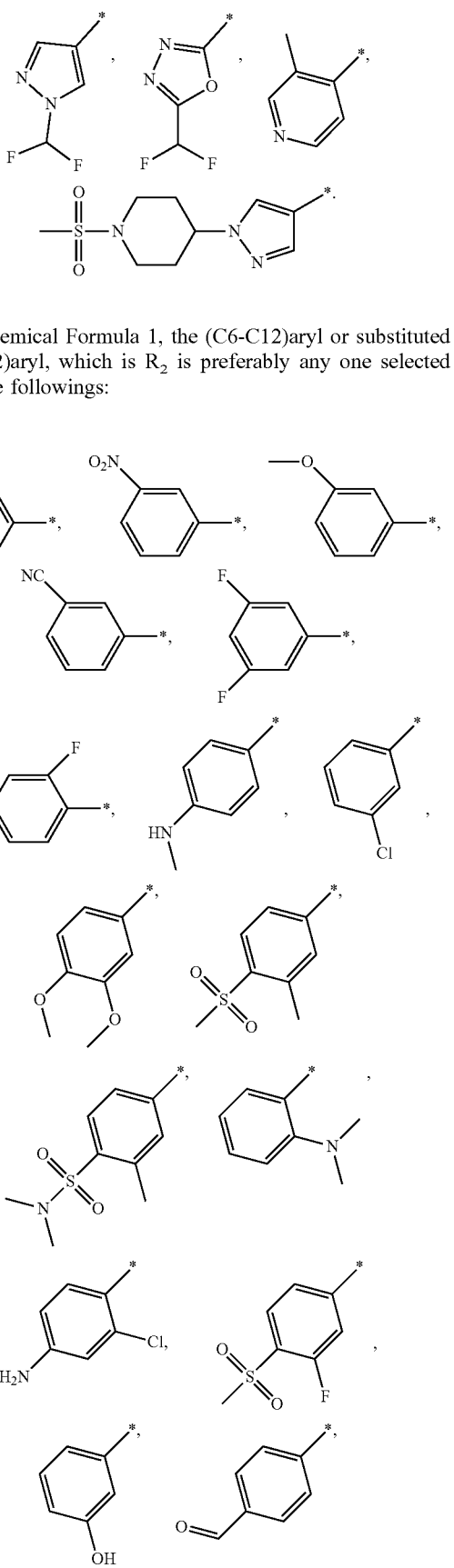
In Chemical Formula 1, the (C6-C12)aryl or substituted (C6-C12)aryl, which is $R_2$ is preferably any one selected from the followings:

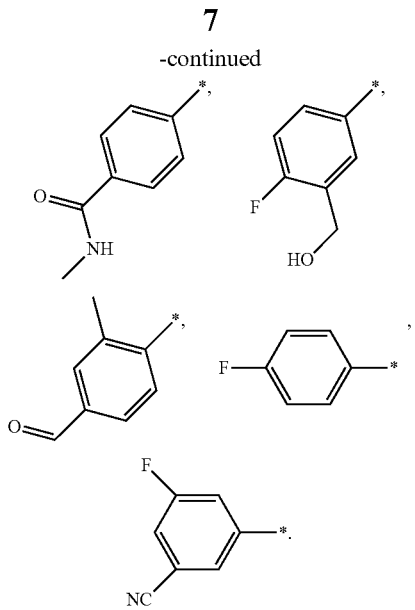
In Chemical Formula 1, the (C6-C12)aryl or substituted (C6-C12)aryl, which is $R_3$ is preferably
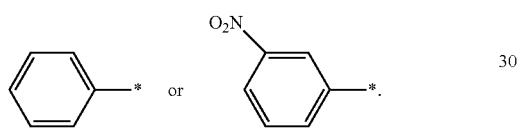
In Chemical Formula 1, $R_4$ is preferably any one selected from the followings:
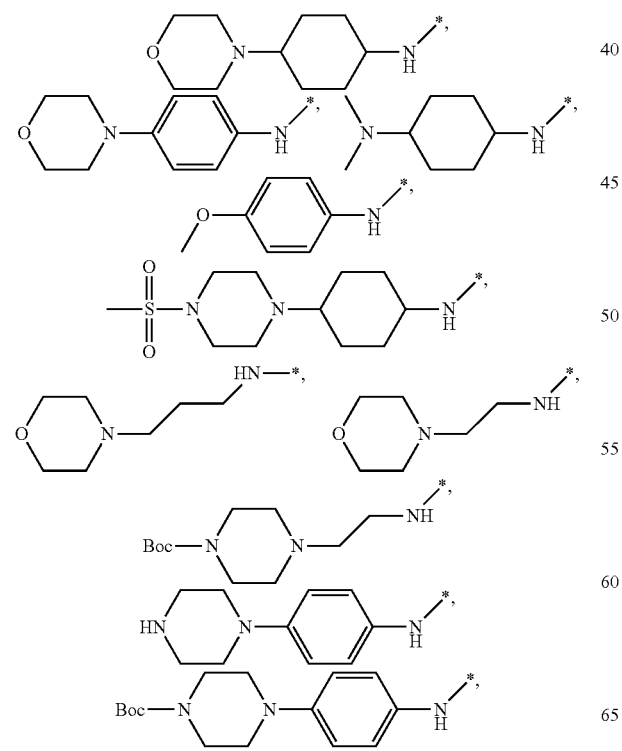
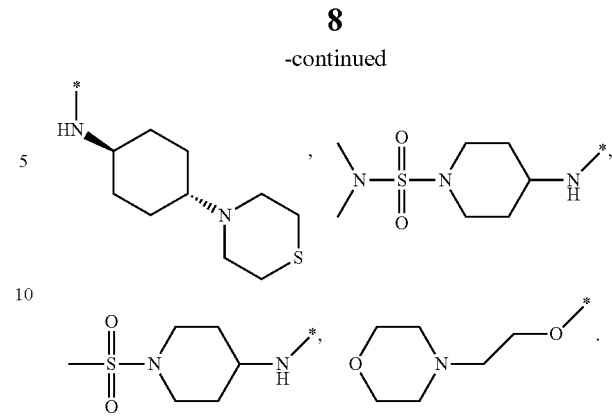
A more specific example of the tricyclic compound represented by Chemical Formula 1 according to the present invention is as follows:
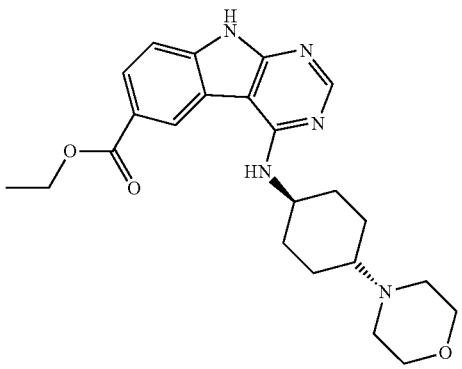
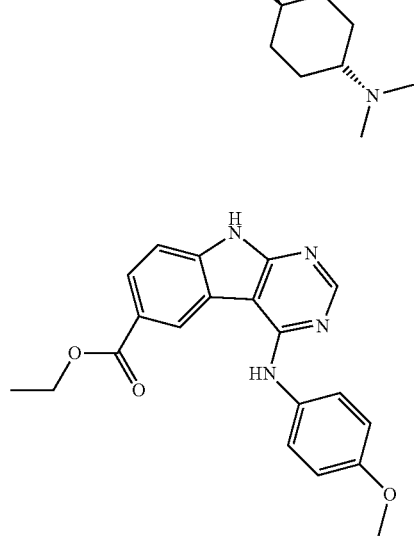

9
-continued
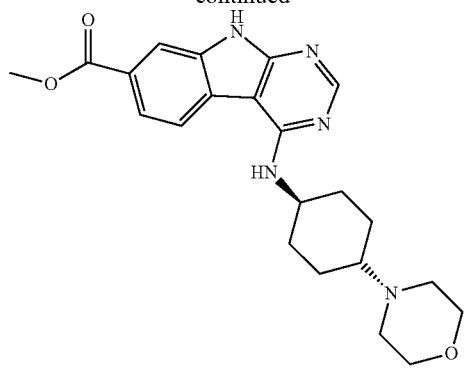
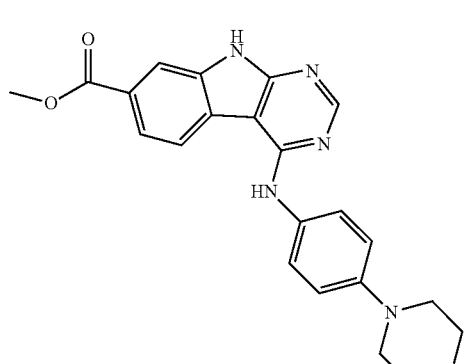
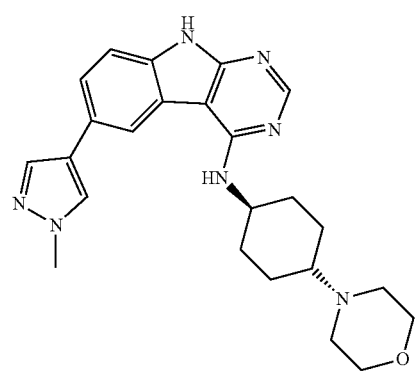
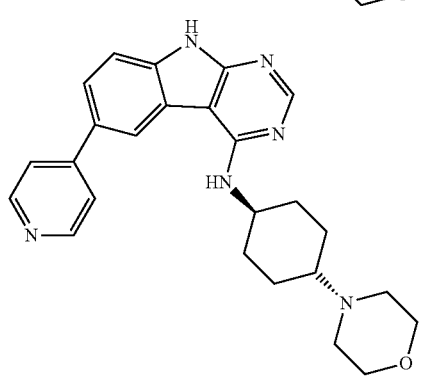
10
-continued
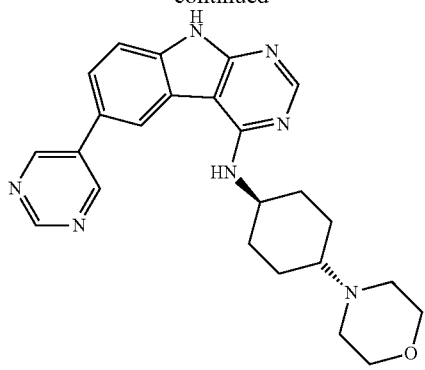
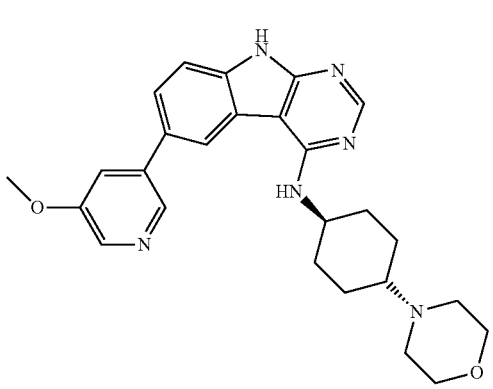
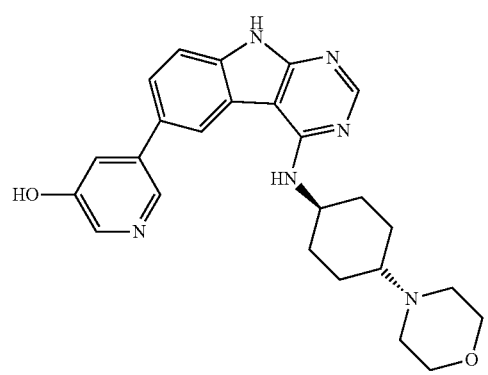

11
-continued
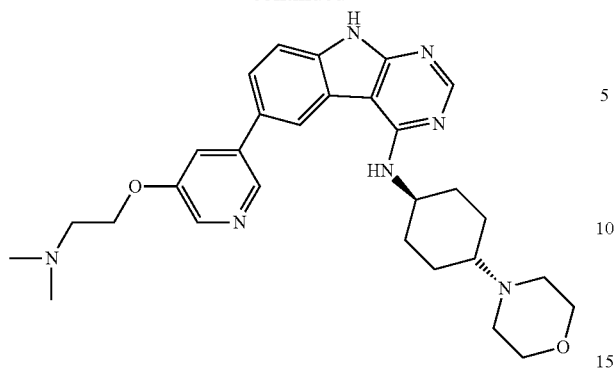
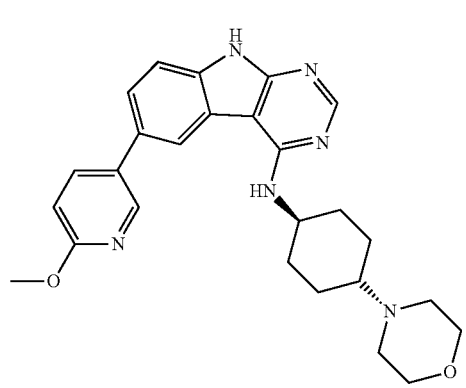
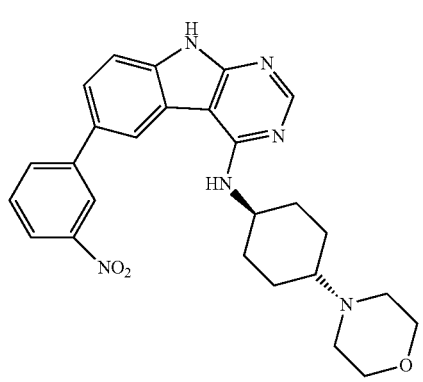
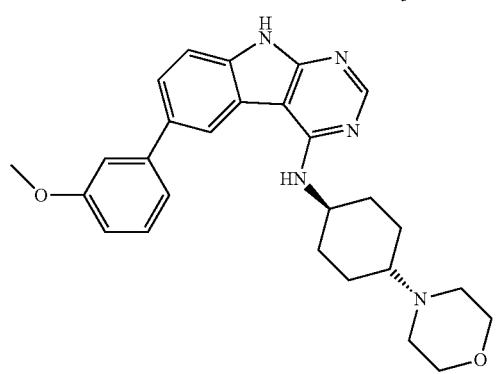
12
-continued
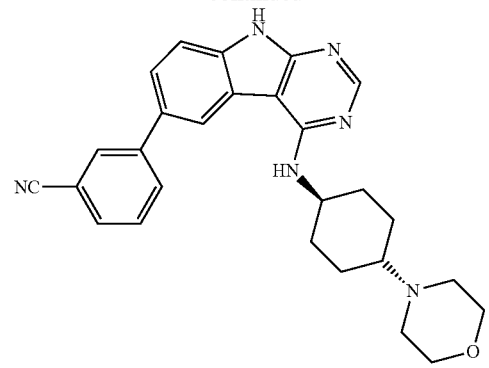
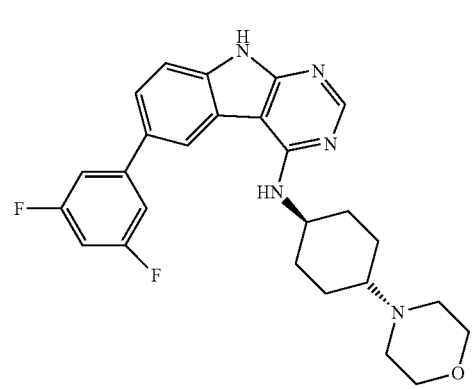
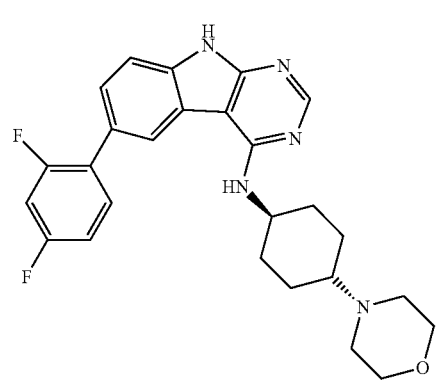
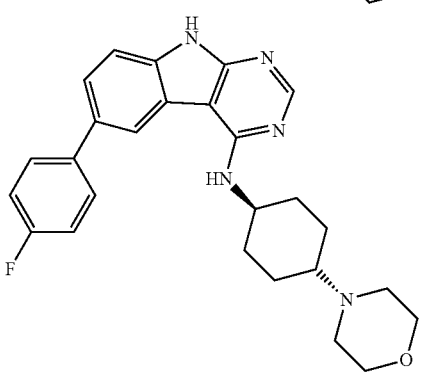

13
-continued
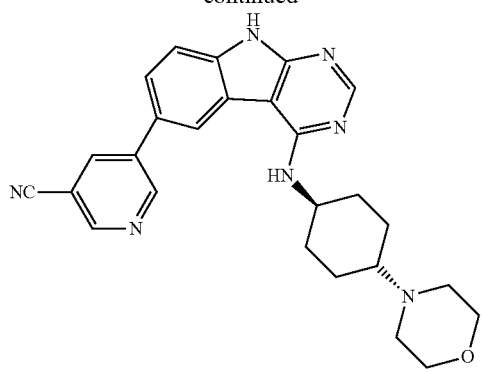
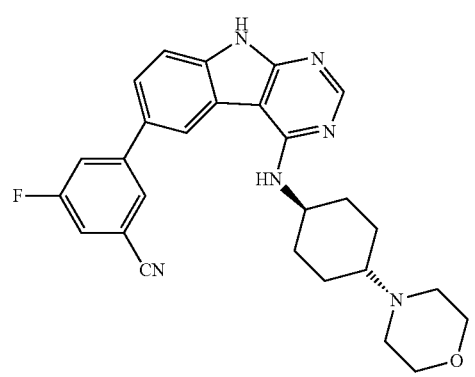
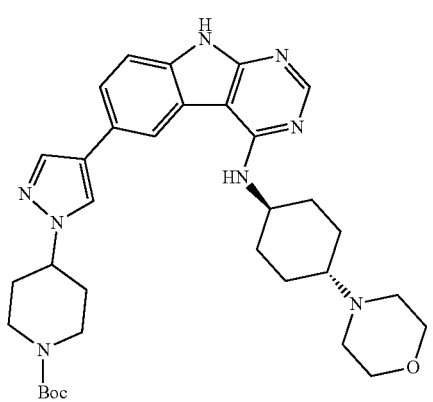
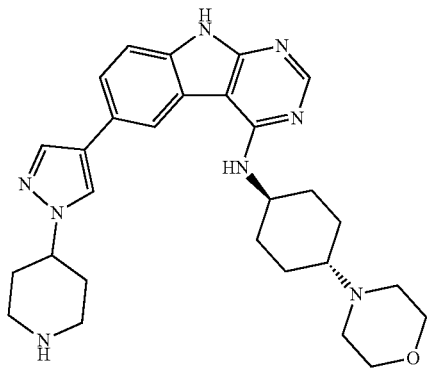
14
-continued
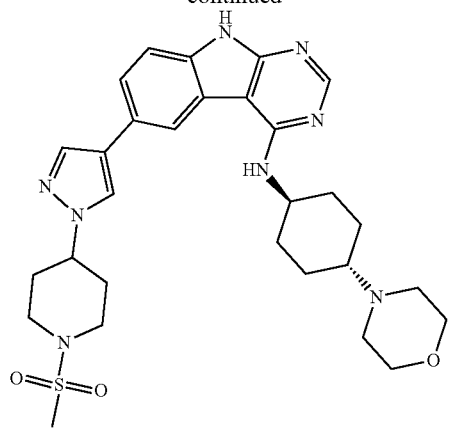
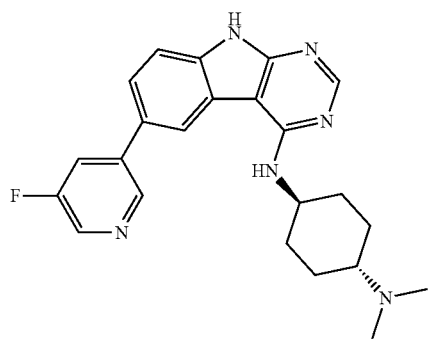
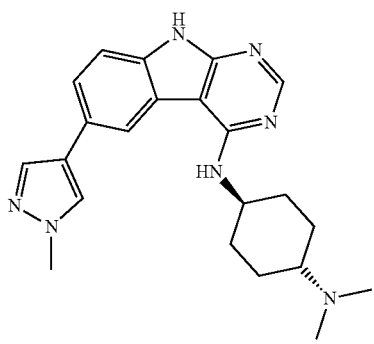
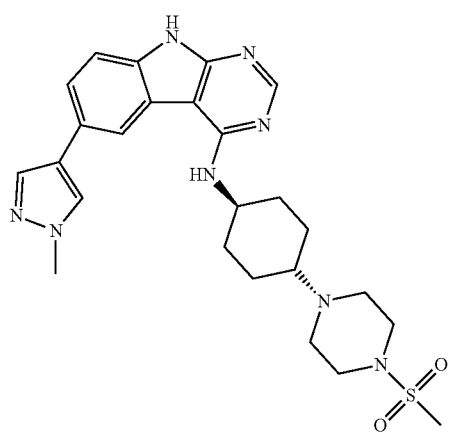

15
-continued
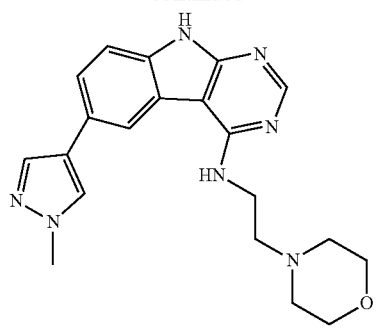
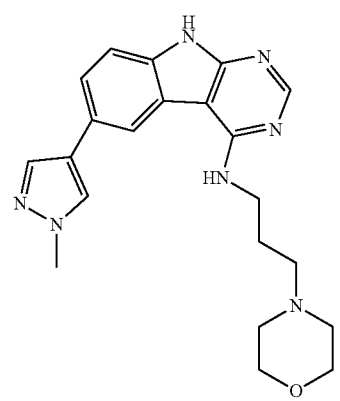
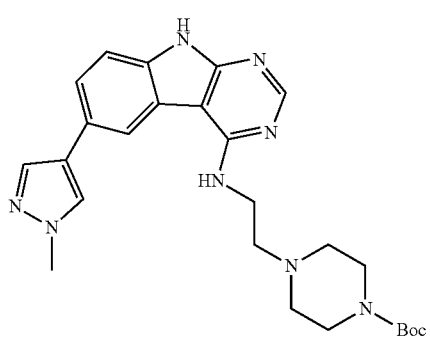
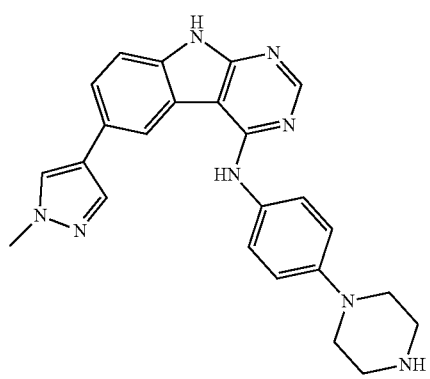
16
-continued
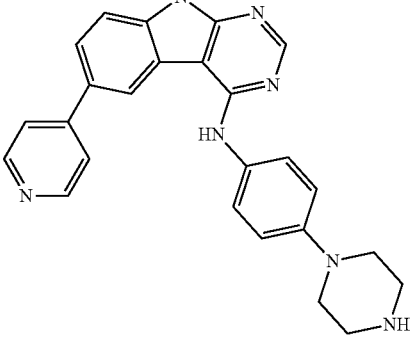
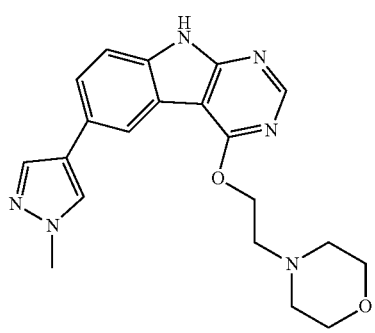
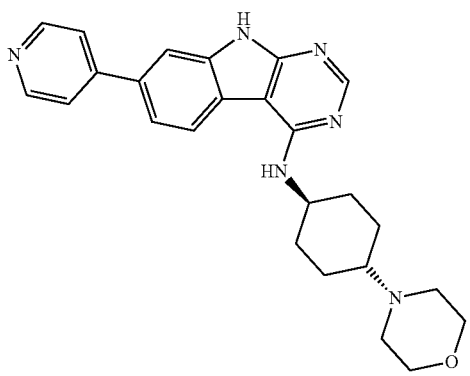
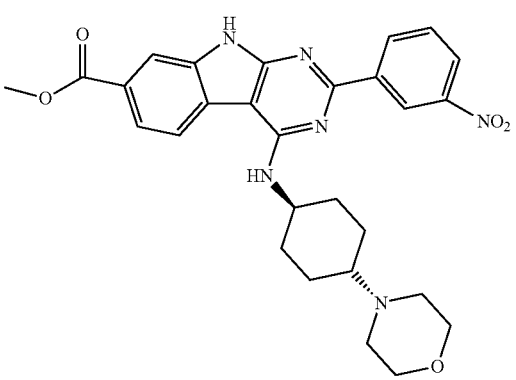

17
-continued
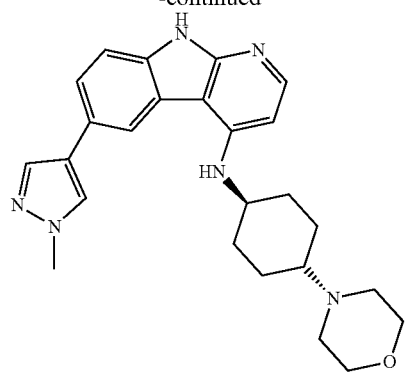
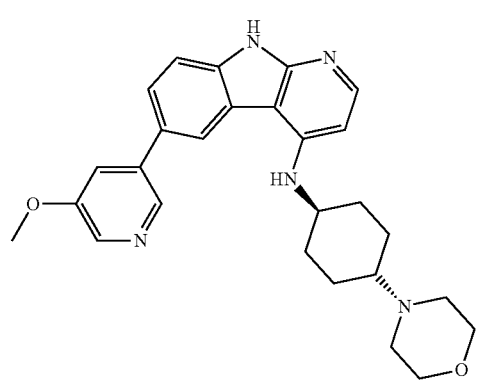
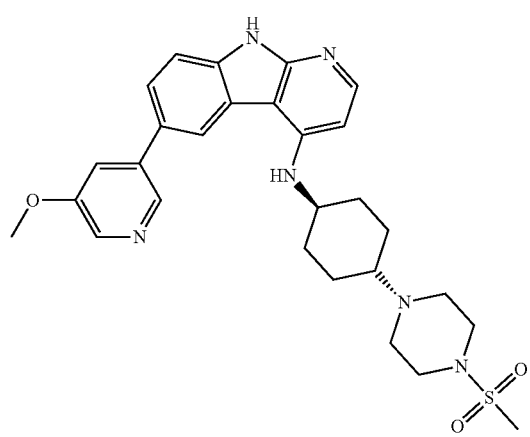
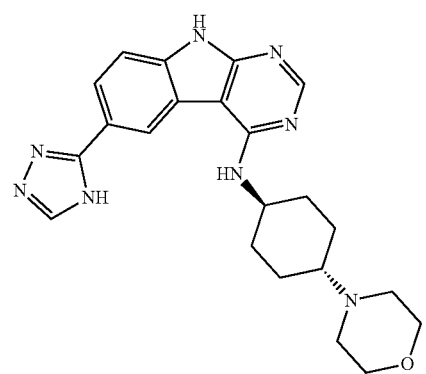
18
-continued
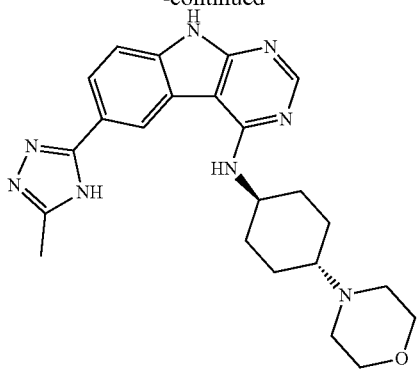
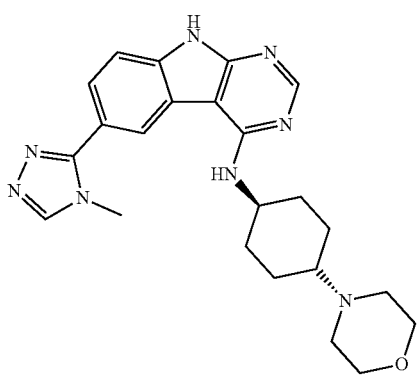
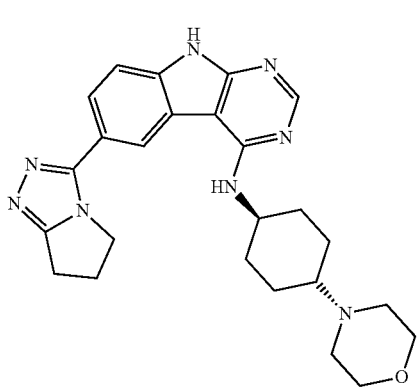
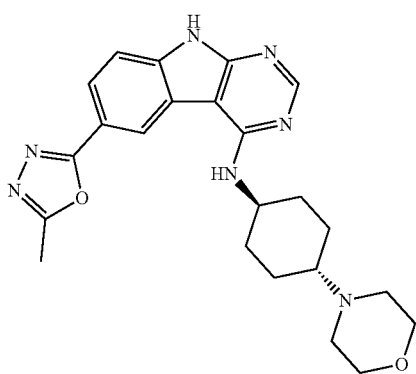

-continued
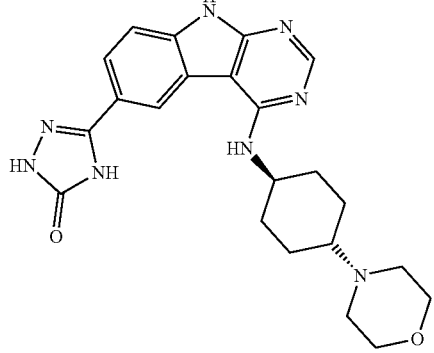
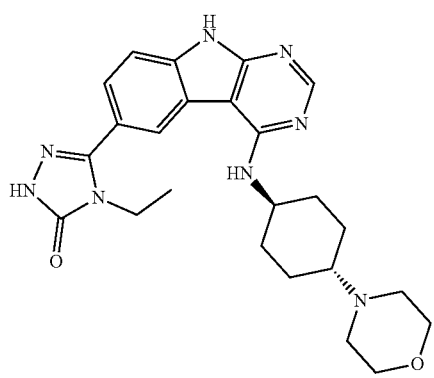
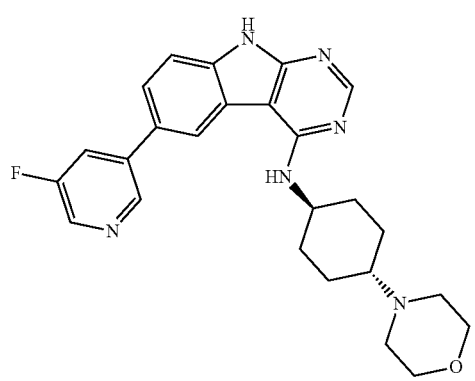
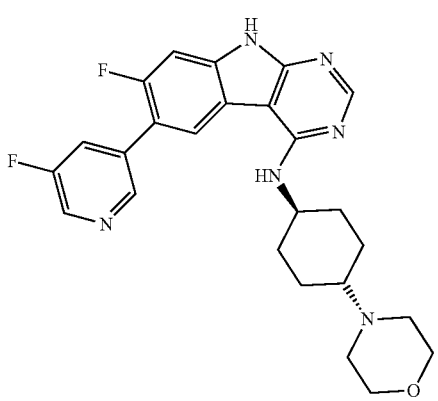
-continued
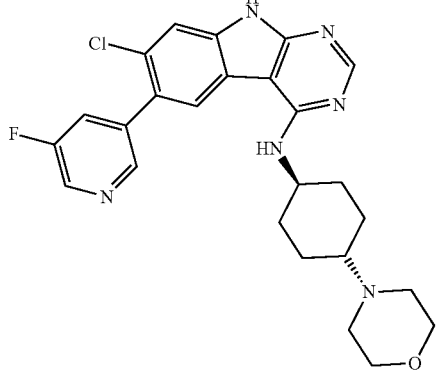
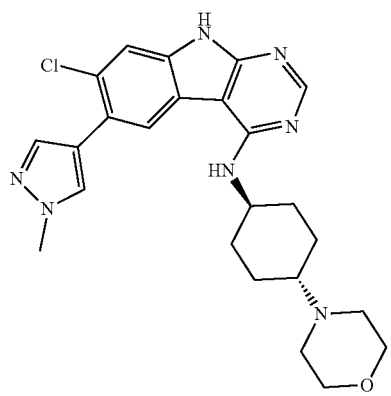
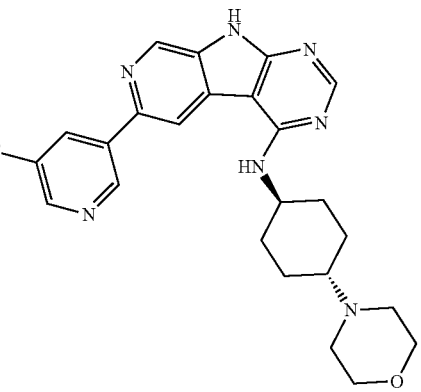
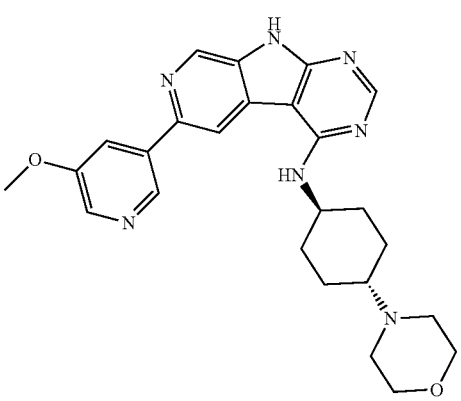

-continued
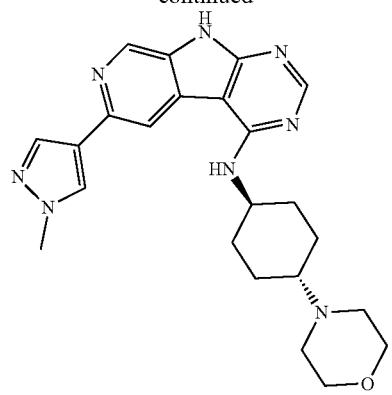
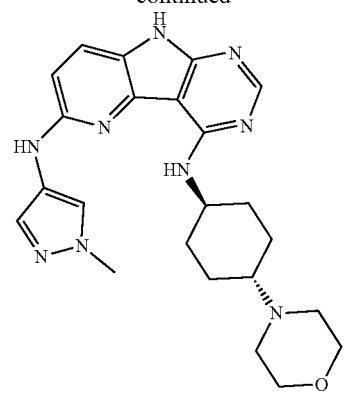
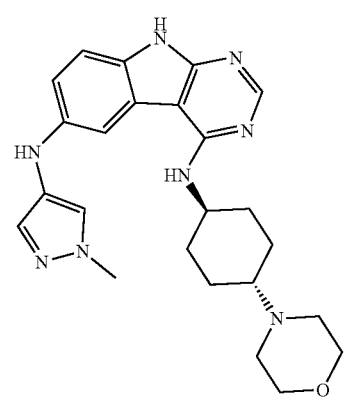
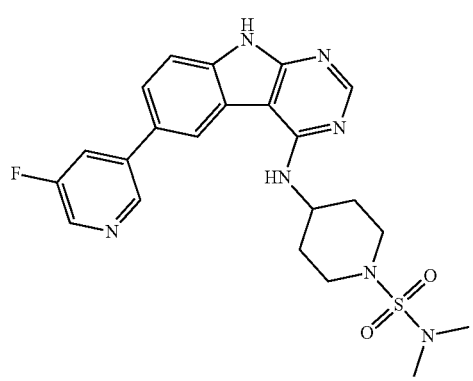
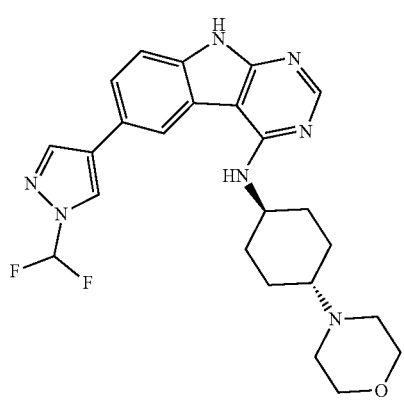
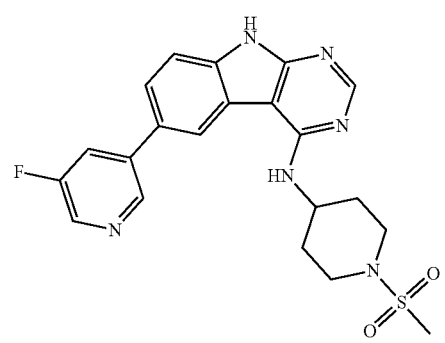
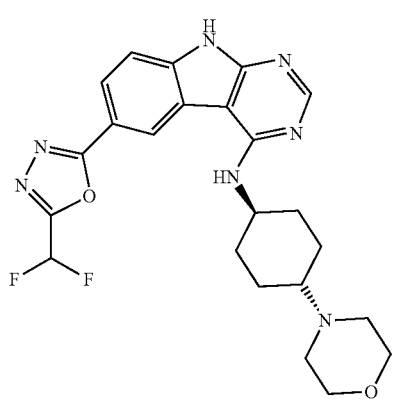
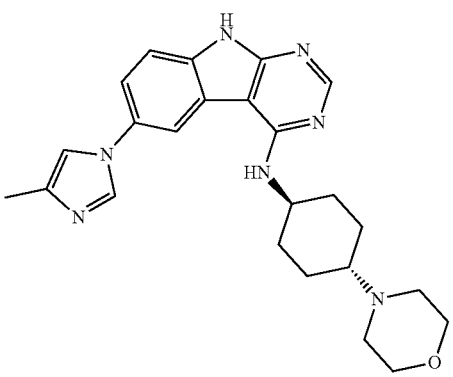

-continued
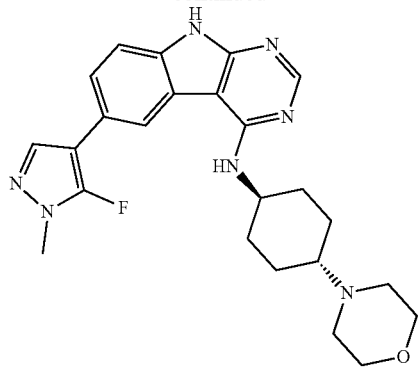
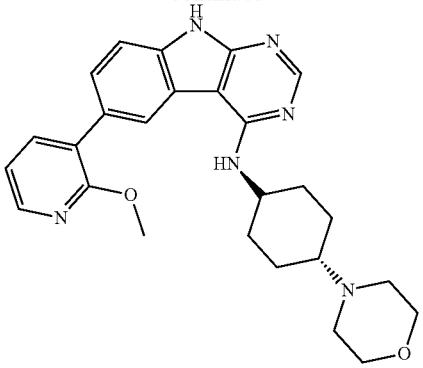
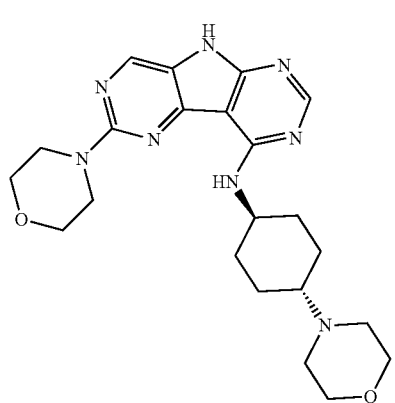
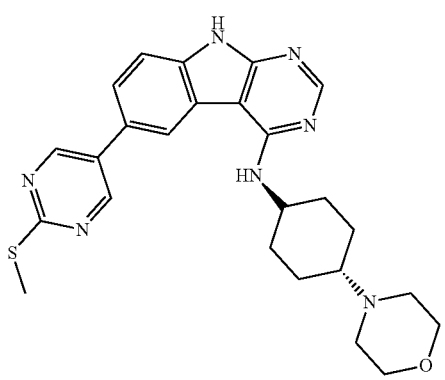
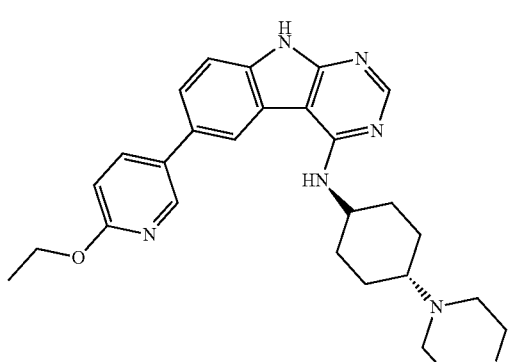
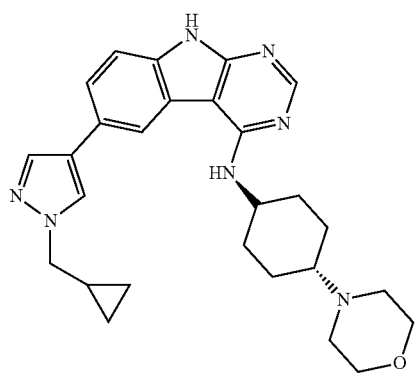
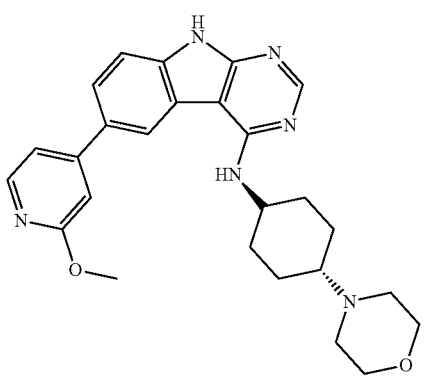
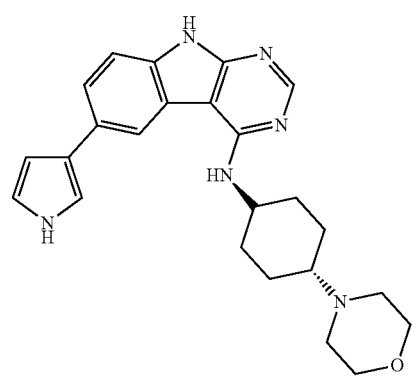

25
-continued
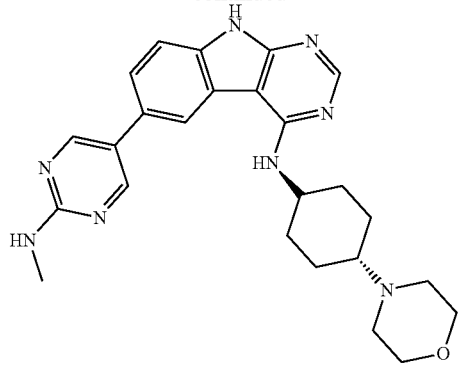
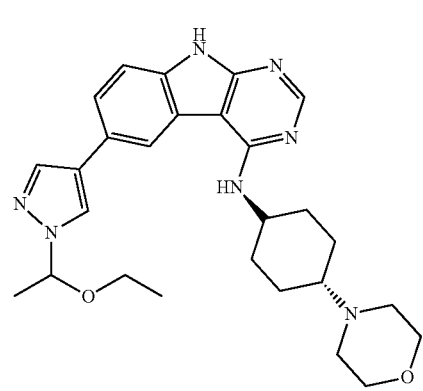
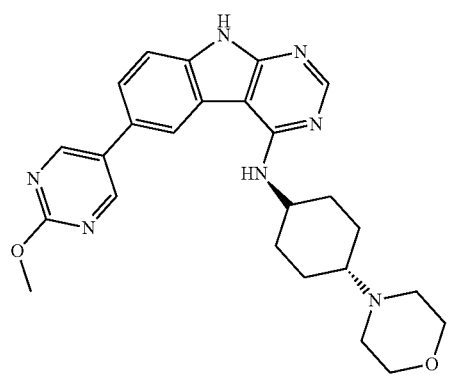
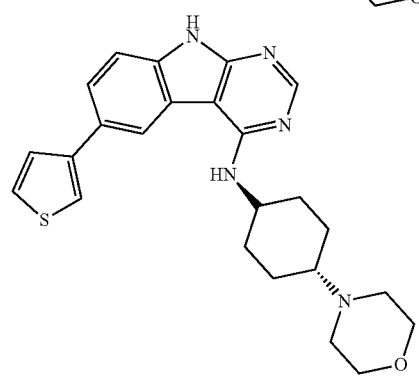
26
-continued
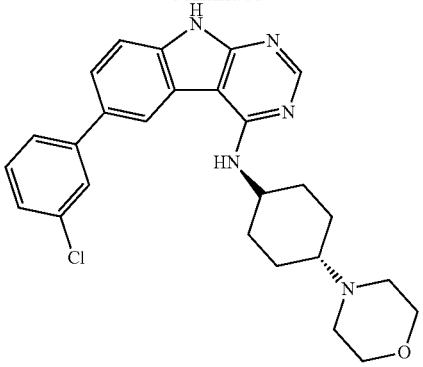
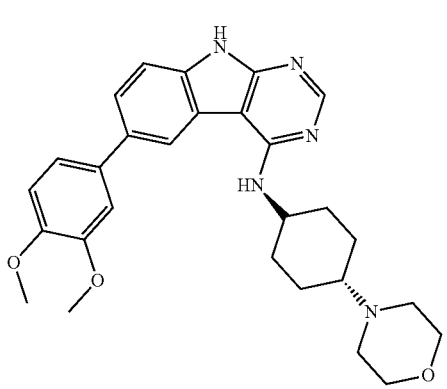
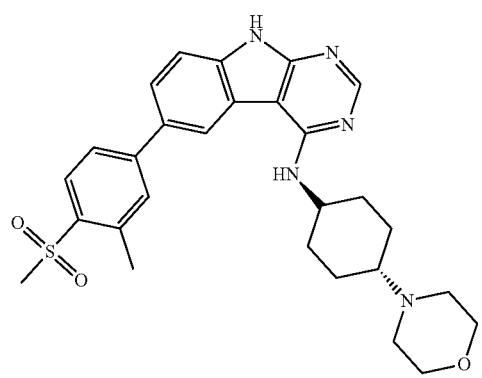
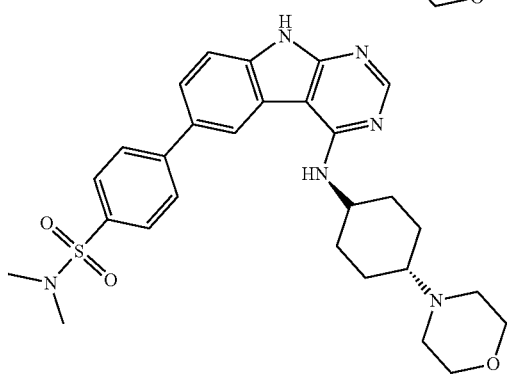

27
-continued
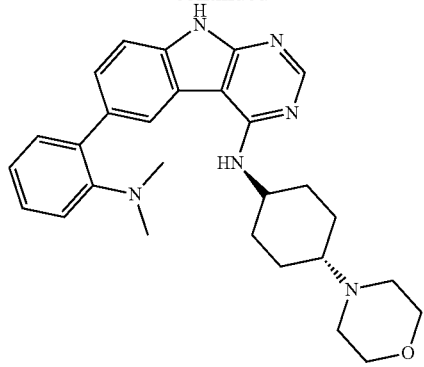
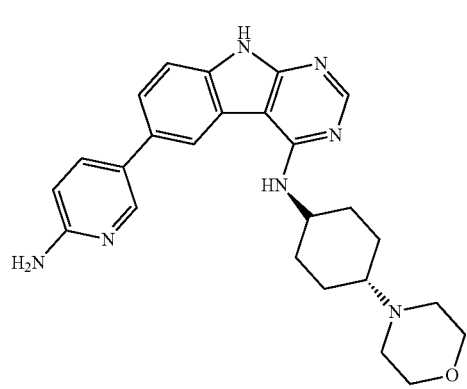
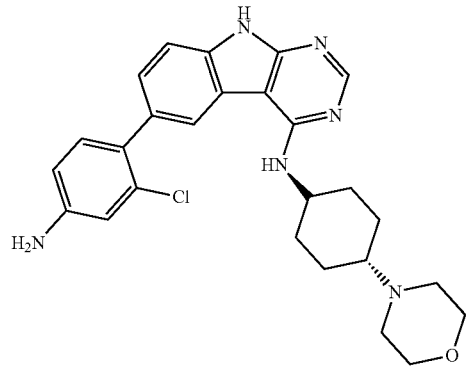
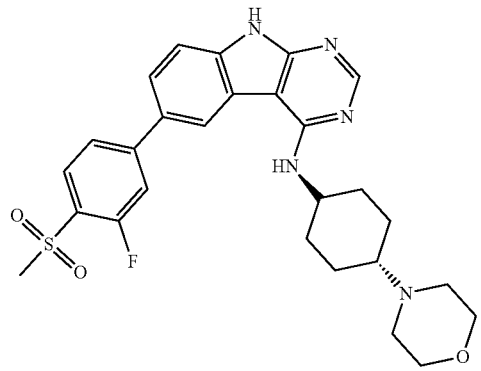
28
-continued
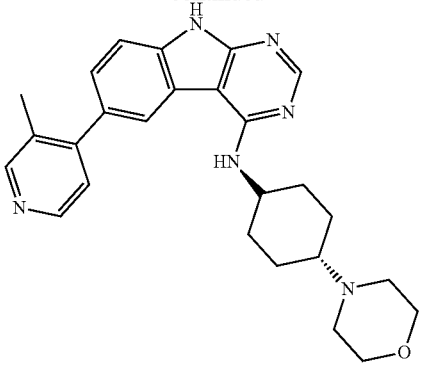
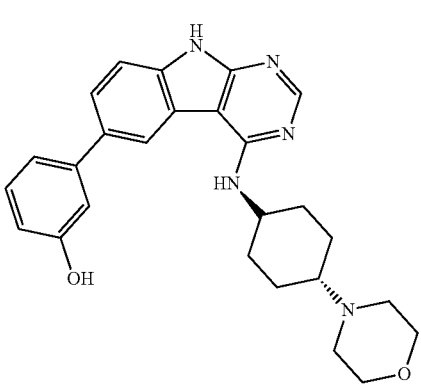
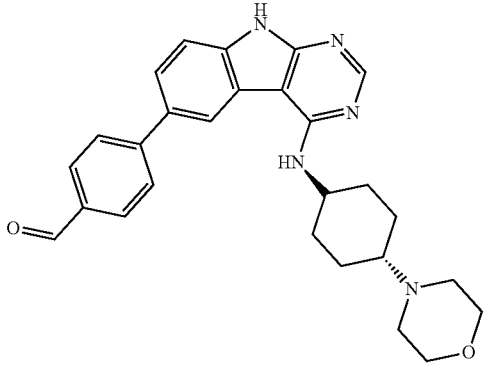
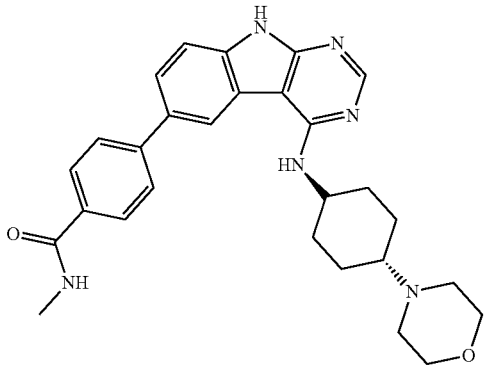

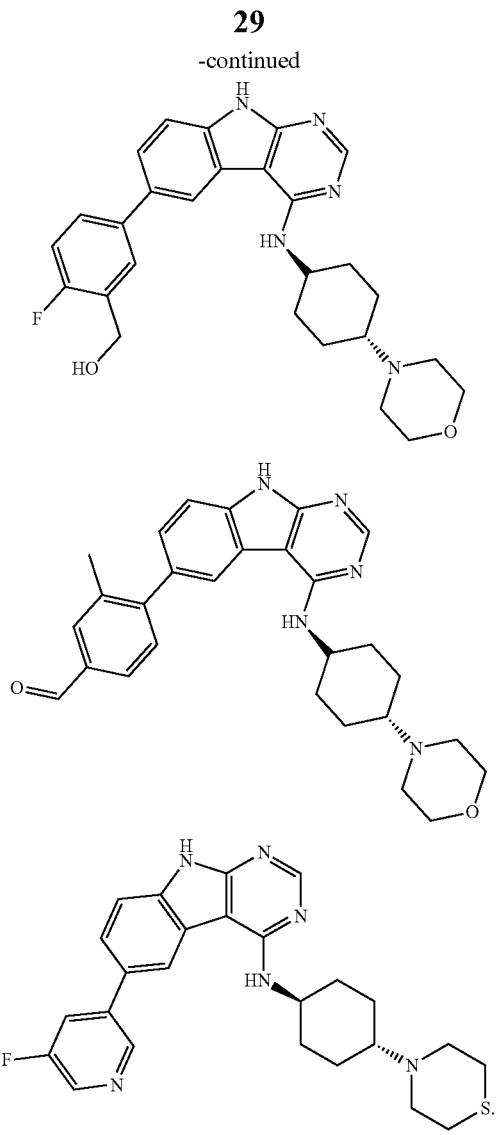

The tricyclic compound represented by Chemical Formula 1 of the present invention may be preferably prepared by the following [Reaction Scheme 1-1], [Reaction Scheme 1-2], [Reaction Scheme 2], [Reaction Scheme 3] or [Reaction Scheme 4].

[Reaction Scheme 1-1]

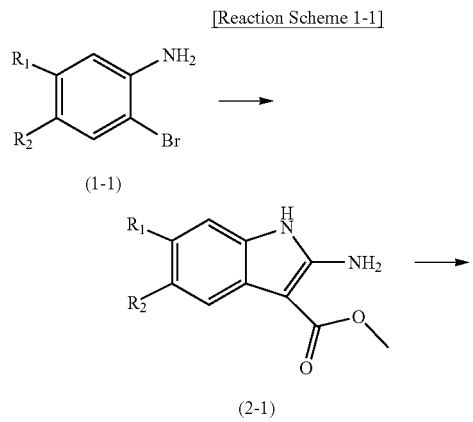

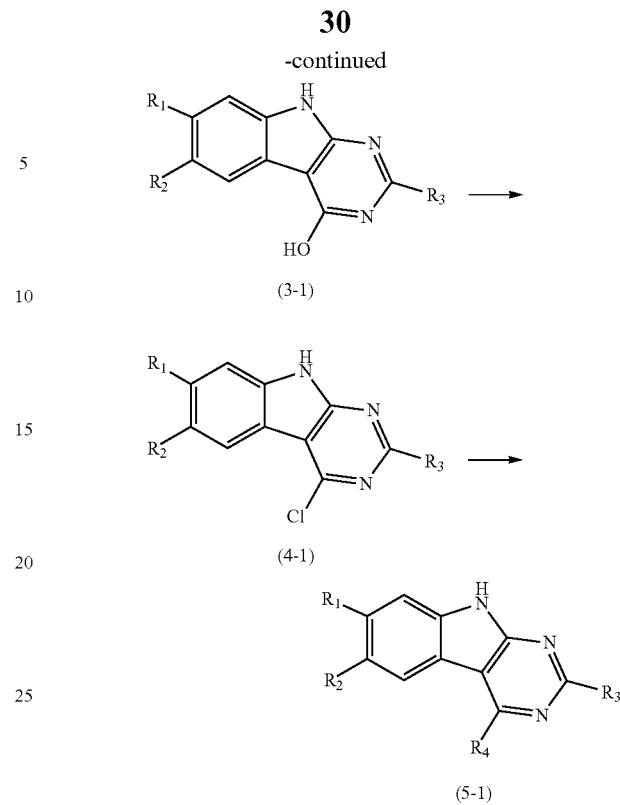

In Reaction Scheme 1-1, $R_1$, $R_2$, $R_3$ and $R_4$ are the same as defined in Chemical Formula 1. Reaction Scheme 1-1 corresponds to a preparation when $A_1$, $A_2$ and $A_3$ of Chemical Formula 1 are CH, N, and $CR_1$, respectively, and is carried out by including the following four-step process:

1) preparing an indole compound of Compound (2-1) from Compound (1-1) using a known method (Adv. Synth. Catal. 2010, 352, 1033-1038);

2) preparing Compound (3-1) from Compound (2-1) using a known method (BioOrg. Med Chem. 2012, 20, 6123);

3) preparing Compound (4-1) by reacting Compound (3-1) with phosphorus oxychloride; and 4) preparing Compound (5-1) by substituting a chlorine (—Cl) group at No. 4 position of Compound (4-1) with $R_4$ using a known method.

[Reaction Scheme 1-2]

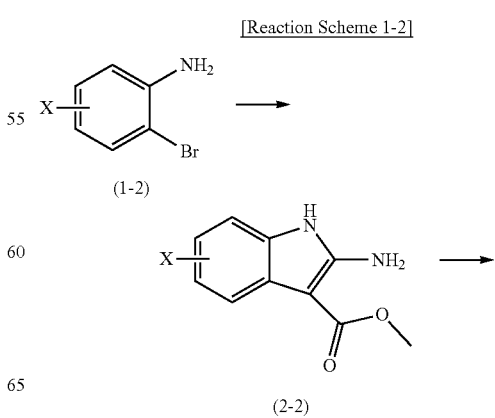

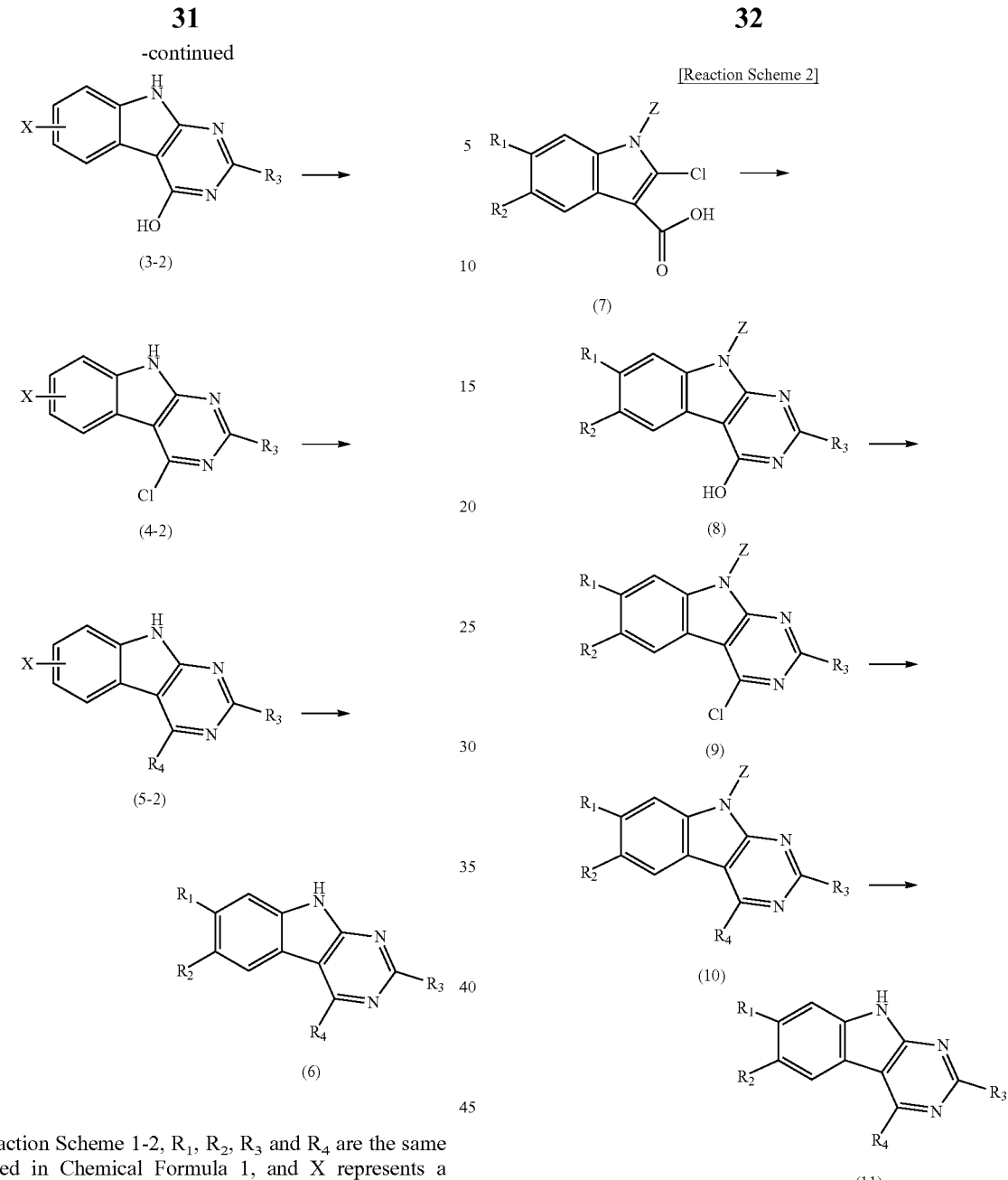

In Reaction Scheme 1-2, $R_1$, $R_2$, $R_3$ and $R_4$ are the same as defined in Chemical Formula 1, and X represents a halogen. Reaction Scheme 1-2 corresponds to a preparation when $A_1$, $A_2$ and $A_3$ of Chemical Formula 1 are CH, N, and $CR_1$, respectively, and is carried out by including the following five-step process:

1) preparing an indole compound of Compound (2-2) from Compound (1-2) using a known method (Adv. Synth. Catal. 2010, 352, 1033-1038);
2) preparing Compound (3-2) from Compound (2-2) using a known method (BioOrg. Med Chem. 2012, 20, 6123);
3) preparing Compound (4-2) by reacting Compound (3-2) with phosphorus oxychloride;
4) preparing Compound (5-2) by substituting a chlorine (—Cl) group at No. 4 position of Compound (4-2) with $R_4$ using a known method; and
5) preparing Compound (6) by introducing $R_1$ and $R_2$ from a substituent X of Compound (5-2).

In Reaction Scheme 2, $R_1$, $R_2$, $R_3$ and $R_4$ are the same as defined in Chemical Formula 1, and Z represents p-methoxybenzyl (PMB). Reaction Scheme 2 corresponds to a preparation when $A_1$, $A_2$ and $A_3$ of Chemical Formula 1 are CH, N, and $CR_1$, respectively, and is carried out by including the following four-step process:

1) preparing Compound (8) from Compound (7) using a known method (WO2006-111648$A_1$);
2) preparing Compound (9) by reacting Compound (8) with phosphorus oxychloride;
3) preparing Compound (10) by substituting a chlorine (—Cl) group at No. 4 position of Compound (9) with $R_4$ using a known method; and
4) preparing Compound (11) by substituting a Z group of Compound (10) with hydrogen.

[Reaction Scheme 3]

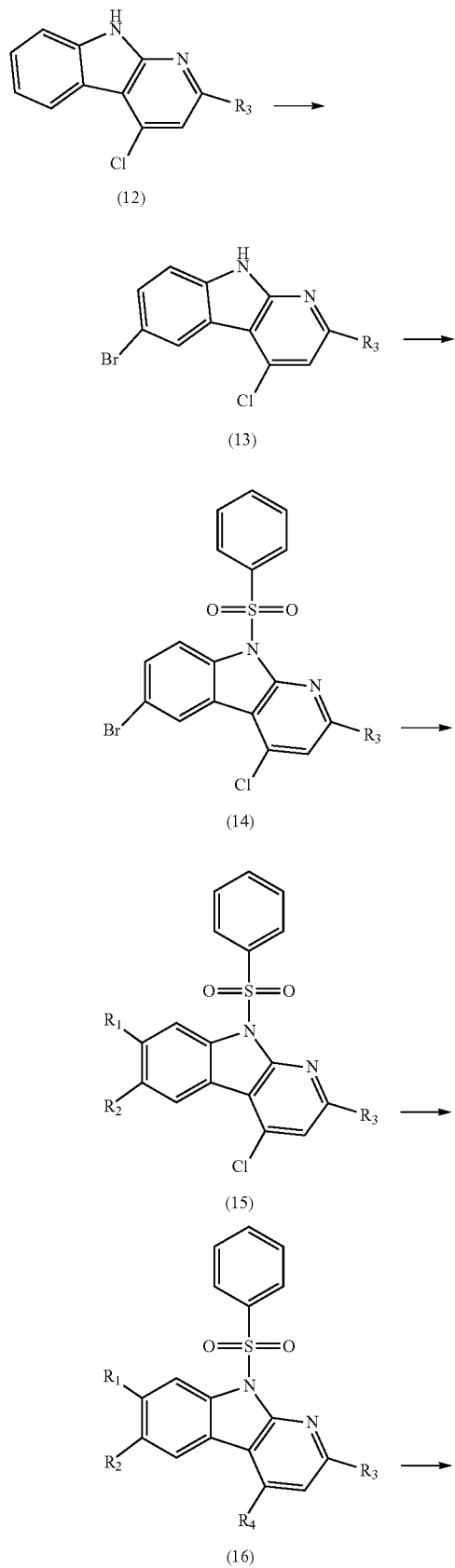

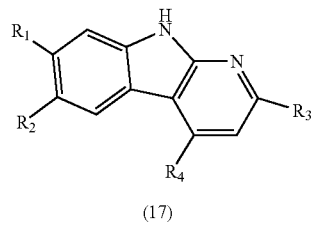

In Reaction Scheme 3, $R_1$, $R_2$, $R_3$ and $R_4$ are the same as defined in Chemical Formula 1. Reaction Scheme 3 corresponds to a preparation when $A_1$, $A_2$ and $A_3$ of Chemical Formula 1 are CH, CH, and $CR_1$, respectively, and is carried out by including the following five-step process:

1) preparing Compound (13) from Compound (12) using a known method (Tetrahedron 65 (2009) 5427-5437);
2) preparing Compound (14) from Compound (13) using a known method (WO2010-025872A$_2$);
3) preparing Compound (15) by introducing $R_1$ and $R_2$ from Compound (14);
4) preparing Compound (16) by substituting a chlorine (—Cl) group at No. 4 position of Compound (15) with $R_4$ using a known method; and
5) preparing Compound (17) by substituting a —SO$_2$Ph group of Compound (16) with hydrogen.

[Reaction Scheme 4]

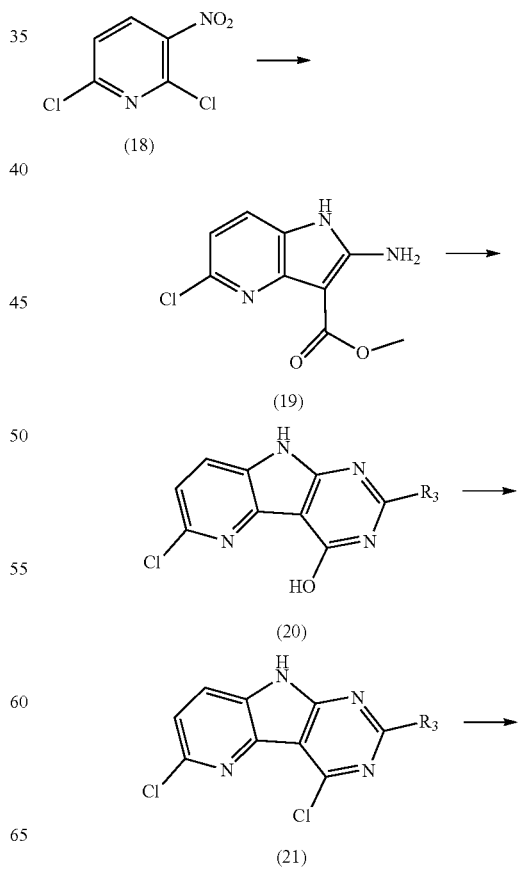

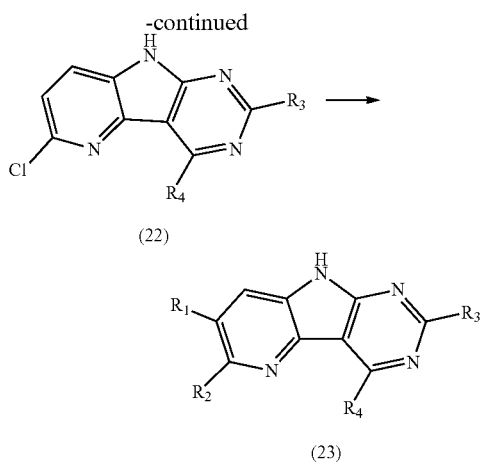

(22)

(23)

In Reaction Scheme 4, $R_1$, $R_2$, $R_3$ and $R_4$ are the same as defined in Chemical Formula 1. Reaction Scheme 4 corresponds to a preparation when $A_1$, $A_2$ and $A_3$ of Chemical Formula 1 are N, N, and $CR_1$, respectively, and is carried out by including the following five-step process:
1) preparing Compound (19) from Compound (18) using a known method (BioOrg. Med Chem. Lett. 2003, 13, 2003-2007);
2) preparing Compound (20) from Compound (19) using a known method (BioOrg. Med Chem. 2012, 20, 6123);
3) preparing Compound (21) by reacting Compound (20) with phosphorus oxychloride; 4) preparing Compound (22) by substituting a chlorine (—Cl) group at No. 4 position of Compound (21) with $R_4$ using a known method; and
5) preparing Compound (23) by introducing $R_1$ and $R_2$ from a substituent chlorine (—Cl) group from Compound (22).

The tricyclic compound represented by Chemical Formula 1 of the present invention can be used in the form of a pharmaceutically acceptable salt. As the salt, acid addition salts formed by various organic or inorganic acids that are pharmaceutically and physiologically acceptable are useful. As a suitable organic salt, it is possible to use, for example, carboxylic acid, phosphonic acid, sulfonic acid, acetic acid, propionic acid, octanoic acid, decanoic acid, glycolic acid, lactic acid, fumaric acid, succinic acid, adipic acid, malic acid, tartaric acid, citric acid, glutamic acid, aspartic acid, maleic acid, benzoic acid, salicylic acid, phthalic acid, phenylacetic acid, benzenesulfonic acid, 2-naphthalenesulfonic acid, methyl sulfuric acid, ethyl sulfuric acid, dodecyl sulfuric acid, and the like, and as a suitable inorganic acid, for example, hydrochloric acid, sulfuric acid, phosphoric acid, or the like can be used. Further, the tricyclic compound represented by Chemical Formula 1 of the present invention can be used in the form of not only a pharmaceutically acceptable salt, but also all salts prepared by typical methods, hydrates and solvates thereof.

Meanwhile, the tricyclic compound represented by Chemical Formula 1 of the present invention has an efficacy of inhibiting IRAK4, and thus is effective for the prevention, treatment and alleviation of autoimmune diseases and tumors.

Thus, the present invention provides a pharmaceutical composition for preventing or treating autoimmune diseases or tumors, containing, as an active ingredient, the tricyclic compound represented by Chemical Formula 1 or a pharmaceutically acceptable salt thereof. The pharmaceutical composition of the present invention may contain one or more active ingredients exhibiting the same or similar functions in addition to the tricyclic compound of Chemical Formula 1 or a pharmaceutically acceptable salt thereof.

In the pharmaceutical composition of the present invention, the tricyclic compound of Chemical Formula 1 or a pharmaceutically acceptable salt thereof may be administered in various oral and parenteral dosage forms at the time of clinical administration, and when the pharmaceutical composition is formulated, the pharmaceutical composition may be prepared using a diluent or excipient such as a filler, a bulking agent, a binder, a wetting agent, a disintegrant, and a surfactant which are usually used.

Examples of a solid preparation for oral administration include a tablet, a pill, a powder, a granule, a capsule, a troche, and the like, and the solid preparation may be prepared by mixing the tricyclic compound of Chemical Formula 1 of the present invention or a pharmaceutically acceptable salt thereof with at least one or more excipients selected from starch, calcium carbonate, sucrose, lactose, gelatin, and the like. Furthermore, in addition to simple excipients, lubricants such as magnesium stearate and talc may also be used. A liquid preparation for oral administration corresponds to a suspension agent, a liquid for internal use, an emulsion, a syrup, and the like, and the liquid preparation may include various excipients, for example, a wetting agent, a sweetener, an aroma, a preservative, and the like, in addition to water and liquid paraffin which are commonly used simple diluents.

Examples of a preparation for parenteral administration include a sterilized aqueous solution, a non-aqueous solvent, a suspension solvent, an emulsion, a freeze-dried preparation, and a suppository. As a non-aqueous solvent and a suspension solvent, it is possible to use propylene glycol, polyethylene glycol, a vegetable oil such as olive oil, an injectable ester such as ethyl oleate, and the like. As a base of the suppository, it is possible to use Witepsol, Macrogol, Tween 61, cacao butter, laurin fat, glycerol, gelatin, and the like.

Further, the dose of the tricyclic compound of Chemical Formula 1 of the present invention or a pharmaceutically acceptable salt thereof administered to the human body may vary depending on the age, body weight, gender, administration form, health status, and level of disease of a patient, and is generally 0.1 to 1,000 mg/day, preferably 1 to 500 mg/day, based on an adult patient having a body weight of 70 kg, and the tricyclic compound of Chemical Formula 1 of the present invention or a pharmaceutically acceptable salt thereof may be administered in divided doses once to several times a day at predetermined time intervals depending on the judgment of a doctor or a pharmacist.

The pharmaceutical composition of the present invention may be used either alone or in combination with surgery, hormone therapy, chemotherapy, and methods using a biological response modifier in order to prevent or treat autoimmune diseases or tumors.

Furthermore, the present invention provides a health food composition for preventing or alleviating autoimmune diseases or tumors, containing the tricyclic compound represented by Chemical Formula 1 as an active ingredient. In the health food composition of the present invention, when the tricyclic compound of Chemical Formula 1 is used as a food additive, the derivative may be added as it is or used with another food or other food ingredients, and may be appropriately used according to a typical method.

In the health food composition of the present invention, a content of the active ingredient may be suitably determined depending on the purpose of use (improvement such as prevention, health or therapeutic treatment). In general, when a food or beverage is prepared, the tricyclic compound of Chemical Formula 1 of the present invention is added in an amount of 15 wt % or less, preferably 10 wt % or less based on raw materials. However, in the case of long-term intake for the purpose of health and hygiene, or for the purpose of controlling health, the content of the active ingredient may be within the above range, but the content of the effective ingredient may be equal to or more than the above range when there is no problem in terms of safety.

In the pharmaceutical composition and the health food composition of the present invention, the autoimmune disease is preferably multiple sclerosis, psoriasis, a systemic inflammatory disease, a small intestinal inflammatory disease, ulcerative colitis, Crohn's disease, rheumatoid arthritis and polyarthritis, topical and systemic pachydermia, systemic lupus erythematosus, discoid lupus erythematosus, cutaneous lupus, dermatomyositis, polymyositis, Sjogren syndrome, panarteritis nodosa, autoimmune enteropathy, atopic dermatitis, proliferative glomerulonephritis, or the like.

In the pharmaceutical composition and the health food composition of the present invention, the tumor is preferably acute myeloid leukemia, myelodysplastic syndrome, acute lymphoblastic leukemia, chronic myeloid leukemia, or the like.

Advantageous Effects

The tricyclic compound represented by Chemical Formula 1 of the present invention has an excellent inhibitory activity against IRAK4, and thus is effective for preventing, treating or alleviating various diseases related thereto, and can be usefully used for the prevention, treatment, or alleviation of autoimmune diseases or tumors, which are known to be associated with IRAK4 inhibitory activity.

DESCRIPTION OF DRAWINGS

FIG. 1 illustrates the suppressive effects of the tricyclic compound of the present invention on systemic inflammatory diseases.

FIG. 2 illustrates the suppressive effects of the tricyclic compound of the present invention on systemic inflammatory diseases.

FIG. 3 illustrates the antitumor effects of the tricyclic compound of the present invention.

FIG. 4 illustrates the antitumor effects of the tricyclic compound of the present invention.

MODES OF THE INVENTION

Hereinafter, the present invention will be described in detail through Examples and Experimental Examples. However, the following Examples and Experimental Examples are only for illustrating the present invention, and the content of the present invention is not limited by the following Examples.

[Preparation Example 1] Preparation of 6-bromo-4-chloro-9H-pyrimido[4,5-b]indole (Compound 4a)

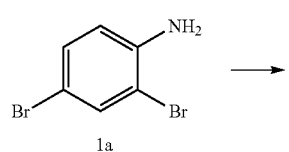

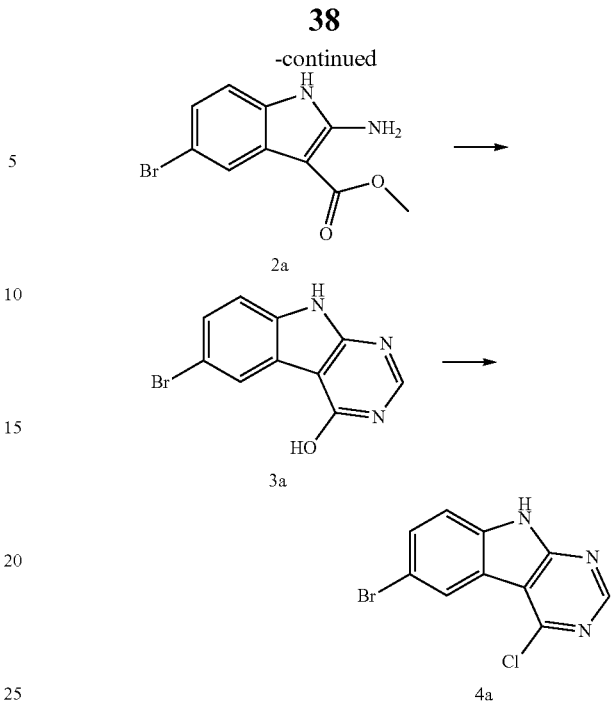

Step 1. Preparation of Compound 2a

After Compound 1a (36 g, 143 mmol) was dissolved in dichloromethane (300 mL), triethylamine (40 mL, 287 mmol) was added thereto, and trifluoroacetic anhydride (30 mL, 216 mmol) was slowly added thereto at 0° C. After the reaction was completed, the resulting product was washed with distilled water (2×300 mL), and then moisture was removed with sodium sulfate ($Na_2SO_4$), and the resulting product was concentrated under reduced pressure to obtain 50 g of a trifluoroacetamide derivative.

The trifluoroacetamide derivative was dissolved in dimethyl sulfoxide (DMSO)-distilled water (1:1; 280 mL), methylcyanoacetate (15 mL, 170 mmol), DL-proline (3.3 g, 18.8 mmol), $K_2CO_3$ (40 g, 289 mmol), and CuI (2.73 g, 14.3 mmol) were added thereto, and the resulting mixture was stirred at 60° C. for 14 hours. After the reaction product was cooled to room temperature, the solid was filtered and washed with methanol (2×100 mL), and then the filtrate was concentrated under reduced pressure. Ethyl acetate (EA, 500 mL) and tetrahydrofuran (200 mL) were added to the residue, the resulting mixture was washed with distilled water (2×200 mL), and then moisture was removed with sodium sulfate ($Na_2SO_4$), and the resulting product was concentrated under reduced pressure. The residue was separated by silica gel column chromatography (hexane:ethyl acetate=1:5→1:2) to obtain Compound 2a (white solid, 32 g, yield 83%).

2a: $^1$H-NMR (300 MHz, DMSO-$d_6$) δ 3.76 (s, 3H), 6.82 (s, 2H), 6.99 (dd, J=8.3, 2.0 Hz, 1H), 7.06 (d, J=8.3 Hz, 1H), 7.61 (d, J=1.8 Hz, 1H), 10.77 (s, 1H).

Step 2. Preparation of Compound 3a

After Compound 2a (15 g, 55.7 mmol) was dissolved in formamide (100 mL), the resulting solution was stirred in the presence of nitrogen at 185° C. for 3 hours. After the reaction product was cooled to room temperature, distilled water (100 mL) was added thereto, and the solid was filtered and then washed with distilled water (2×100 mL) to obtain a brown solid. After the brown solid was dried, the residue was separated by silica gel column chromatography (hexane:ethyl acetate=1:1) to obtain Compound 3a (brown solid, 9.6 g, yield 65%).

3a: $^1$H-NMR (300 MHz, DMSO-$d_6$) δ 7.46 (d, J=2.0 Hz, 2H), 8.06 (s, 1H), 8.16 (s, 1H), 12.33 (s, 1H), 12.37 (s, 1H).

Step 3. Preparation of Compound 4a

After Compound 3a (9.2 g, 34.8 mmol) was dispersed in phosphorus oxychloride (POCl$_3$)(800 mL), the resulting dispersion was stirred at 110° C. for 14 hours. After the reaction product was concentrated under reduced pressure, ice water (100 mL) was added thereto, and the solid was filtered and then washed with ice water (2×100 mL) to obtain a brown solid. The solid was dried, and then separated by silica gel column chromatography (hexane:ethyl acetate=1:3) to obtain Compound 4a (brown solid, 8.4 g, yield 85%).

4a: $^1$H-NMR (300 MHz, DMSO-$d_6$) δ 7.62 (d, J=8.7 Hz, 1H), 7.79 (dd, J=8.5, 1.7 Hz, 1H), 8.38 (d, J=1.6 Hz, 1H), 8.83 (s, 1H), 12.96 (s, 1H).

[Preparation Example 2] Preparation of methyl 4-chloro-9H-pyrimido[4,5-b]indole-6-carboxylate (Compound 4b)

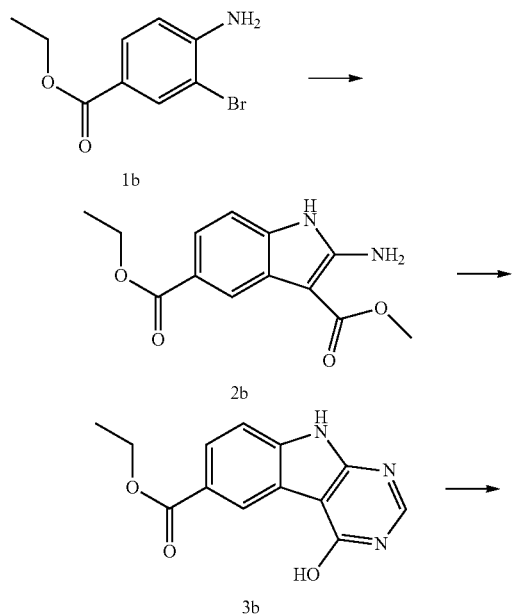

Compound 4b was prepared from Compound 1b by three steps in the same manner as in Preparation Example 1.

4b: $^1$H-NMR (300 MHz, DMSO-$d_6$) δ 1.38 (t, J=7.1 Hz, 3H), 4.38 (q, J=7.1 Hz, 2H), 7.70 (d, J=8.6 Hz, 1H), 8.19 (dd, J=8.6, 1.3 Hz, 1H), 8.80 (s, 1H), 8.85 (s, 1H), 13.13 (s, 1H).

[Preparation Example 3] Preparation of 7-bromo-4-chloro-9H-pyrimido[4,5-b]indole (Compound 4c)

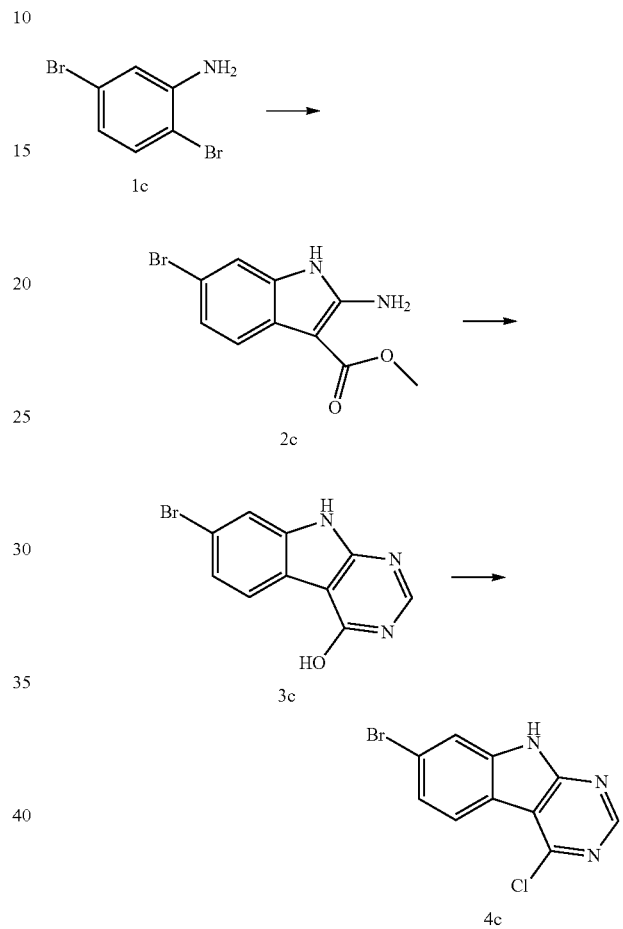

Compound 4c was prepared from Compound 1c by three steps in the same manner as in Preparation Example 1.

4c: $^1$H-NMR (300 MHz, DMSO-$d_6$) δ 7.60 (dd, J=8.4, 1.8 Hz, 1H), 7.81 (d, J=1.7 Hz, 1H), 8.22 (d, J=8.5 Hz, 1H), 8.83 (s, 1H), 12.94 (s, 1H).

[Preparation Example 4] Preparation of methyl 4-chloro-9H-pyrimido[4,5-b]indole-7-carboxylate (Compound 4d)

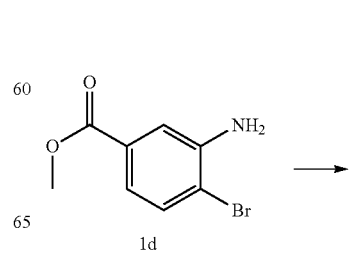

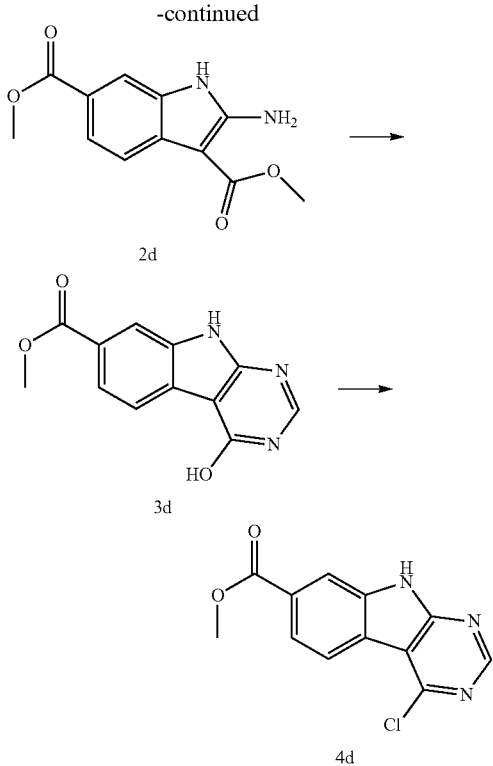

Compound 4d was prepared from Compound 1d by three steps in the same manner as in Preparation Example 1.

4d: $^1$H-NMR (300 MHz, DMSO-$d_6$) δ 3.93 (s, 3H), 8.02 (dd, J=8.4, 1.2 Hz, 1H), 8.20 (s, 1H), 8.41 (d, J=8.2 Hz, 1H), 8.86 (s, 1H).

[Preparation Example 5] Preparation of 6-bromo-N-(trans-4-morpholinocyclohexyl)-9H-pyrimido[4,5-b]indole-4-amine (Compound 5aa)

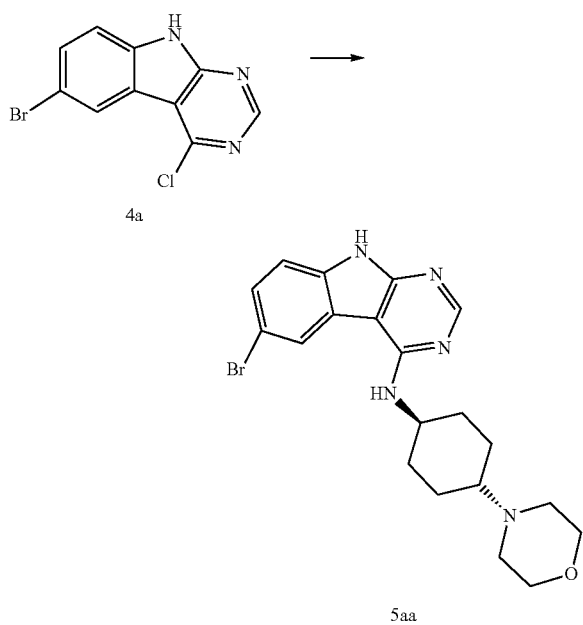

After Compound 4a (1.0 g, 1.76 mmol), trans-4-morpholinocyclohexan-1-amine hydrochloride (496 mg, 1.91 mmol), and triethylamine (0.75 mL, 5.38 mmol) were dissolved in DMSO (7 mL), the resulting solution was stirred at 110° C. After the completion of the reaction was confirmed, ethyl acetate (20 mL) was added thereto, the resulting mixture was washed with water (10 mL), and water (10 mL) was extracted with ethyl acetate (20 mL). After ethyl acetate (40 mL) was washed using water (2×10 mL), moisture was removed with sodium sulfate (Na$_2$SO$_4$) and the resulting product was concentrated under reduced pressure. The residue was separated by silica gel column chromatography (dichloromethane:ethyl acetate:methanol=1:20:1→1:6:1) to obtain 896 mg (58%) of Compound 5aa as a white solid.

5aa: $^1$H-NMR (300 MHz, DMSO-$d_6$) δ 1.25-1.40 (m, 2H), 1.56-1.68 (m, 2H), 1.90-2.03 (m, 4H), 2.20-2.27 (m, 1H), 2.50 (m, 4H), 3.56-3.59 (m, 4H), 4.28-4.30 (m, 1H), 6.86 (d, J=8.2 Hz, 1H), 7.38 (d, J=8.5 Hz, 1H), 7.48 (dd, J=8.6, 1.8 Hz, 1H), 8.34 (s, 1H), 8.62 (d, J=1.5 Hz, 1H), 12.01 (s, 1H).

[Preparation Example 6] Preparation of trans-N1-(6-bromo-9H-pyrimido[4,5-b]indol-4-yl)-N4,N4-dimethylcyclohexane-1,4-diamine (Compound 5ab)

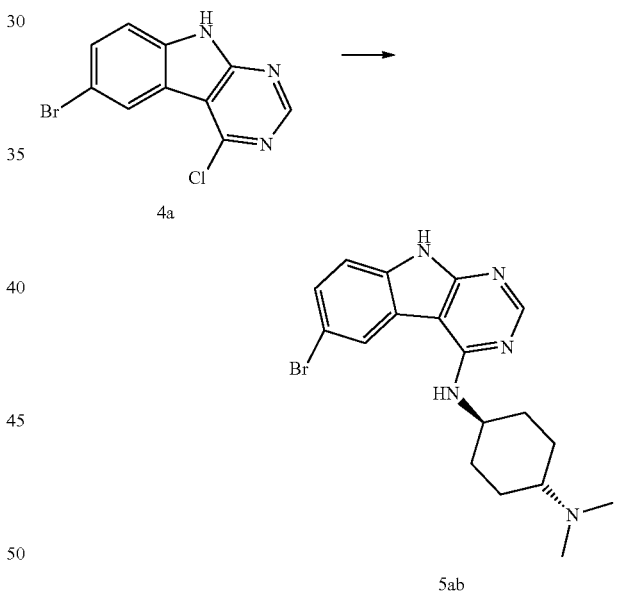

After Compound 4a (200 mg, 0.70 mmol), trans-N1,N1-dimethylcyclohexane-1,4-diamine dihydrochloride (213 mg, 0.77 mmol), and triethylamine (0.49 mL, 3.5 mmol) were dissolved in DMSO (6 mL) in the same manner as in Preparation Example 5, the resulting solution was stirred at 110° C. After the completion of the reaction was confirmed, ethyl acetate (20 mL) was added thereto, the resulting mixture was washed with water (10 mL), and water (10 mL) was extracted with ethyl acetate (15×3 mL). After ethyl acetate (65 mL) was washed using water (2×10 mL), moisture was removed with sodium sulfate (Na$_2$SO$_4$) and the resulting product was concentrated under reduced pressure. The residue was separated by silica gel column chromatography (methanol), and then washed with tetrahydrofuran.

The residue was washed with diethyl ether (20 mL) to obtain 182 mg (66%) of a light brown solid.

5ab: $^1$H-NMR (300 MHz, DMSO-d$_6$) δ1.24-2.02 (m, 9H), 2.20 (s, 9H), 4.26-4.30 (m, 1H), 6.86 (d, J=8.5 Hz, 1H), 7.38 (d, J=8.6 Hz, 1H), 7.47 (dd, J=8.6, 1.6 Hz, 1H), 8.33 (s, 1H), 8.62 (d, J=1.5 Hz, 1H), 12.00 (s, 1H).

[Preparation Example 7] Preparation of 6-bromo-N-(trans-4-(4-(methylsulfonyl)piperazin-1-yl)cyclohexyl)-9H-pyrimido[4,5-b]indole-4-amine (Compound 5ac)

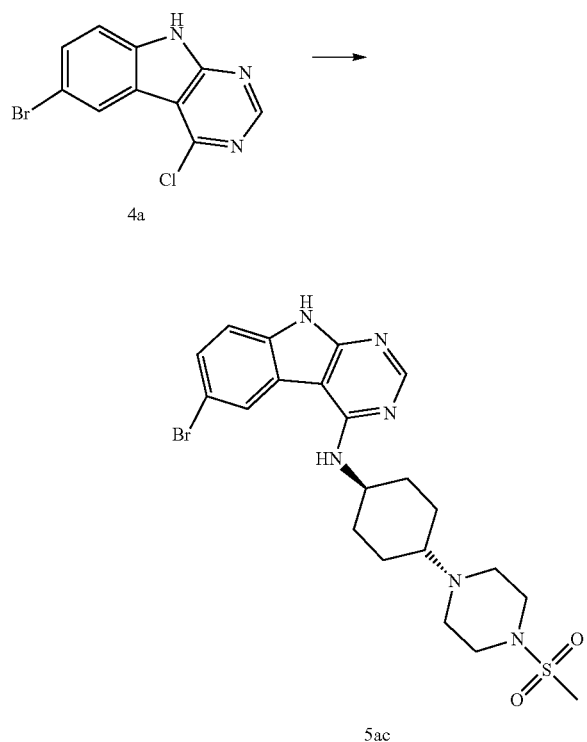

After Compound 4a (278 mg, 0.98 mmol), trans-4-(4-(methylsulfonyl)piperazin-1-yl)cyclohexan-1-amine (260 mg, 0.99 mmol), and N,N-diisopropylethylamine (2.6 mL, 15 mmol) were dissolved in N-methyl-2-pyrrolidone (NMP)(3 mL), the resulting solution was heated to 215° C. using microwaves and stirred for 30 minutes. After the completion of the reaction was confirmed, ethyl acetate (30 mL) was added thereto, and then the resulting mixture was washed with water (2×35 mL). After water (70 mL) was washed with ethyl acetate (20 mL), moisture was removed from ethyl acetate (50 mL) with sodium sulfate (Na$_2$SO$_4$), the resulting product was concentrated under reduced pressure, and then the residue was washed with methanol (10 mL) to obtain 311 mg (62%) of a light brown solid which is Compound 5ac.

5ac: $^1$H-NMR (300 MHz, DMSO-d$_6$) δ 1.33-1.45 (m, 2H), 1.57-1.69 (m, 2H), 1.86-1.90 (m, 2H), 1.99-2.03 (m, 2H), 2.61-2.64 (m, 4H), 2.87 (s, 3H), 3.08-3.11 (m, 4H), 4.27-4.91 (m, 1H), 6.88 (d, J=7.6 Hz, 1H), 7.38 (d, J=8.5 Hz, 1H), 7.47 (d, J=8.8 Hz, 1H). 8.34 (s, 1H), 8.62 (s, 1H), 12.00 (s, 1H).

[Preparation Example 8] Preparation of 6-bromo-N-(2-morpholinoethyl)-9H-pyrimido[4,5-b]indole-4-amine (Compound 5ad)

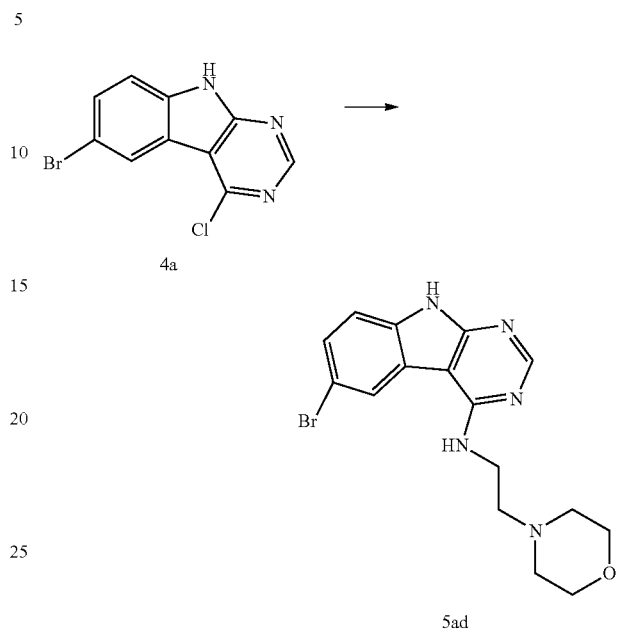

After Compound 4a (100 mg, 0.35 mmol), 2-morpholinoethan-1-amine (68 mg, 0.52 mmol), and N,N-diisopropylethylamine (0.12 mL, 0.7 mmol) were dissolved in N-methyl-2-pyrrolidone (NMP)(3 mL), the resulting solution was heated to 215° C. using microwaves and stirred for 30 minutes. After the completion of the reaction was confirmed, ethyl acetate (25 mL) was added thereto, and then the resulting mixture was washed with water (25 mL). After ethyl acetate (25 mL) was washed with water (25 mL), ethyl acetate (50 mL) was washed with water (2×25 mL), and then moisture was removed with sodium sulfate (Na$_2$SO$_4$), and the resulting product was concentrated under reduced pressure. The residue was separated by silica gel column chromatography (dichloromethane:ethyl acetate:methanol=15:1:1→10:1:1) to obtain 102 mg (76%) of a light yellow solid which is Compound 5aa.

5ad: $^1$H-NMR (300 MHz, DMSO-d$_6$) δ 2.50 (m, 4H), 2.58-2.63 (m, J=7.2 Hz, 2H), 3.58-3.61 (m, 4H), 3.73 (q, J=6.6 Hz, 2H), 7.25 (t, J=5.4 Hz, 1H), 7.39-7.42 (m, 1H), 7.47-7.51 (m, 1H), 8.35 (s, 1H), 8.52-8.53 (m, 1H), 12.03 (s, 1H).

[Preparation Example 9] Preparation of 6-bromo-N-(3-morpholinopropyl)-9H-pyrimido[4,5-b]indole-4-amine (Compound 5ae)

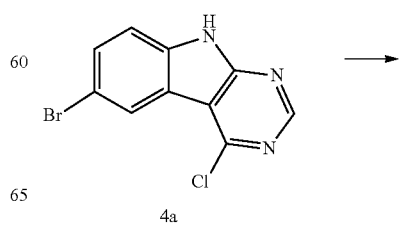

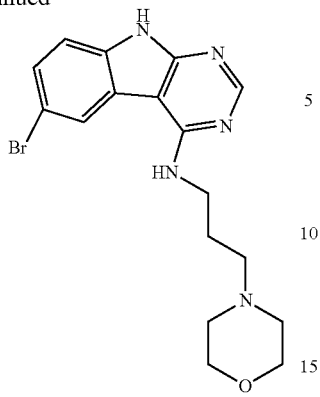

5ae

After Compound 4a (100 mg, 0.35 mmol), 2-morpholinopropyl-1-amine (0.08 mL, 0.52 mmol), and N,N-diisopropylethylamine (0.12 mL, 0.7 mmol) were dissolved in N-methyl-2-pyrrolidone (NMP)(3 mL), the gas was removed, and then the resulting product was heated to 215° C. using microwaves and stirred for 30 minutes. After the completion of the reaction was confirmed, ethyl acetate (25 mL) was added thereto, and then the resulting mixture was washed with water (25 mL). After water (25 mL) was washed with ethyl acetate (2×25 mL), ethyl acetate (75 mL) was washed with water (2×25 mL), and then moisture was removed with sodium sulfate ($Na_2SO_4$), and the resulting product was concentrated under reduced pressure. The residue was separated by silica gel column chromatography (dichloromethane:ethyl acetate:methanol=15:1:1→10:1:1) to obtain 127 mg (91%) of a light yellow solid which is Compound 5ae.

5ae: $^1$H-NMR (300 MHz, DMSO-$d_6$) δ 1.78-1.88 (m, 2H), 2.36-2.38 (m, 6H), 3.55-3.58 (m, 4H), 3.63 (q, J=6.5 Hz, 2H), 7.33 (t, J=5.7 Hz, 1H), 7.39 (d, J=8.5 Hz, 1H), 7.48 (dd, J=8.6, 1.8 Hz, 1H), 8.34 (s, 1H), 8.57 (d, J=1.6 Hz, 1H), 12.00 (s, 1H).

[Preparation Example 10] Preparation of tert-butyl 4-(2-((6-bromo-9H-pyrimido[4,5-b]indol-4-yl)amino)ethyl)piperazine-1-carboxylate (Compound 5af)

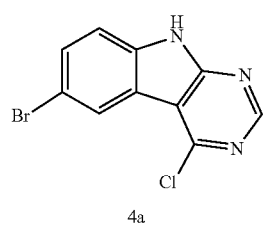

4a

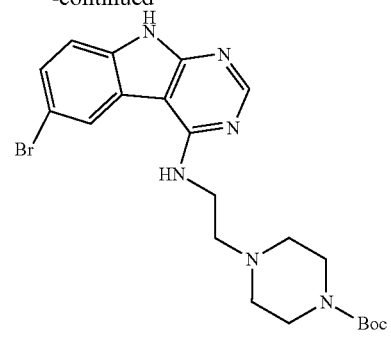

5af

After Compound 4a (200 mg, 0.70 mmol), tert-butyl 4-(2-aminoethyl)piperazine-1-carboxylate (240 mg, 1.05 mmol), and N,N-diisopropylethylamine (0.24 mL, 1.4 mmol) were dissolved in N-methyl-2-pyrrolidone (NMP)(6 mL), the resulting solution was heated to 215° C. using microwaves and stirred for 30 minutes. After the completion of the reaction was confirmed, ethyl acetate (25 mL) was added thereto, and then the resulting mixture was washed with water (25 mL). Water (25 mL) was extracted with ethyl acetate (2×25 mL). After ethyl acetate (50 mL) was washed with water (25×2 mL), moisture was removed with sodium sulfate ($Na_2SO_4$) and the resulting product was concentrated under reduced pressure. The residue was separated by silica gel column chromatography (dichloromethane:ethyl acetate:methanol=20:1:1→10:1:1) to obtain 79 mg (23%) of a light yellow solid which is Compound 5af.

5af: $^1$H-NMR (300 MHz, DMSO-$d_6$) δ 1.40 (s, 9H), 2.42-2.46 (m, 4H), 2.62 (t, J=7.0 Hz, 2H), 3.73 (q, J=6.2 Hz, 2H), 7.26 (t, J=5.8 Hz, 1H), 7.40 (d, J=8.6 Hz, 1H), 7.49 (dd, $J_1$=8.6, 1.8 Hz, 1H), 8.35 (s, 1H), 8.53 (d, J=1.6 Hz, 1H), 12.02 (s, 1H).

[Preparation Example 11] Preparation of tert-butyl 4-(4-(((6-bromo-9H-pyrimido[4,5-b]indol-4-yl)amino)phenyl)piperazine-1-carboxylate (Compound 5ag)

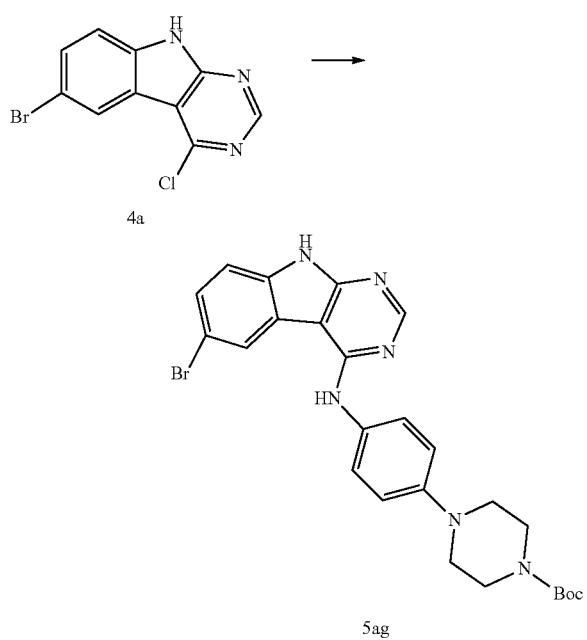

After Compound 4a (200 mg, 0.70 mmol), tert-butyl 4-(4-aminophenyl)piperazine-1-carboxylate (213 mg, 0.76 mmol), and triethylamine (0.4 mL, 2.1 mmol) were dissolved in DMSO (10 mL), the resulting solution was stirred at 110° C. After the completion of the reaction was confirmed, ethyl acetate (20 mL) was added thereto, the resulting mixture was washed with water (10 mL), and water (10 mL) was extracted with ethyl acetate (20 mL). After ethyl acetate (40 mL) was washed using water (2×10 mL), moisture was removed with sodium sulfate (Na$_2$SO$_4$) and the resulting product was concentrated under reduced pressure. The residue was separated by silica gel column chromatography (hexane:ethyl acetate=12:1→1:4) to obtain 174 mg (46%) of a light brown solid which is Compound 5ag.

5ag: $^1$H-NMR (300 MHz, DMSO-d$_6$) δ 1.43 (s, 9H), 3.3.08-3.12 (m, 4H), 3.47-3.50 (m, 4H), 6.99 (d, J=8.7 Hz, 2H), 7.41-7.54 (m, 4H), 8.35 (s, 1H), 8.57 (s, 1H), 8.86 (s, 1H), 12.17 (s, 1H).

[Preparation Example 12] Preparation of 4-(2-((6-bromo-9H-pyrimido[4,5-b]indol-4-yl)oxy)ethyl)morpholine (Compound 5ah)

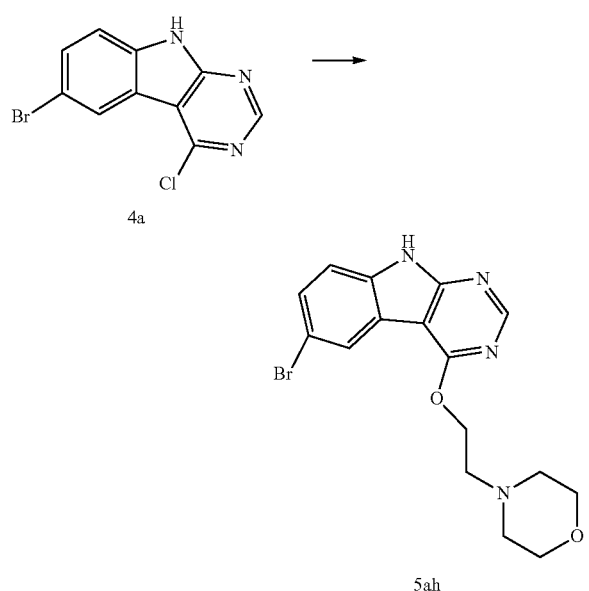

After 2-morpholinoethyl alcohol (92 mg, 0.7 mmol) was dissolved in diglyme (3 mL), NaH (60%, 28 mg, 0.7 mmol) was added thereto at 0° C., and then the resulting mixture was stirred at room temperature for 1 hour. Compound 4a (100 mg, 0.35 mmol) was added thereto, and the resulting mixture was stirred at 100° C. After the completion of the reaction was confirmed, water (25 mL) was added thereto, then extraction was performed with ethyl acetate (3×25 mL), and then the extract was washed with water (2×25 mL), moisture was removed with sodium sulfate (Na$_2$SO$_4$), and the resulting product was concentrated under reduced pressure. The residue was separated by silica gel column chromatography (dichloromethane:ethyl acetate:methanol=30:1:1→20:1:1) to obtain 115 mg (86%) of a light yellow solid.

5ah: $^1$H-NMR (300 MHz, DMSO-d$_6$) δ 2.54-2.57 (m, 4H), 2.87 (t, J=5.8 Hz, 2H), 3.57-3.60 (m, 4H), 4.73 (t, J=5.8 Hz, 2H), 7.52 (d, J=8.6 Hz, 1H), 7.61 (dd, J=8.7, 1.9 Hz, 1H), 8.11 (d, J=1.8 Hz, 1H), 8.61 (s, 1H), 12.46 (s, 1H).

[Example 1] Preparation of ethyl 4-((trans-4-morpholinocyclohexyl)amino)-9H-pyrimido[4,5-b]indole-6-carboxylate (Compound 5ba)

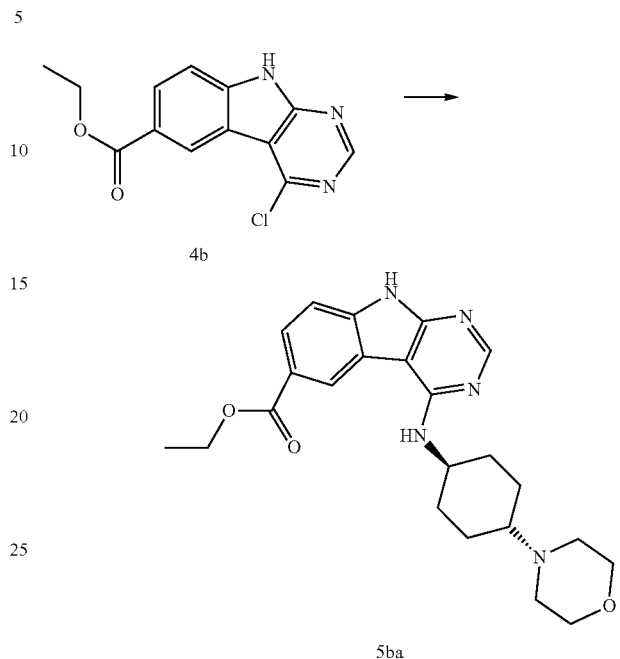

After Compound 4b (500 mg, 1.81 mmol), trans-4-morpholinocyclohexan-1-amine hydrochloride (507 mg, 1.97 mmol), and triethylamine (0.76 mL, 5.44 mmol) were dissolved in DMSO (6 mL), the resulting solution was stirred at 110° C. for 20 hours. After the completion of the reaction was confirmed, ethyl acetate (20 mL) was added thereto, the resulting mixture was washed with water (10 mL), and water (10 mL) was extracted with ethyl acetate (20 mL). After ethyl acetate (40 mL) was washed using water (2×10 mL), moisture was removed with sodium sulfate (Na$_2$SO$_4$) and the resulting product was concentrated under reduced pressure. The residue was separated by silica gel column chromatography (dichloromethane:ethyl acetate:methanol=1:10:1→1:8:1) to obtain 338 mg (44%) of a white solid which is Compound 5ba.

5ba: $^1$H-NMR (300 MHz, DMSO-d$_6$) δ 1.35-1.40 (m, 6H), 1.60-1.72 (m, 2H), 1.90-2.05 (m, 4H), 2.27 (m, 1H), 2.50 (m, 4H), 3.56-3.59 (m, 4H), 4.25-4.27 (m, 1H), 4.37 (q, J=7.0 Hz, 2H), 7.12 (d, J=7.2 Hz, 1H), 7.50 (d, J=8.6 Hz, 1H), 7.98 (d, J=7.5 Hz, 1H), 8.37 (s, 1H), 8.93 (s, 1H), 12.25 (s, 1H).

[Example 2] Preparation of ethyl 4-((trans-4-(dimethylamino)cyclohexyl)amino)-9H-pyrimido[4,5-b]indole-6-carboxylate (Compound 5bb)

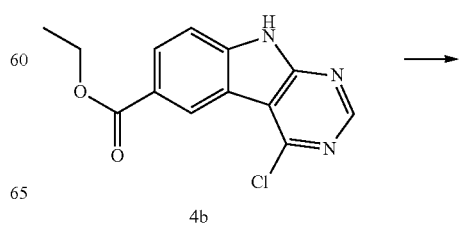

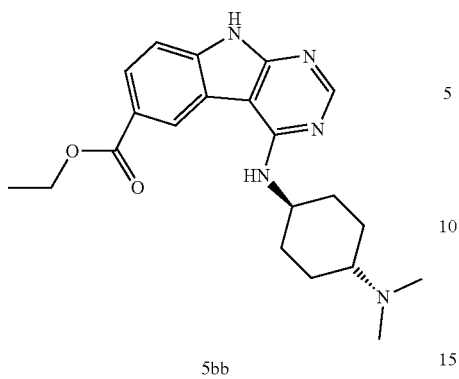

5bb

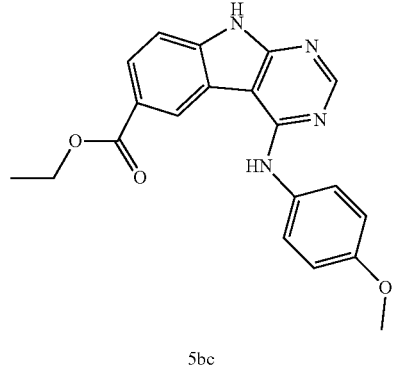

5bc

After Compound 4b (500 mg, 1.81 mmol), trans-N1,N1-dimethylcyclohexane-1,4-diamine dihydrochloride (425 mg, 1.97 mmol), and triethylamine (0.76 mL, 5.44 mmol) were dissolved in DMSO (6 mL), the resulting solution was stirred at 110° C. for 20 hours. After the completion of the reaction was confirmed, ethyl acetate (50 mL) was added thereto, the resulting mixture was washed with water (50 mL), and water (50 mL) was extracted with ethyl acetate (2×30 mL). After ethyl acetate (110 mL) was washed using water (3×50 mL), moisture was removed with sodium sulfate ($Na_2SO_4$) and the resulting product was concentrated under reduced pressure. After the residue was separated by silica gel column chromatography (dichloromethane:ethyl acetate:methanol=1:3:1→methanol→methanol+10% triethylamine), the separated product was concentrated under reduced pressure, and then washed with diethyl ether to obtain 392 mg (56%) of a light yellow solid which is Compound 5bb.

5bb: $^1$H-NMR (500 MHz, DMSO-$d_6$) δ 1.29-1.38 (m, 6H), 1.64 (q, J=12.4, 11.3 Hz, 2H), 1.87-1.90 (m, 2H), 2.01-2.03 (m, 2H), 2.20 (s, 6H), 4.25-4.27 (m, 1H), 4.37 (q, J=7.1 Hz, 2H), 7.11 (d, J=8.2 Hz, 1H), 7.50 (d, J=8.5 Hz, 1H), 7.98 (dd, J=8.5, 1.3 Hz, 1H), 8.37 (s, 1H), 8.93 (s, 1H), 12.25 (s, 1H).

[Example 3] Preparation of ethyl 4-((4-methoxyphenyl)amino)-9H-pyrimido[4,5-b]indole-6-carboxylate (Compound 5bc)

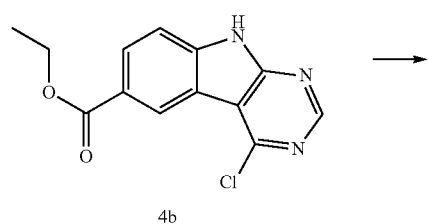

4b

After Compound 4b (500 mg, 1.81 mmol), 4-methoxyaniline (0.22 mL, 1.97 mmol), and triethylamine (0.76 mL, 5.44 mmol) were dissolved in DMSO (6 mL), the resulting solution was stirred at 110° C. for 20 hours. After the completion of the reaction was confirmed, ethyl acetate (30 mL) was added thereto, the resulting mixture was washed with water (10 mL), and water (10 mL) was extracted with ethyl acetate (10 mL). After ethyl acetate (40 mL) was washed using water (3×15 mL), moisture was removed with sodium sulfate ($Na_2SO_4$) and the resulting product was concentrated under reduced pressure. The residue was washed with diethyl ether to obtain 525 mg (79%) of a brown solid.

5bc: $^1$H-NMR (500 MHz, DMSO-$d_6$) δ 1.36 (t, J=7.1 Hz, 3H), 3.78 (s, 3H), 4.35 (q, J=7.0 Hz, 2H), 6.97 (d, J=8.8 Hz, 2H), 7.49 (d, J=8.8 Hz, 2H), 7.56 (d, J=8.5 Hz, 1H), 8.03 (d, J=8.5 Hz, 1H), 8.39 (s, 1H), 8.90 (s, 1H), 9.20 (s, 1H), 12.43 (s, 1H).

[Preparation Example 13] Preparation of 7-bromo-N-(trans-4-morpholinocyclohexyl)-9H-pyrimido[4,5-b]indole-4-amine (Compound 5ca)

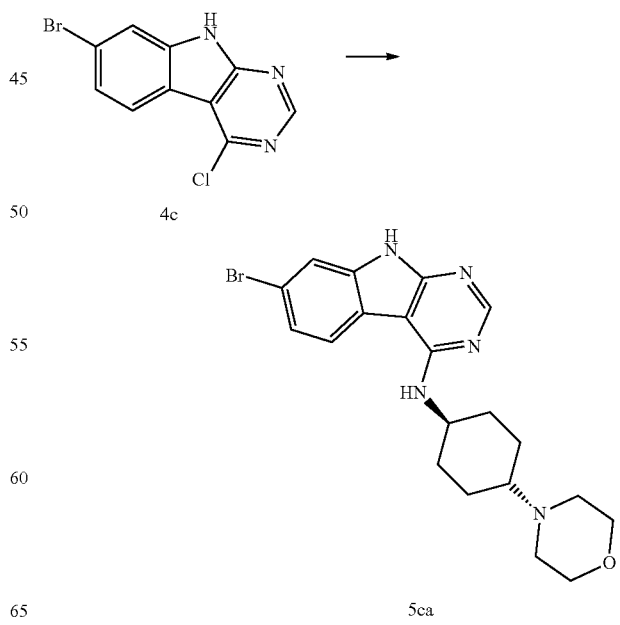

After Compound 4c (52 mg, 0.19 mmol), trans-4-morpholinocyclohexan-1-amine hydrochloride (297 mg, 1.15 mmol), and triethylamine (0.4 mL, 3.18 mmol) were dissolved in DMSO (15 mL), the resulting solution was stirred at 110° C. for 22 hours. After the completion of the reaction was confirmed, ethyl acetate (20 mL) was added thereto, the resulting mixture was washed with water (20 mL), and water (20 mL) was extracted with ethyl acetate (6×15 mL). After ethyl acetate (130 mL) was washed using brine (2×10 mL), moisture was removed with sodium sulfate (Na$_2$SO$_4$) and the resulting product was concentrated under reduced pressure. The residue was separated by silica gel column chromatography (dichloromethane:methanol=30:1→20:1) to obtain 896 mg (65%) of a white solid.

5ca: $^1$H-NMR (300 MHz, CDCl$_3$) δ 1.36-1.60 (m, 3H), 2.02-2.05 (m, 2H), 2.34-2.38 (m, 3H), 2.59-2.62 (m, 4H), 3.73-3.76 (m, 4H), 4.29 (m, 1H), 4.92 (d, J=7.1 Hz, 1H), 7.43 (dd, J=8.2, 1.6 Hz, 1H), 7.54 (d, J=8.5 Hz, 1H), 7.66 (d, J=1.6 Hz, 1H), 8.53 (s, 1H), 9.10 (s, 1H).

[Example 4] Preparation of methyl 4-((trans-4-morpholinocyclohexyl)amino)-9H-pyrimido[4,5-b]indole-7-carboxylate (Compound 5da)

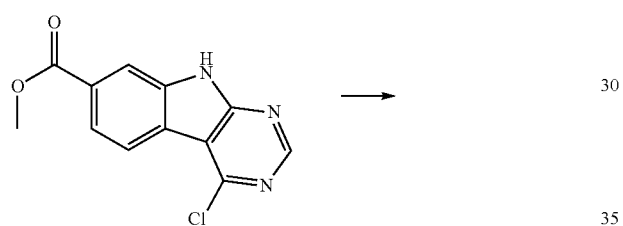
4d

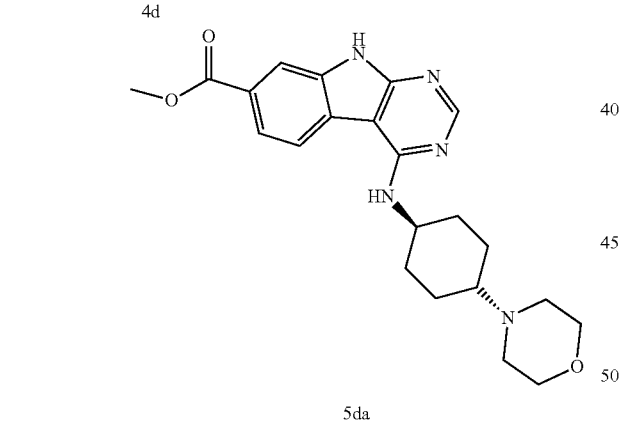
5da

After Compound 4d (52 mg, 0.19 mmol), trans-4-morpholinocyclohexan-1-amine hydrochloride (38 mg, 0.20 mmol), and triethylamine (26 μL, 0.57 mmol) were dissolved in DMSO (9 mL), the resulting solution was stirred at 110° C. for 18 hours. After the completion of the reaction was confirmed, ethyl acetate (10 mL) was added thereto, the resulting mixture was washed with water (10 mL), and water (10 mL) was extracted with ethyl acetate (2×10 mL). After ethyl acetate (40 mL) was washed using brine (2×10 mL), moisture was removed with sodium sulfate (Na$_2$SO$_4$) and the resulting product was concentrated under reduced pressure. The residue was separated by silica gel column chromatography (dichloromethane:methanol=10:1) to obtain 48 mg (59%) of a white solid.

5da: $^1$H-NMR (300 MHz, DMSO-d$_6$) δ 1.29-1.41 (m, 3H), 1.55-1.68 (m, 3H), 1.89-2.04 (m, 5H), 2.24-2.27 (m, 2H), 3.56-3.59 (m, 4H), 3.89 (s, 3H), 4.27-4.30 (m, 1H), 6.90 (d, J=8.3 Hz, 1H), 7.84 (dd, J=8.3, 1.6 Hz, 1H), 8.03 (d, J=1.5 Hz, 1H), 8.38 (s, 1H), 8.46 (d, J=8.4 Hz, 1H), 12.15 (s, 1H).

[Example 5] Preparation of methyl 4-((4-morpholinophenyl)amino)-9H-pyrimido[4,5-b]indole-7-carboxylate (Compound 5db)

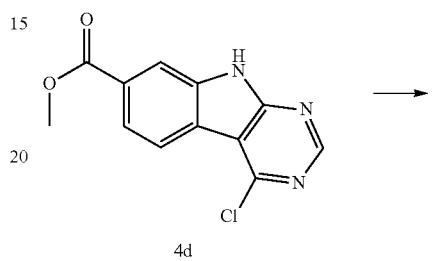
4d

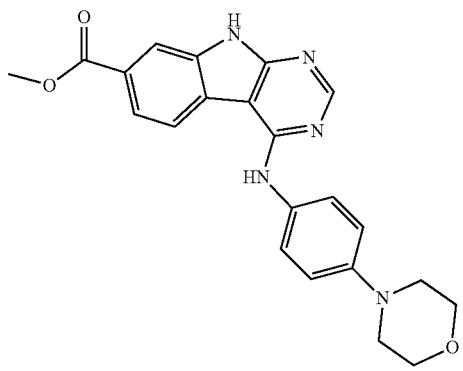
5db

Compound 4d (52 mg, 0.19 mmol) and 4-morpholinoaniline (36 mg, 0.20 mmol) were reacted in the same manner as in Example 4, and the residue after reaction was separated by silica gel column chromatography (dichloromethane:ethyl acetate:methanol=1:20:1) to obtain 45 mg (58%) of a white solid.

5db: $^1$H-NMR (300 MHz, DMSO-d$_6$) δ 3.10-3.13 (m, 4H), 3.75-3.78 (m, 4H), 3.91 (s, 3H), 6.98 (d, J=8.9 Hz, 2H), 7.50 (d, J=8.8 Hz, 2H), 7.72 (d, J=8.1 Hz, 1H), 8.26 (s, 1H), 8.48 (s, 1H), 8.60 (d, J=8.0 Hz, 1H), 9.02 (s, 1H).

[Example 6] Preparation of 6-(1-methyl-1H-pyrazol-4-yl)-N-(trans-4-morpholinocyclohexyl)-9H-pyrimido[4,5-b]indole-4-amine (Compound 6aaa)

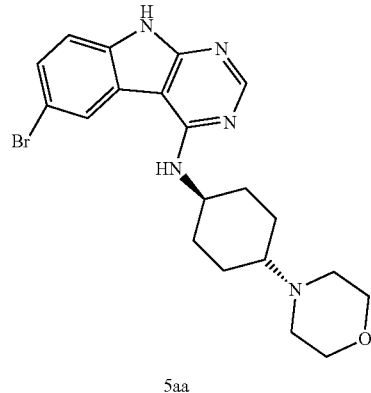

5aa

→

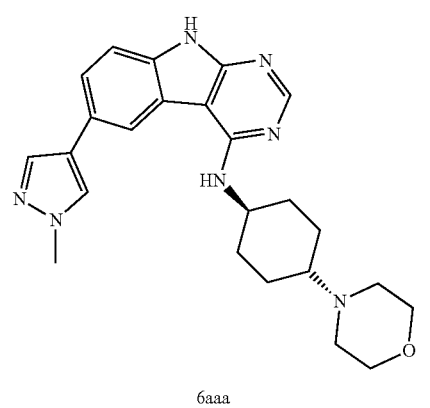

6aaa

By applying the Suzuki coupling reaction, a reaction of substituting Compound 5aa with a halogen group is carried out.

After Compound 5aa (20 mg, 0.04 mmol), 1-methyl-4-(4,4,5,5-tetramethyl-1,3,2-dioxaborolan-2-yl)-1H-pyrazole (9.9 mg, 0.04 mmol), and K$_2$CO$_3$ (16 mg, 0.12 mmol) were dissolved in dioxane:H$_2$O (4:1 in v/v, 1 mL), oxygen was removed by purging with argon gas, Pd(PPh$_3$)$_4$ (2 mg, 0.002 mmol) was added thereto, and then the gas was removed, and the resulting product was stirred at 80° C. for 18 hours. After the completion of the reaction was confirmed, ethyl acetate (10 mL) was added thereto, the resulting mixture was filtered with a celite pad and washed with water (2×10 mL), and then moisture was removed with sodium sulfate (Na$_2$SO$_4$), and the resulting product was concentrated under reduced pressure. The residue was separated by silica gel column chromatography (dichloromethane:methanol=20:1→10:1) to obtain 11 mg (55%) of a light yellow solid.

6aaa: $^1$H-NMR (300 MHz, DMSO-d$_6$) δ 1.62-1.66 (m, 2H), 1.90-2.09 (m, 8H), 3.57-3.60 (m, 4H), 3.90 (s, 3H), 4.24-4.31 (m, 1H), 7.41 (d, J=8.3 Hz, 1H), 7.56 (d, J=8.0 Hz, 1H), 7.96 (s, 1H), 8.13 (s, 1H), 8.34 (d, J=11.5 Hz, 2H), 11.82 (s, 1H).

[Example 7] Preparation of N-(trans-4-morpholinocyclohexyl)-6-(pyridin-4-yl)-9H-pyrimido[4,5-b]indole-4-amine (Compound 6aab)

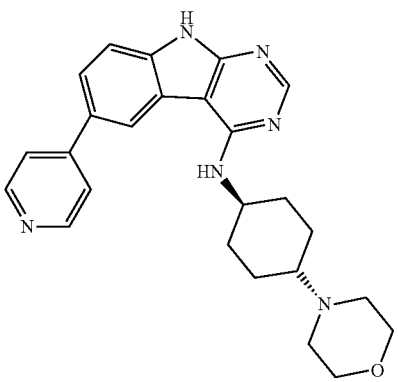

6aab

Compound 5aa (50 mg, 0.12 mmol) and pyridin-4-ylboronic acid (19 mg, 0.15 mmol) were reacted in the same manner as in Example 6, and the residue after reaction was separated by silica gel column chromatography (dichloromethane:methanol=20:1→10:1) to obtain 28 mg (23%) of a white solid.

6aab: $^1$H-NMR (300 MHz, DMSO-d$_6$) δ 1.31-1.43 (m, 2H), 1.58-1.70 (m, 2H), 1.91-1.95 (m, 2H), 2.05-2.09 (m, 2H), 2.23-2.30 (m, 2H), 2.50 (m, 3H), 3.57-3.60 (m, 4H), 4.27-4.31 (m, 1H), 6.86 (d, J=8.7 Hz, 1H), 7.56 (d, J=8.4 Hz, 1H), 7.81 (d, J=8.8 Hz, 1H), 7.85 (d, J=6.0 Hz, 2H), 8.36 (s, 1H), 8.65 (m, 3H), 12.04 (s, 1H).

[Example 8] Preparation of N-(trans-4-morpholinocyclohexyl)-6-(pyrimidin-5-yl)-9H-pyrimido[4,5-b]indole-4-amine (Compound 6aac)

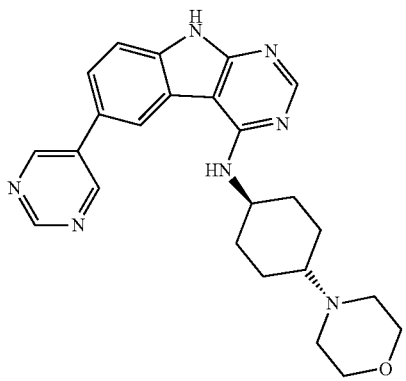

6aac

Compound 5aa (50 mg, 0.11 mmol) and pyrimidin-5-ylboronic acid (17 mg, 0.14 mmol) were reacted in the same manner as in Example 6, and the residue after reaction was separated by silica gel column chromatography (dichloromethane:ethyl acetate:methanol=10:10:1→5:5:1→4:2:1) to obtain 58 mg (99%) of a white solid.

6aac: $^1$H-NMR (300 MHz, DMSO-d$_6$) δ 1.31-1.44 (m, 2H), 1.57-1.70 (m, 2H), 1.91-1.94 (m, 2H), 2.05-2.08 (m, 2H), 2.23-2.30 (m, 2H), 2.50 (m, 3H), 3.56-3.59 (m, 4H), 4.31-4.34 (m, 1H), 6.76 (d, J=8.1 Hz, 1H), 7.58 (d, J=8.4 Hz, 1H), 7.80 (d, J=8.5 Hz, 1H), 8.37 (s, 1H), 8.66 (s, 1H), 9.19 (s, 1H), 9.29 (s, 2H), 12.05 (s, 1H).

[Example 9] Preparation of 6-(5-methoxypyridin-3-yl)-N-(trans-4-morpholinocyclohexyl)-9H-pyrimido[4,5-b]indole-4-amine (Compound 6aad)

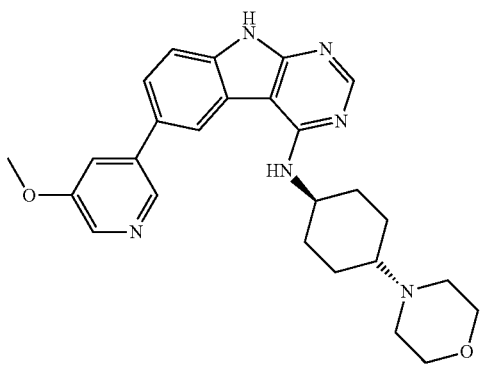

6aad

Compound 5aa (100 mg, 0.23 mmol) and 3-methoxy-5-(4,4,5,5-tetramethyl-1,3,2-dioxaborolan-2-yl)pyridine (70 mg, 0.29 mmol) were reacted in the same manner as in Example 6, and the residue after reaction was separated by silica gel column chromatography (dichloromethane:ethyl acetate:methanol=2:4:1→1:5:1) to obtain 63 mg (59%) of a white solid.

6aad: $^1$H-NMR (300 MHz, DMSO-d$_6$) δ 1.30-1.42 (m, 2H), 1.58-1.70 (m, 2H), 1.91-1.94 (m, 2H), 2.04-2.08 (m, 2H), 2.23-2.29 (m, 2H), 2.50 (m, 3H), 3.56-3.59 (m, 4H), 3.94 (s, 3H), 4.29-4.31 (m, 1H), 6.81 (d, J=8.1 Hz, 1H), 7.54 (d, J=8.3 Hz, 1H), 7.74 (m, 2H), 8.29 (s, 1H), 8.35 (s, 1H), 8.60 (s, 1H), 8.67 (s, 1H), 11.97 (s, 1H).

[Example 10] Preparation of 5-(4-((trans-4-morpholinocyclohexyl)amino)-9H-pyrimido[4,5-b]indol-6-yl)pyridine-3-ol (Compound 6aae)

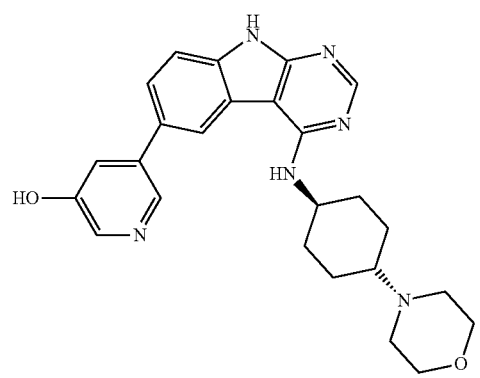

6aae

Compound 6aad (40 mg, 88 μmol) of Example 9 was stirred with a pyridine HCl salt (100 mg) at 120° C. for 1 hour. After the completion of the reaction was confirmed, ethyl acetate (10 mL) was added thereto, the resulting mixture was washed with water (2×10 mL), and then moisture was removed with sodium sulfate (Na$_2$SO$_4$), and the resulting product was concentrated under reduced pressure. The residue was separated by silica gel column chromatography (dichloromethane:methanol=10:1) to obtain 24 mg (62%) of a light yellow solid.

6aae: $^1$H-NMR (300 MHz, DMSO-d$_6$) δ 1.30-1.43 (m, 2H), 1.56-1.71 (m, 2H), 1.91-1.94 (m, 2H), 2.03-2.07 (m, 2H), 2.19-2.22 (m, 2H), 2.50 (m, 3H), 3.56-3.60 (m, 4H), 4.29-4.32 (m, 1H), 6.84 (d, J=8.3 Hz, 1H), 7.49-7.54 (m, 2H), 7.63 (dd, J=8.4, 1.4 Hz, 1H), 8.12 (d, J=2.4 Hz, 1H), 8.35 (s, 1H), 8.50 (d, J=1.5 Hz, 1H), 8.56 (s, 1H), 9.99 (s, 1H), 11.95 (s, 1H).

[Example 11] Preparation of 6-(5-fluoropyridin-3-yl)-N-(trans-4-morpholinocyclohexyl)-9H-pyrimido[4,5-b]indole-4-amine (Compound 6aaf)

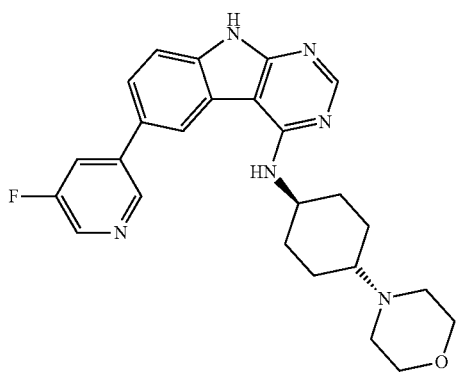

6aaf

Compound 5aa (30 mg, 0.06 mmol) and (5-fluoropyridin-3-yl)boronic acid (10 mg, 0.07 mmol) were reacted in the same manner as in Example 6, and the residue after reaction was separated by silica gel column chromatography (dichloromethane:ethyl acetate:methanol=6:1:1→5:1:1) to obtain 25 mg (81%) of a white solid.

6aaf: $^1$H-NMR (300 MHz, DMSO-d$_6$) δ 1.31-1.44 (m, 2H), 1.58-1.70 (m, 2H), 1.91-1.94 (m, 2H), 2.05-2.09 (m, 2H), 2.24-2.32 (m, 2H), 2.50 (m, 3H), 3.57-3.58 (m, 4H), 4.30-4.33 (m, 1H), 6.79 (d, J=8.3 Hz, 1H), 7.56 (d, J=8.1 Hz, 1H), 7.78 (d, J=9.0 Hz, 1H), 8.16 (m, 1H), 8.36 (s, 1H), 8.56 (d, J=2.7 Hz, 1H), 8.62 (s, 1H), 8.98 (s, 1H), 12.02 (s, 1H).

[Example 12] Preparation of 6-(5-(2-(dimethyl-amino)ethoxy)pyridin-3-yl)-N-(trans-4-morpholino-cyclohexyl)-9H-pyrimido[4,5-b]indole-4-amine (Compound 6aag)

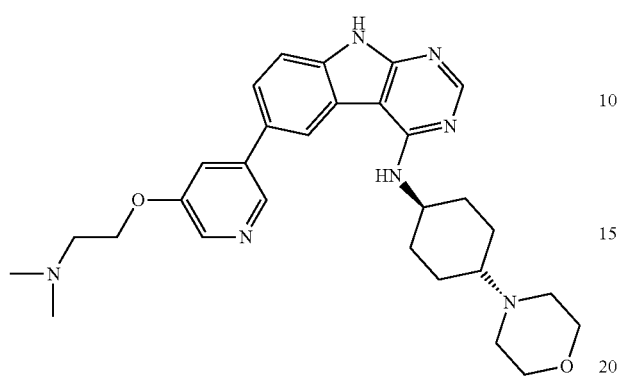

6aag

After N,N-dimethylaminoethyl alcohol (22 μL, 0.22 mmol) was dissolved in DMSO (2 mL), NaH (3.5 mg, 2.0 equivalent weights) was added thereto, and the resulting mixture was stirred at room temperature for 20 minutes. After Compound 6aaf (50 mg, 1.0 equivalent weight) was added thereto, the resulting mixture was stirred at 80° C. After the completion of the reaction was confirmed, water (10 mL) was added thereto, and extraction was performed with ethyl acetate (10 mL). After water (10 mL) was extracted with ethyl acetate (5 mL), ethyl acetate (15 mL) was washed using water (5×3 mL). Moisture was removed from ethyl acetate with sodium sulfate ($Na_2SO_4$), the resulting product was concentrated under reduced pressure, and then the residue was separated by silica gel column chromatography (dichloromethane:methanol=15:1) to obtain 24 mg (41%) of a white solid.

6aag: $^1$H-NMR (300 MHz, DMSO-$d_6$) δ 1.31-1.43 (m, 2H), 1.57-1.70 (m, 2H), 1.91-2.08 (m, 4H), 2.27 (m, 8H), 2.50 (m, 3H), 2.73 (m, 2H), 3.57-3.60 (m, 4H), 4.25-4.32 (m, 3H), 6.83 (d, J=8.1 Hz, 1H), 7.53 (d, J=8.4 Hz, 1H), 7.73-7.75 (m, 2H), 8.29 (d, J=2.6 Hz, 1H), 8.35 (s, 1H), 8.60 (s, 1H), 8.67 (d, J=1.5 Hz, 1H), 11.98 (s, 1H).

[Example 13] Preparation of 6-(6-methoxypyridin-3-yl)-N-(trans-4-morpholinocyclohexyl)-9H-pyrimido[4,5-b]indole-4-amine (Compound 6aah)

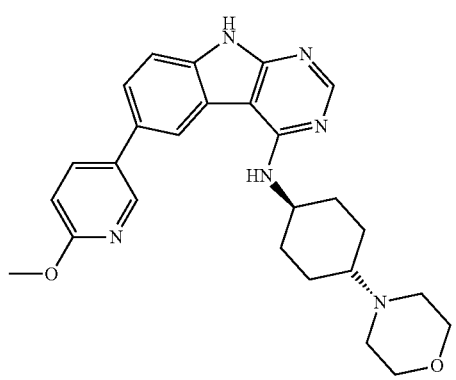

6aah

Compound 5aa (30 mg, 0.06 mmol) and (6-methoxypyridin-3-yl)boronic acid (11 mg, 0.07 mmol) were reacted in the same manner as in Example 6, and the residue after reaction was separated by silica gel column chromatography (dichloromethane:ethyl acetate:methanol=6:1:1→5:1:1) to obtain 25 mg (78%) of a white solid.

6aah: $^1$H-NMR (300 MHz, DMSO-$d_6$) δ 1.32-1.43 (m, 2H), 1.58-1.70 (m, 2H), 1.91-1.94 (m, 2H), 2.04-2.08 (m, 2H), 2.21-2.30 (m, 2H), 2.50 (m, 3H), 3.57-3.58 (m, 4H), 3.92 (s, 3H), 4.27-4.32 (m, 1H), 6.74 (d, J=7.8 Hz, 1H), 6.95 (d, J=8.4 Hz, 1H), 7.51 (d, J=8.6 Hz, 1H), 7.63 (d, J=7.2 Hz, 1H), 8.11 (d, J=7.9 Hz, 1H), 8.34 (s, 1H), 8.50 (s, 1H), 8.62 (s, 1H), 11.91 (s, 1H).

[Example 14] Preparation of N-(trans-4-morpholinocyclohexyl)-6-(3-nitrophenyl)-9H-pyrimido[4,5-b]indole-4-amine (Compound 6aai)

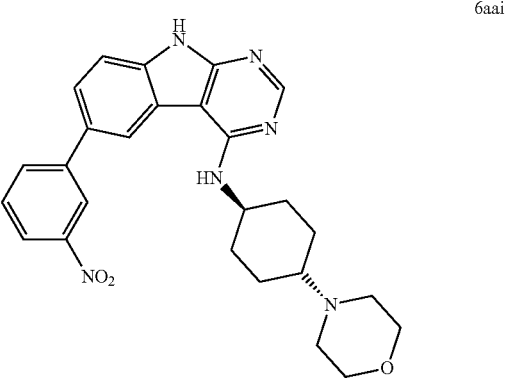

6aai

Compound 5aa (30 mg, 0.06 mmol) and (3-nitrophenyl)boronic acid (13 mg, 0.07 mmol) were reacted in the same manner as in Example 6, and the residue after reaction was separated by silica gel column chromatography (dichloromethane:ethyl acetate:methanol=5.5:1:1) to obtain 24 mg (74%) of a yellow solid.

6aai: $^1$H-NMR (500 MHz, DMSO-$d_6$) δ 1.32-1.41 (m, 2H), 1.60-1.67 (m, 2H), 1.91-1.93 (m, 2H), 2.06-2.09 (m, 2H), 2.24-2.28 (m, 2H), 2.50 (m, 3H), 3.58 (m, 4H), 4.26-4.31 (m, 1H), 6.88 (d, J=8.3 Hz, 1H), 7.57 (d, J=8.0 Hz, 1H), 7.76 (d, J=8.1 Hz, 1H), 7.81 (t, J=8.0 Hz, 1H), 8.21 (d, J=7.6 Hz, 1H), 8.27 (d, J=6.7 Hz, 1H), 8.37 (s, 1H), 8.56 (s, 1H), 8.64 (s, 1H), 12.03 (s, 1H).

[Example 15] Preparation of 6-(3-methoxyphenyl)-N-(trans-4-morpholinocyclohexyl)-9H-pyrimido[4,5-b]indole-4-amine (Compound 6aaj)

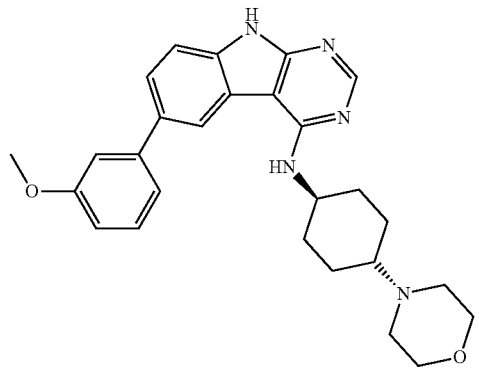

6aaj

Compound 5aa (30 mg, 0.06 mmol) and (3-methoxyphenyl)boronic acid (11 mg, 0.07 mmol) were reacted in the same manner as in Example 6, and the residue after reaction was separated by silica gel column chromatography (dichloromethane:ethyl acetate:methanol=6:1:1) to obtain 42 mg (99%) of a white solid.

6aaj: $^1$H-NMR (300 MHz, DMSO-$d_6$) δ 1.31-1.43 (m, 2H), 1.57-1.69 (m, 2H), 1.91-1.94 (m, 3H), 2.04-2.09 (m, 3H), 2.27-2.30 (m, 1H), 3.57-3.60 (m, 6H), 3.85 (s, 3H), 4.27 (m, 1H), 6.83-6.86 (d, J=8.1 Hz, 1H), 6.92-6.95 (m, 1H), 7.32-7.44 (m, 4H), 7.49-7.52 (d, J=8.4 Hz, 1H), 7.64-7.67 (m, 1H), 8.34 (s, 1H), 8.52 (s, 1H), 11.92 (s, 1H).

[Example 16] Preparation of 3-(4-((trans-4-morpholinocyclohexyl)amino)-9H-pyrimido[4,5-b]indol-6-yl) benzonitrile (Compound 6aak)

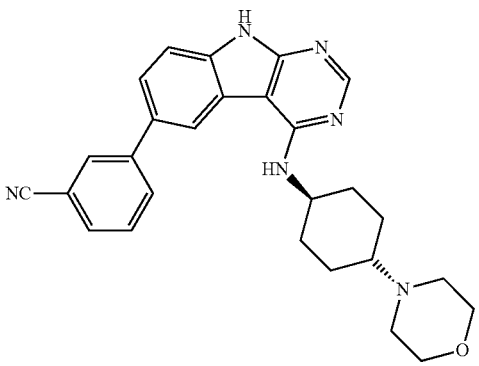

6aak

Compound 5aa (30 mg, 0.06 mmol) and (3-cyanophenyl)boronic acid (11 mg, 0.07 mmol) were reacted in the same manner as in Example 6, and the residue after reaction was separated by silica gel column chromatography (dichloromethane:ethyl acetate:methanol=5.5:1:1) to obtain 24 mg (78%) of a white solid.

6aak: $^1$H-NMR (500 MHz, DMSO-$d_6$) δ 1.33-1.40 (m, 2H), 1.60-1.68 (m, 2H), 1.92-1.94 (m, 2H), 2.06-2.09 (m, 2H), 2.25-2.30 (m, 2H), 2.50 (m, 3H), 3.57-3.58 (m, 4H), 4.26-4.30 (m, 1H), 6.81 (d, J=7.7 Hz, 1H), 7.54 (d, J=8.3 Hz, 1H), 7.70-7.74 (m, 2H), 7.82 (d, J=7.2 Hz, 1H), 8.14 (d, J=7.9 Hz, 1H), 8.26 (s, 1H), 8.36 (s, 1H), 8.58 (s, 1H), 12.00 (s, 1H).

[Example 17] Preparation of 6-(3,5-difluorophenyl)-N-(trans-4-morpholinocyclohexyl)-9H-pyrimido[4,5-b]indole-4-amine (Compound 6aal)

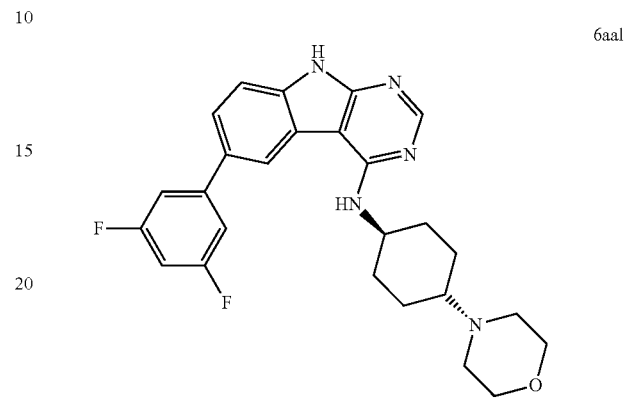

6aal

Compound 5aa (30 mg, 0.06 mmol) and (3,5-difluorophenyl)boronic acid (12 mg, 0.07 mmol) were reacted in the same manner as in Example 6, and the residue after reaction was separated by silica gel column chromatography (dichloromethane:ethyl acetate:methanol=4.5:2:1) to obtain 25 mg (77%) of a white solid.

6aal: $^1$H-NMR (300 MHz, DMSO-$d_6$) δ 1.32-1.44 (m, 2H), 1.58-1.71 (m, 2H), 1.91-1.96 (m, 2H), 2.06-2.09 (m, 2H), 2.24-2.33 (m, 2H), 2.50 (m, 3H), 3.57-3.58 (m, 4H), 4.26-4.29 (m, 1H), 6.82 (d, J=8.9 Hz, 1H), 7.16-7.24 (m, 1H), 7.52 (d, J=8.5 Hz, 1H), 7.55-7.59 (m, 2H), 7.74 (dd, J=8.6, 1.6 Hz, 1H), 8.36 (s, 1H), 8.54-8.55 (m, 1H), 12.00 (s, 1H).

[Example 18] Preparation of 6-(2,4-difluorophenyl)-N-(trans-4-morpholinocyclohexyl)-9H-pyrimido[4,5-b]indole-4-amine (Compound 6aam)

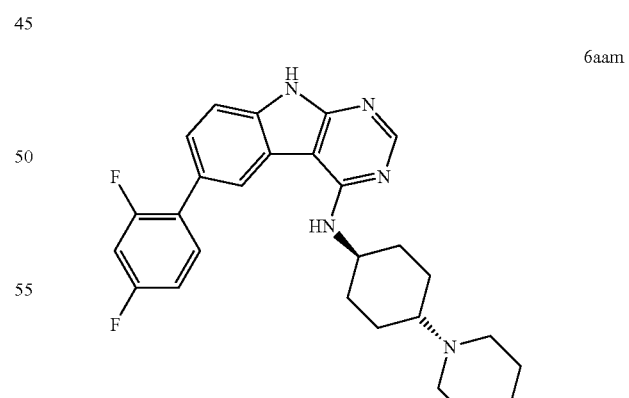

6aam

Compound 5aa (30 mg, 0.06 mmol) and (2,4-difluorophenyl)boronic acid (12 mg, 0.07 mmol) were reacted in the same manner as in Example 6, and the residue after reaction was separated by silica gel column chromatography (dichloromethane:ethyl acetate:methanol=4.5:2:1) to obtain 23 mg (71%) of a white solid.

6aam: $^1$H-NMR (300 MHz, DMSO-d$_6$) δ 1.30-1.42 (m, 2H), 1.53-1.67 (m, 2H), 1.88-1.91 (m, 2H), 2.01-2.04 (m, 2H), 2.21-2.27 (m, 2H), 2.50 (m, 3H), 3.57-3.58 (m, 4H), 4.27-4.31 (m, 1H), 6.73 (d, J=7.9 Hz, 1H), 7.20-7.27 (m, 1H), 7.34-7.42 (m, 1H), 7.44-7.53 (m, 2H), 7.61-7.69 (m, 1H), 8.34 (s, 1H), 8.44 (s, 1H), 11.95 (s, 1H).

[Example 19] Preparation of 6-(4-fluorophenyl)-N-(trans-4-morpholinocyclohexyl)-9H-pyrimido[4,5-b]indol-4-amine (Compound 6aan)

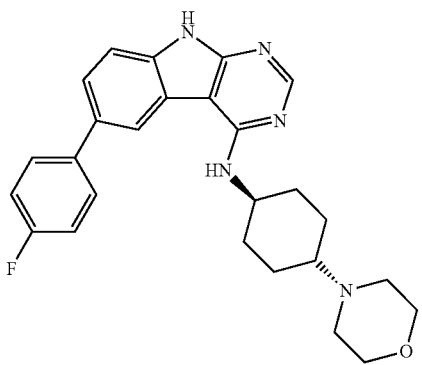

6aan

Compound 5aa (30 mg, 0.06 mmol) and (4-fluorophenyl) boronic acid (10 mg, 0.07 mmol) were reacted in the same manner as in Example 6, and the residue after reaction was separated by silica gel column chromatography (dichloromethane:ethyl acetate:methanol=4.5:2:1) to obtain 16 mg (51%) of a white solid.

6aan: $^1$H-NMR (300 MHz, DMSO-d$_6$) δ 1.30-1.42 (m, 2H), 1.57-1.69 (m, 2H), 1.90-2.09 (m, 4H), 2.21-2.28 (m, 2H), 2.50 (m, 3H), 3.56-3.59 (m, 4H), 4.24-4.31 (m, 1H), 6.79 (d, J=8.6 Hz, 1H), 7.33 (t, J=8.9 Hz, 2H), 7.50 (d, J=8.4 Hz, 1H), 7.62 (dd, J=8.4, 1.6 Hz, 1H), 7.78-7.83 (m, 2H), 8.34 (s, 1H), 8.50 (s, 1H), 11.90 (s, 1H).

[Example 20] Preparation of 5-(4-((trans-4-morpholinocyclohexyl)amino)-9H-pyrimido[4,5-b]indol-6-yl) nicotinonitrile (Compound 6aao)

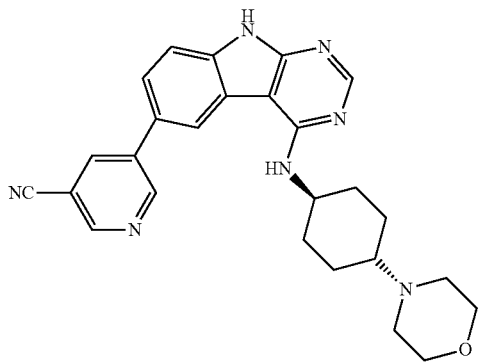

6aao

Compound 5aa (30 mg, 0.06 mmol) and (5-cyanopyridin-3-yl)boronic acid (11 mg, 0.07 mmol) were reacted in the same manner as in Example 6, and the residue after reaction was separated by silica gel column chromatography (dichloromethane:ethyl acetate:methanol=20:1:1→10:1:1→8:1:1) to obtain 29 mg (91%) of a light yellow solid.

6aao: (500 MHz, DMSO-d$_6$) δ 1.34-1.41 (m, 2H), 1.60-1.68 (m, 2H), 1.91-1.94 (m, 2H), 2.06-2.09 (m, 2H), 2.25-2.30 (m, 2H), 2.50 (m, 2H), 3.57-3.59 (m, 4H), 4.28-4.35 (m, 1H), 6.78 (d, J=7.9 Hz, 1H), 7.57 (d, J=8.3 Hz, 1H), 7.82 (d, J=8.5 Hz, 1H), 8.37 (s, 1H), 8.65 (s, 1H), 8.73 (s, 1H), 9.00 (s, 1H), 9.37 (s, 1H), 12.08 (s, 1H).

[Example 21] Preparation of 3-fluoro-5-(4-((trans-4-morpholinocyclohexyl)amino)-9H-pyrimido[4,5-b]indol-6-yl) benzonitrile (Compound 6aap)

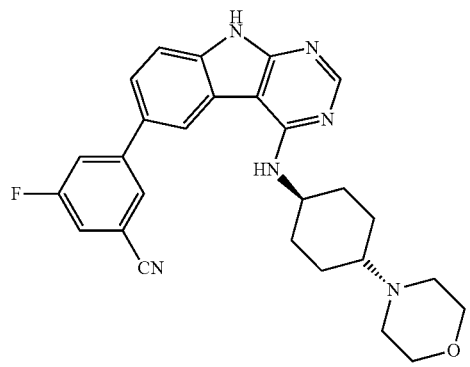

6aap

Compound 6aa (20 mg, 0.044 mmol) and 3-fluoro-5-(4,4,5,5-tetramethyl-1,3,2-dioxaborolan-2-yl)benzonitrile (12 mg, 0.05 mmol) were reacted in the same manner as in Example 6, and the residue after reaction was separated by silica gel column chromatography (dichloromethane:ethyl acetate:methanol=1:4:1) to obtain 11 mg (53%) of a white solid.

6aap: (500 MHz, DMSO-d$_6$) δ 1.23-1.51 (m, 2H), 1.63-1.79 (m, 3H), 1.89-1.94 (m, 2H), 2.07-2.18 (m, 2H), 2.25-2.31 (m, 2H), 2.87-2.89 (m, 1H), 3.57-3.59 (m, 3H), 3.67-3.68 (m, 1H), 4.21 (t, J=11.2 Hz, 1H), 4.28-4.32 (m, 1H), 6.83 (dd, J=29.4, 7.9 Hz, 1H), 7.54 (dd, J=8.4, 3.5 Hz, 1H), 7.79-7.83 (m, 2H), 8.08 (d, J=10.5 Hz, 1H), 8.16-8.20 (m, 1H), 8.37 (d, J=7.6 Hz, 1H), 8.60 (d, J=8.3 Hz, 1H), 12.09 (d, J=8.9 Hz, 1H).

[Example 22] Preparation of tert-butyl 4-(4-(4-((trans-4-morpholinocyclohexyl)amino)-9H-pyrimido[4,5-b]indol-6-yl)-1H-pyrazol-1-yl)piperidine-1-carboxylate (Compound 6aaq)

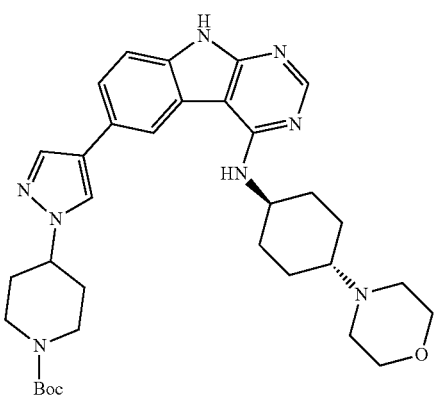

Compound 6aa (30 mg, 0.06 mmol) and tert-butyl 4-(4-(4,4,5,5-tetramethyl-1,3,2-dioxaborolan-2-yl)-1H-pyrazol-1-yl)piperidine-1-carboxylate (22 mg, 0.06 mmol) were reacted in the same manner as in Example 6, and the residue after reaction was separated by silica gel column chromatography (dichloromethane:methanol=1:8:1→1:5:1) to obtain 119 mg (65%) of a white solid.

6aaq: (500 MHz, DMSO-$d_6$) δ 1.33-1.38 (m, 4H), 1.44 (s, 9H), 1.64 (q, J=11.9, 11.4 Hz, 3H), 1.80-1.94 (m, 4H), 2.06-2.07 (m, 4H), 2.27 (t, J=12.8 Hz, 2H), 2.89-3.01 (m, 2H), 3.58-3.59 (m, 4H), 4.09 (s, 2H), 4.24-4.29 (m, 1H), 4.41 (t, J=11.4 Hz, 1H), 6.62 (d, J=7.7 Hz, 1H), 7.41 (d, J=8.2 Hz, 1H), 7.58 (d, J=8.3 Hz, 1H), 8.00 (s, 1H), 8.23 (s, 1H), 8.33 (s, 1H), 8.37 (s, 1H), 11.85 (s, 1H).

[Example 23] Preparation of N-(trans-4-morpholinocyclohexyl)-6-(1-(piperidin-4-yl)-1H-pyrazol-4-yl)-9H-pyrimido[4,5-b]indol-4-amine (Compound 6aar)

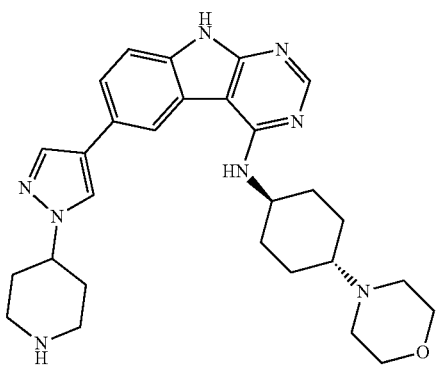

HCl (4M in dioxane, 10 mL) was put into Compound 6aaq (111 mg, 0.20 mmol) of Example 22 at 0° C., and the resulting mixture was stirred at room temperature. After the completion of the reaction was confirmed and the reaction product was concentrated under reduced pressure, the residue was washed with diethyl ether (3 mL) to obtain 121 mg of a white solid, which was used in Example 24.

6aar: (500 MHz, DMSO-$d_6$) δ 1.74 (q, J=13.1 Hz, 2H), 1.95-2.03 (m, 2H), 2.14-2.31 (m, 7H), 3.09-3.18 (m, 4H), 3.37-3.52 (m, 6H), 3.66-3.73 (m, 1H), 3.91 (t, J=12.0 Hz, 2H), 3.99-4.01 (m, 2H), 4.52-4.56 (m, 2H), 7.59 (d, J=8.2 Hz, 1H), 7.76 (d, J=8.2 Hz, 1H), 8.12 (s, 1H), 8.49 (s, 1H), 8.57 (s, 1H), 8.86 (s, 1H), 8.96 (s, 1H), 9.10 (s, 1H), 11.19 (s, 1H), 12.95 (s, 1H).

[Example 24] Preparation of 6-(1-(1-(methylsulfonyl)piperidin-4-yl)-1H-pyrazol-4-yl)-N-(trans-4-morpholinocyclohexyl)-9H-pyrimido[4,5-b]indole-4-amine (Compound 6aas)

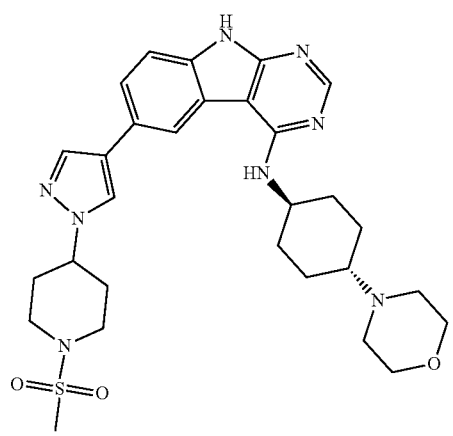

After Compound 6aar (25 mg, 0.04 mmol) of Example 23 and triethylamine (0.03 mL, 0.24 mmol) were dissolved in dichloromethane (2 mL), methanesulfonyl chloride (4.6 μL, 0.05 mmol) was added thereto, and the resulting mixture was stirred at room temperature. After the completion of the reaction was confirmed and the pressure of the reaction product was reduced, the pH was adjusted to 7 with saturated sodium bicarbonate. Ethyl acetate (10 mL) was added thereto, the resulting mixture was washed with water (10 mL), and then moisture was removed with sodium sulfate (Na$_2$SO$_4$), and the resulting product was concentrated under reduced pressure. The residue was washed with diethyl ether (5 mL) to obtain 10 mg (37%) of a white solid.

6aas: (500 MHz, DMSO-$d_6$) δ 1.34-1.41 (m, 2H), 1.61-1.69 (q, J=13.5, 11.8 Hz, 2H), 1.91-1.94 (m, 3H), 2.02-2.09 (m, 5H), 2.18-2.29 (m, 4H), 2.95 (s, 3H), 2.97-3.00 (m, 2H), 3.58 (m, 5H), 3.69-3.72 (m, 2H), 4.24-4.29 (m, 1H), 4.36-4.40 (m, 1H), 6.62 (d, J=7.8 Hz, 1H), 7.41 (d, J=8.1 Hz, 1H), 7.58 (d, J=7.7 Hz, 1H), 8.01 (s, 1H), 8.26 (s, 1H), 8.33 (s, 1H), 8.37 (s, 1H), 11.85 (s, 1H).

[Example 25] Preparation of trans-N1-(6-(5-fluoro-pyridin-3-yl)-9H-pyrimido[4,5-b]indol-4-yl)-N4,N4-dimethylcyclohexane-1,4-diamine (Compound 6aba)

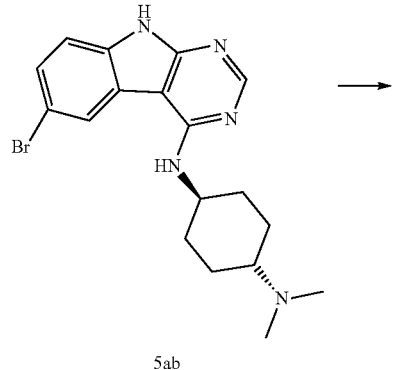

5ab

Compound 5ab (102 mg, 0.26 mmol) and (5-fluoropyridin-3-yl)boronic acid (47 mg, 0.33 mmol) were reacted in the same manner as in Example 6, and the residue after reaction was washed with diethyl ether to obtain 57 mg (53%) of a light brown solid.

6aba: $^1$H-NMR (300 MHz, DMSO-$d_6$) δ 1.28-1.41 (m, 2H), 1.57-1.70 (m, 2H), 1.88-1.92 (m, 3H), 2.03-2.09 (m, 2H), 2.21 (s, 6H), 4.27-4.36 (m, 1H), 6.80 (d, J=8.2 Hz, 1H), 7.55 (d, J=8.4 Hz, 1H), 7.78 (dd, J=8.5, 1.4 Hz, 1H), 8.13-8.18 (m, 1H), 8.36 (s, 1H), 8.55-8.56 (m, 1H), 8.63 (s, 1H), 8.98 (s, 1H), 12.03 (s, 1H).

[Example 26] Preparation of trans-N1,N1-dimethyl-N4-(6-(1-methyl-1H-pyrazol-4-yl)-9H-pyrimido[4,5-b]indol-4-yl)cyclohexane-1,4-diamine (Compound 6abb)

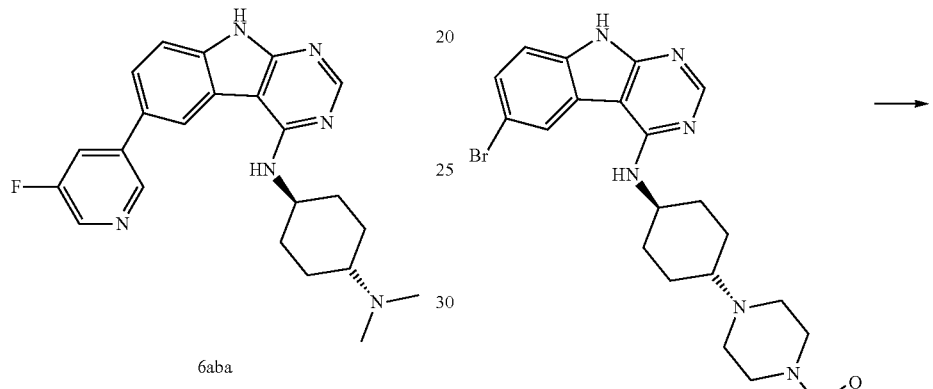

6abb                                          5ac

Compound 5ab (74 mg, 0.19 mmol) and 1-methyl-4-(4,4,5,5-tetramethyl-1,3,2-dioxaborolan-2-yl)-1H-pyrazole (40 mg, 0.19 mmol) were reacted in the same manner as in Example 25, and the residue after reaction was washed with diethyl ether to obtain 19 mg (26%) of a brown solid.

6abb: $^1$H-NMR (300 MHz, DMSO-$d_6$) δ 1.23-2.08 (m, 9H), 2.21 (s, 9H), 3.90 (s, 3H), 4.24-4.31 (m, 1H), 6.62 (d, J=7.7 Hz, 1H), 7.41 (d, J=8.3 Hz, 1H), 7.56 (d, J=8.2 Hz, 1H), 7.96 (s, 1H), 8.14 (s, 1H), 8.32 (s, 1H), 8.37 (s, 1H), 11.82 (s, 1H).

[Example 27] Preparation of 6-(1-methyl-1H-pyrazol-4-yl)-N-(trans-4-(4-(methylsulfonyl)piperazin-1-yl)cyclohexyl)-9H-pyrimido[4,5-b]indole-4-amine (Compound 6aca)

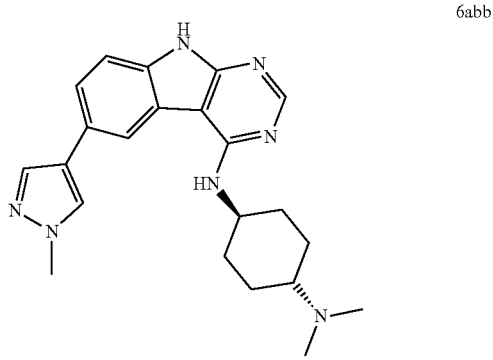

6aca

Compound 5ac (50 mg, 0.09 mmol) and 1-methyl-4-(4,4,5,5-tetramethyl-1,3,2-dioxaborolan-2-yl)-1H-pyrazole (23 mg, 0.11 mmol) were reacted in the same manner as in Example 6, and the residue after reaction was separated by silica gel column chromatography (dichloromethane:methanol=10:1) to obtain 32 mg (63%) of a light yellow solid.

6aca: $^1$H-NMR (300 MHz, CDCl$_3$) δ 1.37-1.56 (m, 4H), 1.98-2.2 (m, 2H), 2.38-2.42 (m, 2H), 2.73-2.74 (m, 4H), 2.79 (s, 3H), 3.26-3.29 (m, 4H), 4.00 (s, 3H), 4.26-4.34 (m, 2H), 4.99 (d, J=7.2 Hz, 1H), 7.51 (d, J=2.8 Hz, 2H), 7.67 (d, J=8.9 Hz, 2H), 7.81 (s, 1H), 8.52 (s, 1H), 9.06 (s, 1H).

[Example 28] Preparation of 6-(1-methyl-1H-pyrazol-4-yl)-N-(2-morpholinoethyl)-9H-pyrimido[4,5-b]indole-4-amine (Compound 6ada)

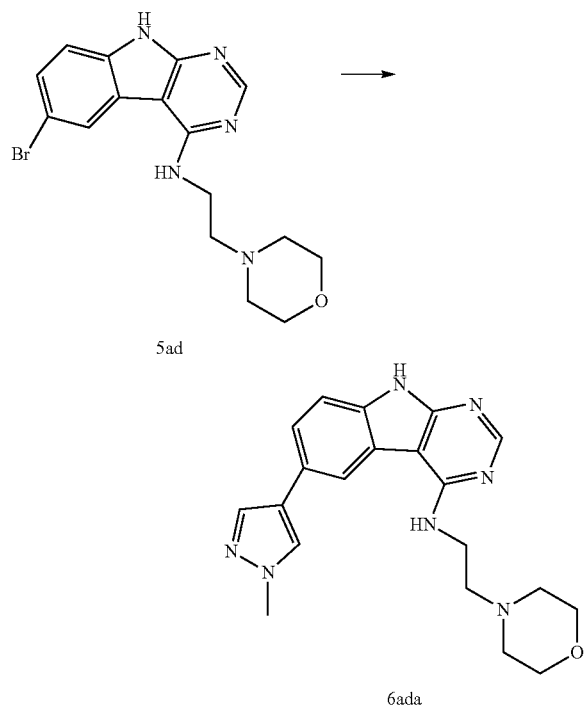

Compound 5ad (50 mg, 0.13 mmol) and 1-methyl-4-(4,4,5,5-tetramethyl-1,3,2-dioxaborolan-2-yl)-1H-pyrazole (35 mg, 0.16 mmol) were reacted in the same manner as in Example 6, and the residue after reaction was separated by silica gel column chromatography (dichloromethane:ethyl acetate:methanol=100:1:1→10:1:1) to obtain 43 mg (85%) of a light yellow solid.

6ada: $^1$H-NMR (300 MHz, DMSO-d$_6$) δ 2.50 (m, 4H), 2.63 (t, J=6.9 Hz, 2H), 3.58-3.61 (m, 4H), 3.78 (q, J=6.8 Hz, 2H), 3.90 (s, 3H), 7.08 (t, J=5.5 Hz, 1H), 7.42 (d, J=8.3 Hz, 1H), 7.56 (dd, J=8.2, 1.5 Hz, 1H), 7.95 (s, 1H), 8.11 (s, 1H), 8.33 (s, 1H), 8.36 (s, 1H), 11.81 (s, 1H).

[Example 29] Preparation of 6-(1-methyl-1H-pyrazol-4-yl)-N-(3-morpholinopropyl)-9H-pyrimido[4,5-b]indole-4-amine (Compound 6aea)

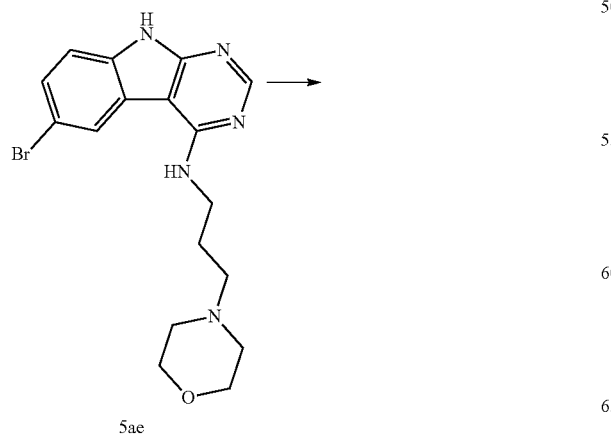

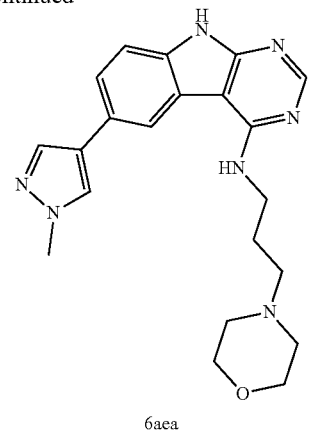

Compound 5ae (30 mg, 0.07 mmol) and 1-methyl-4-(4,4,5,5-tetramethyl-1,3,2-dioxaborolan-2-yl)-1H-pyrazole (18 mg, 0.09 mmol) were reacted in the same manner as in Example 6, and the residue after reaction was separated by silica gel column chromatography (dichloromethane:ethyl acetate:methanol=8:1:1→6:1:1) to obtain 31 mg (99%) of a white solid.

6aea: $^1$H-NMR (300 MHz, DMSO-d$_6$) δ 1.85-1.91 (m, 2H), 2.37-2.41 (m, 6H), 3.55-3.57 (m, 4H), 3.68 (q, 6.5 Hz, 2H), 3.90 (s, 3H), 7.18 (t, J=5.9 Hz, 1H), 7.41 (d, J=8.3 Hz, 1H), 7.55 (d, J=8.3 Hz, 1H), 7.97 (s, 1H), 8.12 (s, 1H), 8.31 (s, 1H), 8.41 (s, 1H), 11.79 (s, 1H).

[Example 30] Preparation of tert-butyl 4-(2-((6-(1-methyl-1H-pyrazol-4-yl)-9H-pyrimido[4,5-b]indol-4-yl)amino)ethyl)piperazine-1-carboxylate (Compound 6afa)

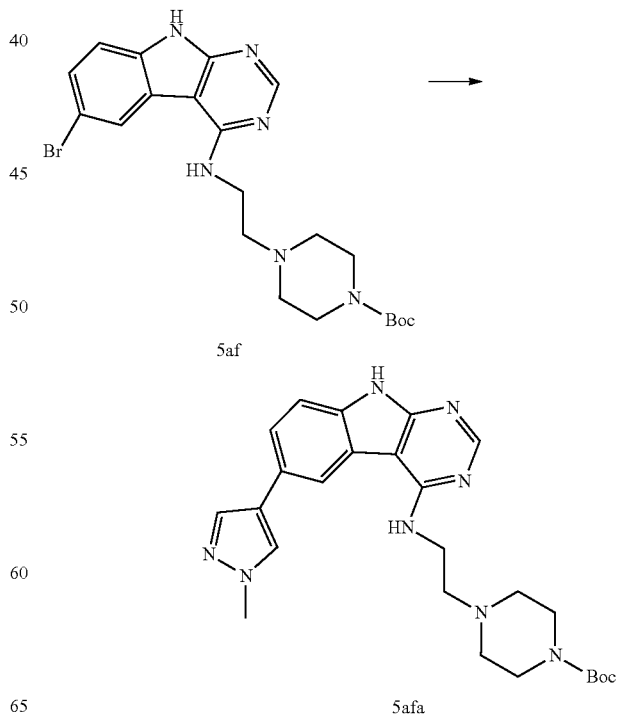

Compound 5af (40 mg, 0.08 mmol) and 1-methyl-4-(4,4,5,5-tetramethyl-1,3,2-dioxaborolan-2-yl)-1H-pyrazole (21 mg, 0.10 mmol) were reacted in the same manner as in Example 6, and the residue after reaction was separated by silica gel column chromatography (dichloromethane:ethyl acetate:methanol=25:1:1→15:1:1) to obtain 26 mg (64%) of a white solid.

6afa: ¹H-NMR (300 MHz, DMSO-d₆) δ 1.39 (s, 9H), 2.26-2.28 (m, 1H), 2.44-2.46 (m, 4H), 2.65 (t, J=6.7 Hz, 3H), 2.72-2.74 (m, 1H), 3.78 (q, J=13.8, 6.6 Hz, 3H), 3.90 (s, 3H), 7.09 (t, J=5.6 Hz, 1H), 7.42 (d, J=8.4 Hz, 1H), 7.56 (dd, J=8.3, 1.2 Hz, 1H), 7.94 (s, 1H), 8.10 (s, 1H), 8.33 (s, 1H), 8.36 (s, 1H), 11.81 (s, 1H).

[Preparation Example 14] Preparation of tert-butyl 4-(4-((6-(1-methyl-1H-pyrazol-4-yl)-9H-pyrimido[4,5-b]indol-4-yl)amino)phenyl)piperazine-1-carboxylate (Compound 6aga)

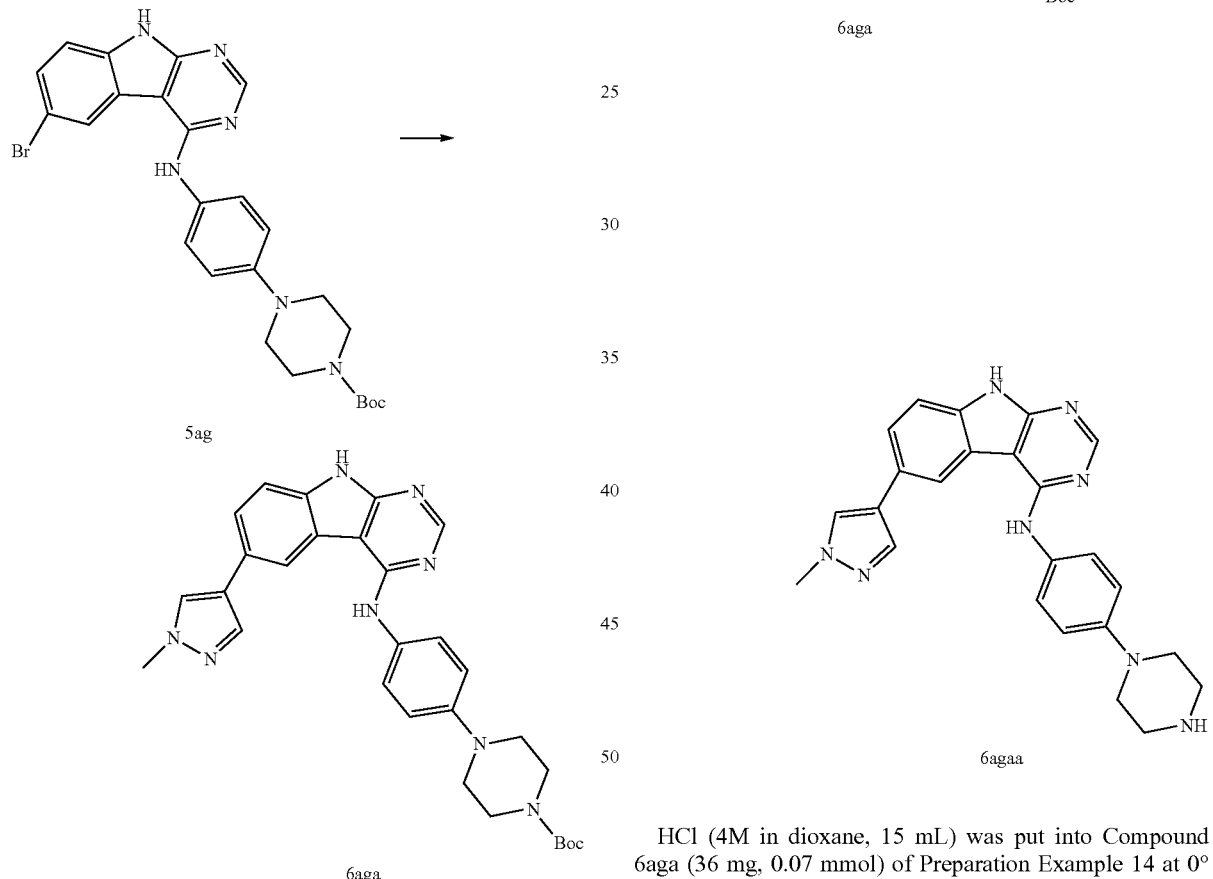

Compound 5ag (81 mg, 0.15 mmol) and 1-methyl-4-(4,4,5,5-tetramethyl-1,3,2-dioxaborolan-2-yl)-1H-pyrazole (35 mg, 0.18 mmol) were reacted in the same manner as in Example 6, and the residue after reaction was separated by silica gel column chromatography (hexane:ethyl acetate=1:2→ethyl acetate) to obtain 50 mg (61%) of a light pink solid.

6aga: ¹H-NMR (300 MHz, DMSO-d₆) δ 3.08-3.11 (m, 4H), 3.48-3.49 (m, 4H), 3.88 (s, 3H), 7.02 (d, J=8.9 Hz, 2H), 7.46 (t, J=7.9 Hz, 3H), 7.60 (d, J=8.5 Hz, 1H), 7.92 (s, 1H), 8.10 (s, 1H), 8.32 (s, 1H), 8.38 (s, 1H), 8.72 (s, 1H), 11.96 (s, 1H).

[Example 31] Preparation of 6-(1-methyl-1H-pyrazol-4-yl)-N-(4-(piperazin-1-yl)phenyl)-9H-pyrimido[4,5-b]indole-4-amine (Compound 6agaa)

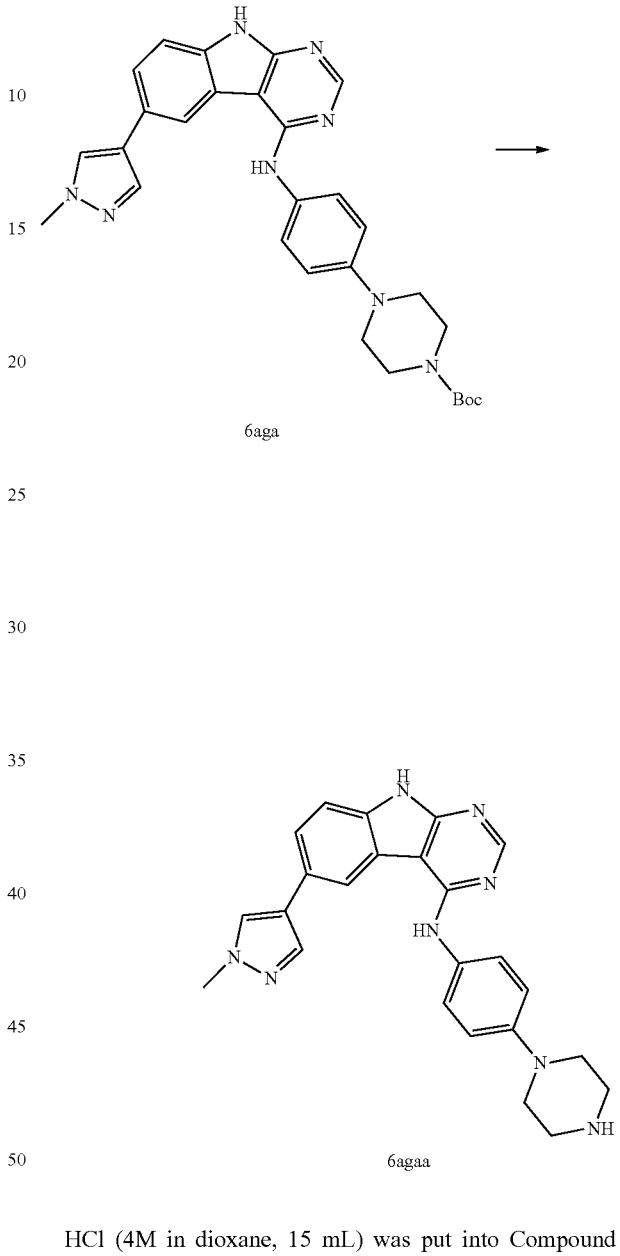

HCl (4M in dioxane, 15 mL) was put into Compound 6aga (36 mg, 0.07 mmol) of Preparation Example 14 at 0° C., and the resulting mixture was stirred at room temperature. After the completion of the reaction was confirmed and the reaction product was concentrated under reduced pressure, the pH was adjusted to 9 with saturated sodium bicarbonate, and then moisture was removed with sodium sulfate (Na₂SO₄), and the resulting product was concentrated under reduced pressure. The residue was washed with diethyl ether (3 mL) to obtain 14 mg (46%) of a white solid.

6agaa: ¹H-NMR (300 MHz, DMSO-d₆) δ 2.95-3.17 (m, 5H), 3.36-3.39 (m, 4H), 3.88 (s, 3H), 6.98 (d, J=8.6 Hz, 2H), 7.41-7.45 (m, 3H), 7.57-7.60 (m, 1H), 7.92 (s, 1H), 8.09 (s, 1H), 8.30 (s, 1H), 8.37 (s, 1H), 8.67 (s, 1H), 11.95 (s, 1H).

[Preparation Example 15] Preparation of tert-butyl 4-(4-((6-(pyridin-4-yl)-9H-pyrimido[4,5-b]indol-4-yl)amino)phenyl)piperazine-1-carboxylate (Compound 6agb)

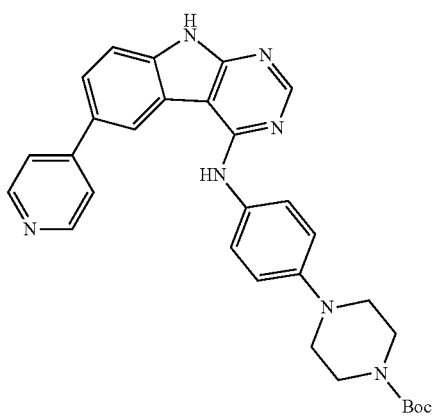

6agb

Compound 5ag (81 mg, 0.15 mmol) and pyridin-4-ylboronic acid (22 mg, 0.18 mmol) were reacted in the same manner as in Example 6, and the residue after reaction was separated by silica gel column chromatography (dichloromethane:ethyl acetate=1:1→ethyl acetate→ethyl acetate:methanol=10:1) to obtain 34 mg (42%) of a light brown solid.

6agb: $^1$H-NMR (300 MHz, DMSO-d$_6$) δ 1.44 (s, 9H), 3.07-3.11 (m, 4H), 3.47-3.50 (m, 4H), 7.01 (d, J=8.8 Hz, 2H), 7.46 (d, J=8.8 Hz, 2H), 7.60 (d, J=8.4 Hz, 1H), 7.82-7.88 (m, 3H), 8.36 (s, 1H), 8.61-8.63 (m, 3H), 8.95 (s, 1H), 12.20 (s, 1H).

[Example 32] Preparation of N-(4-(piperazin-1-yl)phenyl)-6-(pyridin-4-yl)-9H-pyrimido[4,5-b]indole-4-amine (Compound 6agba)

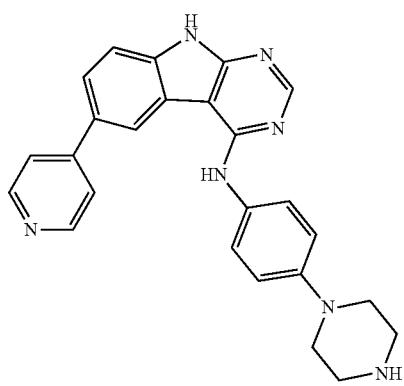

6agba

HCl (4M in dioxane, 10 mL) was put into Compound 6agb (26 mg, 0.04 mmol) of Preparation Example 15 at 0° C., and the resulting mixture was stirred at room temperature. After the completion of the reaction was confirmed and the reaction product was concentrated under reduced pressure, the pH was adjusted to 9 with saturated sodium bicarbonate, then moisture was removed with sodium sulfate (Na$_2$SO$_4$), and the resulting product was concentrated under reduced pressure. The residue was washed with diethyl ether (3 mL) to obtain 46 mg (99%) of a white solid.

6agba: $^1$H-NMR (300 MHz, DMSO-d$_6$) δ 2.73-7.87 (m, 4H), 3.05-3.13 (m, 2H), 3.05-3.13 (m, 4H), 6.96-7.00 (m, 2H), 7.42 (d, J=8.8 Hz, 2H), 7.59 (d, J=8.2 Hz, 2H), 7.81-7.88 (m, 3H), 8.36 (s, 1H), 8.61-8.63 (m, 3H), 8.94 (s, 1H), 12.19 (s, 1H).

[Example 33] Preparation of 4-(2-((6-(1-methyl-1H-pyrazol-4-yl)-9H-pyrimido[4,5-b]indol-4-yl)oxy)ethyl)morpholine (Compound 6aha)

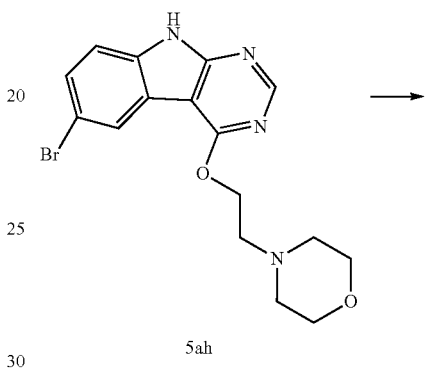

5ah

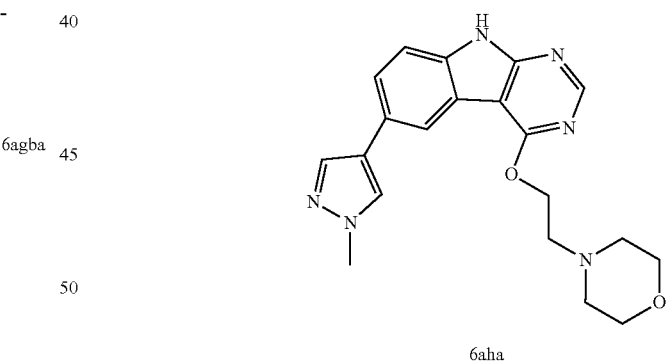

6aha

Compound 5ah (30 mg, 0.07 mmol) and 1-methyl-4-(4,4,5,5-tetramethyl-1,3,2-dioxaborolan-2-yl)-1H-pyrazole (18 mg, 0.09 mmol) were reacted in the same manner as in Example 6, and the residue after reaction was separated by silica gel column chromatography (dichloromethane:ethyl acetate:methanol=25:1:1→20:1:1→15:1:1) to obtain 31 mg (99%) of a light yellow solid.

6aha: $^1$H-NMR (300 MHz, DMSO-d$_6$) δ 2.58-2.61 (m, 4H), 2.91 (t, J=5.7 Hz, 2H), 3.57-3.60 (m, 4H), 3.90 (s, 3H), 4.75 (t, J=5.7 Hz, 2H), 7.53 (d, J=8.4 Hz, 1H), 7.66 (dd, J=8.4, 1.6 Hz, 1H), 7.83 (s, 1H), 8.11 (s, 2H), 8.56 (s, 1H), 12.24 (s, 1H).

[Preparation Example 16] Preparation of 4-((trans-4-morpholinocyclohexyl)amino)-9H-pyrimido[4,5-b]indole-6-carbohydrazide (Compound 6ba)

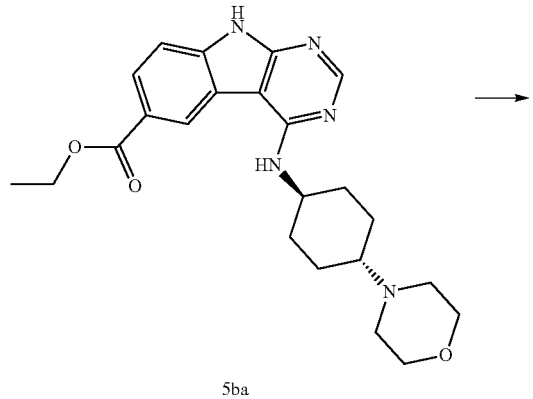

5ba

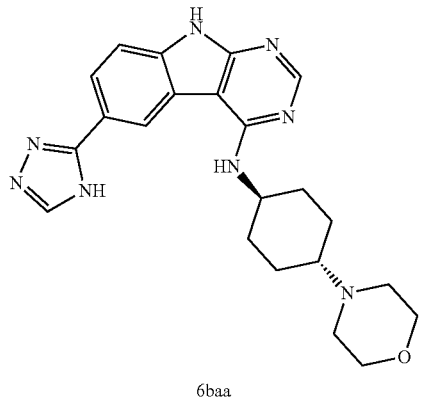

6ba

After Compound 5ba (423 mg, 1 mmol) was dissolved in ethanol (10 mL), a hydrazine hydrate (5 mL) was added thereto, and the resulting mixture stirred at 80° C. for 14 hours. After the reaction product was concentrated under reduced pressure, distilled water (20 mL) was added thereto, and the resulting solid was filtered, then washed with distilled water (2×10 mL), and dried to obtain 385 mg (94%) of a light brown solid.

6ba: $^1$H-NMR (300 MHz, DMSO-$d_6$) δ 1.38 (q, J=11.9 Hz, 2H), 1.59 (q, J=12.3 Hz, 2H), 1.91-1.95 (m, 2H), 2.07-2.11 (m, 2H), 2.24-2.31 (m, 2H), 2.49-2.50 (m, 3H), 3.57-3.60 (m, 4H), 4.27-4.31 (m, 1H), 4.53 (s, 2H), 6.55 (d, J=8.2 Hz, 1H), 7.48 (d, J=8.4 Hz, 1H), 7.88 (dd, J=8.5, 1.5 Hz, 1H), 8.37 (s, 1H), 8.66 (d, J=1.6 Hz, 1H), 9.63 (s, 1H).

[Example 34] Preparation of N-(trans-4-morpholinocyclohexyl)-6-(4H-1,2,4-triazol-3-yl)-9H-pyrimido[4,5-b]indole-4-amine (Compound 6baa)

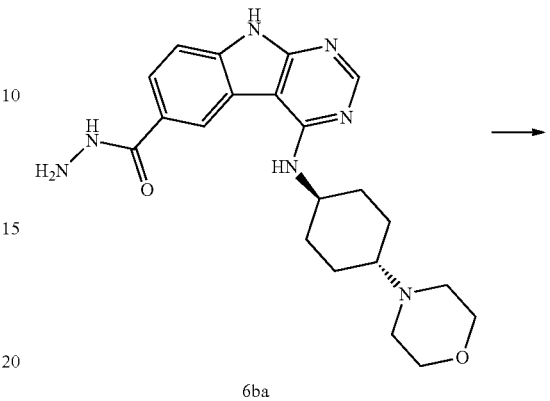

6ba

6baa

Ethyl formimidate hydrochloride (12 mg, 0.11 mmol) and triethylamine (31 μl, 0.22 mmol) were added to a solution in which Compound 6ba (41 mg, 0.1 mmol) was dissolved in acetonitrile (2 mL), and the resulting mixture was heated to 150° C. using microwaves and stirred for 30 minutes. After the completion of the reaction was confirmed, ethyl acetate (20 mL) was added thereto, then the resulting mixture was washed with water (10 mL), moisture was removed with sodium sulfate (Na$_2$SO$_4$), and the resulting product was concentrated under reduced pressure. The residue was separated by silica gel column chromatography (dichloromethane:methanol=6:1) to obtain 15 mg (36%) of a white solid.

6baa: $^1$H-NMR (300 MHz, DMSO-$d_6$) δ 1.35-1.44 (m, 2H), 1.60-1.73 (m, 2H), 1.91-2.08 (m, 4H), 2.28-2.43 (m, 4H), 3.58-3.61 (m, 4H), 4.10-4.17 (m, 1H), 4.25-4.30 (m, 1H), 6.72-6.94 (m, 1H), 7.51-7.55 (m, 1H), 8.02 (d, J=7.8 Hz, 1H), 8.35 (d, J=4.6 Hz, 1H), 8.82-8.89 (m, 1H). 11.96-12.08 (m, 1H), 13.62-13.99 (m, 1H).

[Example 35] Preparation of 6-(5-methyl-4H-1,2,4-triazol-3-yl)-N-(trans-4-morpholinocyclohexyl)-9H-pyrimido[4,5-b]indole-4-amine (Compound 6bab)

[Example 36] Preparation of 6-(4-methyl-4H-1,2,4-triazol-3-yl)-N-(trans-4-morpholinocyclohexyl)-9H-pyrimido[4,5-b]indole-4-amine (Compound 6bac)

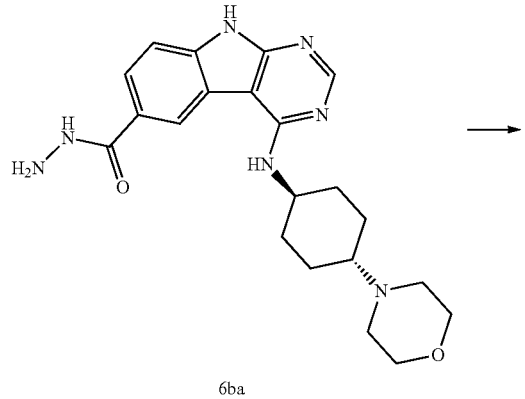

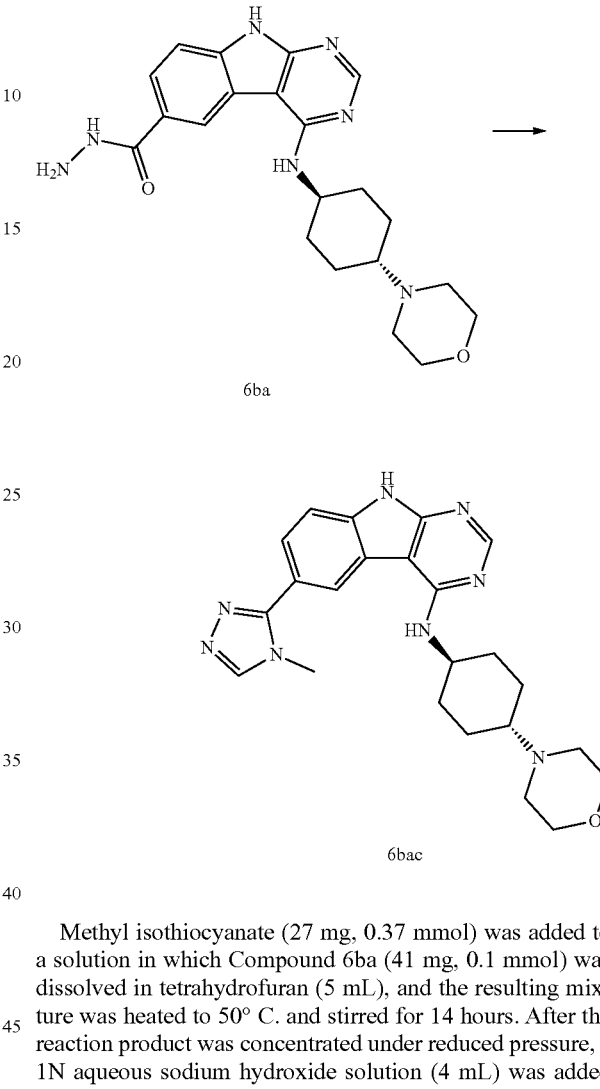

Ethyl acetimidate hydrochloride (15 mg, 0.12 mmol) and a 1 N sodium hydroxide methanol solution (0.12 mL, 0.12 mmol) were added to a solution in which Compound 6ba (41 mg, 0.1 mmol) was dissolved in methanol (2 mL), and the resulting mixture was heated to 70° C. and stirred for 14 hours. After the completion of the reaction was confirmed, ethyl acetate (20 mL) was added thereto, then the resulting mixture was washed with water (10 mL), moisture was removed with sodium sulfate ($Na_2SO_4$), and the resulting product was concentrated under reduced pressure. The residue was separated by silica gel column chromatography (dichloromethane:methanol=7:1) to obtain 21 mg (49%) of a white solid.

6bab: $^1$H-NMR (300 MHz, DMSO-$d_6$) δ 1.63-1.76 (m, 5H), 1.94-1.97 (m, 4H), 2.28-2.41 (m, 3H), 3.57-3.60 (m, 4H), 3.67 (s, 3H), 4.17-4.28 (m, 2H), 6.87 (s, 1H), 7.50 (d, J=8.6 Hz, 1H), 7.99 (d, J=8.1 Hz, 1H), 8.35 (d, J=4.4 Hz, 1H), 8.80 (d, J=6.6 Hz, 1H), 12.02 (s, 1H), 13.63 (s, 1H).

Methyl isothiocyanate (27 mg, 0.37 mmol) was added to a solution in which Compound 6ba (41 mg, 0.1 mmol) was dissolved in tetrahydrofuran (5 mL), and the resulting mixture was heated to 50° C. and stirred for 14 hours. After the reaction product was concentrated under reduced pressure, a 1N aqueous sodium hydroxide solution (4 mL) was added thereto, and the resulting mixture was heated to 50° C. and stirred for 3 hours. After dichloromethane (20 mL) was added to the reaction product, a 35% aqueous hydrogen peroxide solution (0.22 mL) and acetic acid (1.5 mL) were added thereto, and the resulting mixture was stirred at room temperature for 2 hours. After the completion of the reaction was confirmed, the reaction product was neutralized with a 1N aqueous sodium hydroxide solution, then ethyl acetate (20 mL) was added thereto, and after the resulting mixture was washed with water (10 mL), moisture was removed with sodium sulfate ($Na_2SO_4$), and the resulting product was concentrated under reduced pressure. The residue was separated by silica gel column chromatography (dichloromethane:methanol=7:1) to obtain 11 mg (26%) of a white solid.

6bac: $^1$H-NMR (300 MHz, DMSO-$d_6$) δ 1.23-1.41 (m, 3H), 1.54-1.67 (m, 3H), 1.88-2.04 (m, 4H), 2.19-2.28 (m, 2H), 3.56-3.59 (m, 4H), 3.74 (s, 1H), 4.25-4.36 (m, 1H), 6.85 (d, J=8.8 Hz, 1H), 7.61 (q, J=8.4 Hz, 2H), 8.37 (s, 1H), 8.64 (d, J=15.7 Hz, 2H), 12.12 (s, 1H).

[Example 37] Preparation of 6-(6,7-dihydro-5H-pyrrolo[2,1-c][1,2,4]triazol-3-yl)-N-(trans-4-morpholinocyclohexyl)-9H-pyrimido[4,5-b]indole-4-amine (Compound 6bad)

[Example 38] Preparation of 6-(5-methyl-1,3,4-oxadiazol-2-yl)-N-(trans-4-morpholinocyclohexyl)-9H-pyrimido[4,5-b]indole-4-amine (Compound 6bae)

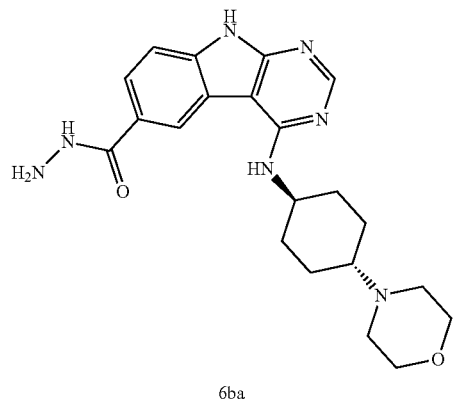

6ba

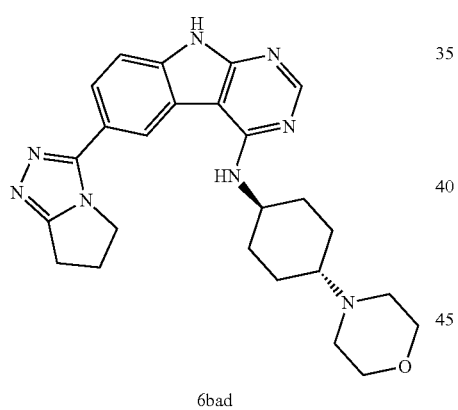

6bad

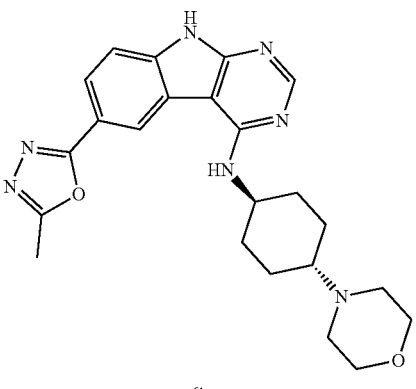

6bae

2-Methoxy-1-pyrroline (12 mg, 0.12 mmol) was added to a solution in which Compound 6ba (41 mg, 0.1 mmol) was dissolved in 2-propanol (2 mL), and the resulting mixture was heated to 80° C. and stirred for 2 hours. After the completion of the reaction was confirmed, ethyl acetate (20 mL) was added thereto, then the resulting mixture was washed with water (10 mL), moisture was removed with sodium sulfate ($Na_2SO_4$), and the resulting product was concentrated under reduced pressure. The residue was separated by silica gel column chromatography (dichloromethane:methanol=6:1) to obtain 16 mg (35%) of a white solid.

6bad: $^1$H-NMR (300 MHz, $CD_3OD$) δ 1.63-1.69 (m, 5H), 2.01-2.04 (m, 2H), 2.22-2.30 (m, 5H), 2.83-3.08 (m, 6H), 3.83-3.86 (m, 4H), 4.41 (t, J=7.0 Hz, 2H), 7.65 (d, J=8.4 Hz, 1H), 7.81 (dd, J=8.4, 1.7 Hz, 1H), 8.37 (s, 1H), 8.62 (d, J=1.6 Hz, 1H).

A catalytic amount of para-toluenesulfonic acid (1 mg) was added to a solution in which Compound 6ba (41 mg, 0.1 mmol) was dissolved in triethyl orthoacetate (2 mL), and the resulting mixture was heated to 120° C. and stirred for 12 hours. After the completion of the reaction was confirmed, the resulting product was concentrated under reduced pressure. The residue was separated by silica gel column chromatography (dichloromethane:methanol=9:1) to obtain 28 mg (65%) of a white solid.

6bae: $^1$H-NMR (300 MHz, $CD_3OD$) δ 1.53-1.70 (m, 3H), 2.01-2.04 (m, 3H), 2.13-2.18 (m, 2H), 2.24-2.29 (m, 2H), 2.66 (s, 3H), 2.77-2.80 (m, 4H), 3.76-3.79 (m, 4H), 7.64-7.67 (m, 1H), 8.06 (dd, J=8.5, 1.7 Hz, 1H), 8.37 (s, 1H), 8.83-8.84 (m, 1H).

[Example 39] Preparation of 5-(4-((trans-4-morpholinocyclohexyl)amino)-9H-pyrimido[4,5-b]indol-6-yl)-2,4-dihydro-3H-1,2,4-triazole-3-one (Compound 6baf)

[Example 40] Preparation of 4-ethyl-5-(4-((trans-4-morpholinocyclohexyl)amino)-9H-pyrimido[4,5-b]indol-6-yl)-2,4-dihydro-3H-1,2,4-triazole-3-one (Compound 6bag)

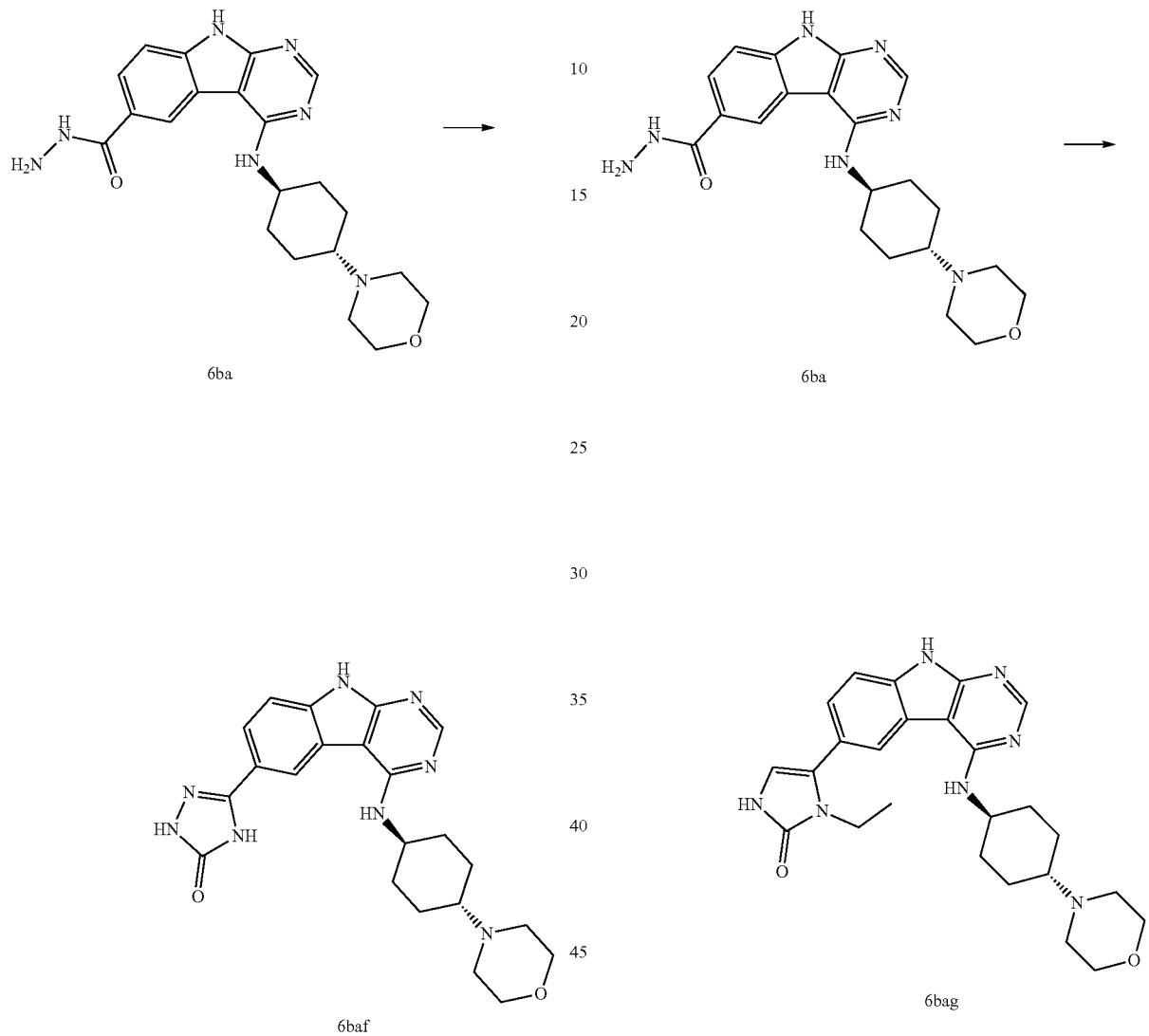

Trimethylsilyl isocyanate (25 μL, 0.15 mmol) was added to a solution in which Compound 6ba (41 mg, 0.1 mmol) was dissolved in tetrahydrofuran (5 mL), and the resulting mixture was heated to 40° C. and stirred for 14 hours. After the reaction product was concentrated under reduced pressure, a 1N aqueous sodium hydroxide solution (2 mL) was added thereto, and then the resulting mixture was heated to 100° C., stirred for 14 hours, and then concentrated under reduced pressure. The residue was separated by silica gel column chromatography (dichloromethane:methanol=4:1) to obtain 4 mg (9%) of a white solid.

6baf: $^1$H-NMR (300 MHz, CD$_3$OD) 1.69-1.73 (m, 5H), 2.28-2.34 (m, 4H), 3.16-3.19 (m, 4H), 3.34-3.35 (m, 4H), 3.70-3.76 (m, 1H), 7.55 (d, J=8.4 Hz, 1H), 8.11 (d, J=8.5 Hz, 1H), 8.36 (s, 1H), 8.78 (s, 1H).

Ethyl isocyanate (10 μL, 0.12 mmol) was added to a solution in which Compound 6ba (41 mg, 0.1 mmol) was dissolved in tetrahydrofuran (5 mL), and the resulting mixture was heated to 40° C. and stirred for 14 hours. After the reaction product was concentrated under reduced pressure, a 1N aqueous sodium hydroxide solution (2 mL) was added thereto, and then the resulting mixture was heated to 100° C., stirred for 14 hours, and then concentrated under reduced pressure. The residue was separated by silica gel column chromatography (dichloromethane:methanol=6:1) to obtain 9 mg (19%) of a white solid.

6bag: $^1$H-NMR (300 MHz, DMSO-d$_6$) δ 1.18 (t, J=7.1 Hz, 3H), 1.63-1.76 (m, 5H), 2.10-2.22 (m, 5H), 3.19-3.23 (m, 2H), 3.72-3.80 (m, 4H), 4.00-4.07 (m, 3H), 4.23-4.40 (m, 1H), 7.23 (d, J=8.1 Hz, 1H), 7.52 (d, J=8.5 Hz, 1H), 7.99 (d, J=8.4 Hz, 1H), 8.39 (s, 1H), 8.95 (s, 1H), 10.68 (s, 1H), 11.33 (s, 1H).

[Preparation Example 17] Preparation of 4-((4-methoxyphenyl)amino)-9H-pyrimido[4,5-b]indole-6-carboxylic acid (Compound 6bc)

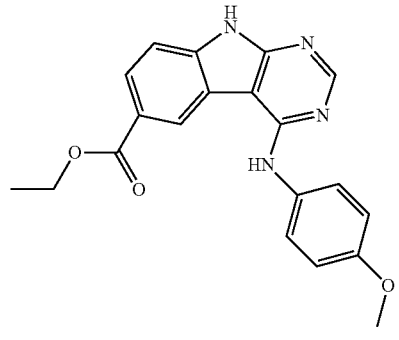

5bc

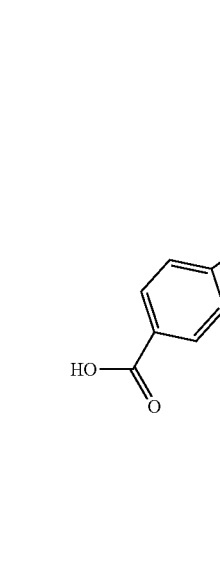

6bc

After Compound 5bc (525 mg, 1.44 mmol) was dissolved in tetrahydrofuran:methanol (1:1 in v/v, 50 mL), LiOH·H$_2$O (607 mg, 14.48 mmol) was added thereto, and then the resulting mixture was stirred at 60° C. After the completion of the reaction was confirmed and the reaction product was concentrated under reduced pressure, 3N HCl (4.8 mL) was added thereto, and then moisture was removed with sodium sulfate (Na$_2$SO$_4$), and the resulting product was concentrated under reduced pressure. After ethyl acetate (30 mL) was added to the residue, the resulting mixture was washed with water, the pH of water was adjusted to 9 with saturated sodium bicarbonate, and then the resulting product was washed with water to obtain 393 mg (81%) of a light brown solid.

6bc: $^1$H-NMR (500 MHz, DMSO-d$_6$) δ 3.78 (s, 3H), 6.96 (d, J=8.9 Hz, 2H), 7.50-7.53 (m, 3H), 8.02 (dd, J=8.5, 1.3 Hz, 1H), 8.37 (s, 1H), 8.99 (s, 1H), 9.16 (s, 1H), 12.36 (s, 1H).

[Preparation Example 18] Preparation of (4-((4-methoxyphenyl)amino)-9H-pyrimido[4,5-b]indol-6-yl)(morpholino)methanone (Compound 6bca)

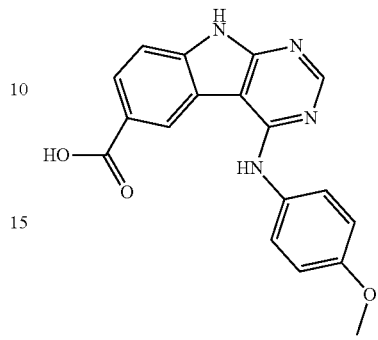

6bc

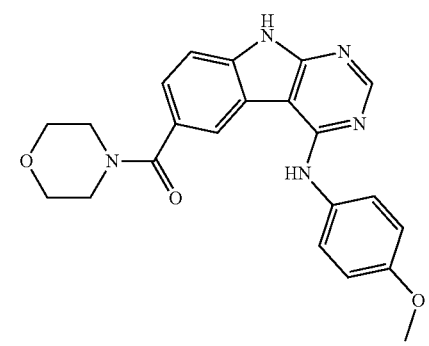

6bca

After Compound 6bc (40 mg, 0.10 mmol), morpholine (0.01 mL, 0.20 mmol) and 1-[bis(dimethylamino)methylene]-1H-1,2,3-triazolo[4,5-b]pyridinium 3-oxide hexafluorophosphate (HATU)(53 mg, 0.14 mmol) were dissolved in dimethylformamide (2 mL), the resulting solution was stirred at room temperature. After the completion of the reaction was confirmed, water was added thereto, and then the resulting solid was filtered and then washed with water to obtain 31 mg (76%) of a light brown solid.

6bca: $^1$H-NMR (500 MHz, DMSO-d$_6$) δ 3.62 (m, 8H), 3.78 (s, 3H), 6.96 (d, J=8.9 Hz, 2H), 7.44 (dd, J=8.2, 1.5 Hz, 1H), 7.52 (d, J=9.0 Hz, 3H), 8.37 (s, 1H), 8.46 (s, 1H), 8.90 (s, 1H), 12.23 (s, 1H).

[Preparation Example 19] Preparation of (4-((4-methoxyphenyl)amino)-9H-pyrimido[4,5-b]indol-6-yl)(4-methylpiperazin-1-yl)methanone (Compound 6bcb)

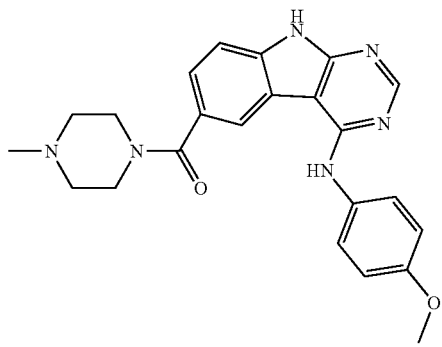

Compound 6bc (40 mg, 0.10 mmol) was reacted with N-methylpiperazine (0.01 mL, 0.20 mmol) in a manner similar to Preparation Example 18 to obtain 31 mg (76%) of a light brown solid.

6bcb: $^1$H-NMR (300 MHz, DMSO-$d_6$) δ 2.20 (s, 3H), 2.33 (m, 4H), 3.50 (m, 4H), 3.78 (s, 3H), 6.95 (d, J=9.0 Hz, 2H), 7.41 (dd, J=8.0, 1.3 Hz, 1H), 7.51 (d, J=8.8 Hz, 3H), 8.36 (s, 1H), 8.43 (s, 1H), 8.90 (s, 1H), 12.21 (s, 1H).

[Preparation Example 20] Preparation of 4-((4-methoxyphenyl)amino)-N-(pyridin-3-ylmethyl)-9H-pyrimido[4,5-b]indole-6-carboxamide (Compound 6bcc)

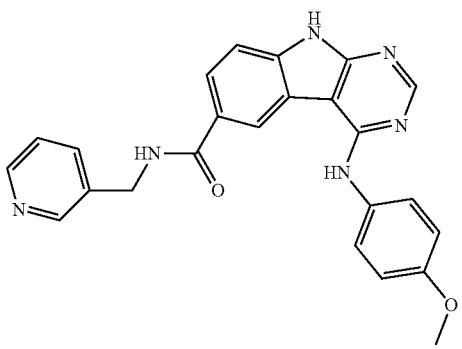

Compound 6bc (40 mg, 0.10 mmol) was reacted with pyridin-3-ylmethanamine (0.02 mL, 0.20 mmol) in a manner similar to Preparation Example 18 to obtain 32 mg (76%) of a light yellow solid.

6bcc: $^1$H-NMR (500 MHz, DMSO-$d_6$) δ 3.78 (s, 3H), 4.58 (d, J=5.8 Hz, 2H), 6.97 (d, J=8.9 Hz, 2H), 7.36-7.39 (m, 1H), 7.53-7.57 (m, 3H), 7.77-7.79 (m, 1H), 7.96 (dd, J=8.6, 1.3 Hz, 1H), 8.39 (s, 1H), 8.46-8.47 (m, 1H), 8.60-8.62 (m, 1H), 8.83 (s, 1H), 8.91 (s, 1H), 8.99 (t, J=6.0 Hz, 1H), 12.30 (s, 1H).

[Preparation Example 21] Preparation of 4-((4-methoxyphenyl)amino)-N-(2-morpholinoethyl)-9H-pyrimido[4,5-b]indole-6-carboxamide (Compound 6bcd)

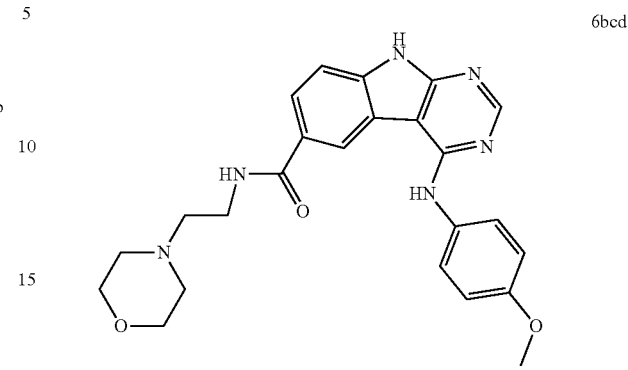

Compound 6bc (40 mg, 0.10 mmol) was reacted with 2-morpholinoethan-1-amine (0.02 mL, 0.20 mmol) in a manner similar to Preparation Example 18 to obtain 33 mg (74%) of a brown solid.

6bcd: $^1$H-NMR (300 MHz, DMSO-$d_6$) δ 2.43-2.46 (m, 4H), 2.50 (m, 2H), 3.46 (q, J=6.4 Hz, 2H), 3.57-3.60 (m, 4H), 3.78 (s, 3H), 6.98 (d, J=9.0 Hz, 2H), 7.52 (d, J=8.4 Hz, 1H), 7.58 (d, J=8.9 Hz, 2H), 7.89-7.93 (m, 1H), 8.29 (t, J=5.9 Hz, 1H), 8.38 (s, 1H), 8.82 (d, J=7.7 Hz, 2H), 12.27 (s, 1H).

[Example 41] Preparation of N-(trans-4-morpholinocyclohexyl)-7-(pyridin-4-yl)-9H-pyrimido[4,5-b]indole-4-amine (Compound 6caa)

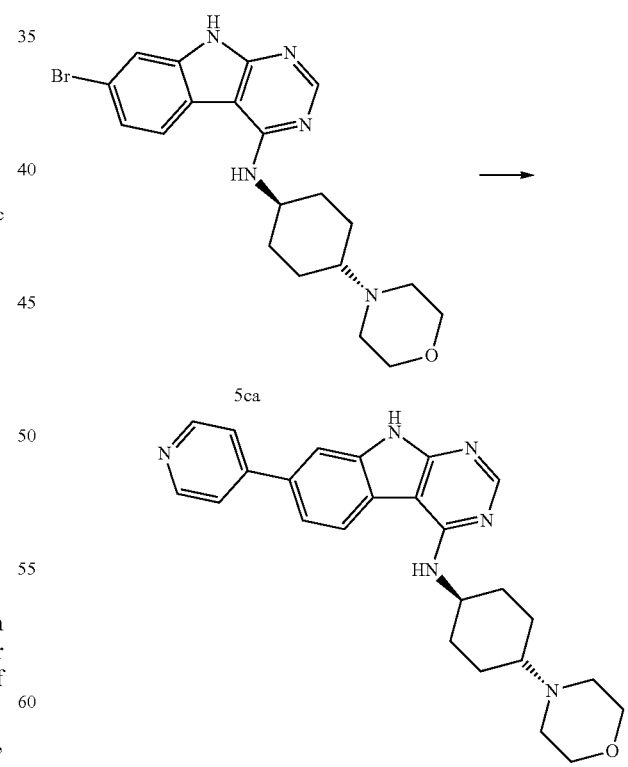

Compound 5ca (30 mg, 0.06 mmol) and 4-pyridylboronic acid (1.1 equivalent weights) were reacted in a manner similar to Example 6, and the residue after reaction was separated by silica gel column chromatography (ethyl acetate:dichloromethane:methanol=0.5:5:1) to obtain 21 mg (70%) of a brown solid.

6caa: $^1$H-NMR (300 MHz, MeOD-d$_4$+DMSO-d$_6$) δ 1.59-1.75 (m, 4H), 1.95-2.02 (m, 2H), 2.19-2.28 (m, 4H), 2.90-3.05 (m, 4H), 3.79-3.91 (m, 4H), 6.46 (d, J=7.5 Hz, 1H), 7.71 (d, J=8.0 Hz, 1H), 7.81-7.83 (m, 3H), 7.91 (s, 1H), 8.30-8.35 (m, 2H), 8.61 (d, J=5.0 Hz, 2H).

LC-MS(ESI, m/z): [M+H]$^+$=428.9, 429.9.

[Preparation Example 22] Preparation of methyl 2-(3-nitrophenyl)-4-(1-(piperidin-4-yl)-1H-pyrazol-4-yl)-9H-pyrimido[4,5-b]indole-7-carboxylate (Compound 11a)

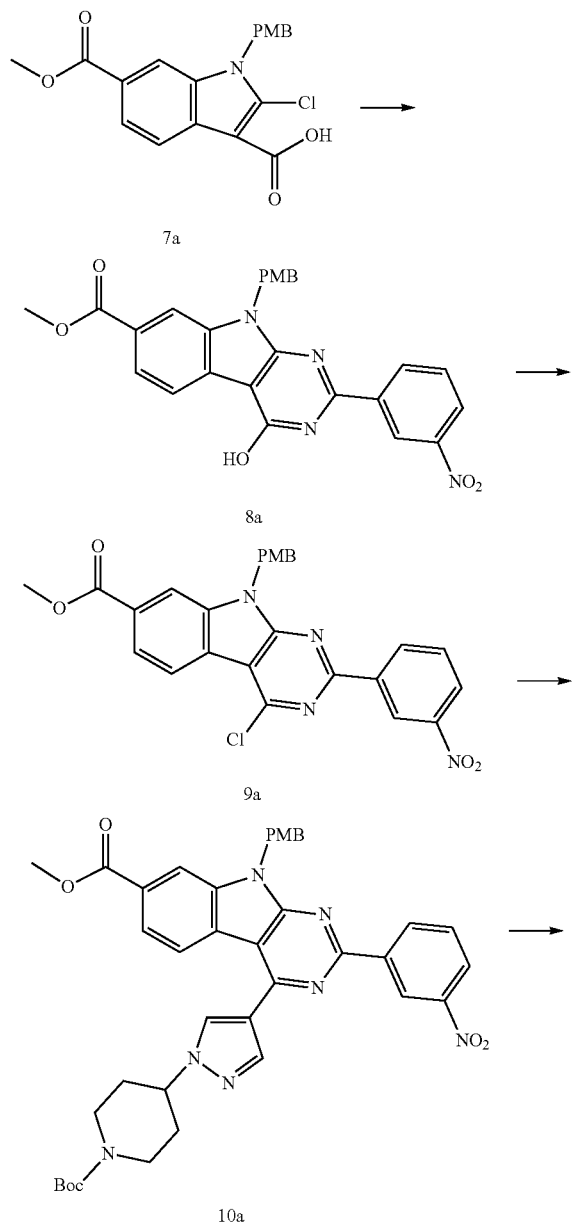

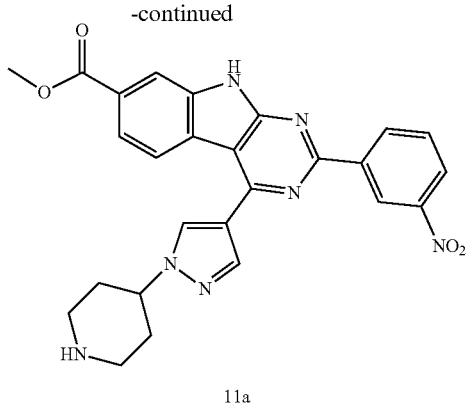

11a

In the chemical formula of Preparation Example 22, PMB represents p-methoxybenzyl.

Step 1. Preparation of Compound 8a

Oxalyl chloride (0.11 mL, 1.2 mmol) was added to a solution in which an indole carboxylic acid Compound 7a (European Journal of Medicinal Chemistry 39 (2004) 785-791)(225 mg, 0.6 mmol) was dissolved in dichloromethane (30 mL) by a known method (WO2006-111648A1), a catalytic amount of N,N-dimethylformamide (2 drops) was added thereto, and the resulting mixture was stirred at room temperature for 2 hours. The reaction product was concentrated under reduced pressure, and then dissolved in anhydrous tetrahydrofuran (20 mL), 2-nitrophenylamidine hydrochloride (390 mg, 0.72 mmol) and triethylamine (0.25 mL, 1.8 mmol) were added thereto, and the resulting mixture was stirred at room temperature for 15 hours. After the completion of the reaction was confirmed, ethyl acetate (40 mL) was added thereto, the resulting mixture was washed with water (20 mL), water (20 mL) was extracted with ethyl acetate (20 mL), and then moisture was removed with sodium sulfate (Na$_2$SO$_4$), the resulting product was concentrated under reduced pressure, and the resulting solid was washed with ether (20 mL) to obtain a yellow solid. The solid was dissolved in diphenyl ether (20 mL) without separation and purification, the resulting solution was stirred at 200° C. for 2 hours, and then cooled to room temperature, and then the resulting solid was filtered, and then washed with ether (20 mL) to obtain 213 mg (73%) of a grey solid.

8a: $^1$H-NMR (300 MHz, DMSO-d$_6$) δ 3.68 (s, 3H), 3.88 (s, 3H), 5.75 (s, 2H), 6.87 (d, J=8.6 Hz, 2H), 7.28 (d, J=8.6 Hz, 2H), 7.86-7.93 (m, 2H), 8.16 (d, J=8.3 Hz, 1H), 8.21 (s, 1H), 8.44-8.47 (m, 1H), 8.71 (d, J=8.3 Hz, 1H), 9.11 (s, 1H), 13.06 (s, 1H).

Step 2. Preparation of Compound 9a

Compound 8a (195 mg, 0.40 mmol) was reacted with phosphorus oxychloride (POCl$_3$)(10 mL) in the same manner as in Step 3 of Preparation Example 1 to obtain 180 mg (89%) of Compound 9a.

9a: $^1$H-NMR (300 MHz, DMSO-d$_6$) δ 3.67 (s, 3H), 3.91 (s, 3H), 5.86 (s, 2H), 6.87 (d, J=8.6 Hz, 2H), 7.33 (d, J=8.6 Hz, 2H), 7.88 (t, J=8.0 Hz, 1H), 7.99-8.04 (m, 1H), 8.32 (s, 1H), 8.41 (d, J=8.3 Hz, 2H), 8.93 (d, J=7.9 Hz, 1H), 9.18 (t, J=2.1 Hz, 1H).

Step 3. Preparation of Compound 10a

After Compound 9a (138 mg, 0.30 mmol), tert-butyl 4-(4-(4,4,5,5-tetramethyl-1,3,2-dioxaborolan-2-yl)-1H- pyrazol-1-yl)piperidine-1-carboxylate (147 mg, 0.39 mmol), and K$_3$PO$_4$ (191 mg, 90 mmol) were dissolved in dioxane:H$_2$O (3:1 in v/v, 4 mL), oxygen was removed by purging with argon gas, Pd(PPh$_3$)$_4$ (17 mg, 0.01 mmol) was added thereto, and then the gas was removed, and the resulting product was stirred at 130° C. for 20 minutes using microwaves. After the completion of the reaction was confirmed, ethyl acetate (20 mL) was added thereto, the resulting mixture was filtered with a celite pad and washed with water (3×20 mL), and then moisture was removed with sodium sulfate (Na$_2$SO$_4$), and the resulting product was concentrated under reduced pressure. The residue was separated by silica gel column chromatography (ethyl acetate:hexane=1:1.5→1:1→2:1→3:1) to obtain 132 mg (65%) of a yellow solid.

10a: $^1$H-NMR (300 MHz, CDCl$_3$) δ 1.51 (s, 9H), 2.04-2.17 (m, 3H), 2.27-2.33 (m, 2H), 2.98 (t, J=12.7 Hz, 2H), 3.75 (s, 3H), 3.98 (s, 3H), 4.33-4.51 (m, 2H), 5.77 (s, 2H), 6.85 (d, J=8.7 Hz, 2H), 7.36 (d, J=8.6 Hz, 2H), 7.69 (t, J=8.0 Hz, 1H), 7.99 (dd, J=8.4, 1.2 Hz, 1H), 8.23 (d, J=1.4 Hz, 1H), 8.31-8.37 (m, 4H), 9.00-9.03 (m, 1H), 9.49-9.50 (m, 1H).

Step 4. Preparation of Compound 11a

After Compound 10a (25 mg, 34.8 μmol) was dissolved in methanesulfonic acid (2 mL) at 0° C., the resulting solution was stirred at 80° C. After the completion of the reaction was confirmed, the reaction product was concentrated under reduced pressure, and then the pH was adjusted to 9 with saturated sodium bicarbonate, and after extraction was performed with ethyl acetate (2×7 mL), moisture was removed with sodium sulfate (Na$_2$SO$_4$), and the resulting product was concentrated under reduced pressure. The residue was separated by silica gel column chromatography (dichloromethane:methanol=5:1) to obtain 1.3 mg (8%) of a brown oil.

11a: $^1$H-NMR (300 MHz, DMSO-d$_6$) δ 1.91-1.97 (m, 4H), 2.27-2.36 (m, 4H), 3.94 (s, 3H), 4.74-4.81 (m, 1H), 7.86-7.94 (m, 2H), 8.18 (s, 1H), 8.34-8.43 (m, 3H), 8.75 (s, 1H), 9.01 (d, J=7.9 Hz, 1H), 9.32 (s, 1H), 12.95 (s, 1H).

[Example 42] Preparation of methyl 4-((trans-4-morpholinocyclohexyl)amino)-2-(3-nitrophenyl)-9H-pyrimido[4,5-b]indole-7-carboxylate (Compound 11b)

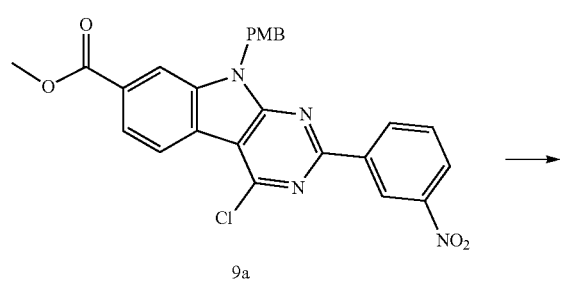

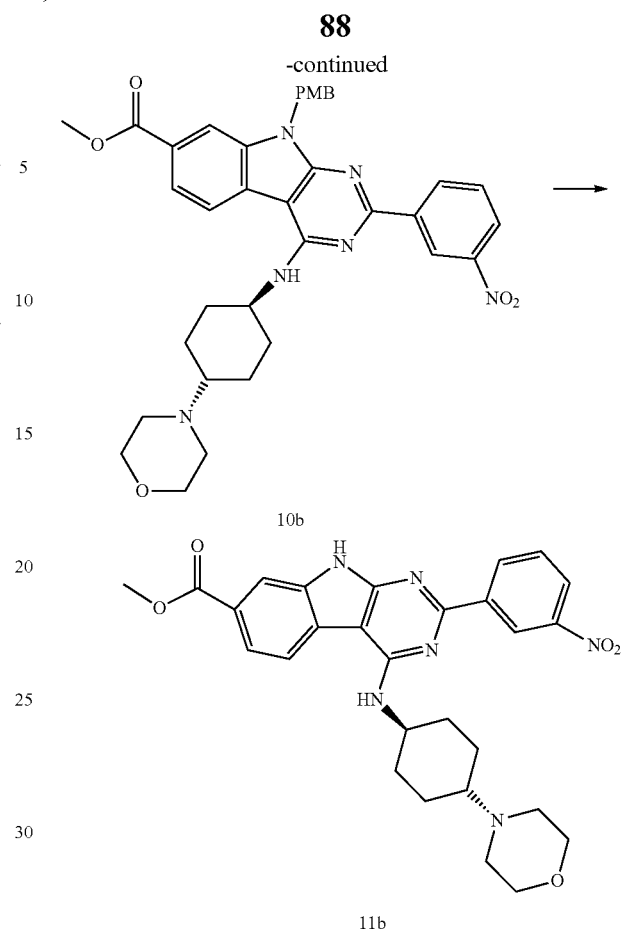

In the chemical formula of Example 42, PMB represents p-methoxybenzyl.

Step 1. Preparation of Compound 10b

Compound 9a (45 mg, 0.08 mmol) and trans-4-morpholinocyclohexan-1-amine hydrochloride (22 mg, 0.08 mmol) were reacted in the same manner as in Step 3 of Preparation Example 22, and the residue after reaction was separated by silica gel column chromatography (dichloromethane:methanol=10:1) to obtain 17 mg (29%) of a yellow solid.

10b: $^1$H-NMR (300 MHz, CDCl$_3$) δ 1.42-1.72 (m, 3H), 2.00-2.04 (m, 1H), 2.12-2.16 (m, 2H), 2.46-2.49 (m, 3H), 2.69-2.72 (m, 4H), 3.74 (s, 3H), 3.78-3.81 (m, 4H), 3.96 (s, 3H), 4.43-4.45 (m, 1H), 5.17 (d, J=7.4 Hz, 1H), 5.67 (s, 2H), 6.82 (d, J=8.6 Hz, 2H), 7.31 (d, J=8.6 Hz, 2H), 7.64 (t, J=8.0 Hz, 1H), 7.73 (d, J=8.2 Hz, 1H), 7.99-8.02 (m, 1H), 8.16 (s, 1H), 8.28-8.31 (m, 1H), 8.88-8.91 (m, 1H), 9.41 (t, J=2.0 Hz, 1H).

Step 2. Preparation of Compound 11b

After Compound 10b (17 mg, 0.13 mmol) was added thereto, the resulting mixture was dissolved in methanesulfonic acid (2 mL) at 0° C., and then the resulting solution was stirred at 80° C. After the completion of the reaction was confirmed, the reaction product was concentrated under reduced pressure, and then the pH was adjusted to 9 with saturated sodium bicarbonate, and after extraction was performed with ethyl acetate (2×7 mL), moisture was removed with sodium sulfate (Na$_2$SO$_4$), and the resulting product was concentrated under reduced pressure. The residue was separated by silica gel column chromatography (dichloromethane:methanol=5:1) to obtain 1.2 mg (1%) of a brown oil.

Compound 11b: ¹H-NMR (300 MHz, CD$_3$OD) δ 1.28-1.33 (m, 3H), 1.85-1.93 (m, 2H), 1.99-2.03 (m, 4H), 2.52-2.55 (m, 3H), 3.73-3.86 (m, 4H), 3.96 (s, 3H), 4.04-4.18 (m, 2H), 7.21 (d, J=8.4 Hz, 1H), 7.75 (t, J=7.9 Hz, 1H), 7.96-7.99 (m, 1H), 8.19 (s, 1H), 8.27 (d, J=8.3 Hz, 1H), 8.34-8.37 (m, 1H), 8.87 (d, J=7.8 Hz, 1H), 9.32 (s, 1H).

[Example 43] Preparation of 6-(1-methyl-1H-pyrazol-4-yl)-N-(trans-4-morpholinocyclohexyl)-9H-pyrimido[2,3-b]indole-4-amine (Compound 17a)

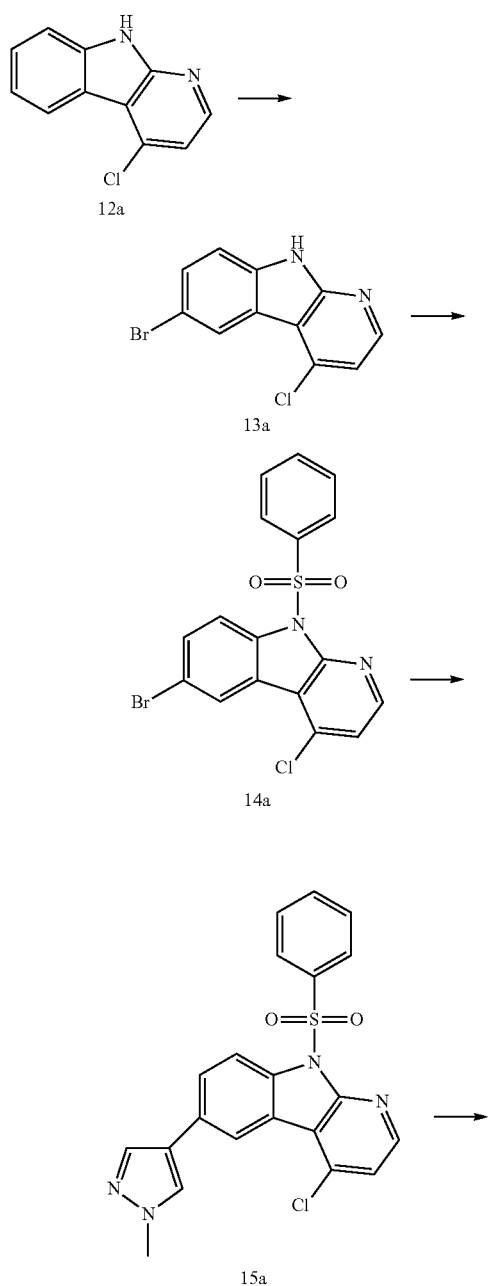

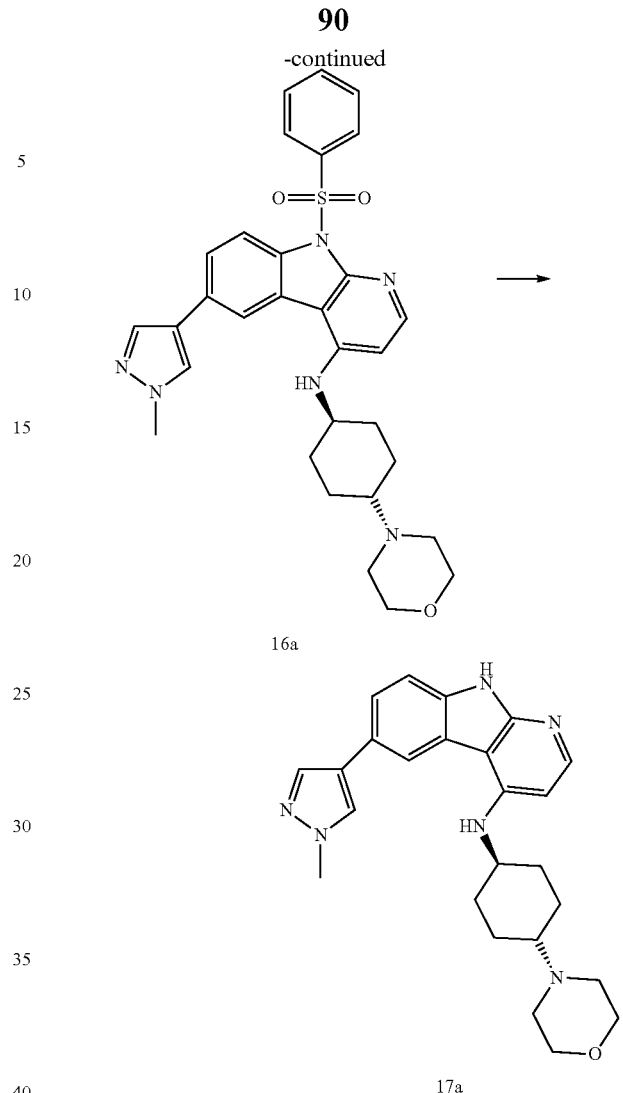

Step 1. Preparation of Compound 13a

After Compound 12a (Tetrahedron 65 (2009) 5427-5437) (677 mg, 3.34 mmol) was dissolved in dichloromethane (20 mL) in a 250 mL round-bottom flask, the resulting solution was stirred at room temperature. After bromine (0.2 mL, 4.0 mmol) was dissolved in dichloromethane (1.5 mL), the resulting solution was slowly added to the 250 mL round-bottom flask, and the resulting solution was stirred at room temperature. After the completion of the reaction was confirmed, ethyl acetate (30 mL) was added thereto, the resulting mixture was washed with water (2×25 mL), and then moisture was removed with sodium sulfate (Na$_2$SO$_4$), and the resulting product was concentrated under reduced pressure. The residue was recrystallized with tetrahydrofuran to obtain 270 mg (28%) of a light orange solid.

13a: ¹H-NMR (300 MHz, DMSO-d$_6$) δ 7.37-7.39 (d, J=5.4 Hz, 1H), 7.54-7.56 (d, J=8.7 Hz, 1H), 7.68-7.71 (dd, J$_1$=8.4 Hz, J$_2$=1.5 Hz, 1H), 8.42-8.44 (m, 2H), 12.41 (brs, 1H).

Step 2. Preparation of Compound 14a

Compound 13a (1.0 g, 4.93 mmol) was put into a 100 mL round-bottom flask, and then dissolved in tetrahydrofuran (50 mL), and then NaH (142 mg, 1.2 equivalent weights) was added thereto at 0° C., and then the resulting mixture was stirred for 20 minutes. After benzenesulfonyl chloride (0.94 mL, 1.5 equivalent weights) was put into the 100 mL round-bottom flask, the resulting mixture was stirred at room temperature. After the completion of the reaction was confirmed, water (100 mL) was added thereto. The resulting solid was filtered with water (150 mL) to obtain 1.07 g (51%) of a white solid.

14a: $^1$H-NMR (300 MHz, DMSO-$d_6$) δ 7.56-7.65 (m, 3H), 7.69-7.74 (t, J=7.5 Hz, 1H), 7.91-7.95 (dd, $J_1$=9.0 Hz, $J_2$=2.1 Hz, 1H), 8.08-8.10 (m, 2H), 8.40-8.43 (d, J=9.0 Hz, 1H), 8.50-8.51 (d, J=1.8 Hz, 1H), 8.53-8.55 (d, J=5.4 Hz, 1H).

Step 3. Preparation of Compound 15a

After Compound 14a (400 mg, 0.94 mmol), 1-methyl-4-(4,4,5,5-tetramethyl-1,3,2-dioxaborolan-2-yl)-1H-pyrazole (256 mg, 1.22 mmol), and $K_2CO_3$ (93 mg, 2.82 mmol) were dissolved in dioxane:$H_2O$ (4:1 in v/v, 9 mL), the resulting solution was degassed. Pd(PPh$_3$)$_4$ (109 mg, 10 mol %) was added thereto, and the resulting mixture was degassed, and then stirred at 110° C. After the reaction was completed, ethyl acetate (20 mL) was added thereto, the resulting mixture was filtered with a celite pad, and then washed with water (20 mL), and the aqueous layer was again extracted with ethyl acetate (20 mL). After the ethyl acetate layer was combined, the resulting mixture was washed with water (25 mL), moisture was removed with sodium sulfate (Na$_2$SO$_4$), and the resulting product was concentrated under reduced pressure. The residue was separated by silica gel column chromatography (ethyl acetate:hexane=1:6→ethyl acetate) to obtain 218 mg (54%) of a white solid.

15a: $^1$H-NMR (300 MHz, DMSO-$d_6$) δ 3.90 (s, 3H), 7.55-7.62 (m, 3H), 7.67-7.72 (m, 1H), 7.93-7.97 (m, 2H), 8.06-8.06 (m, 1H), 8.09 (m, 1H), 8.29 (s, 1H), 8.40-8.43 (d, J=8.7 Hz, 1H), 8.49-8.51 (m, 2H).

Step 4. Preparation of Compound 16a

After Compound 15a (805 mg, 1.90 mmol), trans-4-morpholinocyclohexan-1-amine (450.9 mg, 2.45 mmol), Cs$_2$CO$_3$ (1.24 g, 3.8 mmol), and Xantphos (176.2 mg, 16 mol %) were dissolved in 1,4-dioxane (63 mL), the resulting solution was degassed, and stirred at room temperature. After Pd$_2$(dba)$_3$ (139 mg, 8 mol %) was added thereto, the resulting mixture was degassed, and stirred at 110° C. After the completion of the reaction was confirmed, ethyl acetate (50 mL) was added thereto, the resulting mixture was filtered with a celite pad, the organic layer was washed with water (50 mL), moisture was removed with sodium sulfate (Na$_2$SO$_4$), and the resulting product was concentrated under reduced pressure. The residue was separated by silica gel column chromatography (dichloromethane:ethyl acetate:methanol=20:20:1→5:5:1) to obtain 420 mg (38%) of a yellow oil.

16a: $^1$H-NMR (300 MHz, CDCl$_3$) δ 1.33-1.49 (m, 3H), 2.02-2.07 (m, 3H), 2.31-2.36 (m, 3H), 2.59-2.60 (m, 4H), 3.46-3.49 (m, 1H), 3.73-3.75 (m, 4H), 3.99 (s, 3H), 4.70-4.71 (d, J=7.5, 1H), 6.48-6.49 (d, J=5.5, 1H), 7.37-7.40 (t, J=7.5, 2H), 7.48-7.51 (t, J=7.5, 1H), 7.54-7.56 (d, J=9.0, 1H), 7.62 (s, 1H), 7.64 (s, 1H), 7.78 (s, 1H), 8.11-8.13 (d, J=8.0, 2H), 8.23-8.24 (d, J=6.0, 1H), 8.48-8.49 (d, J=8.5, 1H).

Step 5. Preparation of Compound 17a

Compound 16a (420 mg, 0.73 mmol) was put into a 50 mL round-bottom flask, and then dissolved in tetrahydrofuran (12 mL), and the resulting solution was stirred at room temperature. After 1.5M CH$_3$ONa (2.4 mL, 5.0 equivalent weights) was added thereto, the resulting mixture was stirred a 40° C. After the completion of the reaction was confirmed, an aqueous saturated NaCl solution (20 mL) was added thereto, and then extraction was performed with ethyl acetate (2×30 mL). Moisture in the ethyl acetate layer was removed with sodium sulfate (Na$_2$SO$_4$), the resulting product was concentrated under reduced pressure, and then the residue was separated by silica gel column chromatography (dichloromethane:methanol=10:1) to obtain 199 mg (63%) of a white solid.

17a: $^1$H-NMR (300 MHz, DMSO-$d_6$) δ 1.36-1.48 (m, 2H), 1.56-1.68 (m, 2H), 1.91-1.95 (m, 2H), 2.12-2.16 (m, 2H), 2.24-2.31 (m, 1H), 2.50 (m, 5H), 3.57-3.60 (m, 4H), 3.90 (s, 3H), 5.83-5.85 (d, J=8.4, 1H), 6.43-6.45 (d, J=5.7, 1H), 7.35-7.37 (d, J=8.1, 1H), 7.51-7.53 (d, J=8.1, 1H), 7.93 (s, 1H), 7.98-8.00 (d, J=5.7, 1H), 8.11 (s, 1H), 8.23 (s, 1H), 11.37 (s, 1H).

[Example 44] Preparation of 6-(5-methoxypyridin-3-yl)-N-(trans-4-morpholinocyclohexyl)-9H-pyrimido[2,3-b]indole-4-amine (Compound 17b)

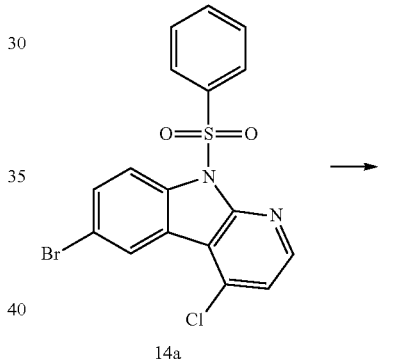

14a

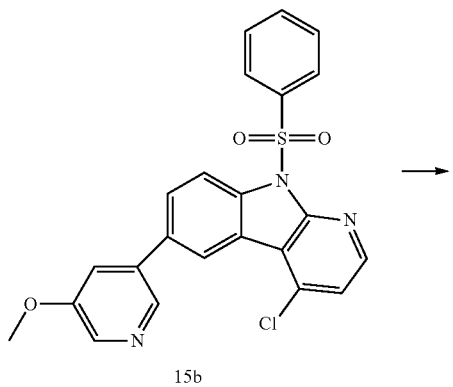

15b

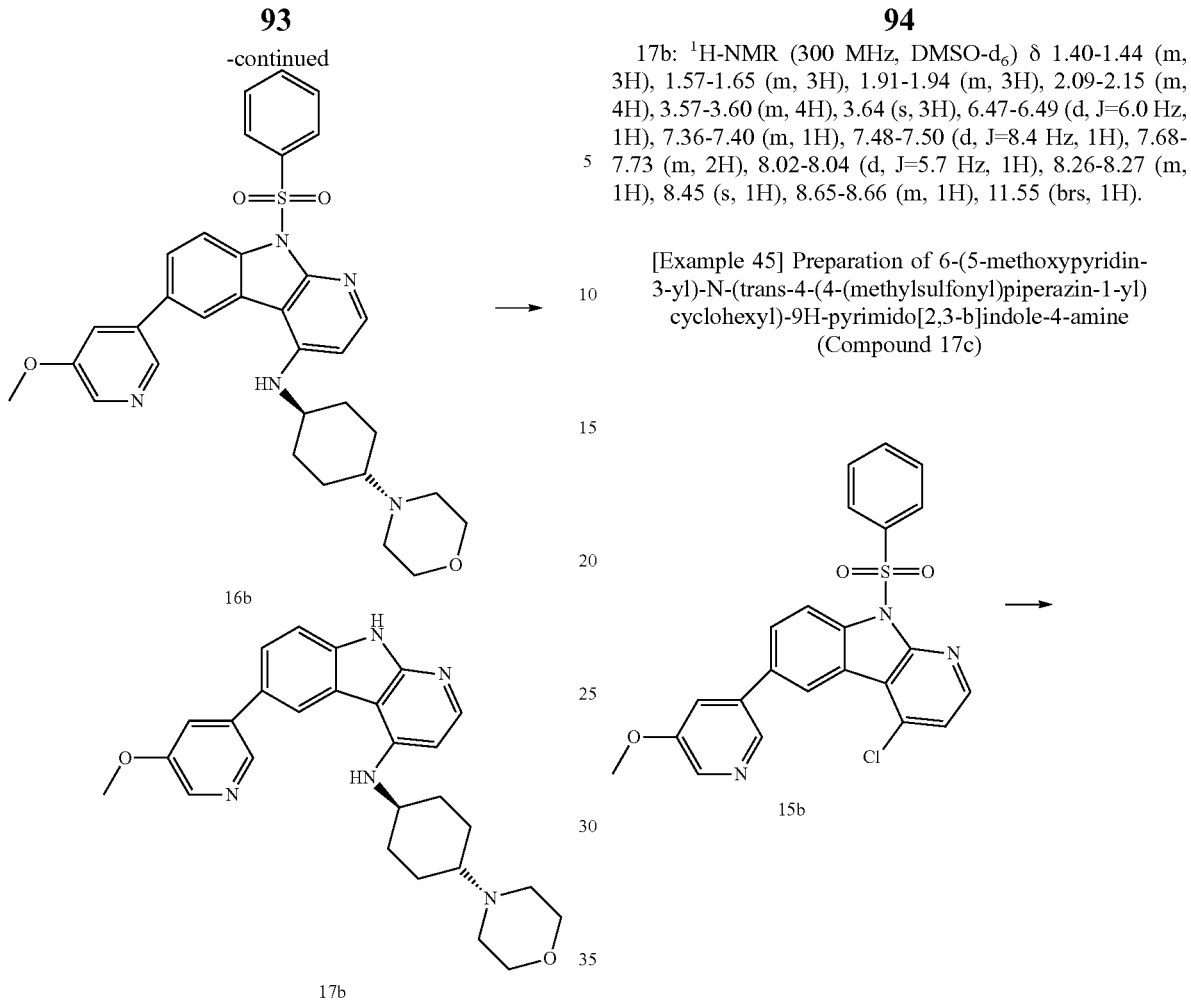

16b

17b

Step 1. Preparation of Compound 15b

Compound 14a (264 mg, 0.62 mmol) and 3-methoxy-5-(4,4,5,5-tetramethyl-1,3,2-dioxaborolan-2-yl)pyridine (189 mg, 0.80 mmol) were reacted in the same manner as in Step 3 of Example 43, and the residue after reaction was separated by silica gel column chromatography (ethyl acetate:hexane=1:6→ethyl acetate) to obtain 140 mg (49%) of a white solid.

15b: $^1$H-NMR (300 MHz, DMSO-$d_6$) δ 3.95 (s, 3H), 7.58-7.72 (m, 5H), 8.10-8.15 (m, 3H), 8.34-8.36 (m, 1H), 8.54-8.58 (m, 3H), 8.66 (s, 1H).

Step 2. Preparation of Compound 16b

Compound 15b (60 mg, 0.12 mmol) and trans-4-morpholinocyclohexan-1-amine (44 mg, 0.24 mmol) were reacted in the same manner as in Step 4 of Example 43 to obtain 13 mg (17%) of a yellow oil, which was used in Step 3 without separation and purification.

Step 3. Preparation of Compound 17b

The same method as in Step 5 of Example 43 was applied to Compound 16b (13 mg, 0.02 mmol), and the residue was separated by silica gel column chromatography (dichloromethane:methanol=11:1→10:1) to obtain 3 mg (32%) of a white solid.

17b: $^1$H-NMR (300 MHz, DMSO-$d_6$) δ 1.40-1.44 (m, 3H), 1.57-1.65 (m, 3H), 1.91-1.94 (m, 3H), 2.09-2.15 (m, 4H), 3.57-3.60 (m, 4H), 3.64 (s, 3H), 6.47-6.49 (d, J=6.0 Hz, 1H), 7.36-7.40 (m, 1H), 7.48-7.50 (d, J=8.4 Hz, 1H), 7.68-7.73 (m, 2H), 8.02-8.04 (d, J=5.7 Hz, 1H), 8.26-8.27 (m, 1H), 8.45 (s, 1H), 8.65-8.66 (m, 1H), 11.55 (brs, 1H).

[Example 45] Preparation of 6-(5-methoxypyridin-3-yl)-N-(trans-4-(4-(methylsulfonyl)piperazin-1-yl)cyclohexyl)-9H-pyrimido[2,3-b]indole-4-amine (Compound 17c)

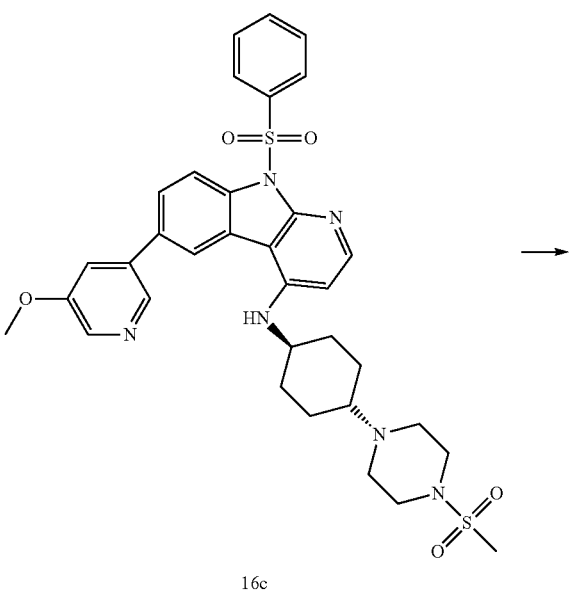

15b

16c

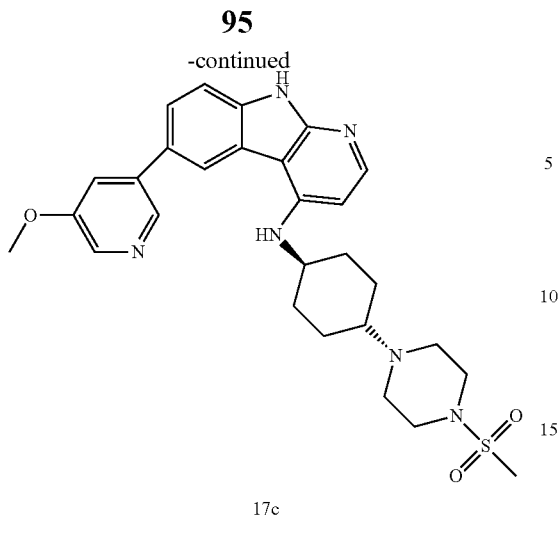

17c

Step 1. Preparation of Compound 16c

Compound 15b (60 mg, 0.12 mmol) and trans-4-(4-(methylsulfonyl)piperazin-1-yl)cyclohexan-1-amine (64 mg, 0.24 mmol) were reacted in the same manner as in Step 4 of Example 43, and the residue after reaction was separated by silica gel column chromatography (dichloromethane:ethyl acetate:methanol=6:4:1) to obtain 7 mg (8%) of a yellow oil.

16c: $^1$H-NMR (300 MHz, DMSO-$d_6$) δ 1.41-1.58 (m, 4H), 1.83-1.91 (m, 2H), 2.04-2.09 (m, 2H), 2.59-2.62 (m, 6H), 2.86 (s, 3H), 3.08-3.10 (m, 4H), 3.94 (s, 3H), 7.53-7.58 (t, J=7.8 Hz, 2H), 7.64-7.69 (t, J=7.5 Hz, 1H), 7.77-7.78 (m, 1H), 7.88-7.91 (m, 1H), 8.03-8.05 (d, J=7.8 Hz, 1H), 8.08-8.10 (d, J=5.7 Hz, 1H), 8.33-8.34 (d, J=2.7 Hz, 1H), 8.43-8.46 (m, 2H), 8.66-8.67 (m, 1H).

Step 2. Preparation of Compound 17c

The same method as in Step 5 of Example 43 was applied to Compound 16c (7 mg, 0.01 mmol), and the residue was separated by silica gel column chromatography (dichloromethane:methanol=10:1) to obtain 0.6 mg (10%) of a white solid.

17c: $^1$H-NMR (300 MHz, DMSO-$d_6$) δ 1.40-1.68 (m, 5H), 1.88-1.97 (m, 3H), 2.09-2.16 (m, 3H), 2.64 (s, 3H), 2.86-2.87 (m, 2H), 3.11 (m, 4H), 3.56 (m, 1H), 3.94 (s, 3H), 6.06-6.09 (d, J=7.8 Hz, 1H), 6.48-6.50 (d, J=5.7 Hz, 1H), 7.48-7.51 (d, J=8.1 Hz, 1H), 7.69-7.73 (m, 2H), 8.02-8.04 (d, J=5.7 Hz, 1H), 8.27 (d, J=2.3 Hz, 1H), 8.46 (s, 1H), 8.66 (s, 1H), 11.57 (brs, 1H).

[Example 46] Preparation of 6-(5-fluoropyridin-3-yl)-N-(trans-4-morpholinocyclohexyl)-9H-pyrido[2',3':4,5]pyrrolo[2,3-d]pyrimidin-4-amine (Compound 23a)

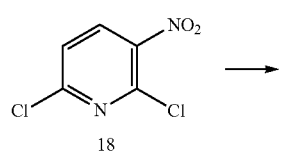

18

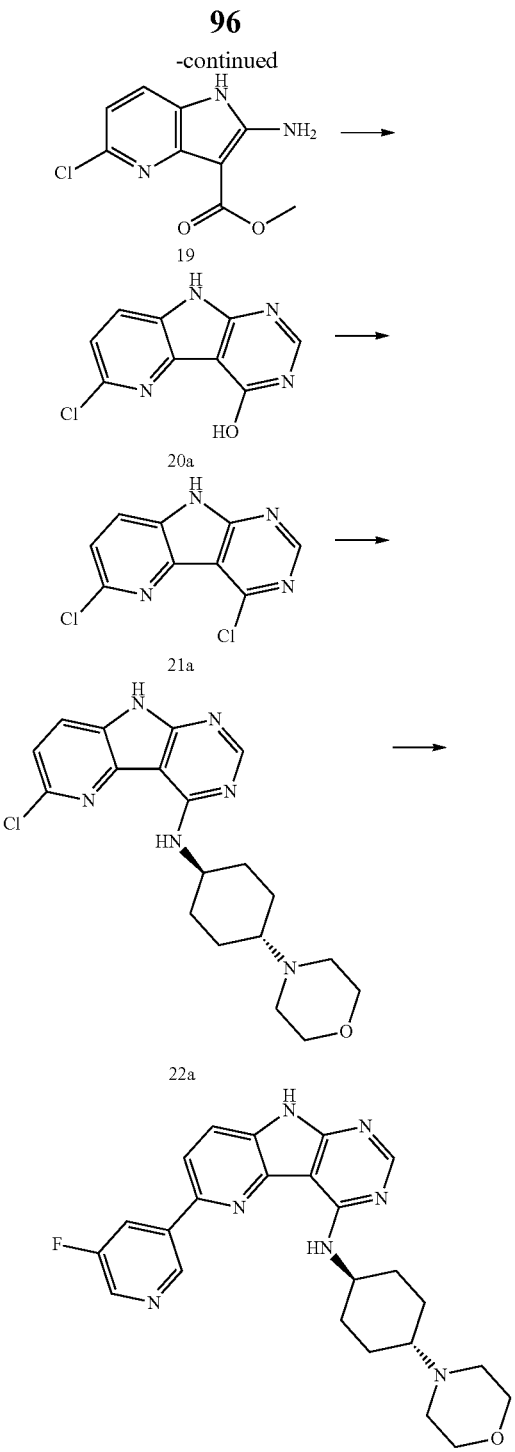

Step 1. Preparation of Compound 19

After 2,6-dichloro-3-nitropyridine (9.65 g, 50 mmol) was dissolved in N,N-dimethylformamide (100 mL) using a known method (BioOrg. Med Chem. Lett. 2003, 13, 2003-2007), methyl cyanoacetate (8.8 mL, 100 mmol) was added thereto. After the reaction solution was cooled to 0° C., sodium tert-butoxide (9.6 g, 100 mmol) was added thereto and the reaction product was stirred at room temperature for 2 hours. The reaction product was poured into ice water (300 mL), the resulting solid was filtered, then washed with water (2×100 mL), and dried to obtain 12.5 g of a white solid. After 12.5 g of the white solid was dissolved in acetic acid (200 mL) without separation and purification, the resulting solution was heated to 70° C., iron (Fe)(13.6 g, 240 mmol) was added thereto in three portions, and the resulting mixture was stirred for 30 minutes. The reaction product was filtered with a celite pad and washed with acetic acid (20 mL), and then the filtrate was concentrated under reduced pressure. After distilled water (200 mL) was added to the residue and extraction was performed with ethyl acetate (2×300 mL), the organic layer was washed with water (2×100 mL), and then moisture was removed with sodium sulfate ($Na_2SO_4$), and the resulting product was concentrated under reduced pressure. The residue was separated by silica gel column chromatography (hexane:ethyl acetate=2:3) to prepare 17.0 g (62%) of a light yellow solid.

19: $^1$H-NMR (500 MHz, DMSO-$d_6$) δ 3.74 (s, 3H), 6.87 (d, J=8.0 Hz, 1H), 7.19 (s, 2H), 7.39 (d, J=8.1 Hz, 1H), 10.93 (s, 1H).

Step 2. Preparation of Compound 20a

After Compound 19 (5 g, 22.2 mmol) was dissolved in formamide (30 mL) in the same manner as in Step 2 of Preparation Example 1, the resulting solution was stirred in the presence of nitrogen at 185° C. for 3 hours. After the reaction product was cooled to room temperature, distilled water (50 mL) was added thereto, and the solid was filtered and then washed with distilled water (2×100 mL) to obtain a brown solid. The solid was dried, and then separated by silica gel column chromatography (hexane:ethyl acetate=1:1) to prepare 3.1 g (63%) of Compound 20a.

20a: $^1$H-NMR (400 MHz, DMSO-$d_6$) δ 7.36 (d, J=8.5 Hz, 1H), 7.89 (d, J=8.4 Hz, 1H), 8.22 (s, 1H).

Step 3. Preparation of Compound 21a

After Compound 20a (3.0 g, 13.6 mmol) was dispersed in phosphorus oxychloride ($POCl_3$)(50 mL) in the same manner as in Step 3 of Preparation Example 1, the resulting dispersion was stirred at 110° C. for 14 hours. After the reaction product was concentrated under reduced pressure, ice water (100 mL) was added thereto, and the solid was filtered, and then washed with ice water (2×100 mL) to obtain a brown solid. The solid was dried, and then separated by silica gel column chromatography (hexane:ethyl acetate=1:3) to prepare 1.25 g (38%) of Compound 21a.

21a: $^1$H-NMR (300 MHz, DMSO-$d_6$) δ 7.69 (d, J=8.6 Hz, 1H), 8.12 (d, J=8.6 Hz, 1H), 8.91 (s, 1H). 13.17 (s, 1H).

Step 4. Preparation of Compound 22a

After Compound 21a (120 mg, 0.5 mmol), trans-4-morpholinocyclohexan-1-amine hydrochloride (156 mg, 0.6 mmol), and triethylamine (0.24 mL, 1.69 mmol) were dissolved in DMSO (3 mL) in the same manner as in Preparation Example 5, the resulting solution was stirred at 110° C. After the completion of the reaction was confirmed, ethyl acetate (20 mL) was added thereto, the resulting mixture was washed with water (10 mL), and water (10 mL) was extracted with ethyl acetate (20 mL). After ethyl acetate (40 mL) was washed using water (2×10 mL), moisture was removed with sodium sulfate ($Na_2SO_4$) and the resulting product was concentrated under reduced pressure. The residue was separated by silica gel column chromatography (dichloromethane:ethyl acetate:methanol=1:6:1) to prepare 160 mg (82%) of Compound 22a.

22a: $^1$H-NMR (500 MHz, $CDCl_3$) δ 1.54-1.67 (m, 4H), 2.03-2.11 (m, 2H), 2.33-2.44 (m, 3H), 2.63-2.65 (m, 4H), 3.77-3.79 (m, 4H), 4.24-4.31 (m, 1H), 6.53 (d, J=8.2 Hz, 1H), 7.34 (d, J=8.4 Hz, 1H), 7.73 (d, J=8.3 Hz, 1H), 8.55 (s, 1H), 10.70 (s, 1H).

Step 5. Preparation of Compound 23a

Compound 22a (50 mg, 0.11 mmol) and (5-fluoropyridin-3-yl)boronic acid (20 mg, 0.14 mmol) were reacted in the same manner as in Example 6, and the residue after reaction was separated by silica gel column chromatography (dichloromethane:ethyl acetate:methanol=6:1:1) to obtain 38 mg (65%) of a white solid.

23a: $^1$H-NMR (300 MHz, DMSO-$d_6$) δ 1.33-1.45 (m, 2H), 1.50-1.62 (m, 2H), 1.91-1.95 (m, 2H), 2.17-2.21 (m, 2H), 2.28-2.36 (m, 1H), 2.42-2.50 (m, 4H), 3.56-3.59 (m, 4H), 4.12-4.15 (m, 1H), 6.80 (d, J=7.9 Hz, 1H), 7.96 (d, J=8.8 Hz, 1H), 8.11 (d, J=8.5 Hz, 1H), 8.45 (s, 1H), 8.50 (d, J=10.6 Hz, 1H), 8.62-8.63 (m, 1H), 9.30 (s, 1H).

[Example 47] Preparation of 7-fluoro-6-(5-fluoropyridin-3-yl)-N-(trans-4-morpholinocyclohexyl)-9H-pyrimido[4,5-b]indole-4-amine (Compound 29a)

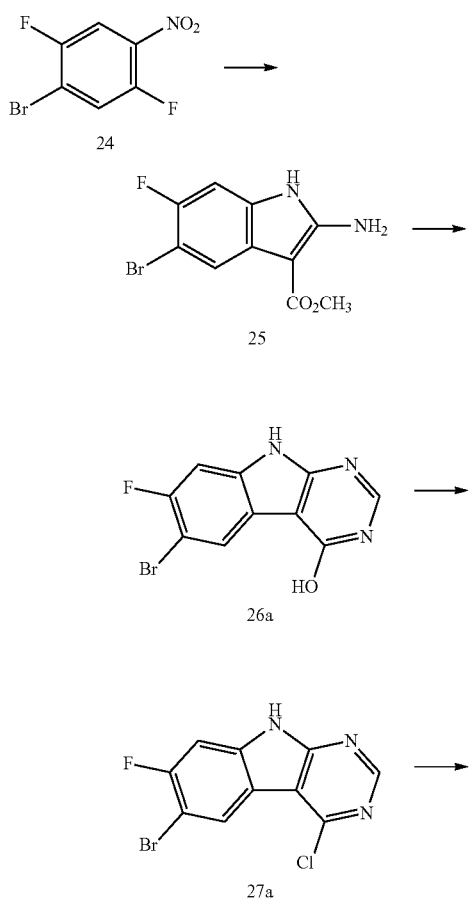

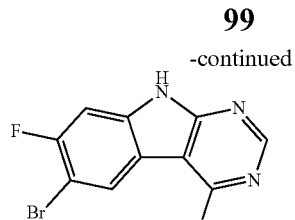

28a

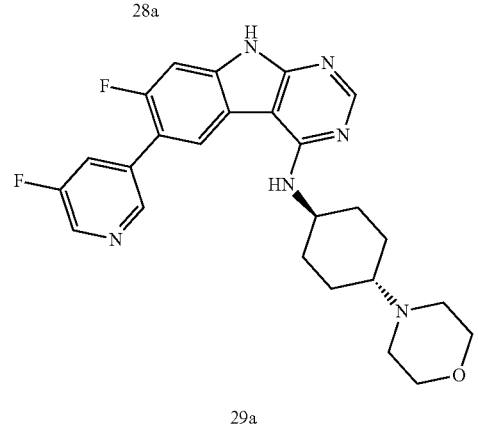

29a

Step 1. Preparation of Compound 25

1-Bromo-2,5-difluoro-4-nitrobenzene 24 (2.26 g, 9.5 mmol) was reacted in a manner similar to Step 1 of Example 46 to prepare 1.25 g (45%) of a light brown solid.

25: $^1$H-NMR (300 MHz, DMSO-$d_6$) δ 3.76 (s, 3H), 6.88 (s, 2H), 7.12 (d, J=9.4 Hz, 1H), 7.64 (d, J=6.9 Hz, 1H), 10.83 (s, 1H).

Step 2. Preparation of Compound 26a

Compound 25 (1.25 g, 4.35 mmol) was reacted in a manner similar to Step 2 of Example 46 to prepare 860 mg (70%) of a light brown solid.

Step 3. Preparation of Compound 27a

Compound 26a (810 mg, 3.05 mmol) was reacted in a manner similar to Step 3 of Example 46 to prepare 816 mg (89%) of a brown solid.

Step 4. Preparation of Compound 28a

Compound 27a (805 mg, 1.80 mmol) was reacted in a manner similar to Step 4 of Example 46 to prepare 753 mg (92%) of a white solid.

28a: $^1$H-NMR (300 MHz, MeOD-$d_4$) δ 1.50 (q, J=12.4 Hz, 2H), 1.64 (q, J=12.4 Hz, 2H), 2.07-2.13 (m, 2H), 2.16-2.23 (m, 2H), 2.40-2.47 (m, 1H), 2.70 (t, J=4.8 Hz, 4H), 3.74 (t, J=4.7 Hz, 4H), 4.25-4.33 (m, 1H), 7.34 (d, J=9.2 Hz, 1H), 8.31 (s, 1H), 8.52 (d, J=6.7 Hz, 1H).

Step 5. Preparation of Compound 29a

Compound 28a (30 mg, 0.06 mmol) was reacted in a manner similar to Step 5 of Example 46 to prepare 6.1 mg (19%) of a white solid.

29a: $^1$H-NMR (300 MHz, DMSO-$d_6$) δ 1.35 (q, J=11.5, 10.8 Hz, 3H), 1.59 (q, J=12.3 Hz, 3H), 1.86-1.95 (m, 2H), 1.99-2.10 (m, 2H), 2.18-2.30 (m, 1H), 2.40-2.60 (m, 2H), 3.57 (t, J=4.5 Hz, 4H), 4.21-4.38 (m, 1H), 6.81 (d, J=8.2 Hz, 1H), 7.38 (d, J=11.2 Hz, 1H), 8.02 (d, J=10.1 Hz, 1H), 8.36 (s, 1H), 8.52 (d, J=7.4 Hz, 1H), 8.64 (d, J=2.8 Hz, 1H), 8.76 (d, J=1.8 Hz, 1H), 12.16 (s, 1H).

[Example 48] Preparation of 7-chloro-6-(5-fluoro-pyridin-3-yl)-N-(trans-4-morpholinocyclohexyl)-9H-pyrimido[4,5-b]indole-4-amine (Compound 35a)

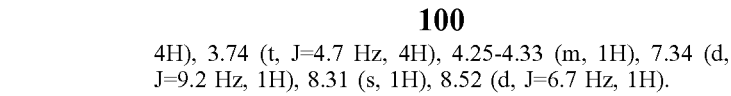

30

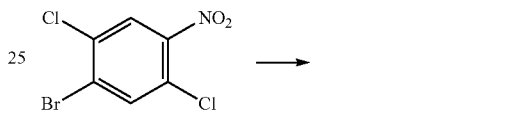

31

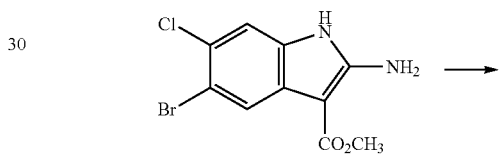

32a

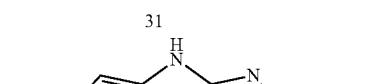

33a

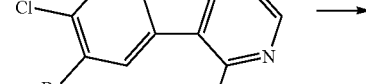

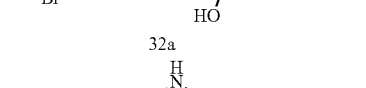

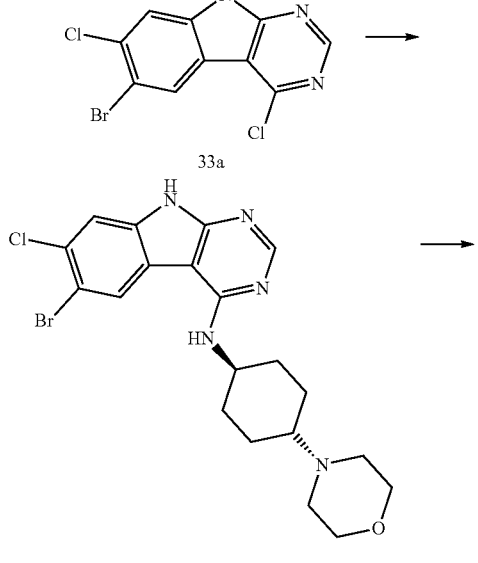

34a 4.25-4.33 (m, 1H), 6.99 (d, J=8.2 Hz, 1H), 7.62 (s, 1H), 8.33-8.39 (s, 1H), 8.83 (s, 1H), 12.13 (s, 1H).

[Example 49] Preparation of 7-chloro-6-(1-methyl-1H-pyrazol-4-yl)-N-(trans-4-morpholinocyclohexyl)-9H-pyrimido[4,5-b]indole-4-amine (Compound 35b)

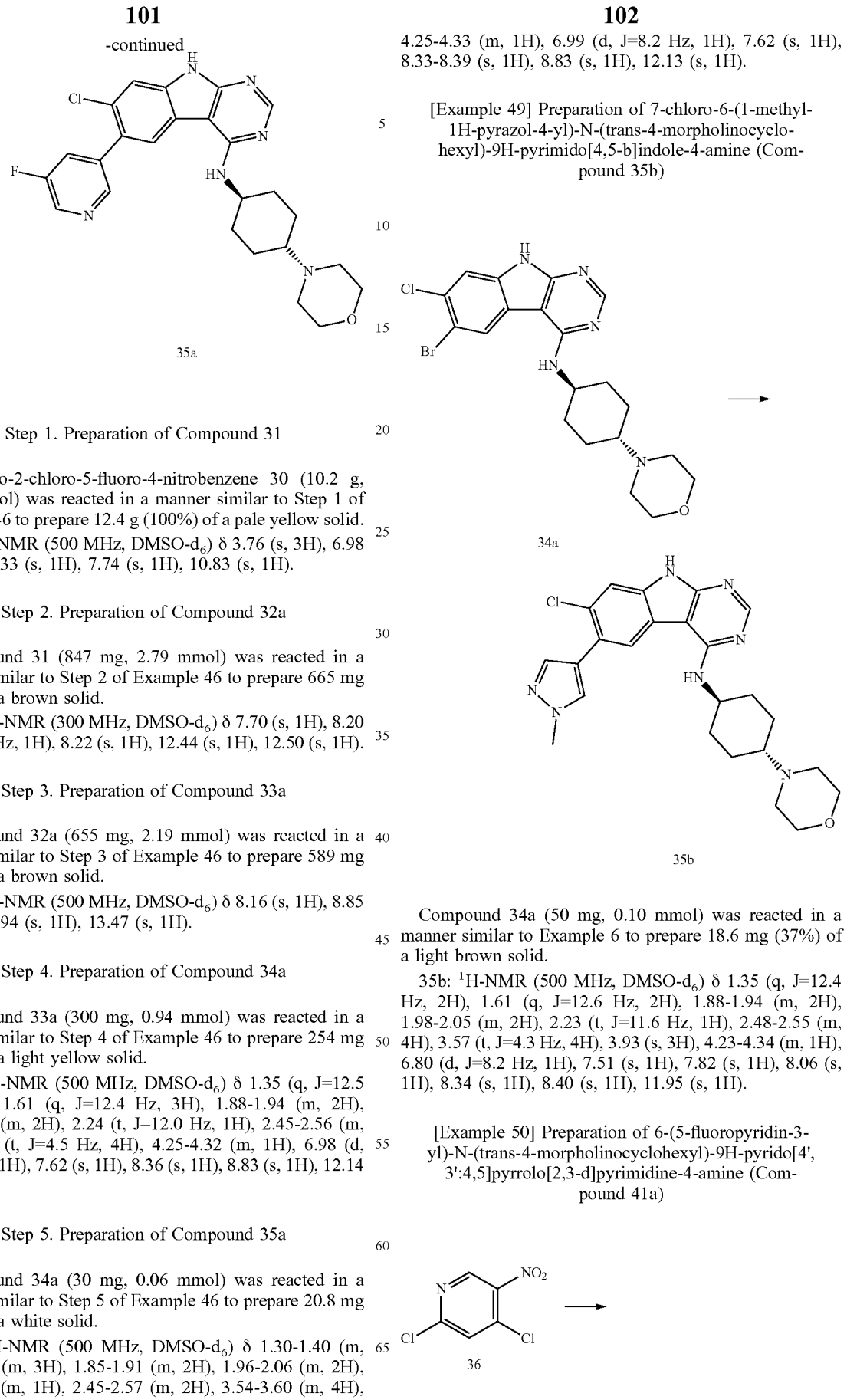

35a

Step 1. Preparation of Compound 31

1-Bromo-2-chloro-5-fluoro-4-nitrobenzene 30 (10.2 g, 48.73 mmol) was reacted in a manner similar to Step 1 of Example 46 to prepare 12.4 g (100%) of a pale yellow solid.

31: $^1$H-NMR (500 MHz, DMSO-$d_6$) δ 3.76 (s, 3H), 6.98 (s, 2H), 7.33 (s, 1H), 7.74 (s, 1H), 10.83 (s, 1H).

Step 2. Preparation of Compound 32a

Compound 31 (847 mg, 2.79 mmol) was reacted in a manner similar to Step 2 of Example 46 to prepare 665 mg (79%) of a brown solid.

32a: $^1$H-NMR (300 MHz, DMSO-$d_6$) δ 7.70 (s, 1H), 8.20 (d, J=2.9 Hz, 1H), 8.22 (s, 1H), 12.44 (s, 1H), 12.50 (s, 1H).

Step 3. Preparation of Compound 33a

Compound 32a (655 mg, 2.19 mmol) was reacted in a manner similar to Step 3 of Example 46 to prepare 589 mg (84%) of a brown solid.

33a: $^1$H-NMR (500 MHz, DMSO-$d_6$) δ 8.16 (s, 1H), 8.85 (s, 1H), 8.94 (s, 1H), 13.47 (s, 1H).

Step 4. Preparation of Compound 34a

Compound 33a (300 mg, 0.94 mmol) was reacted in a manner similar to Step 4 of Example 46 to prepare 254 mg (57%) of a light yellow solid.

34a: $^1$H-NMR (500 MHz, DMSO-$d_6$) δ 1.35 (q, J=12.5 Hz, 3H), 1.61 (q, J=12.4 Hz, 3H), 1.88-1.94 (m, 2H), 1.97-2.05 (m, 2H), 2.24 (t, J=12.0 Hz, 1H), 2.45-2.56 (m, 2H), 3.58 (t, J=4.5 Hz, 4H), 4.25-4.32 (m, 1H), 6.98 (d, J=8.2 Hz, 1H), 7.62 (s, 1H), 8.36 (s, 1H), 8.83 (s, 1H), 12.14 (s, 1H).

Step 5. Preparation of Compound 35a

Compound 34a (30 mg, 0.06 mmol) was reacted in a manner similar to Step 5 of Example 46 to prepare 20.8 mg (67%) of a white solid.

35a: $^1$H-NMR (500 MHz, DMSO-$d_6$) δ 1.30-1.40 (m, 3H), 1.60 (m, 3H), 1.85-1.91 (m, 2H), 1.96-2.06 (m, 2H), 2.18-2.26 (m, 1H), 2.45-2.57 (m, 2H), 3.54-3.60 (m, 4H),

Compound 34a (50 mg, 0.10 mmol) was reacted in a manner similar to Example 6 to prepare 18.6 mg (37%) of a light brown solid.

35b: $^1$H-NMR (500 MHz, DMSO-$d_6$) δ 1.35 (q, J=12.4 Hz, 2H), 1.61 (q, J=12.6 Hz, 2H), 1.88-1.94 (m, 2H), 1.98-2.05 (m, 2H), 2.23 (t, J=11.6 Hz, 1H), 2.48-2.55 (m, 4H), 3.57 (t, J=4.3 Hz, 4H), 3.93 (s, 3H), 4.23-4.34 (m, 1H), 6.80 (d, J=8.2 Hz, 1H), 7.51 (s, 1H), 7.82 (s, 1H), 8.06 (s, 1H), 8.34 (s, 1H), 8.40 (s, 1H), 11.95 (s, 1H).

[Example 50] Preparation of 6-(5-fluoropyridin-3-yl)-N-(trans-4-morpholinocyclohexyl)-9H-pyrido[4',3':4,5]pyrrolo[2,3-d]pyrimidine-4-amine (Compound 41a)

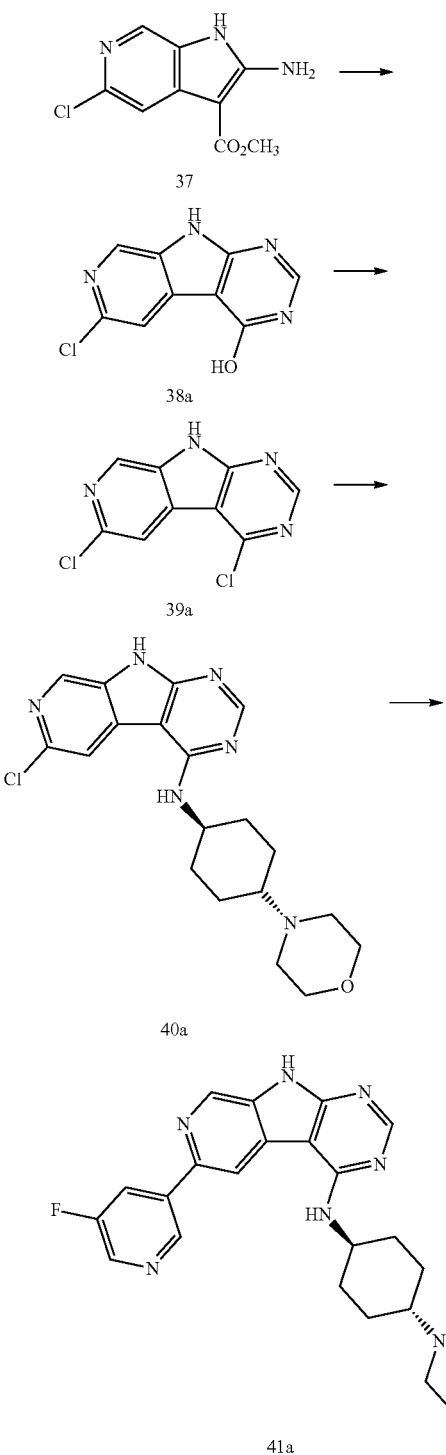

37

38a

39a

40a

41a

Step 1. Preparation of Compound 37

2,4-Dichloro-5-nitropyridine 36 (9.65 g, 50.0 mmol) was reacted in a manner similar to Step 1 of Example 46 to prepare 7.56 g (67%) of a light brown solid.

37: $^1$H-NMR (500 MHz, DMSO-d$_6$) δ 3.77 (s, 3H), 7.25 (s, 2H), 7.35 (s, 1H), 8.07 (s, 1H).

Step 2. Preparation of Compound 38a

Compound 37 (2.57 g, 11.39 mmol) was reacted in a manner similar to Step 2 of Example 46 to prepare 1.4 g (55%) of a brown solid.

38a: $^1$H-NMR (500 MHz, DMSO-d$_6$) δ 7.84 (s, 1H), 8.30 (s, 1H), 8.62 (s, 1H), 12.63 (s, 1H).

Step 3. Preparation of Compound 39a

Compound 38a (1.4 g, 6.34 mmol) was reacted in a manner similar to Step 3 of Example 46 to prepare 1.32 g (87%) of a brown solid.

39a: $^1$H-NMR (300 MHz, DMSO-d$_6$) δ 8.17 (s, 1H), 8.83 (s, 1H), 8.95 (s, 1H), 12.76 (s, 1H).

Step 4. Preparation of Compound 40a

Compound 39a (300 mg, 1.25 mmol) was reacted in a manner similar to Step 4 of Example 46 to prepare 390 mg (81%) of a brown solid.

40a: $^1$H-NMR (500 MHz, DMSO-d$_6$) δ 1.35 (q, J=12.1 Hz, 2H), 1.61 (q, J=12.4 Hz, 2H), 1.88-1.95 (m, 2H), 1.97-2.03 (m, 2H), 2.24 (t, J=11.6 Hz, 1H), 2.48-2.56 (m, 4H), 3.58 (t, J=4.3 Hz, 4H), 4.26-4.36 (m, 1H), 7.18 (d, J=8.1 Hz, 1H), 8.43 (s, 1H), 8.55 (s, 1H), 8.58 (s, 1H), 12.36 (s, 1H).

Step 5. Preparation of Compound 41a

Compound 40a (50 mg, 0.12 mmol) was reacted in a manner similar to Step 5 of Example 46 to prepare 27 mg (46%) of a white solid.

41a: $^1$H-NMR (500 MHz, DMSO-d$_6$) δ 1.33-1.43 (m, 3H), 1.66 (q, J=12.4 Hz, 3H), 1.91-1.97 (m, 2H), 2.05-2.13 (m, 2H), 2.29 (t, J=11.6 Hz, 1H), 2.48-2.55 (m, 2H), 3.58 (t, J=4.5 Hz, 4H), 4.27-4.48 (m, 1H), 7.08 (d, J=8.2 Hz, 1H), 8.41 (d, J=10.0 Hz, 1H), 8.46 (s, 1H), 8.62 (t, J=2.2 Hz, 1H), 8.90 (s, 1H), 8.95 (s, 1H), 9.36 (s, 1H), 12.41 (s, 1H).

[Example 51] Preparation of 6-(5-methoxypyridin-3-yl)-N-(trans-4-morpholinocyclohexyl)-9H-pyrido[4',3':4,5]pyrrolo[2,3-d]pyrimidine-4-amine (Compound 41b)

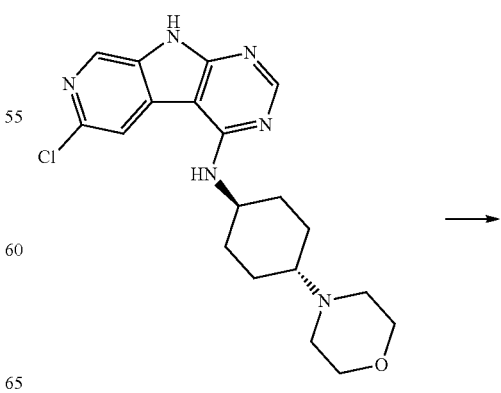

40a

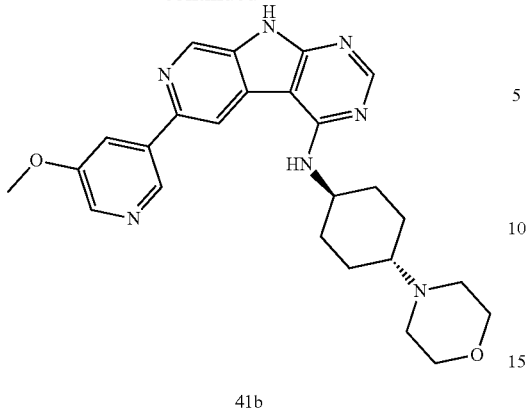

41b

Compound 40a (50 mg, 0.12 mmol) was reacted in a manner similar to Example 9 to prepare 23.9 mg (40%) of a white solid.

41b: $^1$H-NMR (500 MHz, DMSO-d$_6$) δ 1.38 (q, J=12.2, 11.7 Hz, 2H), 1.66 (q, J=12.6 Hz, 2H), 1.90-1.97 (m, 2H), 2.04-2.10 (m, 2H), 2.28 (t, J=11.7 Hz, 1H), 2.49-2.53 (m, 4H), 3.58 (t, J=4.5 Hz, 4H), 3.95 (s, 3H), 4.30-4.39 (m, 1H), 7.12 (d, J=8.1 Hz, 1H), 8.11 (s, 1H), 8.34 (s, 1H), 8.45 (s, 1H), 8.90 (s, 1H), 8.91 (s, 1H), 9.08 (s, 1H), 12.34 (s, 1H).

[Example 52] Preparation of 6-(1-methyl-1H-pyrazol-4-yl)-N-(trans-4-morpholinocyclohexyl)-9H-pyrido[4',3':4,5]pyrrolo[2,3-d]pyrimidine-4-amine (Compound 41c)

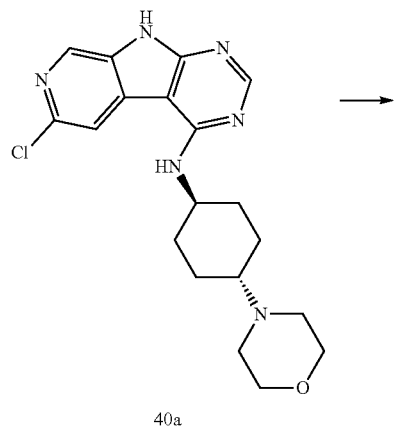

40a

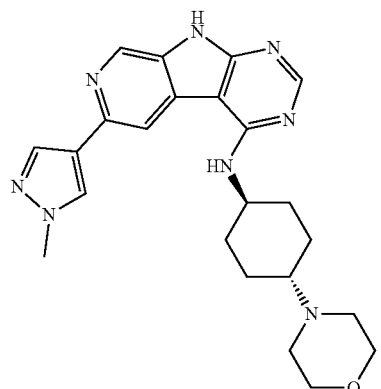

41c

Compound 40a (50 mg, 0.12 mmol) was reacted in a manner similar to Example 6 to prepare 6.9 mg (12%) of a light brown solid.

41c: $^1$H-NMR (500 MHz, DMSO-d$_6$) δ 1.32-1.43 (m, 2H), 1.65 (q, J=13.4, 12.3 Hz, 2H), 1.90-1.99 (m, 2H), 2.05-2.12 (m, 2H), 2.28 (t, J=12.2 Hz, 1H), 2.48-2.56 (m, 4H), 3.59 (t, J=4.6 Hz, 4H), 3.93 (s, 3H), 4.27-4.36 (m, 1H), 6.89 (d, J=8.4 Hz, 1H), 8.07 (s, 1H), 8.21 (s, 1H), 8.42 (s, 1H), 8.48 (s, 1H), 8.71 (s, 1H), 12.13 (s, 1H).

[Example 53] Preparation of 6-(1-methyl-1H-pyrazol-4-yl)-N-(trans-4-morpholinocyclohexyl)-9H-pyrimido[4,5-b]indole-4-diamine (Compound 6aat)

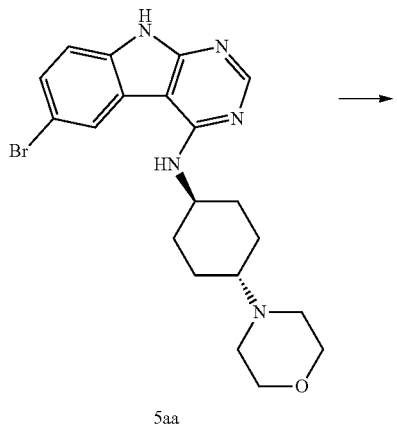

5aa

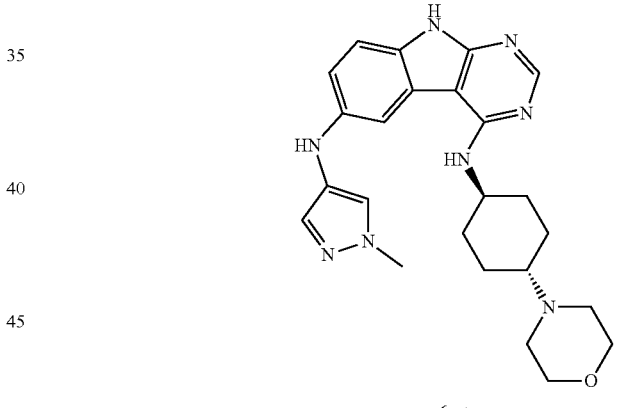

6aat

After Pd(OAc)$_2$ (2.9 mg, 10 mol %) and XPhos (16.6 mg, 30 mol %) were put into 1,4-dioxane (2.3 mL), the resulting mixture was degassed, and stirred at 110° C. for 2 minutes. After Compound 5aa (50 mg, 0.11 mmol), 1-methyl-1H-pyrazol-4-amine (11.5 μL, 0.13 mmol), and NaO$^t$Bu (36.8 mg, 0.38 mmol) were added thereto, the resulting mixture was degassed and stirred at 110° C. After the completion of the reaction was confirmed, ethyl acetate (5 mL) was added thereto, and then the resulting mixture was filtered with a celite pad and concentrated under reduced pressure. The residue was separated by silica gel column chromatography (ethyl acetate:dichloromethane:methanol=3:1:1) to obtain 11.8 mg (22%) of a red solid.

6aat: $^1$H-NMR (400 MHz, DMSO-d$_6$) δ 1.36 (q, J=11.8, 10.8 Hz, 2H), 1.52 (q, J=12.3, 11.4 Hz, 2H), 1.85-1.95 (m, 2H), 2.05-2.15 (m, 2H), 2.24 (t, J=11.4 Hz, 1H), 2.49-2.51 (m, 4H), 3.58 (t, J=4.4 Hz, 4H), 3.79 (s, 3H), 4.06-4.19 (m, 1H), 6.31 (d, J=8.0 Hz, 1H), 6.93 (dd, J=8.6, 2.1 Hz, 1H), 7.20-7.27 (m, 2H), 7.34 (s, 1H), 7.57 (d, J=2.2 Hz, 1H), 7.63 (s, 1H), 8.26 (s, 1H), 11.48 (s, 1H).

[Example 54] Preparation of 6-(1-(difluoromethyl)-1H-pyrazol-4-yl)-N-(trans-4-morpholinocyclohexyl)-9H-pyrimido[4,5-b]indole-4-amine (Compound 6aau)

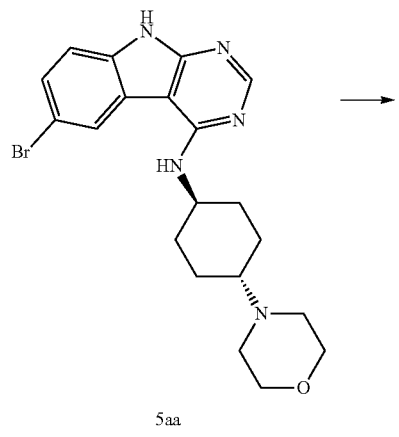

After Compound 5aa (50 mg, 0.11 mmol), 1-(difluoromethyl)-4-(4,4,5,5-tetramethyl-1,3,2-dioxaborolan-2-yl)-1H-pyrazole (34 mg, 0.13 mmol), $^{t}Bu_3PBF_4$ (2 mg, 6 mol %), and $K_2CO_3$ (32 mg, 0.23 mmol) were dissolved in dioxane:$H_2O$ (4:1 in v/v, 2 mL), the resulting solution was degassed. $Pd_2(dba)_3$ (3.5 mg, 3.3 mol %) was added thereto, and the resulting mixture was degassed, and then stirred at 90° C. After the completion of the reaction was confirmed, ethyl acetate (5 mL) was added thereto, the resulting mixture was filtered with a celite pad, and then washed with water (5 mL), and the aqueous layer was again extracted with ethyl acetate (3 mL). After the ethyl acetate layer was combined, the resulting mixture was washed with water (5 mL), moisture was removed with sodium sulfate ($Na_2SO_4$), and the resulting product was concentrated under reduced pressure. The residue was separated by silica gel column chromatography (ethyl acetate:dichloromethane:methanol=3:1:1) to obtain 15.0 mg (27%) of a white solid.

6aau: (500 MHz, DMSO-$d_6$) δ 1.38 (q, J=12.5 Hz, 2H), 1.65 (q, J=12.9, 12.1 Hz, 2H), 1.90-1.98 (m, 2H), 2.05-2.14 (m, 2H), 2.27 (t, J=11.8 Hz, 1H), 2.45-2.57 (m, 4H), 3.58 (t, J=4.3 Hz, 4H), 4.25-4.33 (m, 1H), 6.63 (d, J=8.1 Hz, 1H), 7.46 (d, J=8.3 Hz, 1H), 7.70 (d, J=8.3 Hz, 1H), 7.89 (t, J=59.3 Hz, 1H), 8.34 (s, 1H), 8.38 (s, 1H), 8.49 (s, 1H), 8.70 (s, 1H), 11.94 (s, 1H).

[Example 55] Preparation of 6-(5-(difluoromethyl)-1,3,4-oxadiazol-2-yl)-N-(trans-4-morpholinocyclohexyl)-9H-pyrimido[4,5-b]indole-4-amine (Compound 6baha)

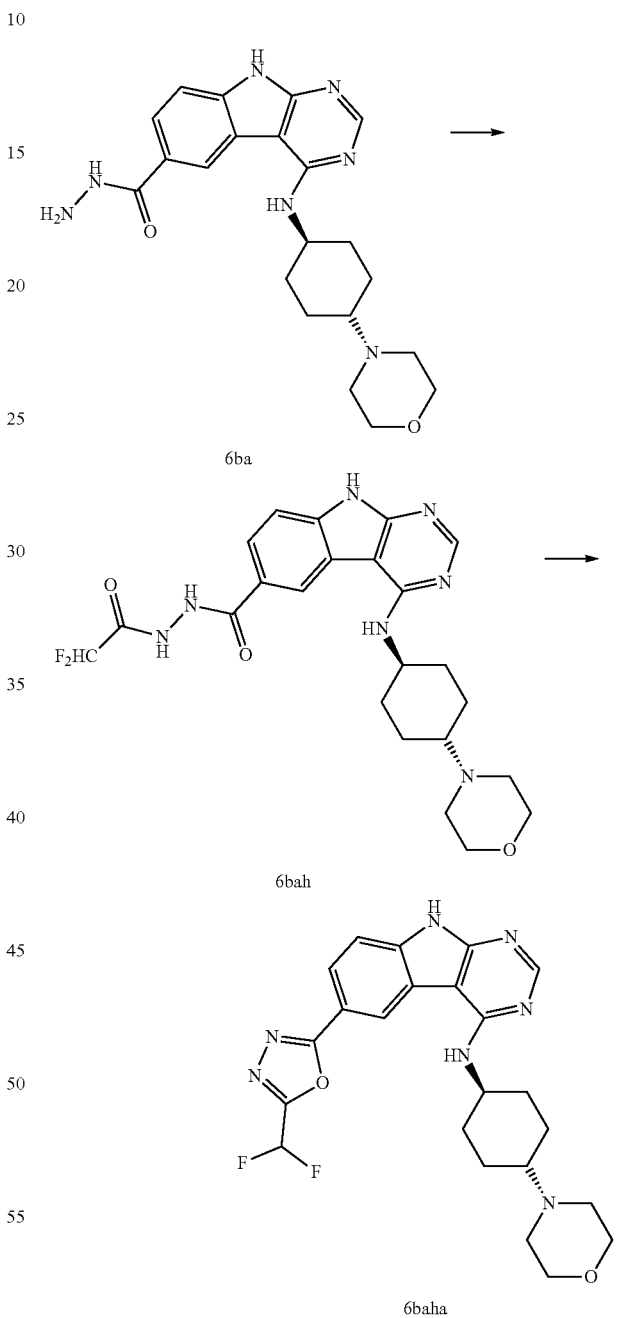

Step 1. Preparation of Compound 6bah

After Compound 6ba (100 mg, 0.24 mmol), hydrazide (100 mg, 0.24 mmol), N,N-diisopropylethylamine (DIPEA) (85 μL, 0.48 mmol), and difluoroacetic anhydride (53 μL, 0.48 mmol) were dissolved in acetonitrile (2 mL), the resulting solution was stirred at 80° C. After the completion of the reaction was confirmed, the reaction product was put into water, and extraction was performed with ethyl acetate (3×10 mL). Moisture was removed from the organic layer with sodium sulfate (Na$_2$SO$_4$), the organic layer was concentrated under reduced pressure, and then the residue was washed with diethyl ether to obtain 101 mg (85%) of a light yellow solid.

Step 2. Preparation of Compound 6baha

Compound 6bah (95 mg, 0.19 mmol) was put into thionyl chloride (3 mL), and the resulting solution was stirred under reflux. After the completion of the reaction was confirmed, the resulting product was concentrated under reduced pressure, and the residue was put into ice water (5 mL). After the resulting mixture was neutralized using sodium bicarbonate, the solid was washed with water. The solid was separated by silica gel column chromatography (dichloromethane:methanol=6:1) to obtain 73 mg (80%) of a pale yellow solid.

6baha: $^1$H-NMR (400 MHz, DMSO-d$_6$) δ 1.36 (q, J=13.1, 11.9 Hz, 3H), 1.67 (q, J=11.8, 10.7 Hz, 3H), 1.88-1.96 (m, 3H), 2.00-2.10 (m, 3H), 2.20-2.31 (m, 1H), 3.58 (t, J=4.6 Hz, 4H), 4.24-4.37 (m, 1H), 7.24 (d, J=8.1 Hz, 1H), 7.58 (t, J=51.6 Hz, 1H), 7.64 (d, J=8.4 Hz, 1H), 8.02-8.08 (m, 1H), 8.40 (s, 1H), 9.07 (s, 1H), 12.39 (s, 1H).

[Example 56] Preparation of 6-(1-methyl-1H-pyrazol-4-yl)-N-(trans-4-morpholinocyclohexyl)-9H-pyrido[2',3':4,5]pyrrolo[2,3-d]pyrimidine-4,6-diamine (Compound 23b)

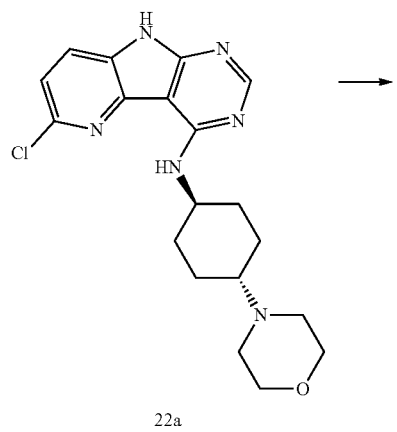

22a

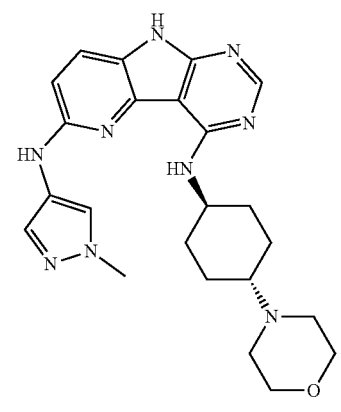

23b

Compound 22a (50 mg, 0.12 mmol) was reacted in a manner similar to Example 53 to prepare 11.1 mg (19%) of a light brown solid.

23b: $^1$H-NMR (400 MHz, DMSO-d$_6$) δ 1.31-1.46 (m, 4H), 1.86-1.98 (m, 2H), 2.25-2.35 (m, 3H), 2.43-2.57 (m, 4H), 3.58 (t, J=4.5 Hz, 4H), 3.85 (s, 3H), 3.98-4.07 (m, 1H), 6.44 (d, J=7.8 Hz, 1H), 6.72 (d, J=8.8 Hz, 1H), 7.50 (s, 1H), 7.64 (d, J=8.8 Hz, 1H), 7.87 (s, 1H), 8.31 (s, 1H), 8.79 (s, 1H), 11.62 (s, 1H).

[Example 57] Preparation of 4-((6-5-fluoropyridin-3-yl)-9H-pyrimido[4,5-b]indol-4-yl)amino)-N,N-dimethylpiperidine-1-sulfonamide (Compound 5aiaaa)

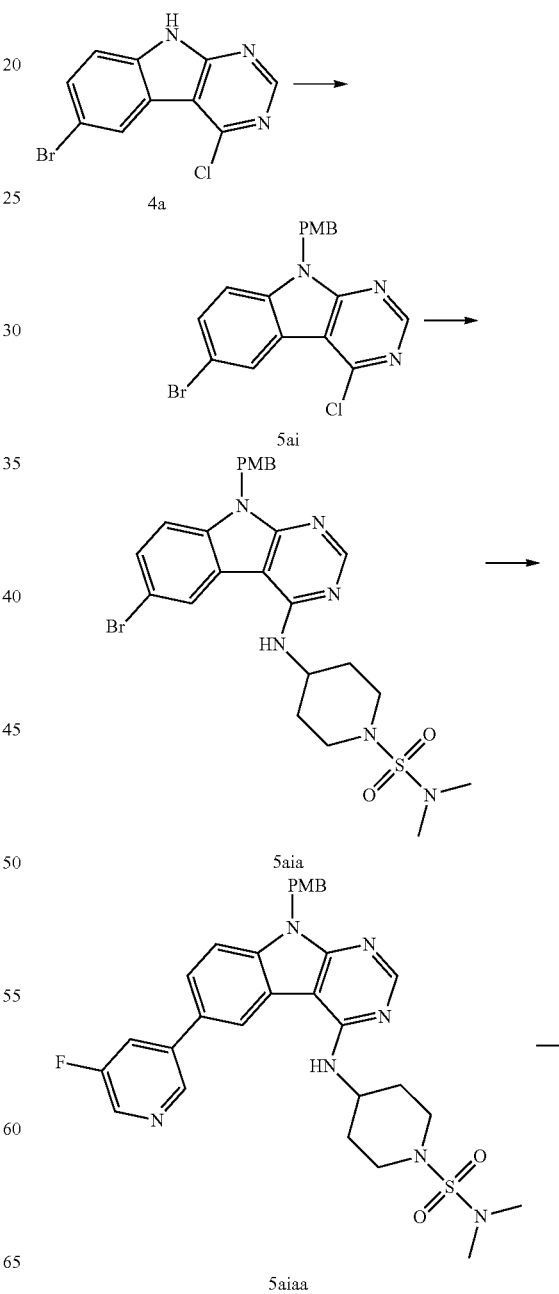

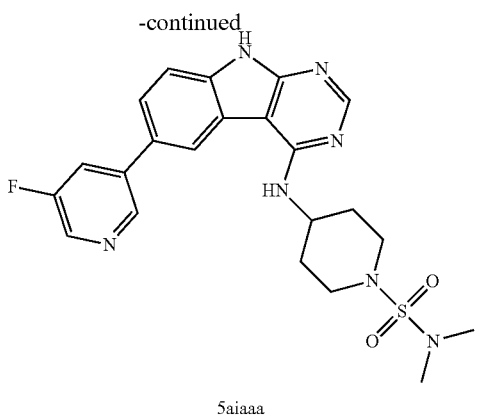

5aiaaa

Step 1. Preparation of Compound 5ai

After Compound 4a (286 mg, 1.01 mmol), potassium carbonate (K$_2$CO$_3$)(280 mg, 2.02 mmol), and 4-methoxybenzyl chloride (0.16 mL, 1.23 mmol) were dissolved in dimethylformamide (DMF)(2 m), the resulting solution was stirred at room temperature. After the completion of the reaction was confirmed, ethyl acetate (5 mL) was added thereto, the resulting mixture was washed with water (8 mL), and the aqueous layer was extracted using ethyl acetate (2×3 mL). After the organic layer was washed with water (2×5 mL), moisture was removed with sodium sulfate (Na$_2$SO$_4$), the organic layer was concentrated under reduced pressure, and then the residue was separated by silica gel column chromatography (hexane:ethyl acetate=1:1) to obtain 399 mg (98%) of a light brown solid. In Compound 5ai, PMB represents p-methoxybenzyl.

5ai: $^1$H-NMR (300 MHz, DMSO-d$_6$) δ 3.68 (s, 3H), 5.67 (s, 2H), 6.84 (d, J=8.7 Hz, 2H), 7.27 (d, J=8.7 Hz, 2H), 7.82 (d, J=1.3 Hz, 2H), 8.40 (t, J=1.3 Hz, 1H), 8.93 (s, 1H).

Step 2. Preparation of Compound 5aia

Compound 5ai (200 mg, 0.49 mmol) and 4-amino-N,N-dimethylpiperidine-1-sulfonamide were reacted in a manner similar to Step 4 of Example 46 to prepare 263 mg (92%) of a white solid.

5aia: $^1$H-NMR (500 MHz, DMSO-d$_6$) δ 1.78-1.89 (m, 2H), 1.97-2.04 (m, 2H), 2.45-2.55 (m, 1H), 2.79 (s, 6H), 3.02 (t, J=12.4 Hz, 2H), 3.67 (s, 3H), 3.68-3.71 (m, 1H), 4.46-4.57 (m, 1H), 5.54 (s, 2H), 6.82 (d, J=8.2 Hz, 2H), 7.09 (d, J=8.2 Hz, 1H), 7.20 (d, J=8.2 Hz, 2H), 7.49-7.61 (m, 2H), 8.47 (s, 1H), 8.68 (s, 1H).

Step 3. Preparation of Compound 5aiaa

Compound 5aia (100 mg, 0.17 mmol) was reacted in a manner similar to Step 5 of Example 46 to prepare 114 mg (99%) of a white solid.

5aiaa: $^1$H-NMR (300 MHz, DMSO-d$_6$) δ 1.80-2.24 (m, 5H), 2.79 (s, 6H), 3.03 (t, J=12.2 Hz, 2H), 3.68 (s, 3H), 3.68-3.78 (m, 1H), 4.47-4.67 (m, 1H), 5.59 (s, 2H), 6.85 (t, J=7.0 Hz, 2H), 7.02 (d, J=8.1 Hz, 1H), 7.24 (d, J=7.9 Hz, 2H), 7.68-7.87 (m, 2H), 8.15 (d, J=10.5 Hz, 1H), 8.53 (d, J=24.0 Hz, 2H), 8.68 (s, 1H), 8.97 (s, 1H).

Step 4. Preparation of Compound 5aiaaa

After Compound 5aiaa (114 mg, 0.19 mmol) was dissolved in methanesulfonyl chloride (0.4 mL) and trifluoroacetic acid (2 mL), the resulting solution was stirred at 60° C. After the completion of the reaction was confirmed, the resulting product was concentrated under reduced pressure, and the residue was put into ice water (5 mL). After the resulting mixture was neutralized using sodium bicarbonate, extraction was performed using ethyl acetate (7 mL), and then moisture was removed with sodium sulfate (Na$_2$SO$_4$), and the resulting product was concentrated under reduced pressure. The residue was separated by silica gel column chromatography (dichloromethane:methanol=10:1) to obtain 5 mg (5%) of a light brown solid.

5aiaaa: $^1$H-NMR (500 MHz, DMSO-d$_6$) δ 1.79-1.90 (m, 2H), 1.99-2.07 (m, 2H), 2.78 (s, 6H), 2.99-3.06 (m, 2H), 3.65-3.73 (m, 2H), 4.47-4.56 (m, 1H), 6.91 (d, J=8.2 Hz, 1H), 7.57 (d, J=8.4 Hz, 1H), 7.79 (dd, J=8.4, 1.7 Hz, 1H), 8.12-8.17 (m, 1H), 8.38 (s, 1H), 8.57 (d, J=2.7 Hz, 1H), 8.63-8.66 (m, 1H), 8.97 (t, J=1.8 Hz, 1H), 12.09 (s, 1H).

[Example 58] Preparation of 6-(5-fluoropyridin-3-yl)-N-(1-(methylsulfonyl)piperidin-4-yl)-9H-pyrimido[4,5-b]indole-4-amine (Compound 5aibaa)

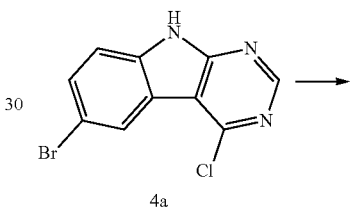

4a

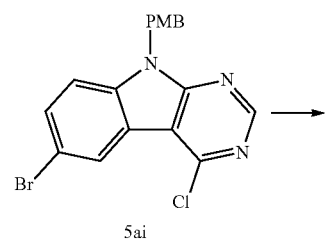

5ai

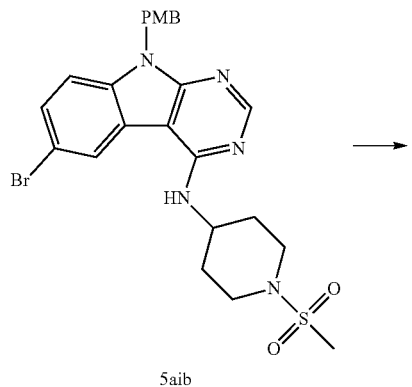

5aib

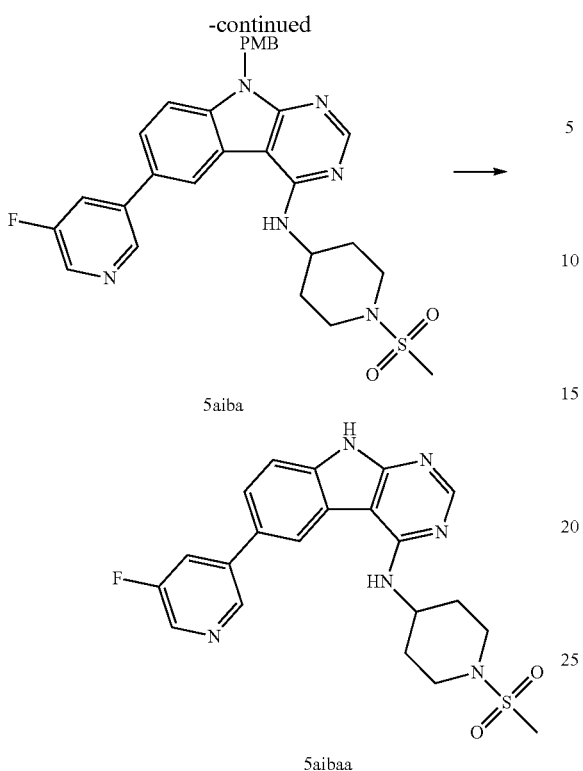

5aiba

5aibaa

Step 2. Preparation of Compound 5aib

Compound 5th (200 mg, 0.49 mmol) and 4-amino-1-(methylsulfonyl)piperidine were reacted in a manner similar to Step 4 of Example 46 to prepare 268 mg (99%) of a white solid.

5aib: $^1$H-NMR (500 MHz, DMSO-d$_6$) δ 1.81-1.91 (m, 2H), 2.00-2.08 (m, 2H), 2.86-2.94 (s, 5H), 3.64-3.71 (m, 5H), 4.45-4.56 (m, 1H), 5.54 (s, 2H), 6.82 (d, J=8.4 Hz, 2H), 7.10 (d, J=8.1 Hz, 1H), 7.20 (d, J=8.5 Hz, 2H), 7.52 (dd, J=8.6, 1.8 Hz, 1H), 7.58 (d, J=8.7 Hz, 1H), 8.47 (s, 1H), 8.68 (d, J=1.8 Hz, 1H).

Step 3. Preparation of Compound 5aiba

Compound 5aib (66.6 mg, 0.12 mmol) was reacted in a manner similar to Step 5 of Example 46 to prepare 62 mg (85%) of a brown solid.

5aiba: $^1$H-NMR (300 MHz, DMSO-d$_6$) δ 1.67-2.28 (m, 5H), 2.84-3.05 (m, 4H), 3.54-3.75 (m, 5H), 4.45-4.65 (s, 1H), 5.60 (s, 2H), 6.79-6.94 (m, 2H), 7.02 (d, J=8.1 Hz, 1H), 7.25 (d, J=8.1 Hz, 2H), 7.68-7.91 (m, 2H), 8.16 (d, J=10.5 Hz, 1H), 8.50 (s, 1H), 8.58 (s, 1H), 8.68 (s, 1H), 8.97 (s, 1H).

Step 4. Preparation of Compound 5aibaa

Compound 5aiba (62.0 mg, 0.14 mmol) was reacted in a manner similar to Step 4 of Example 57 to prepare 21.1 mg (34%) of a white solid.

5aibaa: $^1$H-NMR (500 MHz, DMSO-d$_6$) δ 1.85-1.95 (m, 2H), 2.05-2.13 (m, 2H), 2.87-2.96 (m, 5H), 3.65-3.73 (m, 2H), 4.46-4.57 (m, 1H), 6.93 (d, J=8.2 Hz, 1H), 7.58 (d, J=8.4 Hz, 1H), 7.81 (d, J=8.4 Hz, 1H), 8.16 (d, J=10.5 Hz, 1H), 8.39 (s, 1H), 8.58 (d, J=2.7 Hz, 1H), 8.65 (s, 1H), 8.98 (s, 1H), 12.11 (s, 1H).

[Example 59] Preparation of 6-(4-methyl-1-imidazol-1-yl)-N-(trans-4-morpholinocyclohexyl)-9H-pyrimido[4,5-b]indole-4-amine (Compound 5aicaa)

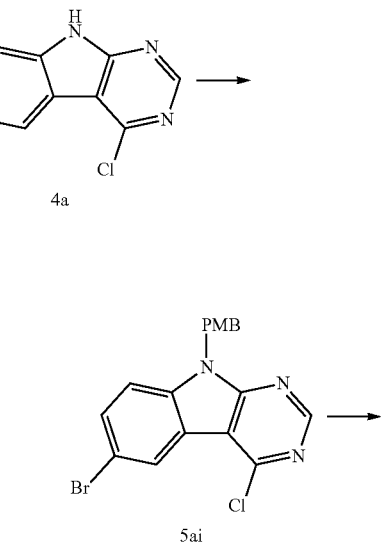

4a

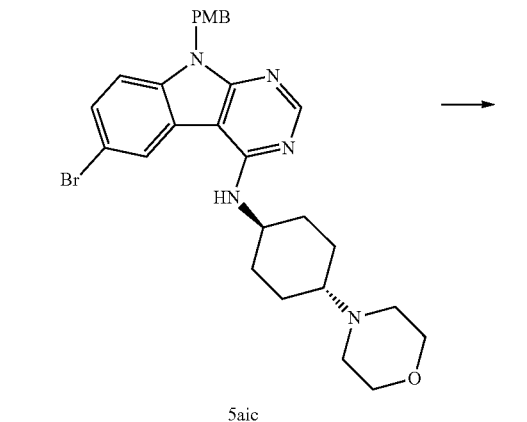

5ai

5aic

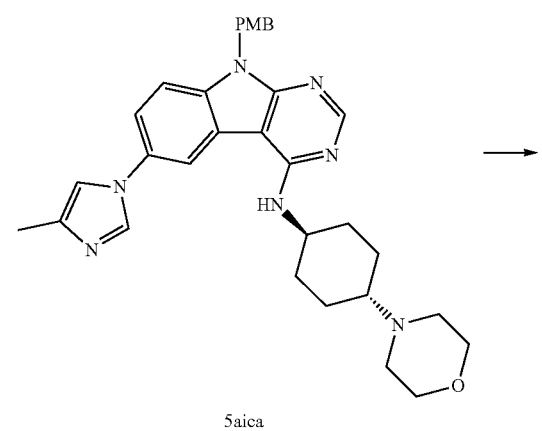

5aica

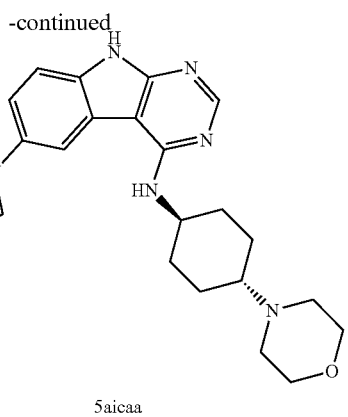

5aicaa

Step 2. Preparation of Compound 5aic

Compound 5ai (103 mg, 0.255 mmol) was reacted in a manner similar to Step 4 of Example 46 to prepare 129 mg (92%) of a light brown solid.

5aic: $^1$H-NMR (500 MHz, CDCl$_3$) δ 1.42 (q, J=12.2 Hz, 3H), 1.48-1.56 (m, 1H), 2.01-2.10 (m, 2H), 2.30-2.42 (m, 3H), 2.56-2.66 (m, 4H), 3.74 (s, 3H), 3.74-3.77 (m, 4H), 4.25-4.347 (m, 1H), 4.91 (d, J=8.0 Hz, 1H), 5.53 (s, 2H), 6.79 (d, J=8.6 Hz, 2H), 7.15 (d, J=8.5 Hz, 2H), 7.25 (s, 1H), 7.46 (dd, J=8.6, 1.8 Hz, 1H), 7.79 (d, J=1.9 Hz, 1H), 8.58 (s, 1H).

Step 3. Preparation of Compound 5aica

After Compound 5aic (30 mg, 0.05 mmol), 4-methyl-1H-imidazole (6.7 mg, 0.08 mmol), potassium tert-butoxide (9.61 mg, 0.10 mmol), and 2-dicyclohexylphosphino-2',6'-dimethoxybiphenyl (SPhos)(2.0 mg, 10 mol %) were put into toluene (2 mL), the resulting mixture was degassed. Pd$_2$(dba)$_3$ (2.3 mg, 0.0025 mmol) was added thereto, and the resulting mixture was degassed, and then stirred at 110° C. After the completion of the reaction was confirmed, ethyl acetate (5 mL) was added thereto, and then the resulting mixture was filtered with a celite pad and concentrated under reduced pressure. The residue was separated by silica gel column chromatography (ethyl acetate:dichloromethane:methanol=6:1:1) to obtain 16 mg (53%) of a yellow solid.

5aica: $^1$H-NMR (300 MHz, CDCl$_3$) δ 1.34-1.63 (m, 5H), 1.97-2.10 (m, 4H), 2.26-2.43 (m, 3H), 2.61 (t, J=4.6 Hz, 4H), 3.67-3.78 (m, 7H), 4.24-4.38 (m, 1H), 5.01 (d, J=7.7 Hz, 1H), 5.58 (s, 2H), 6.78-6.85 (m, 2H), 7.00 (s, 1H), 7.19 (d, J=8.6 Hz, 2H), 7.33 (dd, J=8.6, 1.9 Hz, 1H), 7.43 (d, J=8.9 Hz, 1H), 7.59-7.65 (m, 1H), 7.73 (s, 1H), 8.61 (s, 1H).

Step 4. Preparation of Compound 5aicaa

Compound 5aica (16 mg, 0.02 mmol) was reacted in a manner similar to Step 4 of Example 57 to prepare 4.5 mg (35%) of a white solid.

5aicaa: $^1$H-NMR (500 MHz, DMSO-d$_6$) δ 1.36-1.50 (m, 4H), 1.55-1.68 (m, 3H), 1.93-2.02 (m, 3H), 2.03-2.09 (m, 3H), 2.21 (s, 3H), 3.59-3.69 (m, 4H), 4.28-4.35 (m, 1H), 6.77 (d, J=8.2 Hz, 1H), 7.43 (s, 1H), 7.53 (d, J=1.1 Hz, 2H), 8.08-8.09 (m, 1H), 8.36 (s, 1H), 8.45 (s, 1H), 12.01 (s, 1H).

[Example 60] Preparation of 6-(5-fluoro-1-methyl-1H-pyrazol-4-yl)-N-(trans-4-morpholinocyclohexyl)-9H-pyrimido[4,5-b]indole-4-amine (Compound 5aicba)

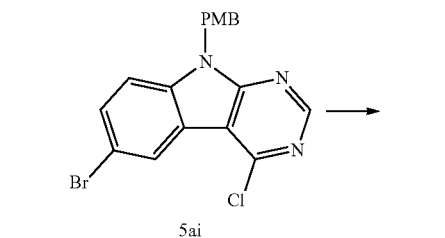

4a

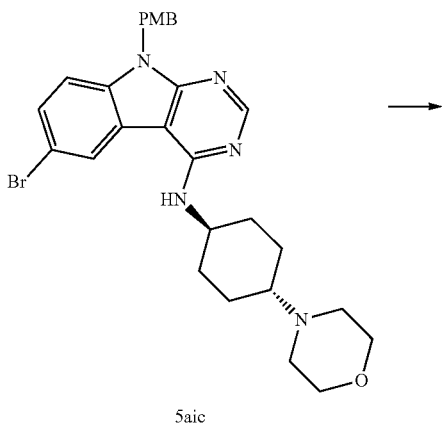

5ai

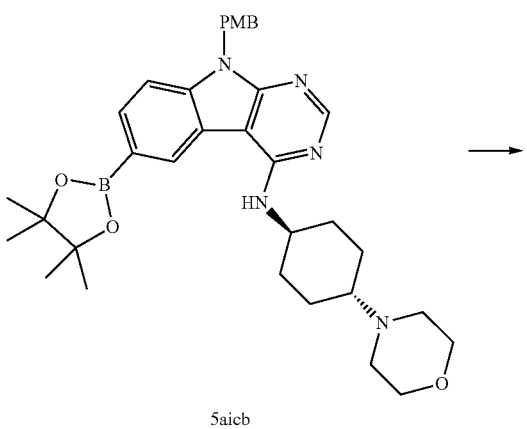

5aic

5aicb

-continued

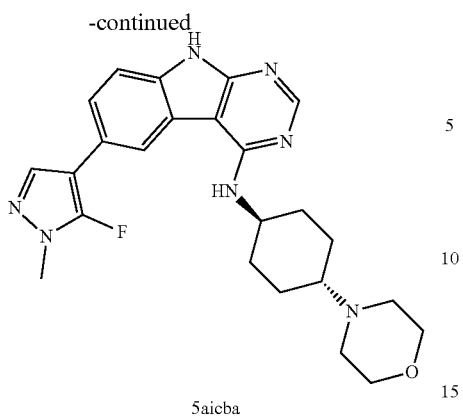

5aicba

Step 3. Preparation of Compound 5aicb

After Compound 5aic (68 mg, 0.123 mmol), bis(pinacolato)diboron (Pin2B)(42 mg, 0.165 mmol), and potassium acetate (AcOK)(36 mg, 0.366 mmol) were put into 1,4-dioxane (2.3 mL), the resulting mixture was degassed. Pd(dppf)Cl$_2$ (9 mg, 0.0123 mmol) was added thereto, and the resulting mixture was degassed, and then stirred at 90° C. After the completion of the reaction was confirmed, ethyl acetate (5 mL) was added thereto, and then the resulting mixture was filtered with a celite pad and concentrated under reduced pressure. The residue was separated by silica gel column chromatography (ethyl acetate:hexane=3:1) to obtain 52 mg (71%) of a white solid.

5aicb: $^1$H-NMR (300 MHz, CDCl$_3$) δ 1.23-1.31 (m, 4H), 1.39 (s, 12H), 1.43-1.54 (m, 4H), 2.00-2.01 (m, 2H), 2.31-2.46 (m, 3H), 2.62 (t, J=4.4 Hz, 4H), 3.73 (s, 3H), 3.74-3.79 (m, 4H), 4.24-4.39 (m, 1H), 5.17 (d, J=8.0 Hz, 1H), 5.56 (s, 2H), 6.77 (d, J=8.6 Hz, 2H), 7.15 (d, J=8.6 Hz, 2H), 7.39 (d, J=8.3 Hz, 1H), 7.84 (d, J=8.2 Hz, 1H), 8.14 (s, 1H), 8.57 (s, 1H). 8.2 Hz, 1H), 8.14 (s, 1H), 8.57 (s, 1H).

Step 4. Preparation of Compound 5aicba

After 5-fluoro-4-iodo-1-methyl-1H-pyrazole (18 mg, 0.085 mmol), Compound 5aicb (35 mg, 0.06 mmol), and K$_2$CO$_3$ (37 mg, 0.26 mmol) were dissolved in dioxane:H$_2$O (4:1 in v/v, 3 mL), the resulting solution was degassed. Pd(PPh$_3$)$_4$ (6 mg, 5.0 mol %) was added thereto, and the resulting mixture was degassed, and then stirred at 90° C. After the completion of the reaction was confirmed, ethyl acetate (5 mL) was added thereto, the resulting mixture was filtered with a celite pad, and then washed with water (5 mL), and the aqueous layer was again extracted with ethyl acetate (3 mL). After the ethyl acetate layer was combined, the resulting mixture was washed with water (5 mL), moisture was removed with sodium sulfate (Na$_2$SO$_4$), and the resulting product was concentrated under reduced pressure. The residue was separated by silica gel column chromatography (ethyl acetate:hexane=5:1) to obtain 25 mg of a white solid.

The white solid compound was added to 2 mL of trifluoroacetic acid, 0.2 mL of methanesulfonic acid was added thereto, and then the resulting mixture was stirred at 60° C. for 14 hours. The reaction product was concentrated under reduced pressure, then neutralized with an aqueous sodium bicarbonate solution, and extracted with ethyl acetate (2×3 mL). After the ethyl acetate layer was combined, the resulting mixture was washed with water (5 mL), moisture was removed with sodium sulfate (Na$_2$SO$_4$), and the resulting product was concentrated under reduced pressure. The residue was separated by silica gel column chromatography (ethyl acetate:dichloromethane:methanol=6:1:1) to obtain 10 mg (37%) of a white solid.

[Example 61] Preparation of 2-morpholino-N-(trans-4-morpholinocyclohexyl)-5H-pyrrolo[2,3-d:4,5-d']dipyrimidine-9-amine (Compound 47a)

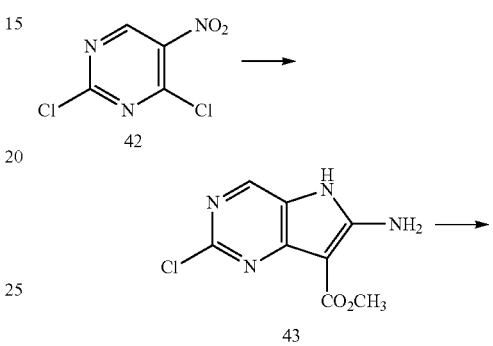

42

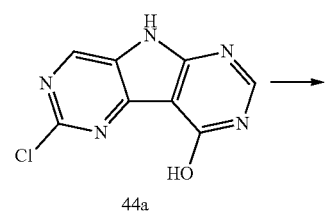

43

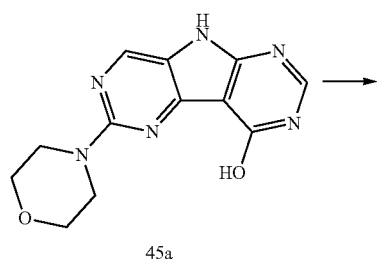

44a

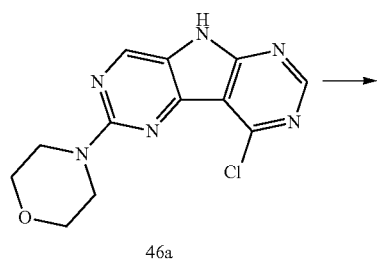

45a

46a

-continued

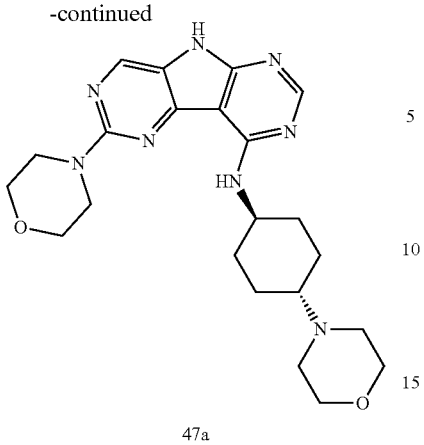

47a

Step 1. Preparation of Compound 43

Compound 42 (2,4-dichloro-5-nitropyrimidine)(9.4 g, 48.76 mmol) was reacted in a manner similar to Step 1 of Example 46 to prepare 5.19 g (45%) of a brown solid.

43: $^1$H-NMR (500 MHz, DMSO-$d_6$) δ 3.76 (s, 3H), 7.63 (s, 2H), 8.16 (s, 1H), 11.17 (s, 1H).

Step 2. Preparation of Compound 44a

Compound 43 (350 mg, 1.54 mmol) was reacted in a manner similar to Step 2 of Example 46 to prepare 495 mg (100%) of a brown solid.

44a: $^1$H-NMR (500 MHz, DMSO-$d_6$) δ 8.36 (s, 1H), 8.87 (s, 1H), 12.72 (s, 2H).

Step 3. Preparation of Compound 45a

After Compound 44a (200 mg, 0.90 mmol), morpholine (0.12 mL, 1.35 mmol), and K$_2$CO$_3$ (249 mg, 1.80 mmol) were dissolved in dimethyl sulfoxide (DMSO)(3 mL), the resulting solution was stirred at 190° C. for 30 minutes. After the completion of the reaction was confirmed, ethyl acetate (5 mL) was added thereto, then the resulting mixture was washed with water (5 mL), and the aqueous layer was again extracted with ethyl acetate (2×5 mL). After the ethyl acetate layer was combined, the resulting mixture was washed with water (2×5 mL), moisture was removed with sodium sulfate (Na$_2$SO$_4$), and the resulting product was concentrated under reduced pressure. The residue was separated by silica gel column chromatography (ethyl acetate:dichloromethane:methanol=10:1:1) to obtain 157 mg (63%) of a yellow solid.

45a: $^1$H-NMR (500 MHz, DMSO-$d_6$) δ 3.56-3.59 (t, J=5.0 Hz, 4H), 3.67 (t, J=4.9 Hz, 4H), 8.17 (s, 1H), 8.59 (s, 1H), 12.21 (s, 2H).

Step 4. Preparation of Compound 46a

Compound 45a (157 mg, 0.57 mmol) was reacted in a manner similar to Step 3 of Example 46 to prepare 10.0 mg (5.9%) of a yellow solid.

46a: $^1$H-NMR (300 MHz, DMSO-$d_6$) δ 3.70-3.75 (m, 5H), 3.76-3.80 (m, 4H), 8.83 (s, 1H), 8.87 (s, 1H).

Step 5. Preparation of Compound 47a

Compound 46a (8.0 mg, 0.02 mmol) was reacted in a manner similar to Step 4 of Example 46 to prepare 8.9 mg (73%) of a light yellow solid.

47a: $^1$H-NMR (300 MHz, DMSO-$d_6$) δ 1.27-1.57 (m, 7H), 1.82-1.95 (m, 3H), 2.07-2.18 (m, 3H), 2.21-2.33 (m, 2H), 3.57 (t, J=4.6 Hz, 4H), 3.68-3.76 (m, 6H), 3.98-4.14 (m, 1H), 6.44 (d, J=8.1 Hz, 1H), 8.39 (s, 1H), 8.59 (s, 1H), 11.83 (s, 1H).

[Example 62] Preparation of 6-(4-ethoxy-3-pyridyl)-N-(trans-4-morpholinocyclohexyl)-6-(pyridin-4-yl)-9H-pyrimido[4,5-b]indole-4-amine (Compound 48a)

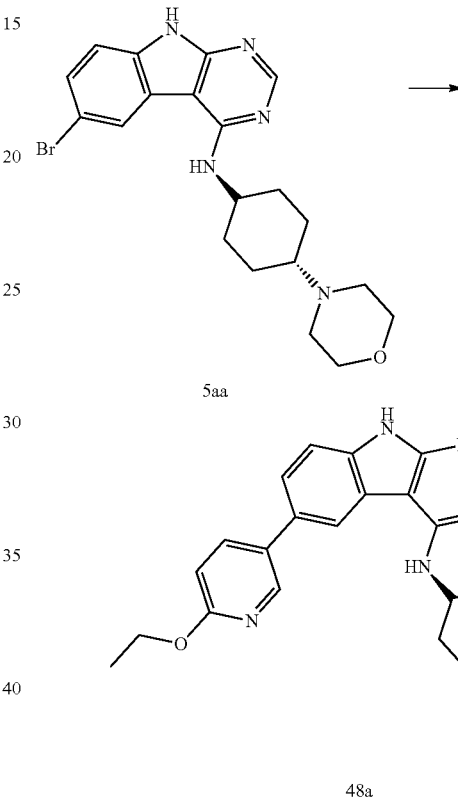

After Compound 5aa (55 mg, 0.13 mmol), 2-ethoxypyridine-5-boronic acid (25.6 mg, 0.15 mmol), and K$_2$CO$_3$ (53 mg, 0.38 mmol) were dissolved in dioxane:water (4:1 in v/v in 5 mL), the resulting solution was sufficiently deoxidized by argon gas. Then, Pd(PPh$_3$)$_4$ (4.4 mg, 0.0038 mmol) was added thereto, the gas was removed, and the resulting product was stirred at 80° C. for 15 hours. After the reaction was completed, the resulting product was diluted in ethyl acetate (30 mL) and filtered with a celite pad, and then washed with water (2×15 mL), and then moisture was removed with sodium sulfate (Na$_2$SO$_4$), and the resulting product was concentrated under reduced pressure. The residue was separated by silica gel column chromatography (dichloromethane:methanol=20:1→10:1.5) to obtain 12.2 mg (20%) of a light yellow solid.

48a: $^1$H-NMR (400 MHz, CD$_3$OD-$d_4$) δ 1.42 (t, J=7.2 Hz, 3H), 1.48-1.66 (m, 4H), 2.07-2.22 (m, 4H), 2.33-2.38 (m, 1H), 2.64-2.65 (m, 4H), 3.71-3.73 (m, 4H), 4.26-4.31 (m, 1H), 4.37 (q, J=7.1 Hz, 2H), 6.89 (d, J=8.4 Hz, 1H), 7.57-7.62 (m, 2H), 8.08 (dd, J=8.4, 2.8 Hz, 1H), 8.31 (s, 1H), 8.36 (s, 1H), 8.47 (d, J=2.4 Hz, 1H).

[Example 63] Preparation of 6-(3-methoxy-4-pyridyl)-N-(trans-4-morpholinocyclohexyl)-6-(pyridin-4-yl)-9H-pyrimido[4,5-b]indole-4-amine (Compound 49a)

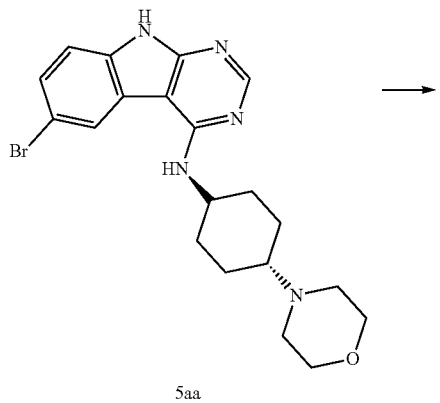

5aa

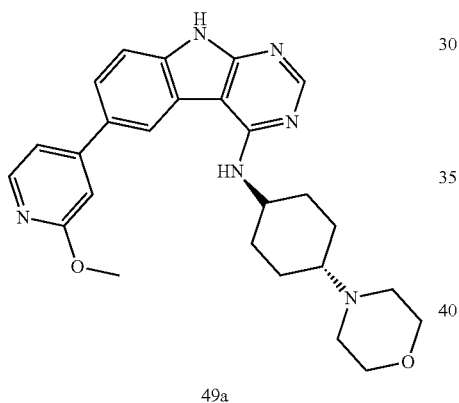

49a

[Example 64] Preparation of 6-(2-methoxy-3-pyridyl)-N-(trans-4-morpholinocyclohexyl)-6-(pyridin-4-yl)-9H-pyrimido[4,5-b]indole-4-amine (Compound 50a)

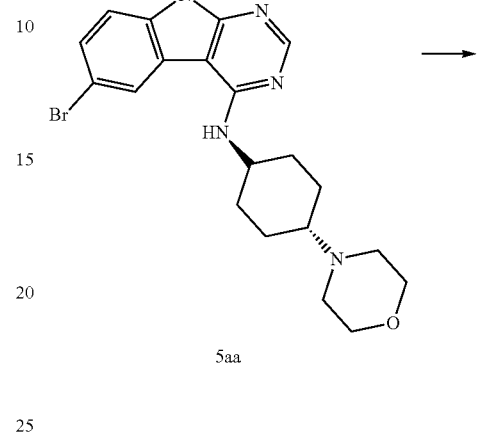

5aa

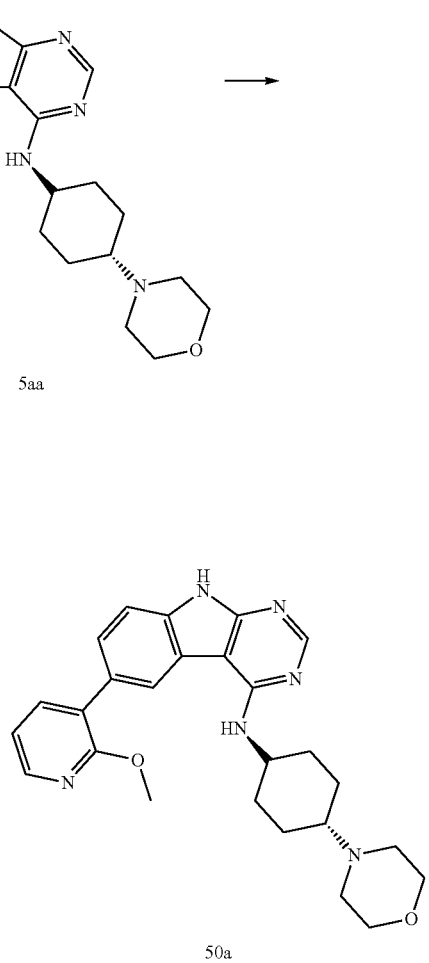

50a

After Compound 5aa (58 mg, 0.14 mmol), 2-methoxy-pyridine-4-boronic acid (62.4 mg, 0.41 mmol), and $K_3PO_4$ (86.6 mg, 0.41 mmol) were dissolved in ethanol:water (4:1 in v/v in 5 mL), oxygen was removed by sufficiently purging with argon gas, and then $Pd(PPh_3)_4$ (15.7 mg, 0.014 mmol) was added thereto, and the resulting mixture was stirred at 55° C. for 15 hours. After the reaction was completed, the reaction mixture was concentrated under reduced pressure, and then dissolved in ethyl acetate (30 mL), and filtered with a celite pad. After the filtrate was washed with water (2×15 mL), moisture was removed with sodium sulfate ($Na_2SO_4$), and the resulting product was concentrated under reduced pressure. The residue was separated by silica gel column chromatography (dichloromethane:methanol=20:1→10:1.5) to obtain 13.1 mg (21%) of a light yellow solid.

49a: $^1$H-NMR (400 MHz, $CD_3OD$-$d_4$) δ 1.48-1.67 (m, 4H), 2.08-2.23 (m, 4H), 2.33-2.40 (m, 1H), 2.64-2.66 (m, 4H), 3.71-3.74 (m, 4H), 3.97 (s, 3H), 4.27-4.34 (m, 1H), 7.24 (s, 1H), 7.42 (d, J=5.6 Hz, 1H), 7.61 (d, J=8.4 Hz, 1H), 7.77 (d, J=8.0 Hz, 1H), 8.17 (d, J=4.8 Hz, 1H), 8.32 (s, 1H), 8.53 (s, 1H).

After Compound 5aa (56 mg, 0.13 mmol), 2-methoxy-pyridine-3-boronic acid (99.4 mg, 0.65 mmol), and $K_3PO_4$ (137.9 mg, 0.65 mmol) were dissolved in 1,2-dimethoxy-ethane:ethanol:water (4:0.5:0.5 in v/v in 5 mL), oxygen was removed by purging with argon gas, and then $Pd(PPh_3)_4$ (15 mg, 0.013 mmol) was added thereto, and the resulting mixture was stirred at 60° C. for 15 hours. The reaction mixture was concentrated under reduced pressure, and then dissolved in ethyl acetate (30 mL), and filtered with a celite pad. After the filtrate was washed with water (2×15 mL), moisture was removed with sodium sulfate ($Na_2SO_4$), and the resulting product was concentrated under reduced pressure. The residue was separated by silica gel column chromatography (dichloromethane:methanol=20:1→10:1.5) to obtain 13.1 mg (22%) of a light yellow solid.

50a: $^1$H-NMR (400 MHz, $CD_3OD$-$d_4$) δ 1.44-1.57 (m, 4H), 2.03-2.20 (m, 4H), 2.33-2.39 (m, 1H), 2.64-2.66 (m, 4H), 3.70-3.73 (m, 4H), 3.95 (s, 3H), 4.21-4.27 (m, 1H), 7.04-7.07 (m, 1H), 7.52-7.60 (m, 2H), 7.82 (d, J=7.2 Hz, 1H), 8.12 (d, J=4.0 Hz, 1H), 8.26 (s, 1H), 8.31 (s, 1H).

[Example 65] Preparation of 6-(2-methylthio)-pyrimidinyl-N-(trans-4-morpholinocyclohexyl)-6-(pyridin-4-yl)-9H-pyrimido[4,5-b]indole-4-amine (Compound 51a)

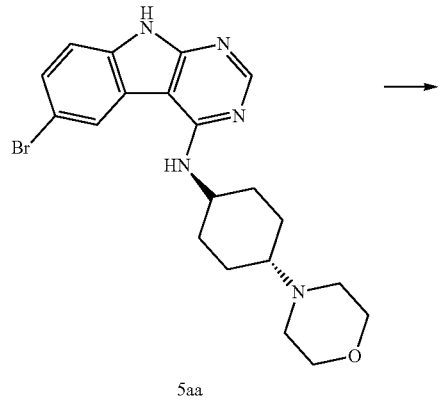

5aa

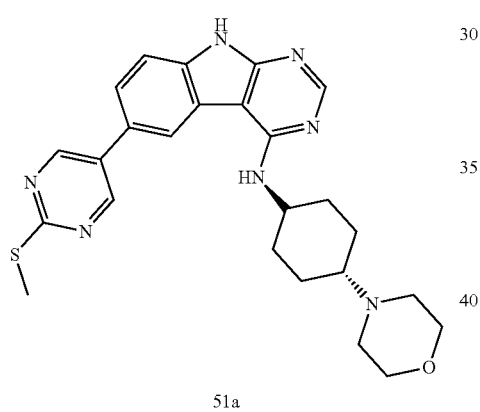

51a

After Compound 5aa (20 mg, 0.04 mmol), 2-(methylthio)-pyrimidinyl-5-boronic acid pinacol ester (10.1 mg, 0.04 mmol), and $K_2CO_3$ (16 mg, 0.12 mmol) were dissolved in dioxane:$H_2O$ (4:1 in v/v, 1 mL), oxygen was removed by purging with argon gas, Pd(PPh$_3$)$_4$ (2 mg, 0.002 mmol) was added thereto, and then gas was removed, and the resulting product was stirred at 80° C. for 18 hours. After the completion of the reaction was confirmed, ethyl acetate (10 mL) was added thereto, the resulting mixture was filtered with a celite pad and washed with water (2×10 mL), and then moisture was removed with sodium sulfate (Na$_2$SO$_4$), and the resulting product was concentrated under reduced pressure. The residue was separated by silica gel column chromatography (dichloromethane:methanol=20:1→10:1) to obtain 12 mg (58%) of a light yellow solid.

51a: $^1$H-NMR (400 MHz, DMSO-d$_6$) δ 1.33-1.41 (m, 2H), 1.58-1.67 (m, 2H), 1.91-2.07 (m, 4H), 2.26 (m, 1H), 2.59 (s, 3H), 3.35 (m, 4H), 3.57 (s, 4H), 4.33 (m, 1H), 6.72 (d, 1H), 7.55 (d, 1H), 7.75 (d, 1H), 8.34 (s, 1H), 8.60 (s, 1H), 9.12 (d, 2H), 12.04 (s, 1H).

[Example 66] Preparation of 6-(1-(cyclopropylmethyl)pyrazol)-N-(trans-4-morpholinocyclohexyl)-6-(pyridin-4-yl)-9H-pyrimido[4,5-b]indole-4-amine (Compound 52a)

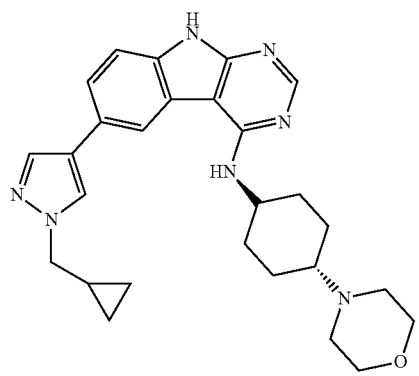

52a

Compound 5aa (60 mg, 0.12 mmol) and 1-(cyclopropylmethyl)pyrazole-4-boronic acid (24.9 mg, 0.15 mmol) were reacted in the same manner as in Example 65, and the residue after reaction was separated by silica gel column chromatography (dichloromethane:methanol=20:1→10:1) to obtain 40 mg (70%) of a white solid.

52a: $^1$H-NMR (400 MHz, DMSO-d$_6$) δ 0.45 (m, 2H), 0.55 (m, 2H), 1.28 (m, 1H), 1.33-1.41 (m, 2H), 1.60-1.68 (m, 2H), 1.91-2.07 (m, 4H), 2.26 (m, 1H), 3.37 (m, 4H), 3.57 (s, 4H), 4.03 (d, 2H), 4.33 (m, 1H), 6.72 (d, 1H), 7.41 (d, 1H), 7.56 (d, 1H), 7.97 (s, 1H), 8.17 (s, 1H), 8.32 (s, 1H), 8.37 (s, 1H), 11.83 (s, 1H).

[Example 67] Preparation of 6-(3-pyrrolo)-N-(trans-4-morpholinocyclohexyl)-6-(pyridin-4-yl)-9H-pyrimido[4,5-b]indole-4-amine (Compound 53a)

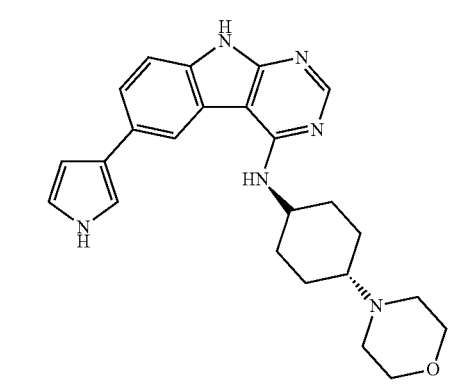

53a

Compound 5aa (60 mg, 0.12 mmol) and pyrrole-3-boronic acid, pinacole ester (28.9 mg, 0.15 mmol) were reacted in the same manner as in Example 65, and the residue after reaction was separated by silica gel column chromatography (dichloromethane:methanol=20:1→10:1) to obtain 42 mg (84%) of a white solid.

53a: $^1$H-NMR (400 MHz, DMSO-d$_6$) δ 1.33-1.41 (m, 2H), 1.60-1.68 (m, 2H), 1.91-2.07 (m, 4H), 2.25 (m, 1H), 3.36 (m, 4H), 3.58 (s, 4H), 4.25 (m, 1H), 6.54 (s, 1H), 6.66

(d, 1H), 6.81 (s, 1H), 7.21 (s, 1H), 7.35 (d, 1H), 7.55 (d, 1H), 8.30 (s, 2H), 10.87 (s, 1H), 11.71 (s, 1H).

[Example 68] Preparation of 6-(4-methylamino-3-phenyl)-N-(trans-4-morpholinocyclohexyl)-6-(pyridin-4-yl)-9H-pyrimido[4,5-b]indole-4-amine (Compound 54a)

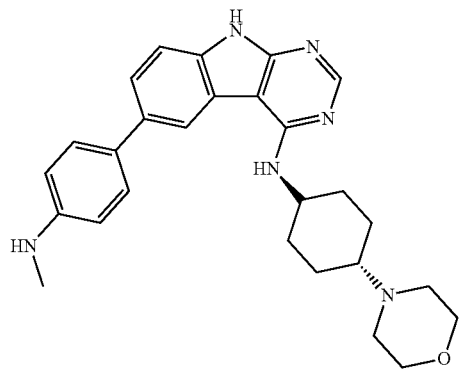

54a

Compound 5aa (60 mg, 0.12 mmol) and 4-(N-methylamino)phenyl boronic acid, pinacol ester (33.5 mg, 0.16 mmol) were reacted in the same manner as in Example 65, and the residue after reaction was separated by silica gel column chromatography (dichloromethane:methanol=20:1→10:1) to obtain 54 mg (78%) of a white solid.

54a: $^1$H-NMR (400 MHz, DMSO-$d_6$) δ 1.33-1.41 (m, 2H), 1.60-1.65 (m, 2H), 1.90-2.02 (m, 4H), 2.25 (m, 1H), 3.36 (m, 4H), 3.58 (s, 4H), 4.25 (m, 1H), 4.52 (s, 3H), 5.72 (brs, 1H), 6.54 (s, 1H), 6.66 (d, 1H), 6.81 (s, 1H), 7.18 (m, 2H), 7.21 (s, 1H), 7.25 (m, 2H), 7.35 (d, 1H), 7.55 (d, 1H), 10.87 (s, 1H), 11.71 (s, 1H).

[Example 69] Preparation of 6-(1-(1-ethoxyethyl)-1H-pyrazol)-N-(trans-4-morpholinocyclohexyl)-6-(pyridin-4-yl)-9H-pyrimido[4,5-b]indole-4-amine (Compound 55a)

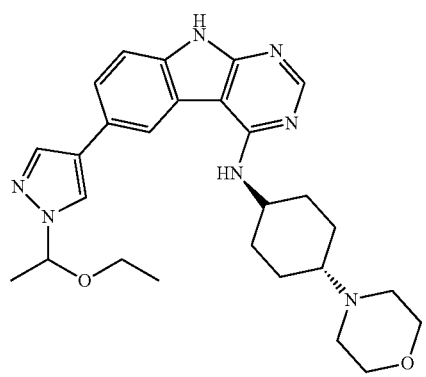

55a

Compound 5aa (60 mg, 0.12 mmol) and 1-(1-ethoxyethyl)-1H-pyrazole-4-boronic acid pinacol ester (36.2 mg, 0.15 mmol) were reacted in the same manner as in Example 65, and the residue after reaction was separated by silica gel column chromatography (dichloromethane:methanol=20:1→10:1) to obtain 36 mg (52%) of a white solid.

55a: $^1$H-NMR (400 MHz, DMSO-$d_6$) δ 1.06 (m, 3H), 1.35-1.38 (m, 2H), 1.66 (m, 5H), 1.94-2.06 (m, 4H), 2.25 (m, 1H), 3.45 (m, 1H), 3.47 (m, 2H), 3.58 (m, 4H), 4.25 (m, 1H), 5.58 (m, 1H), 6.65 (brd, 1H), 7.43 (d, 1H), 7.61 (d, 1H), 8.05 (s, 1H), 8.32 (d, 2H), 8.40 (s, 1H), 11.85 (s, 1H).

[Example 70] Preparation of 6-(2-methoxypyrimidyl)-N-(trans-4-morpholinocyclohexyl)-6-(pyridin-4-yl)-9H-pyrimido[4,5-b]indole-4-amine (Compound 56a)

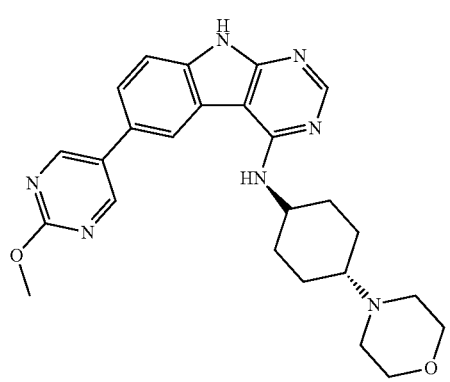

56a

Compound 5aa (60 mg, 0.12 mmol) and 2-methoxypyrimidine-5-boronic acid (25.3 mg, 0.15 mmol) were reacted in the same manner as in Example 65, and the residue after reaction was separated by silica gel column chromatography (dichloromethane:methanol=20:1→10:1) to obtain 36 mg (52%) of a white solid.

56a: $^1$H-NMR (400 MHz, DMSO-$d_6$) δ 1.36-1.38 (m, 2H), 1.66 (m, 4H), 1.91-1.94 (m, 4H), 2.26 (m, 1H), 3.58 (m, 4H), 3.99 (s, 3H), 4.31 (m, 1H), 6.73 (d, 1H), 7.55 (d, 1H), 7.71 (d, 1H), 8.35 (s, 1H), 8.43 (s, 1H), 8.56 (s, 1H), 8.82 (s, 1H), 9.06 (s, 2H), 12.00 (s, 1H).

[Example 71] Preparation of 6-(3-thiophen)-N-(trans-4-morpholinocyclohexyl)-6-(pyridin-4-yl)-9H-pyrimido[4,5-b]indole-4-amine (Compound 57a)

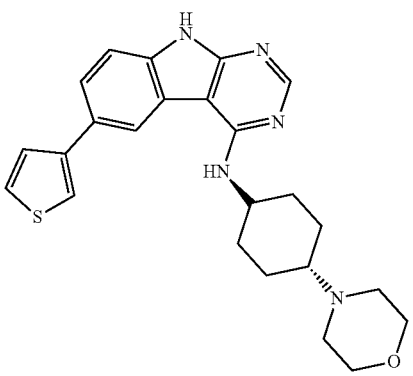

57a

Compound 5aa (60 mg, 0.12 mmol) and thiophene-3-boronic acid (22.5 mg, 0.15 mmol) were reacted in the same manner as in Example 65, and the residue after reaction was separated by silica gel column chromatography (dichloromethane:methanol=20:1→10:1) to obtain 29 mg (48%) of a white solid.

57a: ¹H-NMR (400 MHz, DMSO-d$_6$) δ 1.36-1.38 (m, 2H), 1.62-1.65 (m, 2H), 1.91-1.93 (m, 4H), 2.08 (m, 1H), 3.56 (m, 4H), 4.29 (m, 1H), 6.77 (d, 1H), 7.46 (d, 1H), 7.68 (m, 1H), 7.71 (m, 2H), 7.87 (d, 1H), 8.33 (s, 1H), 8.52 (s, 1H), 11.90 (s, 1H).

[Example 72] Preparation of 6-(3-chlorophenyl)-N-(trans-4-morpholinocyclohexyl)-6-(pyridin-4-yl)-9H-pyrimido[4,5-b]indole-4-amine (Compound 58a)

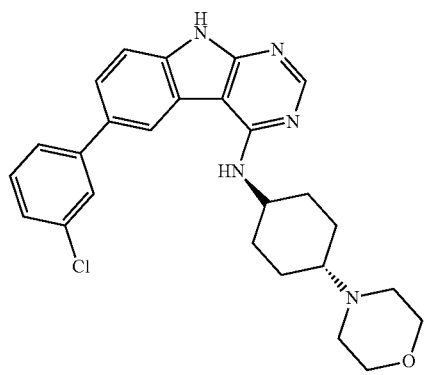

58a

Compound 5aa (60 mg, 0.12 mmol) and 3-chlorophenyl boronic acid (26.7 mg, 0.15 mmol) were reacted in the same manner as in Example 65, and the residue after reaction was separated by silica gel column chromatography (dichloromethane:methanol=20:1→10:1) to obtain 38 mg (55%) of a white solid.

58a: ¹H-NMR (400 MHz, DMSO-d$_6$) δ 1.34-1.37 (m, 2H), 1.62-1.65 (m, 2H), 1.90-1.93 (m, 4H), 2.25 (m, 1H), 3.56 (m, 4H), 4.28 (m, 1H), 6.87 (d, 1H), 7.42 (d, 1H), 7.50 (m, 2H), 7.66 (d, 1H), 7.83 (d, 1H), 7.84 (s, 1H), 8.35 (s, 1H), 8.55 (s, 1H), 11.98 (s, 1H).

[Example 73] Preparation of 6-(3,4-dimethoxyphenyl)-N-(trans-4-morpholinocyclohexyl)-6-(pyridin-4-yl)-9H-pyrimido[4,5-b]indole-4-amine (Compound 59a)

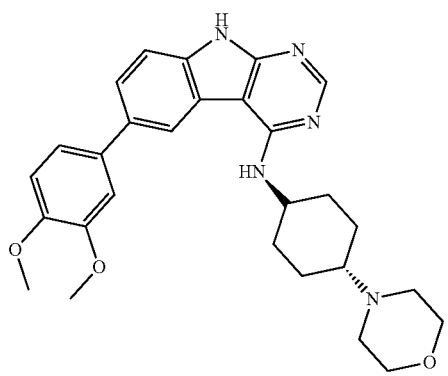

59a

Compound 5aa (60 mg, 0.12 mmol) and 3,4-dimethoxyphenyl boronic acid (33.2 mg, 0.15 mmol) were reacted in the same manner as in Example 65, and the residue after reaction was separated by silica gel column chromatography (dichloromethane:methanol=20:1→10: 1) to obtain 29 mg (45%) of a white solid.

59a: ¹H-NMR (400 MHz, DMSO-d$_6$) δ 1.34-1.37 (m, 2H), 1.62-1.65 (m, 2H), 1.90-1.93 (m, 4H), 2.25 (m, 1H), 3.57 (m, 4H), 3.80 (s, 3H), 3.88 (s, 3H), 4.28 (m, 1H), 6.80 (d, 1H), 7.07 (d, 1H), 7.30 (m, 1H), 7.49 (d, 1H), 7.64 (d, 1H), 8.33 (s, 1H), 8.47 (s, 1H), 11.88 (s, 1H).

[Example 74] Preparation of 6-(4-methanesulfonyl-3-methylphenyl)-N-(trans-4-morpholinocyclohexyl)-6-(pyridin-4-yl)-9H-pyrimido[4,5-b]indole-4-amine (Compound 60a)

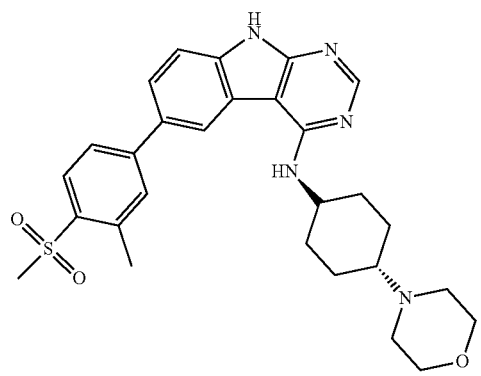

60a

Compound 5aa (60 mg, 0.12 mmol) and (4-methanesulfonyl-3-methylphenyl)boronic acid (33.2 mg, 0.15 mmol) were reacted in the same manner as in Example 65, and the residue after reaction was separated by silica gel column chromatography (dichloromethane:methanol=20:1→10:1) to obtain 28 mg (51%) of a white solid.

60a: ¹H-NMR (400 MHz, DMSO-d$_6$) δ 1.34-1.37 (m, 2H), 1.59-1.65 (m, 2H), 1.91-1.93 (m, 4H), 2.25 (m, 1H), 2.75 (s, 3H), 3.25 (s, 3H), 3.57 (m, 4H), 4.28 (m, 1H), 6.85 (d, 1H), 7.72 (d, 1H), 7.74 (d, 1H), 7.86 (m, 2H), 7.98 (d, 1H), 8.36 (s, 1H), 8.60 (s, 1H), 12.04 (s, 1H).

[Example 75] Preparation of 6-(4-dimethylsulfonamidyl phenyl)-N-(trans-4-morpholinocyclohexyl)-6-(pyridin-4-yl)-9H-pyrimido[4,5-b]indole-4-amine (Compound 61a)

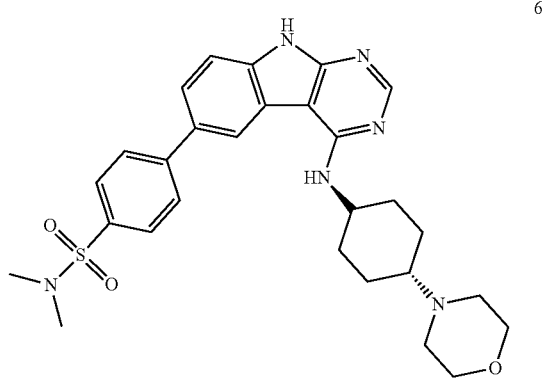

61a

Compound 5aa (60 mg, 0.12 mmol) and N,N-dimethyl-4-boron benzenesulfonamide (45.5 mg, 0.15 mmol) were reacted in the same manner as in Example 65, and the residue after reaction was separated by silica gel column chromatography (dichloromethane:methanol=20:1→10:1) to obtain 58 mg (63%) of a white solid.

61a: $^1$H-NMR (400 MHz, DMSO-$d_6$) δ 1.34-1.37 (m, 2H), 1.59-1.65 (m, 2H), 1.91-1.93 (m, 4H), 2.25 (m, 1H), 2.66 (s, 6H), 3.56 (m, 4H), 4.28 (m, 1H), 6.89 (d, 1H), 7.73 (d, 1H), 7.75 (d, 1H), 7.84 (m, 2H), 7.86 (m, 2H), 8.06 (s, 1H), 8.64 (s, 1H), 12.04 (s, 1H).

[Example 76] Preparation of 6-(2-dimethylaminophenyl)-N-(trans-4-morpholinocyclohexyl)-6-(pyridin-4-yl)-9H-pyrimido[4,5-b]indole-4-amine (Compound 62a)

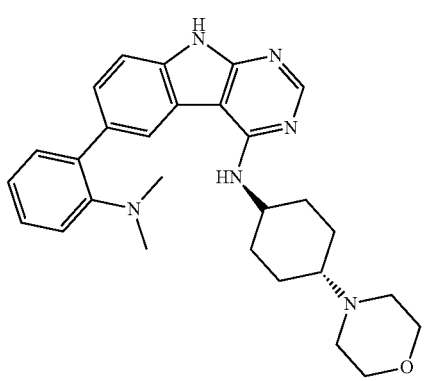

62a

Compound 5aa (60 mg, 0.12 mmol) and 2-dimethylaminophenyl boronic acid pinacol ester (58.6 mg, 0.15 mmol) were reacted in the same manner as in Example 65, and the residue after reaction was separated by silica gel column chromatography (dichloromethane:methanol=20:1→10:1) to obtain 45 mg (56%) of a white solid.

62a: $^1$H-NMR (400 MHz, DMSO-$d_6$) δ 1.34-1.37 (m, 2H), 1.59-1.65 (m, 2H), 1.91-1.93 (m, 4H), 2.25 (m, 1H), 2.46 (s, 6H), 3.56 (m, 4H), 4.28 (m, 1H), 6.72 (d, 1H), 7.09 (m, 2H), 7.27 (m, 2H), 7.42 (d, 1H), 7.56 (d, 1H), 8.32 (s, 1H), 8.40 (s, 1H), 11.85 (s, 1H).

[Example 77] Preparation of 6-(4-amino-3-pyridyl)-N-(trans-4-morpholinocyclohexyl)-6-(pyridin-4-yl)-9H-pyrimido[4,5-b]indole-4-amine (Compound 63a)

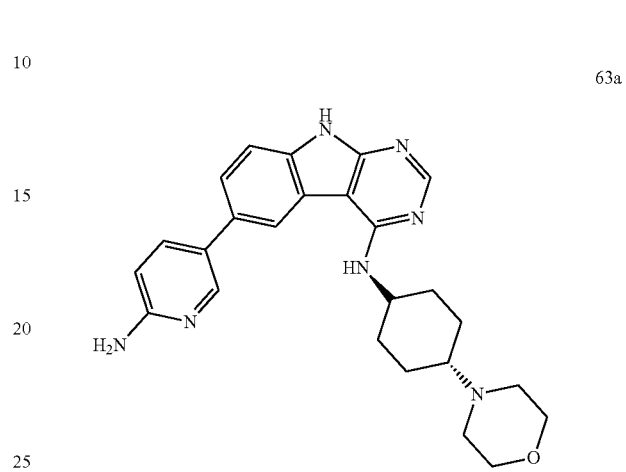

63a

Compound 5aa (60 mg, 0.12 mmol) and 2-aminopyridine boronic acid (28.5 mg, 0.15 mmol) were reacted in the same manner as in Example 65, and the residue after reaction was separated by silica gel column chromatography (dichloromethane:methanol=20:1→10:1) to obtain 18 mg (32%) of a white solid.

63a: $^1$H-NMR (400 MHz, DMSO-$d_6$) δ 1.33-1.36 (m, 2H), 1.59-1.63 (m, 2H), 1.89-1.92 (m, 4H), 2.26 (m, 1H), 3.57 (m, 4H), 4.28 (m, 1H), 5.90 (s, 1H), 6.87 (d, 1H), 7.39 (d, 1H), 7.46 (d, 1H), 8.33 (s, 2H), 12.03 (brs, 1H).

[Example 78] Preparation of 6-(4-amino-2-chlorophenyl)-N-(trans-4-morpholinocyclohexyl)-6-(pyridin-4-yl)-9H-pyrimido[4,5-b]indole-4-amine (Compound 64a)

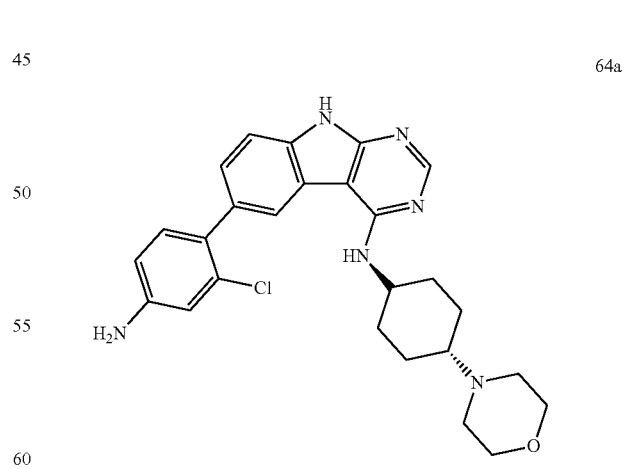

64a

Compound 5aa (60 mg, 0.12 mmol) and 4-amino-2-chlorophenyl boronic acid (41.2 mg, 0.15 mmol) were reacted in the same manner as in Example 65, and the residue after reaction was separated by silica gel column chromatography (dichloromethane:methanol=20:1→10:1) to obtain 33 mg (52%) of a white solid.

64a: ¹H-NMR (400 MHz, DMSO-d₆) δ 1.33-1.37 (m, 2H), 1.59-1.63 (m, 2H), 1.86-1.89 (m, 4H), 2.22 (m, 1H), 3.57 (m, 4H), 4.27 (m, 1H), 5.43 (s, 2H), 6.63 (d, 1H), 6.69 (d, 1H), 6.72 (s, 1H), 7.14 (d, 1H), 7.41 (d, 1H), 7.43 (d, 1H), 8.27 (s, 1H), 8.31 (s, 1H), 11.85 (s, 1H).

[Example 79] Preparation of 6-(3-fluoro-4-(methylsulfonyl)phenyl)-N-(trans-4-morpholinocyclohexyl)-6-(pyridin-4-yl)-9H-pyrimido[4,5-b]indole-4-amine (Compound 65a)

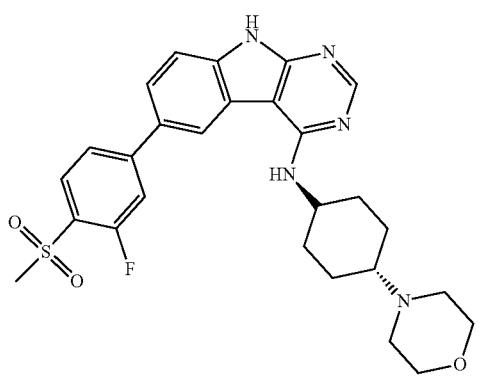

65a

Compound 5aa (60 mg, 0.12 mmol) and 3-fluoro-4-(methylsulfonyl)phenyl boronic acid (42.3 mg, 0.15 mmol) were reacted in the same manner as in Example 65, and the residue after reaction was separated by silica gel column chromatography (dichloromethane:methanol=20:1→10:1) to obtain 44 mg (56%) of a white solid.

65a: ¹H-NMR (400 MHz, DMSO-d₆) δ 1.32-1.37 (m, 2H), 1.59-1.63 (m, 2H), 1.86-1.89 (m, 4H), 2.22 (m, 1H), 3.57 (m, 4H), 3.72 (s, 3H), 4.29 (m, 1H), 6.85 (d, 1H), 7.56 (d, 1H), 7.82 (d, 1H), 7.01 (m, 3H), 8.42 (s, 1H), 8.83 (s, 1H), 12.09 (s, 1H).

[Example 80] Preparation of 6-(2-methyl-4-pyridyl)-N-(trans-4-morpholinocyclohexyl)-6-(pyridin-4-yl)-9H-pyrimido[4,5-b]indole-4-amine (Compound 66a)

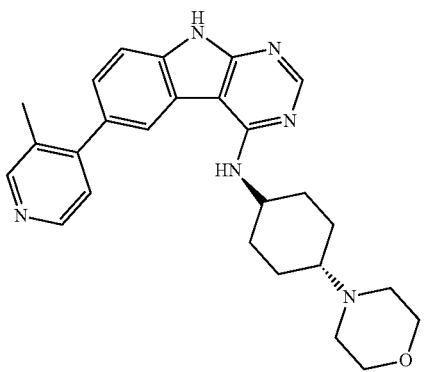

66a

Compound 5aa (60 mg, 0.12 mmol) and 3-picoline-4-boronic acid (35.3 mg, 0.16 mmol) were reacted in the same manner as in Example 65, and the residue after reaction was separated by silica gel column chromatography (dichloromethane:methanol=20:1→10:1) to obtain 35 mg (42%) of a white solid.

66a: ¹H-NMR (400 MHz, DMSO-d₆) δ 1.32-1.37 (m, 2H), 1.59-1.63 (m, 2H), 1.86-1.89 (m, 4H), 2.22 (m, 1H), 2.45 (s, 3H), 3.57 (m, 7H), 4.29 (m, 1H), 6.85 (d, 1H), 7.56 (m, 2H), 7.66 (d, 1H), 8.26 (s, 2H), 8.30 (s, 1H), 8.50 (d, 1H), 8.60 (s, 1H), 12.01 (s, 1H).

[Example 81] Preparation of 6-(3-hydroxy phenyl)-N-(trans-4-morpholinocyclohexyl)-6-(pyridin-4-yl)-9H-pyrimido[4,5-b]indole-4-amine (Compound 67a)

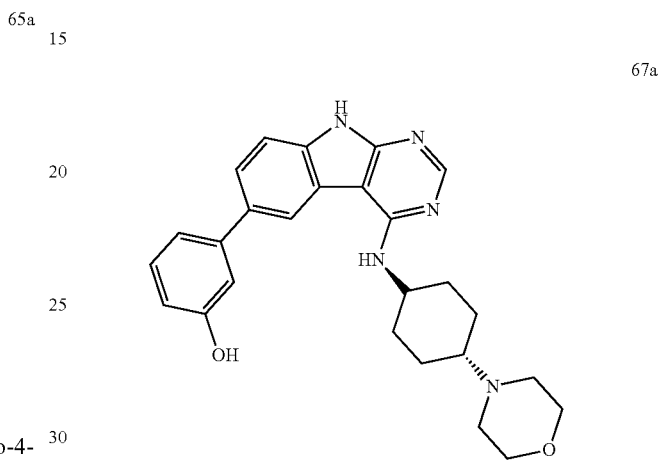

67a

Compound 5aa (60 mg, 0.12 mmol) and 3-hydroxy phenyl boronic acid (33.2 mg, 0.15 mmol) were reacted in the same manner as in Example 65, and the residue after reaction was separated by silica gel column chromatography (dichloromethane:methanol=20:1→10:1) to obtain 40 mg (61%) of a white solid.

67a: ¹H-NMR (400 MHz, DMSO-d₆) δ 1.31-1.35 (m, 2H), 1.59-1.63 (m, 2H), 1.86-1.89 (m, 4H), 2.22 (m, 1H), 3.57 (m, 4H), 4.29 (m, 1H), 6.85 (d, 1H), 6.95 (d, 1H), 7.26 (m, 2H), 7.33 (m, 1H), 7.52 (d, 1H), 7.60 (d, 1H), 8.26 (s, 1H), 8.50 (s, 1H), 9.50 (s, 1H), 11.90 (s, 1H).

[Example 82] Preparation of 6-(3-formyl phenyl)-N-(trans-4-morpholinocyclohexyl)-6-(pyridin-4-yl)-9H-pyrimido[4,5-b]indole-4-amine (Compound 68a)

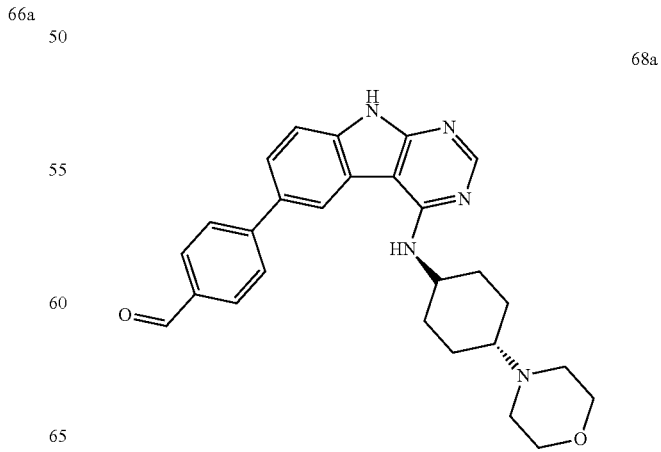

68a

Compound 5aa (60 mg, 0.12 mmol) and 3-formylphenylboronic acid (35.2 mg, 0.15 mmol) were reacted in the same manner as in Example 65, and the residue after reaction was separated by silica gel column chromatography (dichloromethane:methanol=20:1→10:1) to obtain 38 mg (59%) of a white solid.

68a: ¹H-NMR (400 MHz, DMSO-$d_6$) δ 1.31-1.35 (m, 2H), 1.59-1.63 (m, 2H), 1.86-1.89 (m, 4H), 2.22 (m, 1H), 3.57 (m, 4H), 4.29 (m, 1H), 6.85 (d, 1H), 7.52 (d, 1H), 7.60 (d, 1H), 8.02 (m, 4H), 8.33 (s, 1H), 8.72 (s, 1H), 10.06 (s, 1H), 12.04 (s, 1H).

[Example 83] Preparation of 6-(3-N-methylaminocarbonyl)phenyl)-N-(trans-4-morpholinocyclohexyl)-6-(pyridin-4-yl)-9H-pyrimido[4,5-b]indole-4-amine (Compound 69a)

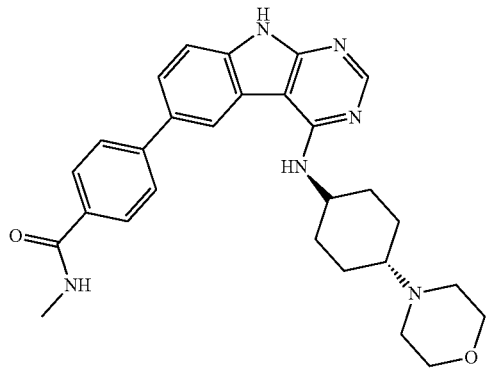

69a

Compound 5aa (60 mg, 0.12 mmol) and 3-(N-methylaminocarbonyl)phenyl boronic acid (40.2 mg, 0.15 mmol) were reacted in the same manner as in Example 65, and the residue after reaction was separated by silica gel column chromatography (dichloromethane:methanol=20:1→10:1) to obtain 25 mg (43%) of a white solid.

69a: ¹H-NMR (400 MHz, DMSO-$d_6$) δ 1.31-1.35 (m, 2H), 1.59-1.63 (m, 2H), 1.86-1.89 (m, 4H), 2.22 (m, 1H), 3.57 (m, 4H), 4.29 (m, 1H), 6.85 (d, 1H), 7.52 (d, 1H), 7.60 (d, 1H), 7.70 (d, 1H), 7.82 (d, 1H), 7.95 (d, 1H), 8.2 (s, 1H), 8.40 (s, 1H), 8.62 (s, 2H), 11.96 (s, 1H).

[Example 84] Preparation of 6-(4-fluoro-3-(hydroxymethyl)-N-(trans-4-morpholinocyclohexyl)-6-(pyridin-4-yl)-9H-pyrimido[4,5-b]indole-4-amine (Compound 70a)

70a

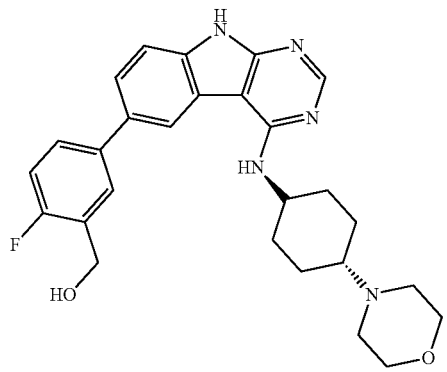

Compound 5aa (60 mg, 0.12 mmol) and 4-fluoro-3-(hydroxymethyl)phenyl boronic acid (45.3 mg, 0.15 mmol) were reacted in the same manner as in Example 65, and the residue after reaction was separated by silica gel column chromatography (dichloromethane:methanol=20:1→10:1) to obtain 33 mg (51%) of a white solid.

70a: ¹H-NMR (400 MHz, DMSO-$d_6$) δ 1.31-1.35 (m, 2H), 1.59-1.63 (m, 2H), 1.86-1.89 (m, 4H), 2.22 (m, 1H), 3.57 (m, 4H), 4.29 (m, 1H), 5.26 (t, 1H), 6.85 (d, 1H), 7.25 (t, 1H), 7.55 (d, 1H), 7.65 (d, 1H), 7.88 (m, 1H), 7.89 (m, 1H), 8.32 (s, 1H), 8.55 (s, 1H), 11.93 (s, 1H).

[Example 85] Preparation of 6-(5-formyl-2-methylphenyl)-N-(trans-4-morpholinocyclohexyl)-6-(pyridin-4-yl)-9H-pyrimido[4,5-b]indole-4-amine (Compound 71a)

71a

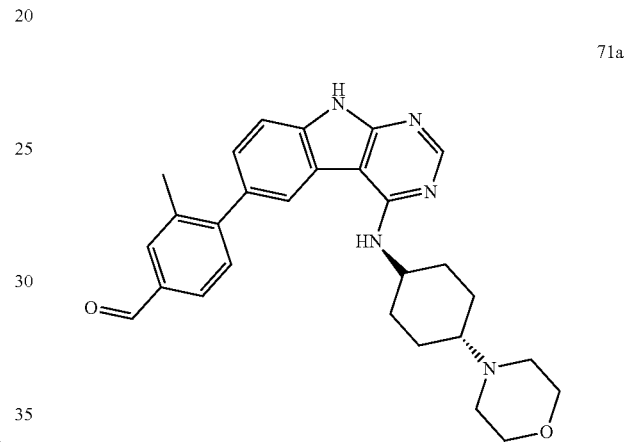

Compound 5aa (60 mg, 0.12 mmol) and 5-formyl-2-methylphenyl boronic acid (46.8 mg, 0.15 mmol) were reacted in the same manner as in Example 65, and the residue after reaction was separated by silica gel column chromatography (dichloromethane:methanol=20:1→10: 1) to obtain 47 mg (58%) of a white solid.

71a: ¹H-NMR (400 MHz, DMSO-$d_6$) δ 1.31-1.35 (m, 2H), 1.59-1.63 (m, 2H), 1.86-1.89 (m, 4H), 2.22 (m, 1H), 2.34 (s, 3H), 3.57 (m, 4H), 4.29 (m, 1H), 6.82 (d, 1H), 7.35 (d, 2H), 7.55 (d, 1H), 7.60 (d, 1H), 7.85 (s, 1H), 8.23 (s, 1H), 8.41 (s, 1H), 10.04 (s, 1H), 11.96 (s, 1H).

[Example 86] Preparation of Compound 73e

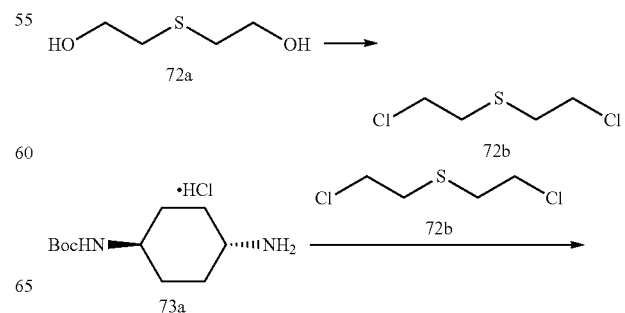

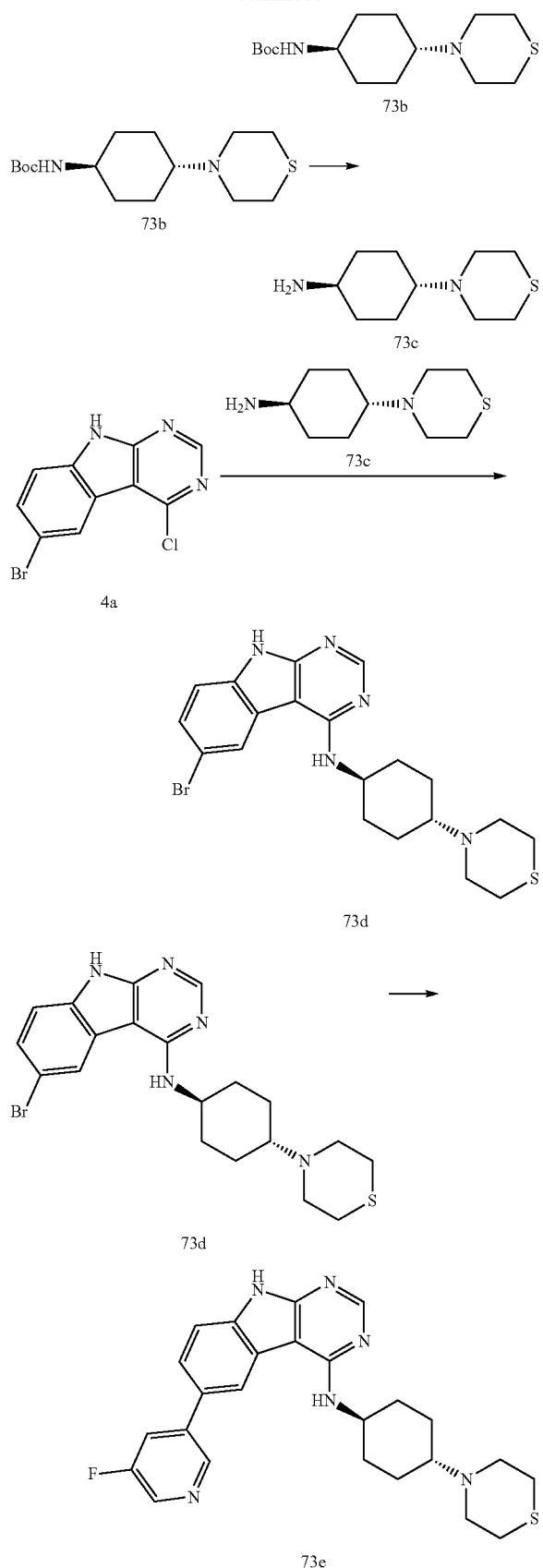

Step 1. Preparation of Compound 72b

After a starting material 72a (2,2'-thiodiethanol) is dissolved in dichloromethane, thionyl chloride was added dropwise thereto at 0° C. for 5 minutes. After the reaction mixture was stirred at 0° C. for 1 hour, cold water was slowly added dropwise thereto when the completion of the reaction was confirmed, and then extraction was performed with dichloromethane. After the extract was filtered with a celite pad, moisture was removed with sodium sulfate ($Na_2SO_4$), and the resulting product was concentrated under reduced pressure to obtain a clear liquid which is a target compound.

72b: $^1$H-NMR (400 MHz, DMSO-$d_6$) δ 2.95 (t, J=3.6 Hz, 4H), 3.77 (t, J=3.8 Hz, 4H).

Step 2. Preparation of Compound 73b

After a starting material 73a (trans-N-Boc-1,4-cyclohexenediamine hydrochloride), and potassium carbonate ($K_2CO_3$) were dissolved in dimethylformamide, the resulting solution was stirred for 2 to 3 minutes. After potassium iodide (KI) and Compound 72b (bis(2-chloroethyl)sulfane) were added to the reaction mixture, the resulting mixture was stirred at room temperature for 15 hours. After the reaction was completed, the resulting product was diluted in ethyl acetate and filtered with a celite pad, and then washed with water, and then moisture was removed with sodium sulfate ($Na_2SO_4$), and the resulting product was concentrated under reduced pressure. The residue was purified by silica gel column chromatography to obtain a light yellow solid which is a target compound.

73b: $^1$H-NMR (400 MHz, DMSO-$d_6$) δ 1.14-1.29 (m, 4H), 1.38 (s, 9H), 1.58-1.74 (m, 4H), 2.57 (m, 1H), 2.67-2.78 (m, 4H), 2.83-2.94 (m, 4H), 3.54 (t, J=4.0 Hz, 1H).

Step 3. Preparation of Compound 73c

After a starting material 73b was dissolved in dichloromethane, a hydrochloric acid solution (4 M dioxane) was slowly added dropwise thereto at 0° C. The reaction mixture was stirred at room temperature for 1 hour, and then concentrated under reduced pressure. Impurities were removed by adding diethyl ether to the concentrate, and the solid was filtered to a light yellow solid which is a target compound.

73c: $^1$H-NMR (400 MHz, DMSO-$d_6$) δ 1.28-1.45 (m, 4H), 1.68-1.94 (m, 4H), 2.57 (m, 1H), 2.73-2.81 (m, 4H), 2.87-2.95 (m, 4H), 3.75 (t, J=3.8 Hz, 1H).

Step 4. Preparation of Compound 73d

After a starting material 4a, Compound 73c, and triethylamine were dissolved in dimethyl sulfoxide, the resulting solution was stirred at room temperature for 24 hours. After the reaction was completed, the reaction mixture was diluted in ethyl acetate and filtered with a celite pad. The filtered product was washed with water, moisture was dried with sodium sulfate ($Na_2SO_4$), the resulting product was concentrated under reduced pressure, and the residue was purified by silica gel column chromatography to obtain a light yellow solid which is a target compound.

73d: $^1$H-NMR (400 MHz, DMSO-$d_6$) δ 1.15-1.26 (m, 4H), 1.57-1.75 (m, 4H), 2.61 (m, 1H), 2.75-2.88 (m, 4H), 2.90-3.15 (m, 4H), 3.45 (m, 1H), 7.46 (d, J=2.8 Hz, 1H), 7.6 (d, J=9.2 Hz, 1H), 8.05 (s, 1H), 8.27 (s, 1H).

Step 5. Preparation of Compound 73e

After a starting material 73d, 5-fluoropyridine-3-boronic acid, and potassium carbonate ($K_2CO_3$) were dissolved in dioxane:water (4:1 in v/v in 5 mL), oxygen was removed by sufficiently purging with argon gas, Pd(PPh$_3$)$_4$ was added thereto, then the gas was removed, and the resulting product was stirred at 80° C. for 18 hours. After the reaction was completed, the resulting product was diluted in ethyl acetate and filtered with a celite pad, and then washed with water, and then moisture was removed with sodium sulfate (Na$_2$SO$_4$), and the resulting product was concentrated under reduced pressure. The residue was separated by silica gel column chromatography to obtain a light yellow solid which is a target compound.

73e: $^1$H-NMR (400 MHz, DMSO-d$_6$) δ 1.42-1.63 (m, 4H), 1.98-2.21 (m, 4H), 2.28-2.35 (m, 1H), 2.45-2.57 (m, 4H), 3.72-3.74 (m, 4H), 4.35-4.38 (m, 1H), 7.68 (d, J=8.8 Hz, 1H), 7.73 (dd, J=8.2, 1.8 Hz, 1H), 7.81 (t, J=2.2, 1H), 8.31 (d, J=2.4 Hz, 1H), 8.41 (s, 1H), 8.49 (d, J=1.2 Hz, 1H), 8.58 (d, J=1.6 Hz, 1H).

[Experimental Example 1] Evaluation of IRAK4 Enzyme Inhibition Degree 2.5 μl of a compound diluted to 4-fold of a final concentration was put into a 384-well white plate (low volume). 2.5 μl of 0.4 ng/μl IRAK4 enzyme was added thereto, and the resulting mixture was totally reacted for 10 minutes. 5 μl of a mixed liquid of a 6 μM peptide substrate (BMKC-2) and 100 μM ATP was added thereto, the resulting mixture was reacted at room temperature for 60 minutes, then 2.5 μl of 10 mM EDTA was added thereto, and the resulting mixture was reacted again for 10 minutes. 40 nM anti-phospho Thr antibody was aliquoted to 2.5 μl each, 5 μl of a mixed solution of a 160 μl/ml acceptor bead and a donor bead was added thereto, and then the resulting mixture was reacted at room temperature for 60 minutes. Fluorescence signals were measured using a bead experimental apparatus (Fusion alpha-FP Microplate Reader, Perkin Elmer Inc.).

From the detected signal, an activity inhibition rate [% inhibition degree=(the average value of a compound−the average value of a negative control)/(the average value of a positive control−the average value of a negative control)× 100] was calculated, and is shown in [Table 1]. Further, a % inhibition degree of the compound at each concentration was obtained, and then a 50% inhibition concentration (IC$_{50}$ value) was analyzed by a non-linear regression analysis.

As shown in [Table 1], the tricyclic compound of the present invention shows an excellent inhibitory activity against IRAK4 by showing an IC$_{50}$ of about 1 to 1,000 nM in an inhibition experiment against IRAK4 enzyme. Therefore, the tricyclic compound of the present invention can be usefully used for the prevention or treatment of diseases associated with the induced activity of IRAK4.

TABLE 1

| Compound | IRAK4 enzyme test | |
|---|---|---|
| | % Inhibition degree @ 1 μM | IC$_{50}$ (nM) |
| 5ba (Example 1) | 83 | 29 |
| 5bb (Example 2) | 83 | 21 |
| 5bc (Example 3) | 9 | — |
| 5da (Example 4) | 99 | 128 |
| 5db (Example 5) | <1 | — |
| 6aaa (Example 6) | 100 | 28 |
| 6aab (Example 7) | 100 | 18.4 |
| 6aac (Example 8) | 100 | 12.6 |
| 6aad (Example 9) | 100 | 4.4 |
| 6aae (Example 10) | 100 | 2.0 |
| 6aaf (Example 11) | 100 | 4.6 |

TABLE 1-continued

| Compound | IRAK4 enzyme test | |
|---|---|---|
| | % Inhibition degree @ 1 μM | IC$_{50}$ (nM) |
| 6aag (Example 12) | 82 | 31 |
| 6aah (Example 13) | 100 | 40.0 |
| 6aai (Example 14) | 98 | 67.6 |
| 6aaj (Example 15) | 99 | 159.2 |
| 6aak (Example 16) | 98 | 104.0 |
| 6aal (Example 17) | 99 | 151.4 |
| 6aam (Example 18) | 37 | 243.7 |
| 6aan (Example 19) | 82 | 61.0 |
| 6aao (Example 20) | 74 | 63 |
| 6aap (Example 21) | 56 | 780 |
| 6aaq (Example 22) | 59 | 565 |
| 6aar (Example 23) | 78 | 137 |
| 6aas (Example 24) | 79 | 50 |
| 6aba (Example 25) | 83 | 4 |
| 6abb (Example 26) | 82 | 10 |
| 6aca (Example 27) | 100 | 13.8 |
| 6ada (Example 28) | 53 | 861 |
| 6aea (Example 29) | 34 | 1,528 |
| 6afa (Example 30) | 36 | 1050 |
| 6agaa (Example 31) | 36 | 1,141 |
| 6agba (Example 32) | 42 | 1,187 |
| 6aha (Example 33) | 41 | 1,042 |
| 6baa (Example 34) | 70 | 308 |
| 6bab (Example 35) | 86 | 210 |
| 6bac (Example 36) | 60 | 842 |
| 6bad (Example 37) | 52 | 928 |
| 6bae (Example 38) | 94 | 8.0 |
| 6baf (Example 39) | 70 | 509 |
| 6bag (Example 40) | 79 | 314 |
| 6caa (Example 41) | 50 | 1,362 |
| 11b (Example 42) | 10 | — |
| 17a (Example 43) | 100 | 10.5 |
| 17b (Example 44) | 100 | 7.2 |
| 17c (Example 45) | 100 | 32.6 |
| 23a (Example 46) | 91 | 79 |

[Experimental Example 2] Experiment of Suppressing Secretion of Cell-Based Inflammatory Cytokines Peripheral blood mononuclear cells (PBMCs) isolated from whole blood were distributed in a 96-well plate. TNF-α was aliquoted at a density of 1×10$^5$ cells/well, IFN-α was aliquoted at a density of 2×10$^5$ cells/well, and TNF-α and IFN-α were treated with a compound diluted to 4-fold of a final concentration and totally cultured for 30 minutes. TNF-α was treated with 100 ng/ml lipopolysaccharide (LPS), IFN-α was treated with 500 nM ODN2216 (CpGTLR9 stimulator), and TNF-α and IFN-α were further cultured for 24 hours and 72 hours, respectively. An enzyme-linked immunosorbent assay (ELISA) was performed on TNF-α and IFN-α using an ELISA kit manufactured by BD Biosciences and an ELISA kit manufactured by PBL Assay Science, Inc., respectively. A cell supernatant and a standard drug were put into the ELISA plates and reacted for 2 hours. The plates were washed and a measurement antibody and streptavidin-HRP were sequentially added thereto. After the plates were washed, a TMB substrate was added thereto and reacted in a dark place. The reaction was stopped by adding a stop solution thereto, and the absorbance at 450 nm and 570 nm was measured using an absorber (OPTIMax tunable microplate reader, molecular devices). The experimental results are shown in [Table 2].

TABLE 2

| | Suppression of cytokine secretion | | | |
|---|---|---|---|---|
| | TNF-α, % inhibition degree | | IFN-α, % inhibition degree | |
| Compound | 1 μM | 0.1 μM | 1 μM | 0.1 μM |
| 5ba (Example 1) | 41.3 | 31.7 | 73.9 | 27.0 |
| 5bb (Example 2) | 47.0 | 7.3 | 90.0 | 27.3 |
| 5da (Example 4) | 40 | 10 | 40 | 10 |
| 6aaa (Example 6) | 42 | 10.5 | 21 | 20 |
| 6aab (Example 7) | 114 | 44 | 94 | 31 |
| 6aac (Example 8) | 86 | 24 | 84 | 21 |
| 6aad (Example 9) | 105 | 42 | 104 | 31 |
| 6aae (Example 10) | 53 | 12 | 92 | 48 |
| 6aaf (Example 11) | 124 | 51 | 96 | 48 |
| 6aag (Example 12) | 51.4 | 16.7 | 89.5 | 6.4 |
| 6aah (Example 13) | 67 | 16 | 79 | 15 |
| 6aai (Example 14) | 62 | 13 | 87 | 32 |
| 6aaj (Example 15) | 30 | 3.2 | 56 | 6.4 |
| 6aak (Example 16) | 70 | 16 | 98 | 53 |
| 6aal (Example 17) | 57 | 13 | 70 | 18 |
| 6aam (Example 18) | 28 | 5 | 55 | 9 |
| 6aan (Example 19) | 32 | 9 | 71 | 28 |
| 6aba (Example 25) | 73.3 | 39.1 | 81.3 | 3.4 |
| 6abb (Example 26) | 79.4 | 17.9 | 90.4 | 54.0 |
| 6aca (Example 27) | 107 | 29 | 99 | 40 |
| 6agaa (Example 31) | 27 | 17 | 65 | 39 |
| 6agba (Example 32) | 87 | 26 | 74 | 56 |
| 6caa (Example 41) | 40 | 5 | 60 | 40 |
| 17a (Example 43) | 75 | 22 | 103 | 67 |
| 17b (Example 44) | 63 | 12 | 110 | 76 |
| 17c (Example 45) | 88 | 7 | 99 | 23 |

As shown in [Table 2], it can be seen that the tricyclic compound of the present invention has an excellent effect of inhibiting TNF-α and IFN-α at micromolar level concentrations.

[Experimental Example 3] Experiment of Cell-Based Inflammatory Promoter Activity A THP1-Lucia™ NF-κB cell line (Invivogen) was used in an NF-κB inhibition experiment, and a THP1-Lucia™ ISG cell line was used in an ISG inhibition experiment. In the NF-κB inhibition experiment, cells were planted at a density of 1×10$^4$ cells/well in a 96-well plate, and in the ISG inhibition experiment, cells were planted at a density of 2×10$^4$ cells/well in a 96-well plate. The cells were treated with a compound diluted to 4-fold of a final concentration, and totally cultured for 30 minutes. NF-κB was treated with 100 ng/ml lipopolysaccharide (LPS), ISG was treated with a stimulator of 1 μg/ml Poly(dA:dT)/LyoVec, and NF-κB and ISG were cultured for 24 hours. 10 μl of a cell supernatant was taken and transferred to a 96-well plate. 50 μl of a Quanti-luc solution was aliquoted using an automatic aliquoter of a measurer (Envision Multilabel Plate Reader, Perkin Elmer, Inc.), and light emission signals were measured.

TABLE 3

| | Promoter inhibition | | | |
|---|---|---|---|---|
| | NF-κB, % inhibition degree | | ISG, % inhibition degree | |
| Compound | 1 μM | 0.1 μM | 1 μM | 0.1 μM |
| 5ba (Example 1) | 89 | 48 | 78 | 37 |
| 5bb (Example 2) | 92 | 58 | 73 | 43 |
| 5da (Example 4) | 30 | 5 | 20 | 1 |
| 6aaa (Example 6) | 71 | 23 | 55 | 17 |
| 6aab (Example 7) | 61 | 8 | 54 | 11 |
| 6aac (Example 8) | 64 | 17 | 45 | 7 |
| 6aad (Example 9) | 78 | 33 | 79 | 37 |
| 6aae (Example 10) | 40 | <1 | 29 | 4 |
| 6aaf (Example 11) | 82 | 43 | 83 | 24 |
| 6aag (Example 12) | 37 | 12 | 52 | 20 |
| 6aah (Example 13) | 63 | 19 | 47 | 10 |
| 6aai (Example 14) | 36 | 6 | 41 | 9 |
| 6aaj (Example 15) | 33 | <1 | 20 | 14 |
| 6aak (Example 16) | 37 | <1 | 30 | <1 |
| 6aal (Example 17) | 15 | <1 | 17 | 1 |
| 6aam (Example 18) | 11 | <1 | <1 | <1 |
| 6aan (Example 19) | 28 | <1 | 6 | <1 |
| 6aba (Example 25) | 87 | 40 | 83 | 33 |
| 6abb (Example 26) | 83 | 50 | 73 | 42 |
| 6aca (Example 27) | 85 | 28 | 73 | 23 |

TABLE 3-continued

| | Promoter inhibition | | | |
| --- | --- | --- | --- | --- |
| | NF-κB, % inhibition degree | | ISG, % inhibition degree | |
| Compound | 1 μM | 0.1 μM | 1 μM | 0.1 μM |
| 6agaa (Example 31) | 24 | <1 | 16 | 7 |
| 6agba (Example 32) | 6 | <1 | 8 | 6 |
| 6caa (Example 41) | 10 | 5 | 10 | 1 |
| 17a (Example 43) | 78 | 31 | 93 | 14 |
| 17b (Example 44) | 62 | 14 | 80 | 4 |
| 17c (Example 45) | 53 | 2 | 52 | 2 |

As shown in Table [Table 3], it can be seen that the tricyclic compound of the present invention has an excellent effect of inhibiting NF-κB 및 ISG promoters at micromolar level concentrations.

[Experimental Example 4] Suppressive Effects of Test Drug on Systemic Inflammatory Diseases in Mice As experimental animals, 8-week-old C57BL/6 (20 to 23 g) mice were supplied from Orient Bio Co., Ltd. (Seongnam, Gyeonggi-do) and used. The mice were acclimatized for 2 weeks or more in an animal room of the Korea Research Institute of Chemical Technology, where temperature (22±1° C.) and humidity (50±10%) were automatically adjusted, and then used for experiments, and allowed to freely ingest water and feed. This animal experiment was performed with the approval of the Animal Care and Use Committee of the Korea Research Institute of Chemical Technology.

A systemic inflammatory disease was induced by administering a dose of 15 mg/kg lipopolysaccharide (LPS, Sigma L2880) intraperitoneally to the mice. A test drug was suspended in a 10% Cremophor solution and administered orally 2 hours prior to LPS injection, the mice were anesthetized with isoflurane 1 hour after LPS administration, and blood was collected from the heart. Serum was obtained by centrifuging the collected blood at 13,000 rpm for 15 minutes, store at −20° C., and then taken if needed to measure the content of cytokine (TNF-α) in serum using an ELISA kit manufactured by BD Biosciences. As a positive control drug, PF-06650833 (AstraTech) was purchased and used, and the statistical significance of the suppressive effects of the test drug on systemic inflammations was verified using a student's T-test or Dunnett's T-test (SigmaStat, Jandel Scientific) program. The test results are illustrated in FIGS. 1 and 2.

According to the test results, when Compounds 6aad and 6aaf of the present invention were administered at doses of 50 and 100 mg/kg, the compounds showed a better suppressive effect than PF-06650833.

[Experimental Example 5] Antitumor Effect in SCID Mice Transplanted with TMD-8

As experimental animals, severe combined immunodeficiency (SCID) mice (C.B-17/IcrCrj-scid, female) were purchased from Charles River Laboratories Japan, Inc., and used. The mice were acclimatized for 2 weeks or more in an animal room, where temperature (22±1° C.) and humidity (50±10%) were automatically adjusted, and then used for experiments, and allowed to freely ingest water and feed. This animal experiment was performed with the approval of the Animal Care and Use Committee of the Korea Research Institute of Chemical Technology. As a TMD-8 cell line, which is a B-cell lymphoma cell line, a cell line whose subculture had been maintained in the Korea Research Institute of Chemical Technology was used.

Tumors in SCID mice were induced by transplanting TMD-8 cells at $9 \times 10^6$ cells/mouse to the right subcutaneous flank of each animal, and when the size of the transplanted tumor reached about 200 mm$^3$, drug administration was started (test period: 1 day). The test drug was suspended in a solution of 20% PEG400 and 3% Tween 80, and orally administered once a day for 14 days. After the test drug was administered, the diameter of the tumor (that is, a long diameter (a) and a short diameter (b) was measured using a calipers every 2 to 3 days, and according to a mathematical formula [size (mm$^3$) of tumor=(a×b$^2$)/2], the size (mm$^3$) of tumor was calculated, and is illustrated in FIGS. 3 and 4. As control drugs, PF-06650833 (Sigma) and ibrutinib (Medichem Express) were purchased and used, and the statistical significance of the antitumor effect of the test drug was verified using a student's T-test (SigmaStat, Jandel Scientific) program.

According to FIGS. 3 and 4, Compound 6aaf of the present invention did not show a significant difference in effect when compared to PF-06650833, but showed a slightly better tendency, and showed an excellent effect when administered in combination with ibrutinib. There was not much change in the body weight of the experimental animals during the test period.

The invention claimed is:

1. A compound represented by the following Chemical Formula 1:

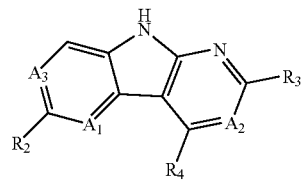

wherein,
$A_1$ is CH,
$A_2$ is N,
$A_3$ is $CR_1$,
$R_1$ is hydrogen, a halogen, —COOR$_5$,
$R_2$ is hydrogen, an amino group, —COOR$_6$,

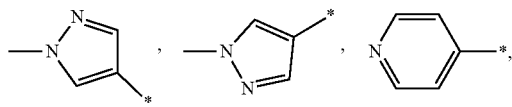

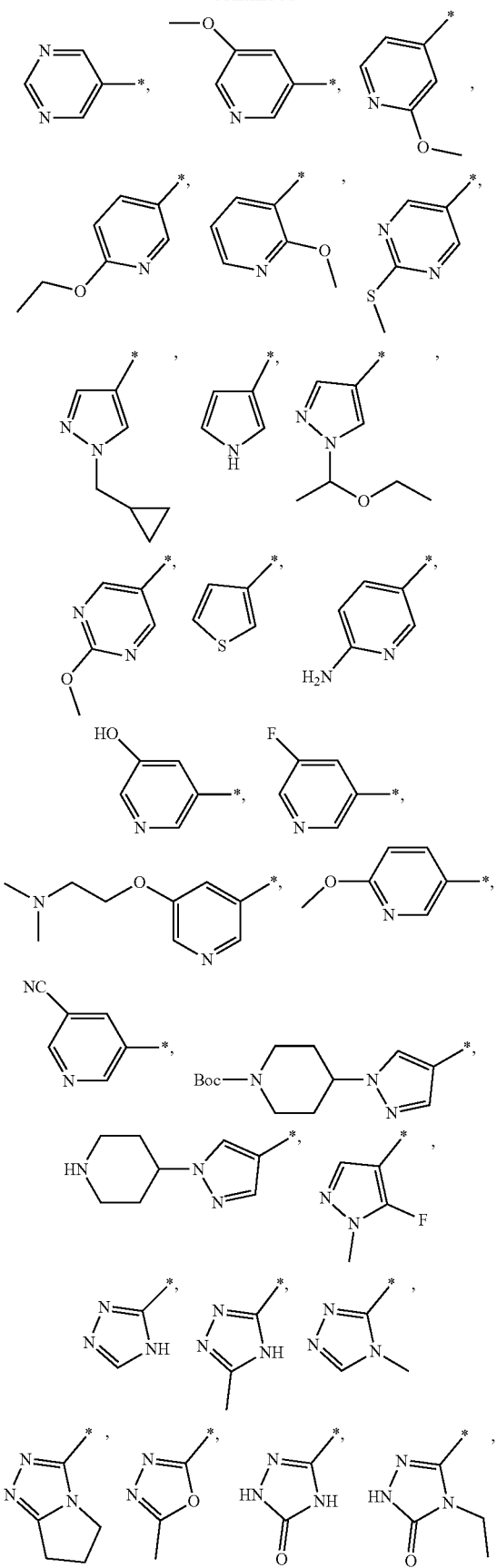

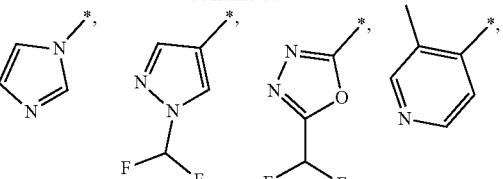

R₃ is hydrogen or a (C6-C12) aryl,

R₄ is -L₁-L₂-R₇, an amino group (—NH₂), a (C1-C12) heteroaryl or a (C6-C12) aryl of R₂ is optionally substituted with at least one or more groups selected from the group consisting of a (C1-C4) alkyl, a (C1-C4) alkyl substituted with a halogen, a (C1-C4) thioalkyl, an amino group (—NH₂), a methylamino group (—NHCH₃), a dimethylamino group (—N(CH₃)₂), —CH₂OH, a (C1-C4) alkoxy, a hydroxyl group (—OH), a halogen, a methanesulfonyl group (—SO₂CH₃), —SO₂N(CH₃)₂, a nitro group (—NO₂), a cyano group (—CN),

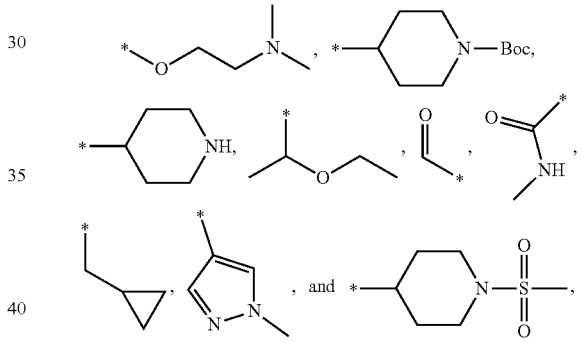

a (C6-C12) aryl of R₃ is optionally substituted with a nitro group (—NO₂),

L₁ is —N(R₈)— or —O—,

L₂ is —(CH₂)ₘ—,

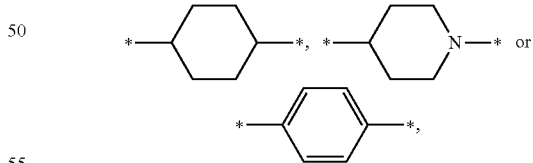

and m is an integer from 2 to 5,

R₇ is —N(R₉)₂, —OR₁₀, —SO₂CH₃, —SO₂N(CH₃)₂, or a monocyclic 5- to 7-membered saturated heterocycle, wherein the heterocycle comprises 1 to 3 heteroatoms selected from nitrogen, oxygen and sulfur, R₅ is a (C1-C4) alkyl, R₆ is a (C1-C4) alkyl, R₈ is hydrogen or a (C1-C4), R₉ is a (C1-C4) alkyl, R₁₀ is a (C1-C4) alkyl, a heterocycloalkyl amino of $R_7$ is optionally substituted with at least one or more groups selected from the group consisting of —SO$_2$CH$_3$ and —COOC(CH$_3$)$_3$ (—Boc).
2. The compound of claim 1, wherein the (C6-C12) aryl or substituted (C6-C12) aryl, which is $R_2$ is selected from the group consisting of:
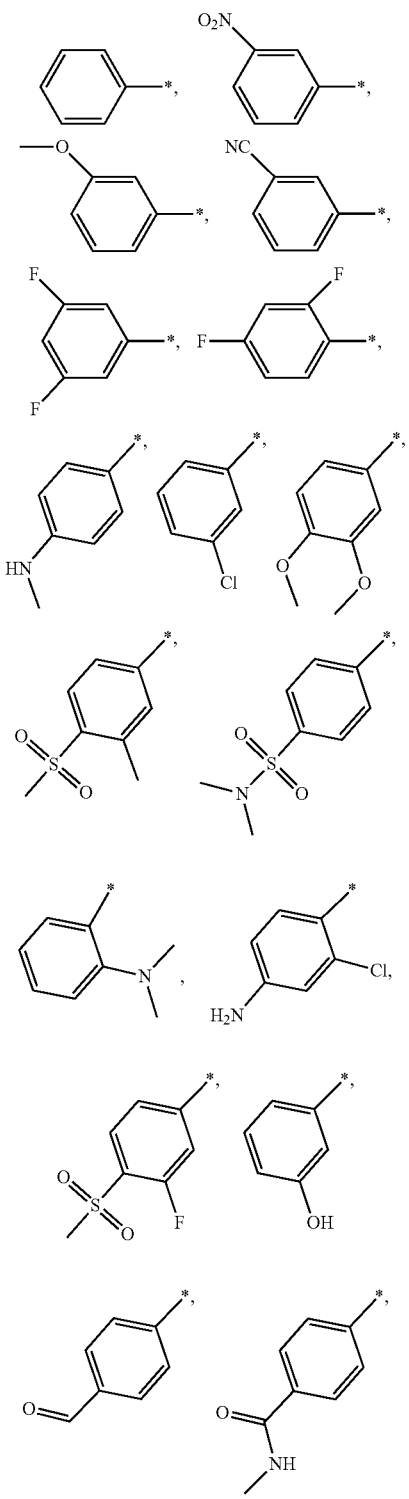
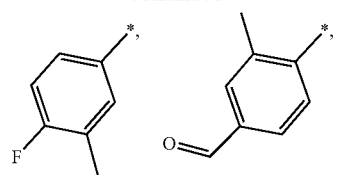
3. The compound of claim 1, wherein $R_4$ is selected from the group consisting of:
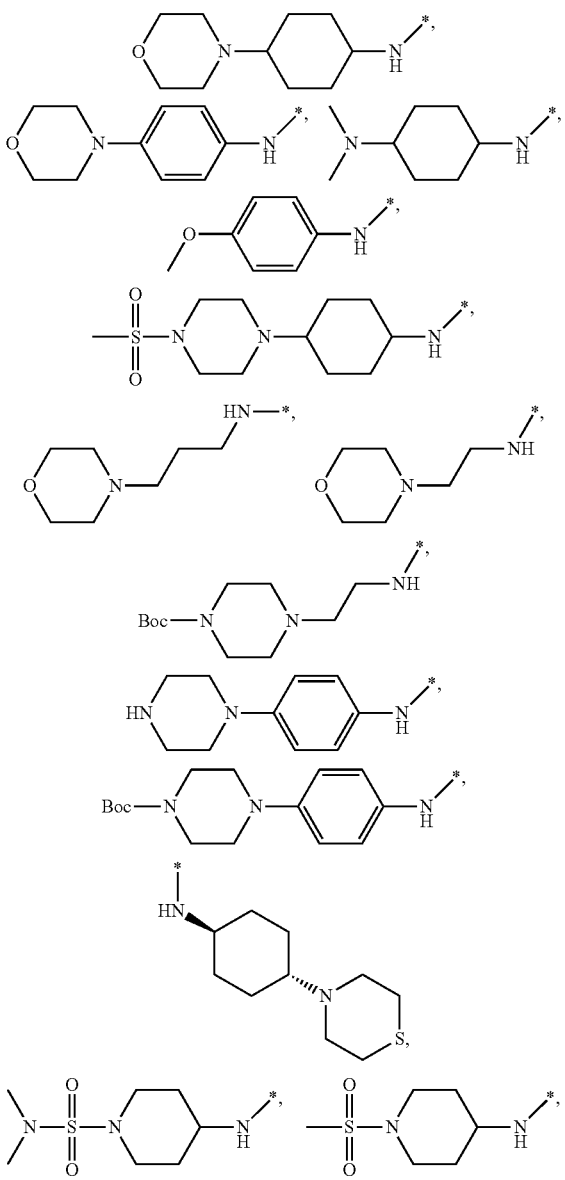

147
-continued
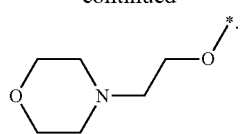
4. The compound of claim 1, wherein the compound is selected from the group consisting of:
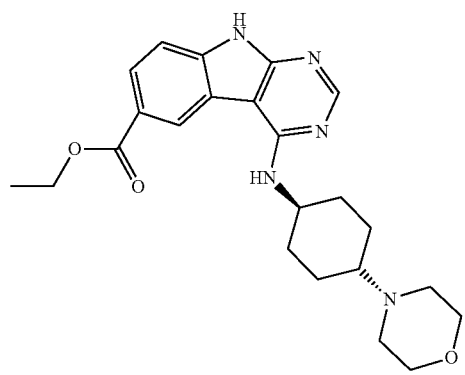
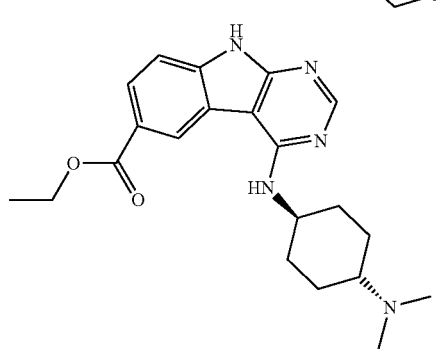
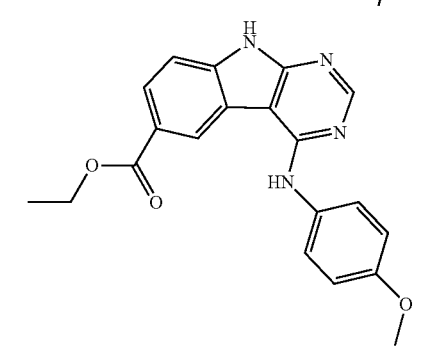
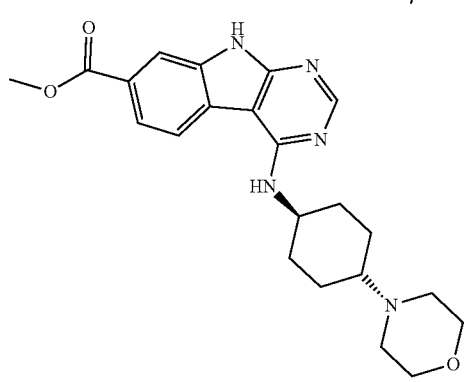
148
-continued
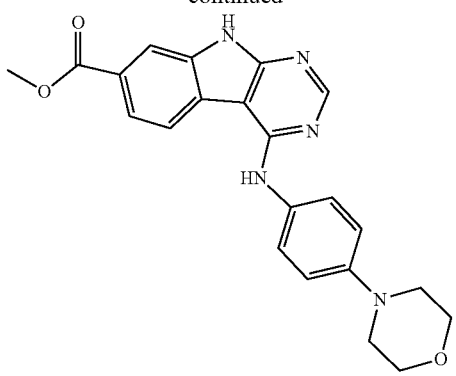
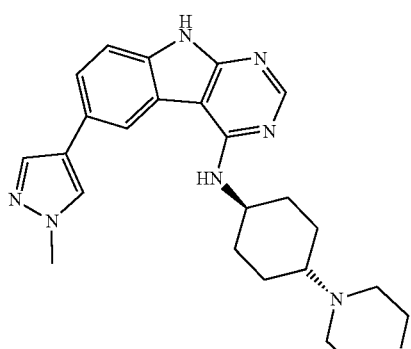
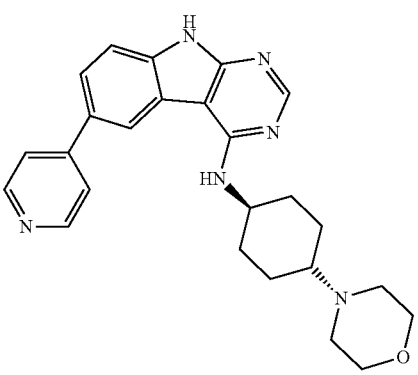
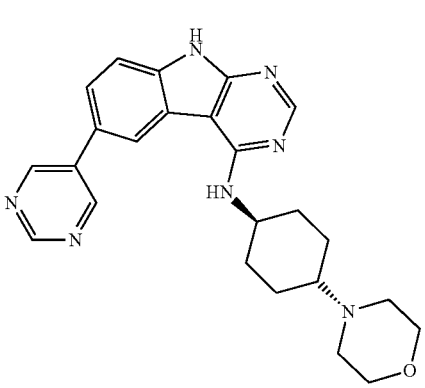

149
-continued
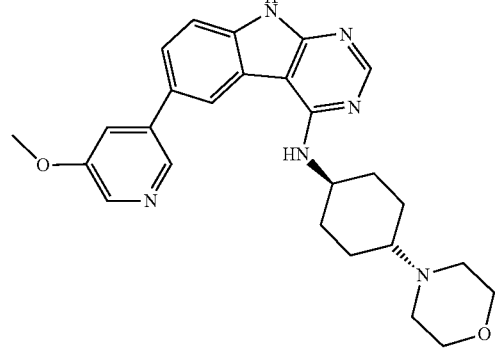
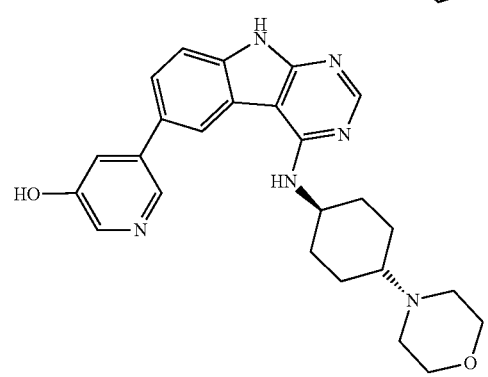
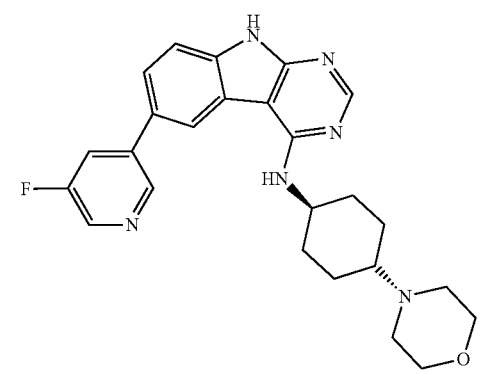
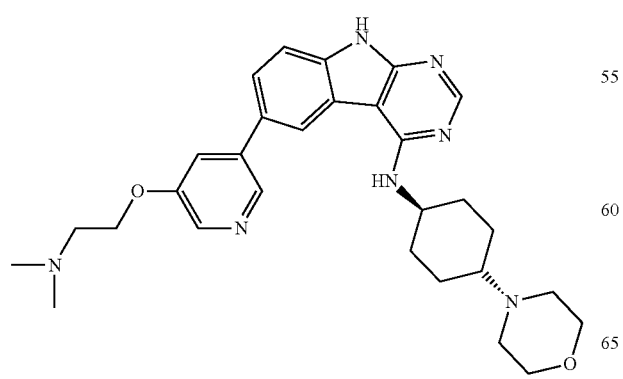
150
-continued
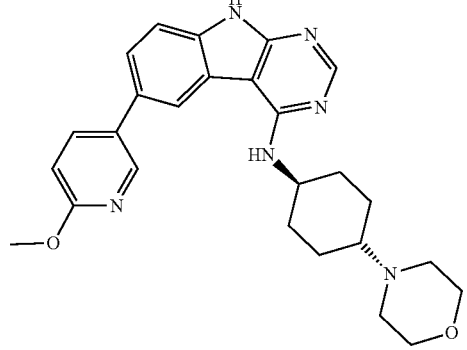
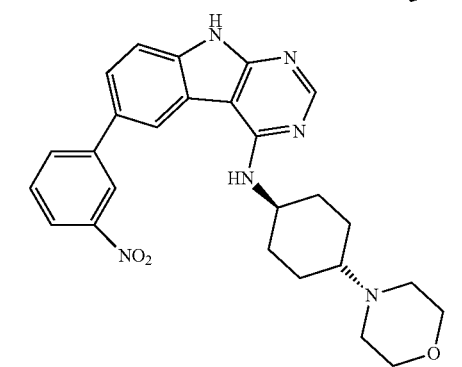
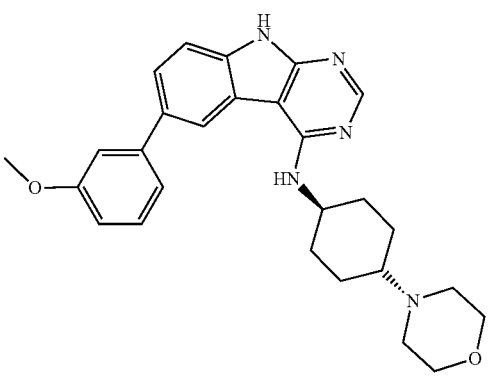
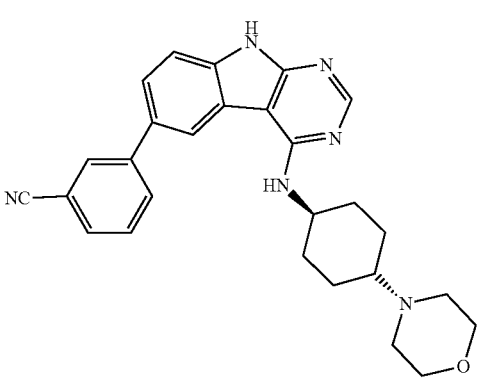

151
-continued
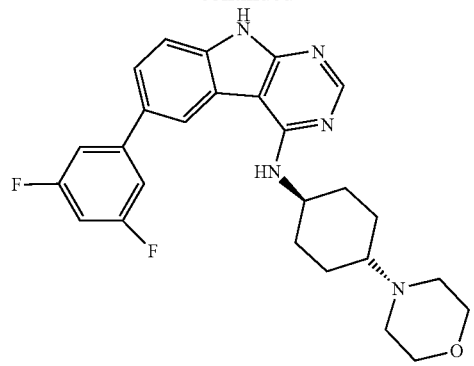
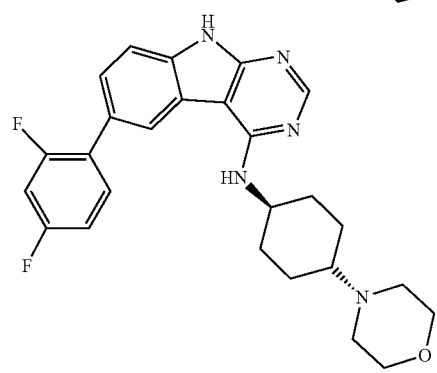
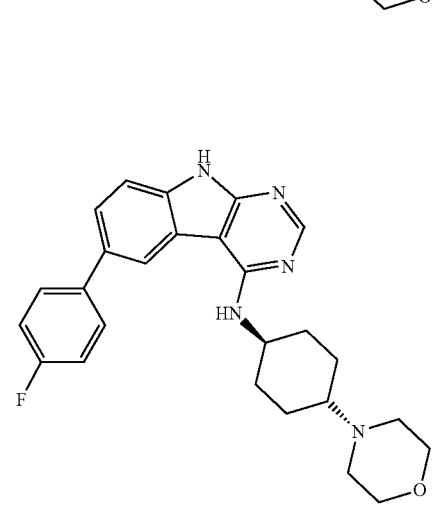
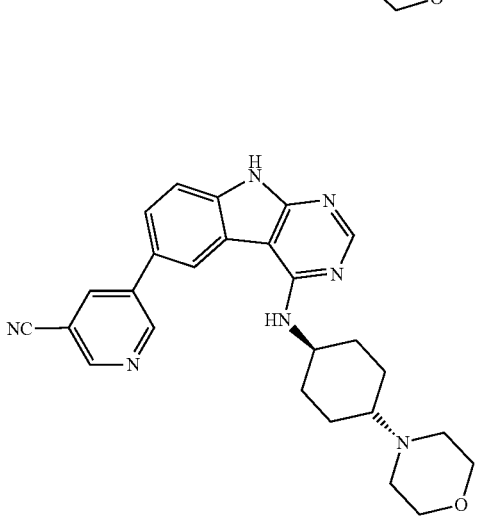
152
-continued
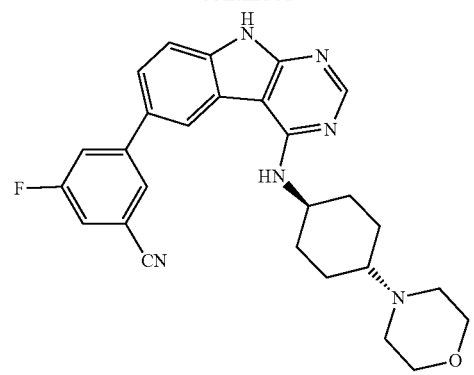
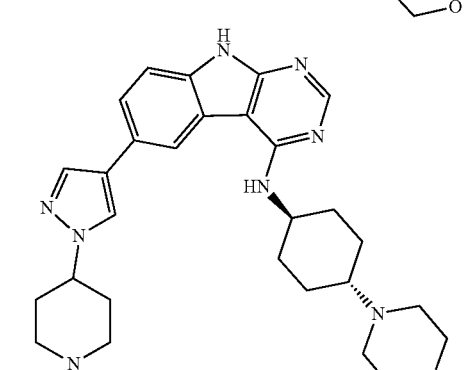
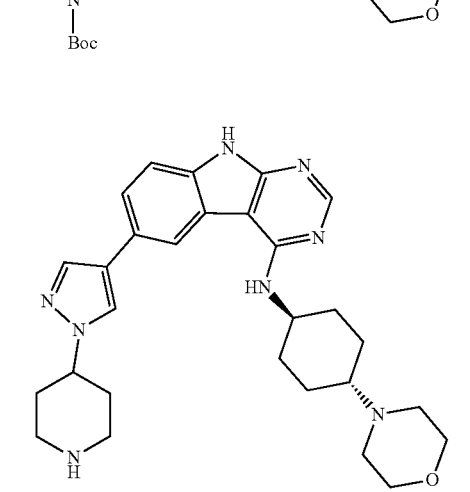
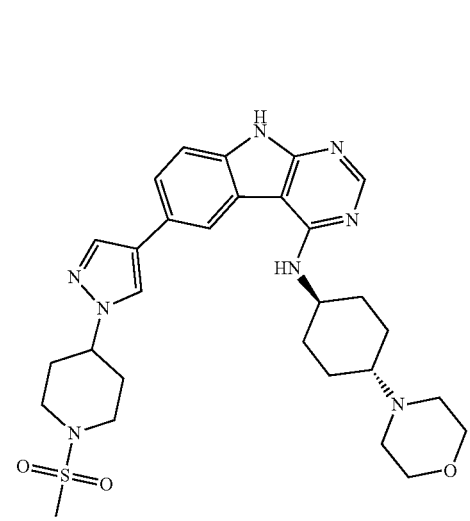

153
-continued
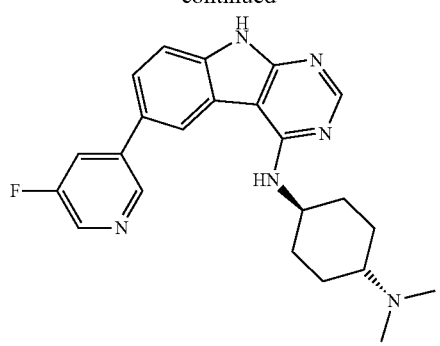
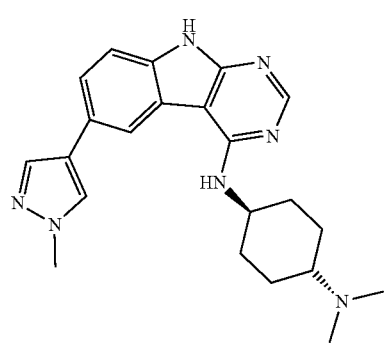
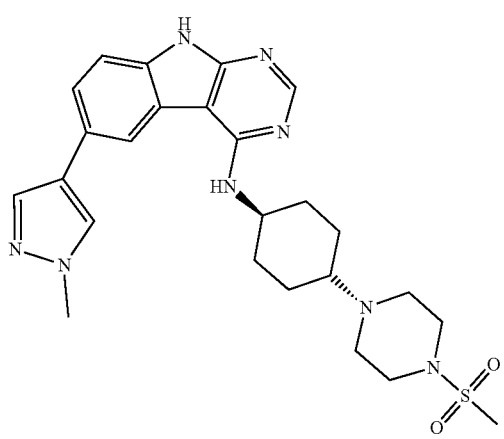
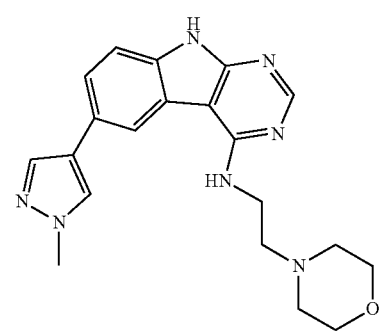
154
-continued
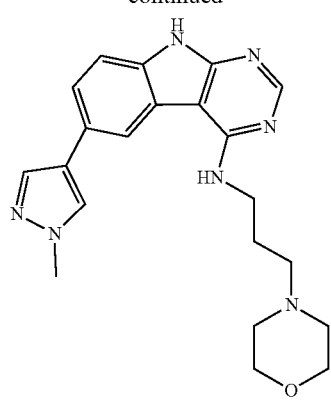
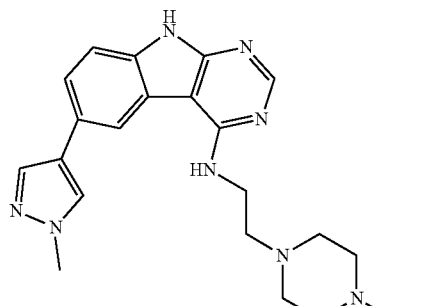
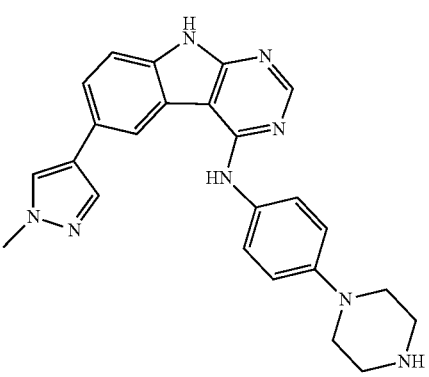
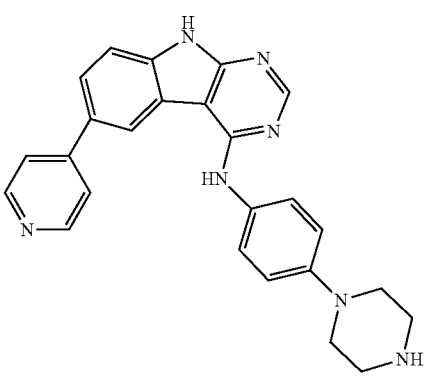

-continued
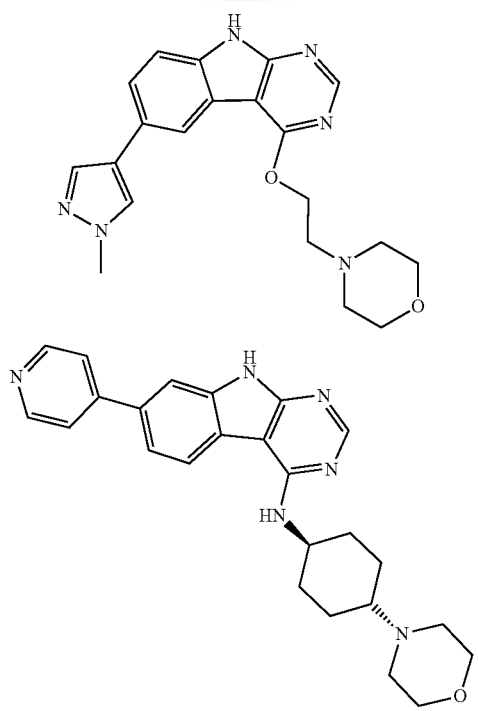
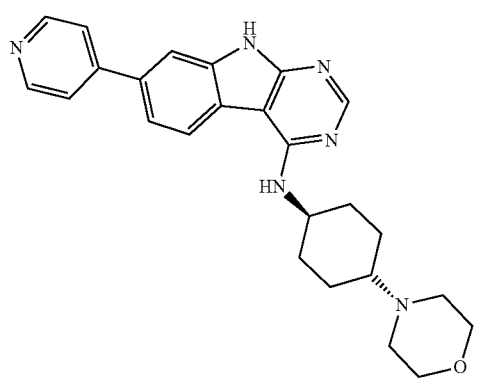
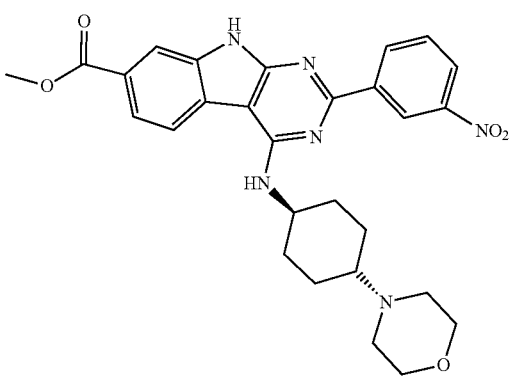
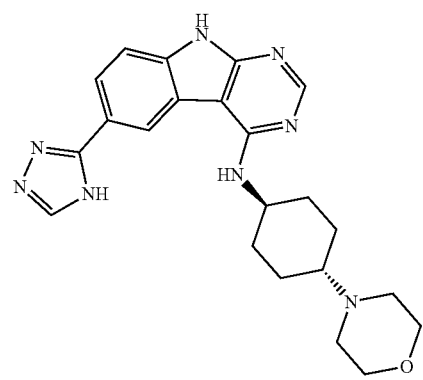
-continued
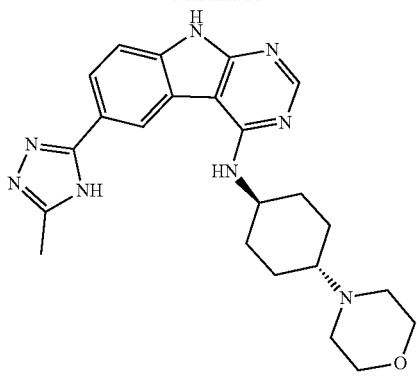
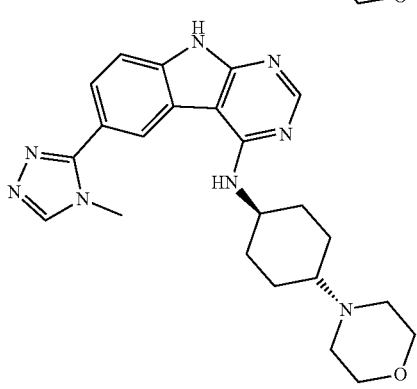
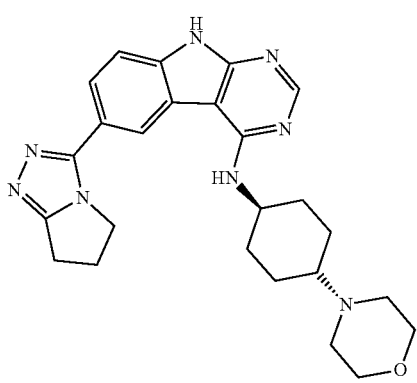
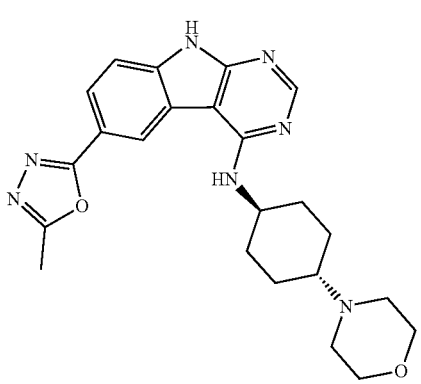

157
-continued
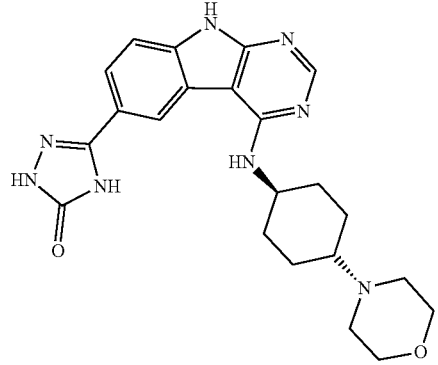
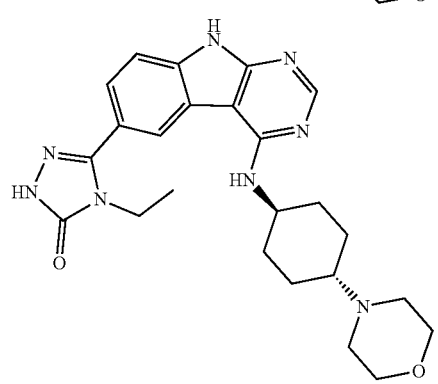
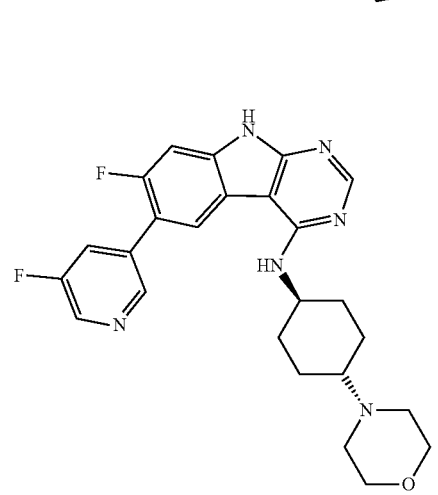
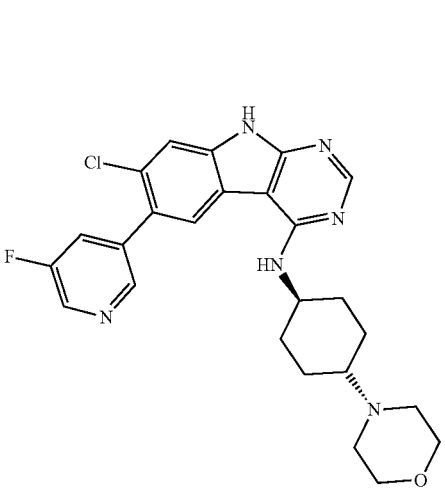
158
-continued
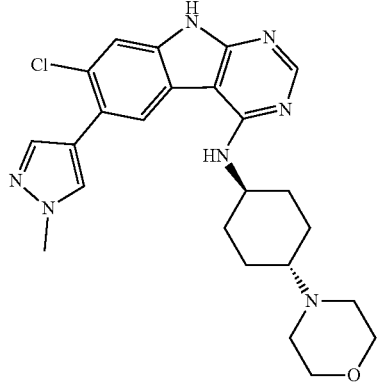 [SMILES: Cn1cc(-c2cc3c(cc2Cl)[nH]c2ncnc(N[C@H]4CC[C@H](N5CCOCC5)CC4)c23)cn1]
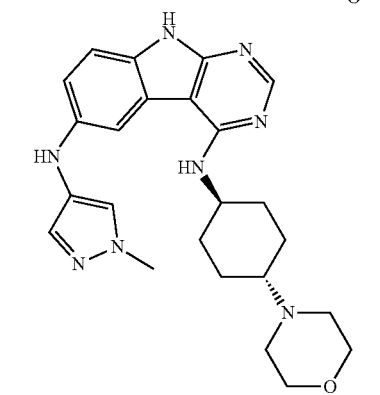
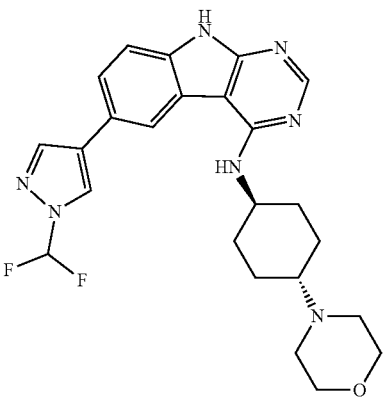
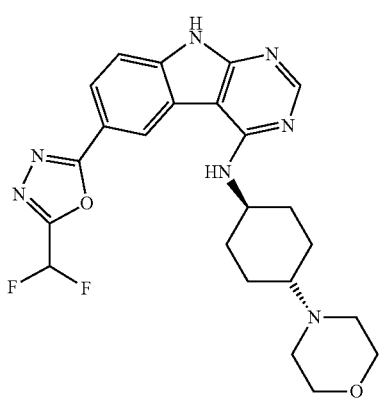

159
-continued
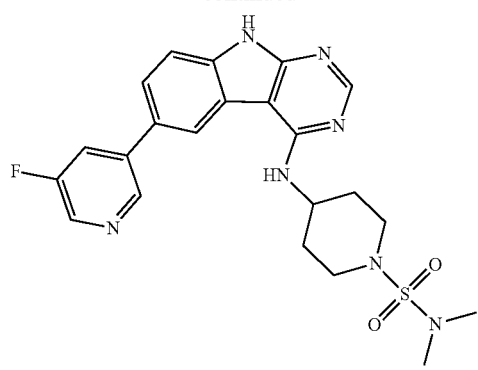
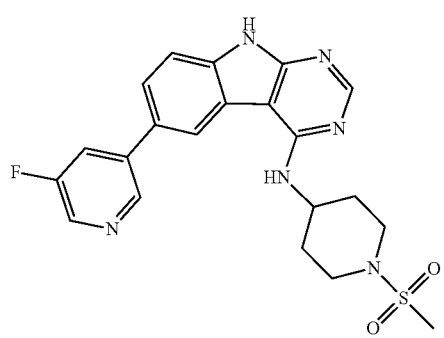
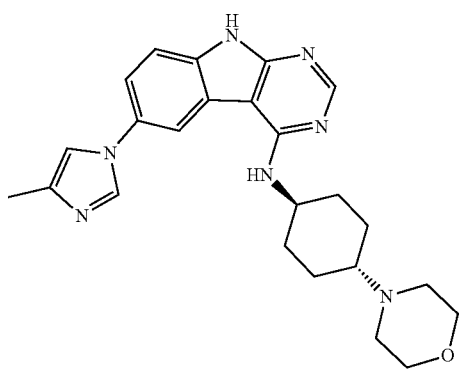
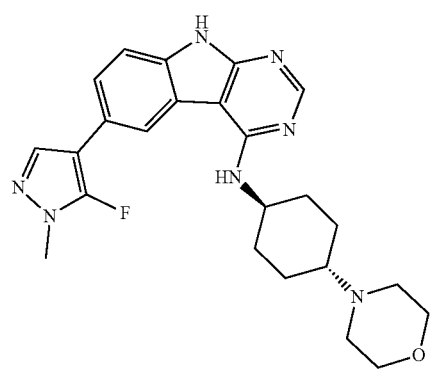
160
-continued
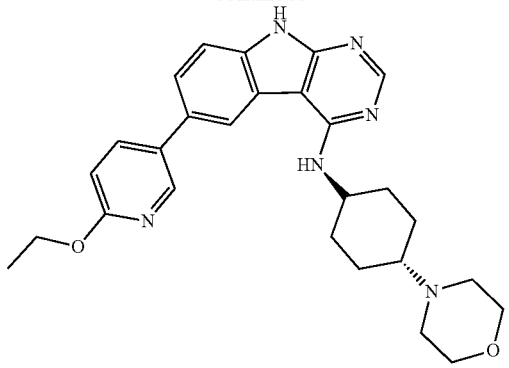
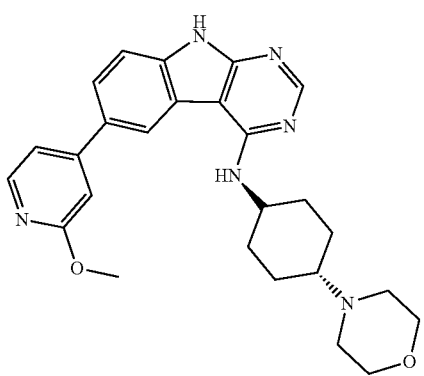
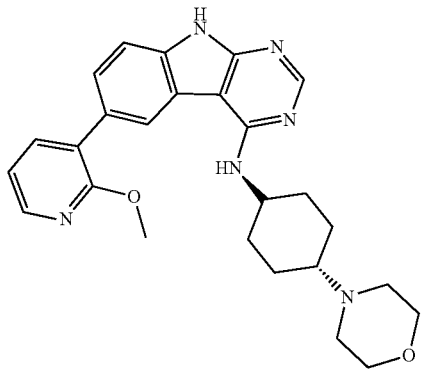
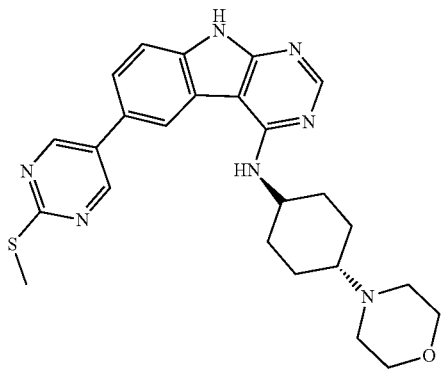

161
-continued
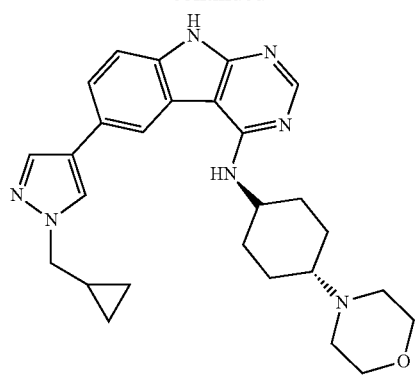
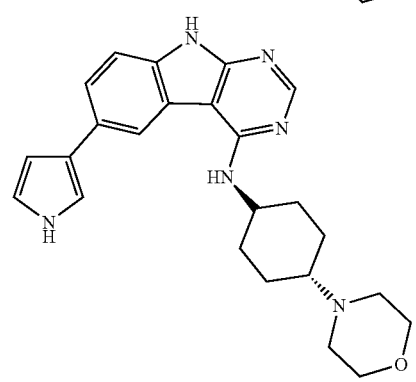
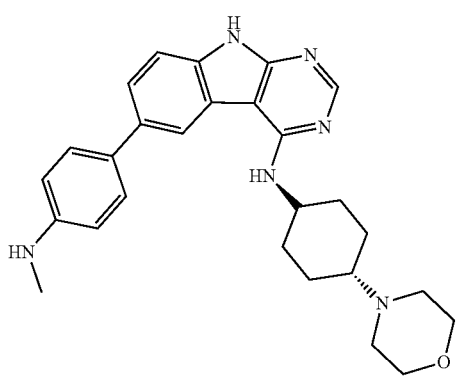
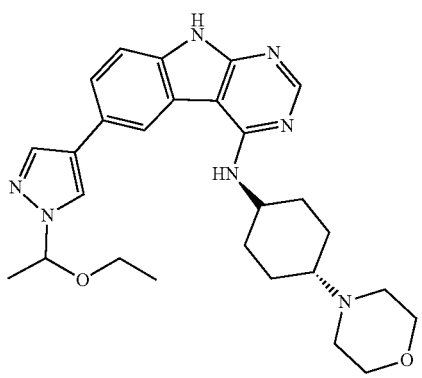
162
-continued
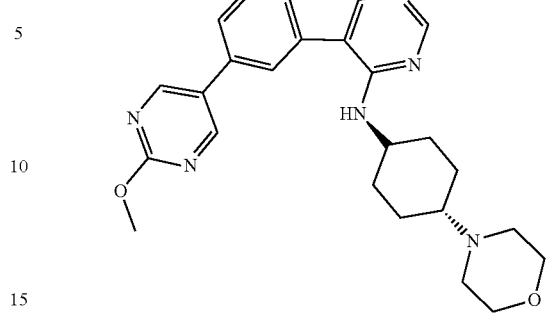
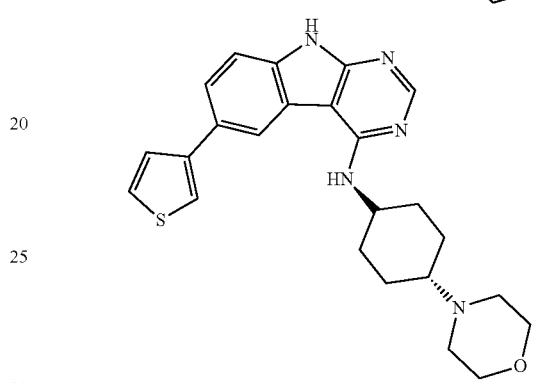
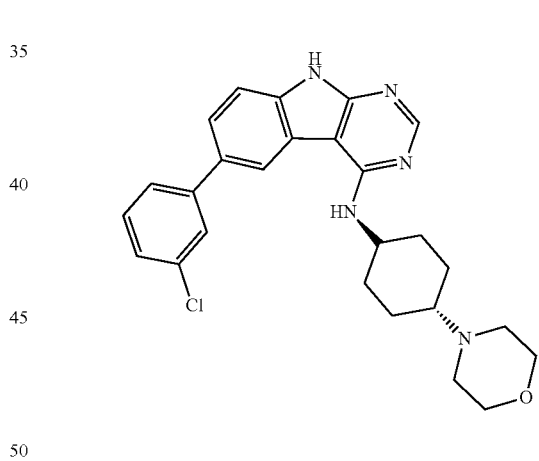
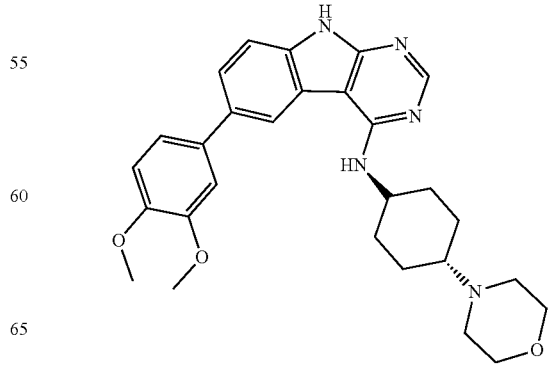

163
-continued
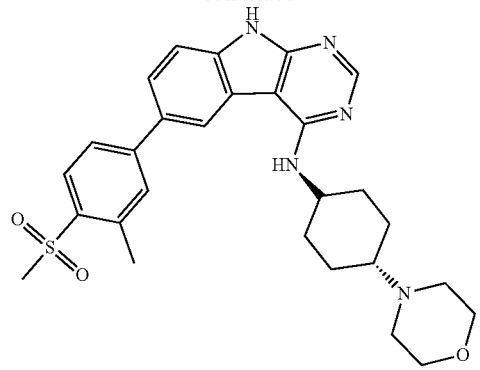
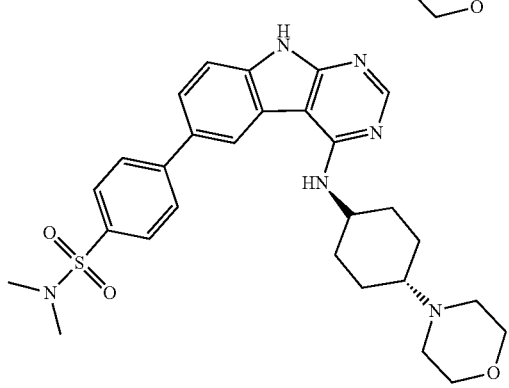
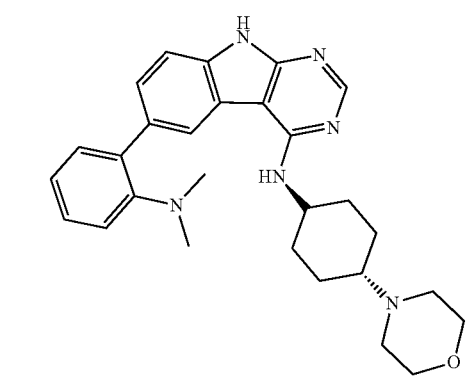
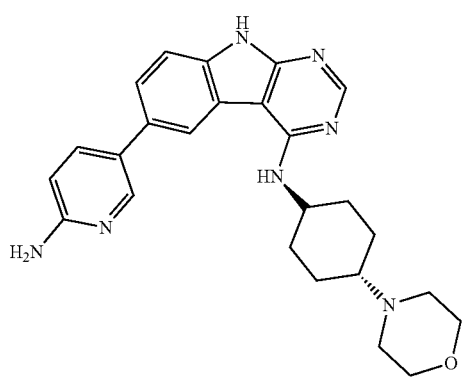
164
-continued
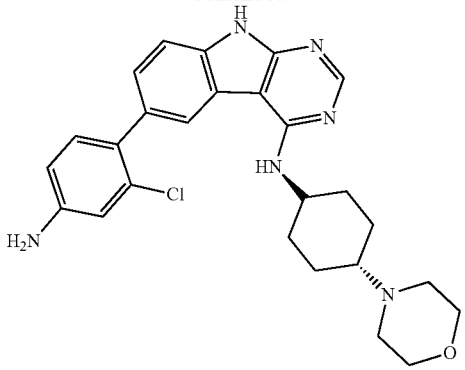
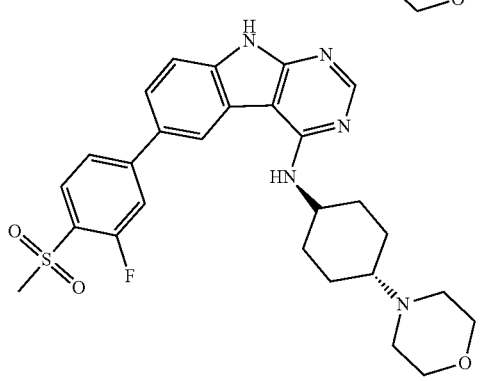
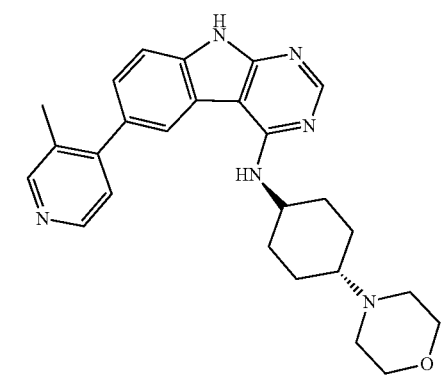
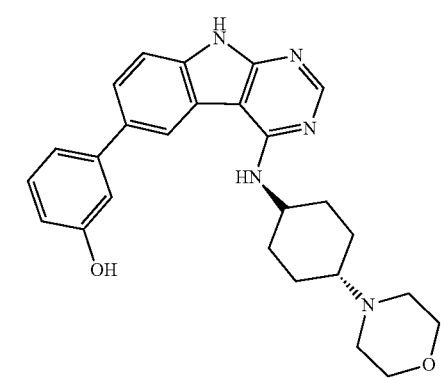

165
-continued
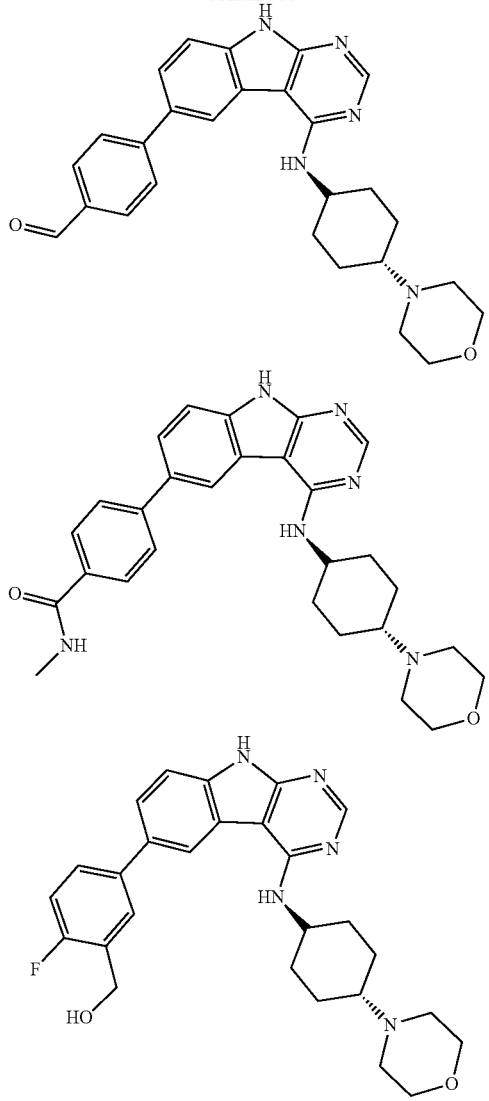
166
-continued
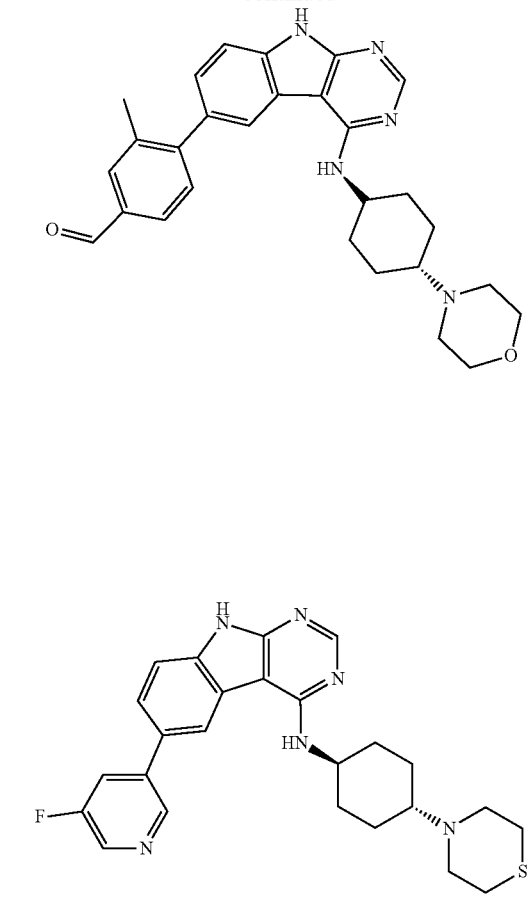
5. A pharmaceutical composition comprising the compound according to claim 1 and a pharmaceutically acceptable carrier.
6. A health food composition comprising the compound according to claim 1 and a food-acceptable carrier.
* * * * *